US012276671B2

(12) United States Patent
Jeromin et al.

(10) Patent No.: US 12,276,671 B2
(45) Date of Patent: Apr. 15, 2025

(54) PHOSPHO-TAU ANTIBODIES AND METHODS OF USE

(71) Applicant: ALZPATH, INC., Carlsbad, CA (US)

(72) Inventors: Andreas Jeromin, Alachua, FL (US); Krish Venkat, Lawrenceville, NJ (US)

(73) Assignee: ALZPATH, INC., Carlsbad, CA (US)

( * ) Notice: Subject to any disclaimer, the term of this patent is extended or adjusted under 35 U.S.C. 154(b) by 0 days.

(21) Appl. No.: 18/599,751

(22) Filed: Mar. 8, 2024

(65) Prior Publication Data

US 2024/0353428 A1 Oct. 24, 2024

Related U.S. Application Data

(63) Continuation of application No. PCT/US2022/042963, filed on Sep. 8, 2022.

(60) Provisional application No. 63/242,437, filed on Sep. 9, 2021.

(51) Int. Cl.
C07K 16/18 (2006.01)
G01N 33/53 (2006.01)
G01N 33/68 (2006.01)

(52) U.S. Cl.
CPC ......... *G01N 33/6896* (2013.01); *C07K 16/18* (2013.01); *G01N 33/53* (2013.01); *G01N 33/6857* (2013.01); *C07K 2317/20* (2013.01); *C07K 2317/24* (2013.01); *C07K 2317/52* (2013.01); *C07K 2317/565* (2013.01); *G01N 2333/4704* (2013.01); *G01N 2333/4709* (2013.01); *G01N 2333/96416* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 4,694,778 A | 9/1987 | Learn et al. | |
| 9,371,376 B2 | 6/2016 | Alderfer et al. | |
| 9,447,179 B2 | 9/2016 | Winderickx et al. | |
| 10,393,759 B2 | 8/2019 | Wilson et al. | |
| 11,275,092 B2 | 3/2022 | Wilson et al. | |
| 2004/0219509 A1 | 11/2004 | Valkirs et al. | |
| 2005/0260697 A1 | 11/2005 | Wang et al. | |
| 2005/0272110 A1 | 12/2005 | Drukier | |
| 2009/0159812 A1 | 6/2009 | Livingston | |
| 2011/0003707 A1 | 1/2011 | Goix et al. | |
| 2014/0094386 A1 | 4/2014 | Wilson et al. | |
| 2016/0376351 A1* | 12/2016 | Adolfsson .......... | G01N 33/6896 424/133.1 |
| 2017/0082641 A1 | 3/2017 | Rhyne et al. | |
| 2017/0106084 A1* | 4/2017 | Bader ................ | A61K 39/3955 |
| 2017/0137502 A1 | 5/2017 | Pfeifer et al. | |
| 2018/0080945 A1* | 3/2018 | Goetzl ............... | G01N 33/6896 |
| 2018/0238910 A1 | 8/2018 | Kang et al. | |
| 2018/0321261 A1 | 11/2018 | Stanley | |
| 2019/0033328 A1 | 1/2019 | Tokuda et al. | |
| 2019/0169275 A1 | 6/2019 | Griswold-Prenner et al. | |
| 2020/0377609 A1 | 12/2020 | Sievers et al. | |
| 2022/0018856 A1 | 1/2022 | Jannes et al. | |
| 2022/0146535 A1 | 5/2022 | Chai et al. | |
| 2022/0229074 A1 | 7/2022 | Wilson et al. | |
| 2022/0244276 A1 | 8/2022 | Wilson et al. | |
| 2024/0360206 A1 | 10/2024 | Jeromin et al. | |

FOREIGN PATENT DOCUMENTS

| | | |
|---|---|---|
| WO | WO-2010011506 A2 | 1/2010 |
| WO | WO-2019085804 A1 | 5/2019 |
| WO | WO-2019094595 A2 | 5/2019 |
| WO | WO-2021178545 A1 | 9/2021 |
| WO | WO-2022115705 A2 | 6/2022 |
| WO | WO-2022150735 A1 | 7/2022 |
| WO | WO-2023039107 A2 | 3/2023 |
| WO | WO-2024192404 A1 | 9/2024 |

OTHER PUBLICATIONS

Kipriyanov et al., Mol Biotechnol. Jan. 2004;26(1):39-60. doi: 10.1385/MB:26:1:39. PMID: 14734823.*
Wegmann et al., Curr Opin Neurobiol. Aug. 2021;69:131-138. doi: 10.1016/j.conb.2021.03.003. Epub Apr. 21, 2021. PMID: 33892381.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al., J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Lescar, et al. Journal of Biological Chemistry 270.30 (1995): 18067-18076.*
Kanyavuz et al., Nat Rev Immunol. Jun. 2019; 19(6):355-368. doi: 10.1038/S41577-019-0126-7.*
Al-Lazikani, Bissan, et al. Standard Conformations for the Canonical Structures of Immunoglobulins. Journal of Molecular Biology, vol. 273, 927-948 (1997).
Bird, Robert E., et al. Single-chain Antigen-Binding Proteins. Science, vol. 242, 423-426 (1988).
Clackson, Tim, et al. Making antibody fragments using phage display libraries. Nature, vol. 352, 624-628 (1991).
Colbere-Garapin, Florence, et al. A New Dominant Hybrid Selective Marker for Higher Eukaryotic Cells. Journal of Molecular Biology, vol. 150, 1-14 (1981).

(Continued)

*Primary Examiner* — Michael Szperka
(74) *Attorney, Agent, or Firm* — Wilson Sonsini Goodrich & Rosati

(57) ABSTRACT

Provided herein are compositions and methods relating to improved assays for establishing Alzheimer's disease. Further provided herein are compositions and methods comprising improved antibodies for assays including immunoassays.

48 Claims, 48 Drawing Sheets
Specification includes a Sequence Listing.

(56) References Cited

OTHER PUBLICATIONS

Cole, S.P.C., et al. The EBV-Hybridoma Technique and its Application to Human Lung Cancer. Monoclonal Antibodies and Cancer Therapy, vol. 27, 77-96 (1985).
Courtenay-Luck, N S. Genetic Manipulation of Monoclonal Antibodies. Monoclonal Antibodies: Production, Engineering and Clinical Application, Chapter 8, 166-179 (1995).
Crouse, Gray F., et al. Expression and Amplification of Engineered Mouse Dihydrofolate Reductase Minigenes. Molecular Cell Biology, vol. 3, 257-266 (1983).
Cummings, Jeffrey, et al. Alzheimer's disease drug development pipeline: 2022. Alzheimer's & Dementia, Translational Research & Clinical Interventions, vol. 8, 1-24 (2022).
Goldspiel, Barry R., et al. Human Gene Therapy. Clinical Pharmacy, vol. 12, 488-505 (1993).
Hanes, Jozef, et al. In Vitro Selection and Evolution of Functional Proteins by Using Ribosome Display. PNAS USA, vol. 94, 4937-4942 (1997).
Honegger, Annemarie, et al. Yet Another Numbering Scheme for Immunoglobulin Variable Domains: An Automatic Modeling and Analysis Tool. Journal of Molecular Biology, vol. 309, 657-670 (2001).
Huse, William D., et al. Generation of a Large Combinatorial Library of the Immunoglobulin Repertoire in Phage Lambda. Science, vol. 246, 1275-1281 (1989).
Huston, James S., et al. Protein engineering of antibody binding sites: recovery of specific activity in an anti-digoxin single-chain Fv analogue produced in *Escherichia coli*. Proceedings of the National Academy of Sciences of the United States of America, Biochemistry, vol. 85, 5879-5883 (1988).
Huston, James S, et al. Protein Engineering of Single-chain Fv Analogs and Fusion Proteins. Methods in Enzymology, vol. 203, 46-96 (1991).
Kabat, Elvin A., et al. Tabulation and Analysis of Amino Acid and Nucleic Acid Sequences of Precursors, V-Regions, C-Regions, J-Chain, T-Cell Receptors for Antigen, T-Cell Surface Antigens, $\beta_2$-Microglobulins, Major Histocompatibility Antigens, Thy-1, Complement, C-Reactive Protein, Thymopoietin, Integrins, Post-gamma Globulin, $\alpha_2$-Macroglobulins, and Other Related Proteins. Sequences of Proteins of Immunological Interest, Fifth Edition, U.S. Department of Health and Human Services NIH Publication No. 91-3242, 1-10 (1991).
Köhler, G., et al. Continuous Cultures of Fused Cells Secreting Antibody of Predefined Specificity. Nature, vol. 256, 495-497 (1975).
Kozbor, Danuta, et al. The production of monoclonal antibodies from human lymphocytes. Immunology Today, vol. 4, No. 3, 72-79 (1983).
Kutemeier, G., et al. Assembly of Humanized Antibody Genes from Synthetic Oligonucleotides Using a Single-round PCR. Biotechniques, vol. 17, 242-246 (1994).
Larrick, James W, et al. PCR Amplification of Antibody Genes. Methods: A Companion to Methods in Enzymology, vol. 2, No. 2, 106-110 (1991).
Lefranc, Marie-Paule. The IMGT Unique Numbering for Immunoglobulins. T-Cell Receptors and Ig-Like Domains. The Immunologist, vol. 7, 132-136 (1999).
Lowy, Israel, et al. Isolation of Transforming DNA: Cloning the Hamster aprt Gene. Cell, vol. 22, 817-823 (1980).
MacCallum, Robert M., et al. Antibody-antigen Interactions: Contact Analysis and Binding Site Topography. Journal of Molecular Biology, vol. 262, 732-745 (1996).
Mielke, Michelle M., Ph.D., et al. Comparison of Plasma Phosphorylated Tau Species With Amyloid and Tau Positron Emission Tomography, Neurodegeneration, Vascular Pathology, and Cognitive Outcomes. JAMA Neurology, vol. 78, 1108-1117 (2021).
Morgan, Richard A., et al. Human Gene Therapy. Annual Review of Biochemistry, vol. 62, 191-217 (1993).
Morrison, Sherie L., et al. Chimeric human antibody molecules: Mouse antigen-binding domains with human constant region domains. Proceedings of the National Academy of Sciences of the United States of America, Immunology, vol. 81, 6851-6855 (1984).
Mulligan, R.C., et al. Selection for animal cells that express the *Escherichia coli* gene coding for xanthine-guanine phosphoribosyltransferase. Proceedings of the National Academy of Sciences of the United States of America, Biochemistry, vol. 78, 2072-2076 (1981).
Mulligan, Richard C. The Basic Science of Gene Therapy. Science, vol. 260, 926-932 (1993).
Neuberger, Michael S., et al. Recombinant antibodies possessing novel effector functions. Nature, vol. 312, 604-608 (1984).
O'Hare, K., et al. Transformation of mouse fibroblasts to methotrexate resistance by a recombinant plasmid expressing a prokaryotic dihydrofolate reductase. Proceedings of the National Academy of Sciences of the United States of America, Biochemistry, vol. 78, 1527-1531 (1981).
PCT/US2022/042963 International Search Report and Written Opinion dated Jun. 14, 2023.
Quanterix Outlines Partner Path With Labs to Expedite Building Global Alzheimer's Disease Testing Infrastructure. Retrieved from internet on Apr. 2, 2024: https://www.businesswire.com/news/home/20240321224578/en/Quanterix-Outlines-Partner-Path-With-Labs-to-Expedite-Building-Global-Alzheimer%E2%80%99s-Disease-Testing-Infrastructure, Mar. 21, 2024, pp. 1-2.
Santerre, Robert F., et al. Expression of prokaryotic genes for hygromycin B and G418 resistance as dominant-selection markers in mouse L cells. Gene, vol. 30, 147-156 (1984).
Skerra, Arne, et al. Assembly of a Functional Immunoglobulin Fv Fragment in *Escherichia coli*. Science, vol. 240, 1038-1041 (1988).
Szybalska, Elizabeth H., et al. Genetics of Human Cell Lines, IV. DNA-Mediated Heritable Transformation of a Biochemical Trait. Proceedings of the National Academy of Sciences of the United States of America, Genetics, vol. 48, 2026-2034 (1962).
Takeda, Shun-Ichi, et al. Construction of chimaeric processed immunoglobulin genes containing mouse variable and human constant region sequences. Nature, vol. 314, 452-454 (1985).
Tolstoshev, Paul. Gene Therapy, Concepts, Current Trials and Future Directions. Annual Review Pharmacology and Toxicology, vol. 32, 573-596 (1993).
Ward, E. Sally, et al. Binding activities of a repertoire of single immunoglobulin variable domains secreted from *Escherichia coli*. Nature, vol. 341, 544-546 (1989).
Ward, E. Sally, et al., Genetic Manipulation and Expression of Antibodies. Monoclonal Antibodies: Principles and Applications, Wiley-Liss Inc., 137-185 (1995).
Whitelegg, Nicholas R. J., et al. WAM: an improved algorithm for modelling antibodies on the WEB. Protein Engineering, vol. 13, 819-824 (2000).
Wigler, Michael, et al. Transfer of Purified Herpes Virus Thymidine Kinase Gene to Cultured Mouse Cells. Cell, vol. 11, 223-232 (1977).
Wigler, Michael, et al. Transformation of mammalian cells with an amplifiable dominant-acting gene. Proceedings of the National Academy of Sciences of the United States of America, Genetics, vol. 77, 3567-3570 (1980).
Wu, George Y., et al. Delivery systems for gene therapy. Biotherapy, vol. 3, 87-95 (1991).
Hampel, Harald et al. Total and phosphorylated tau protein as biological markers of Alzheimer's disease. Exp Gerontol. Jan. 2010;45(1):30-40. doi: 10.1016/j.exger.2009.10.010. Epub Oct. 22, 2009.
Jonaitis, Erin M. et al. Plasma phosphorylated tau 217 in preclinical Alzheimer's disease. Brain Commun. Mar. 6, 2023;5(2):fcad057. doi: 10.1093/braincomms/fcad057. eCollection 2023.
Mintun, M. et al., Donanumab in Early Alzheimer's Disease, N Engl J Med, 2021, vol. 384, No. 18, pp. 1691-1704.
Neddens, Joerg et al. Phosphorylation of different tau sites during progression of Alzheimer's disease. Acta Neuropathol Commun. Jun. 29, 2018;6(1):52. doi: 10.1186/s40478-018-0557-6.
PCT/US2024/020266 International Search Report and Written Opinion dated Jul. 8, 2024.

(56) References Cited

OTHER PUBLICATIONS

Pontecorvo, M. et al., Association of Donanemab Treatment with Exploratory Plasma Biomarkers in Early Symptomatic Alzheimer Disease, JAMA Neurology, 2022, vol. 79, No. 12, pp. 1250-1259.
U.S. Appl. No. 18/770,102 Office Action dated Nov. 18, 2024.

* cited by examiner

| Capture | pTau (pg/mL) | Ave AEB | S/B | LOD (pg/mL) |
|---|---|---|---|---|
| H7L4 | 0 | 0.0059 | - | 6.8 |
| | 1 | 0.0051 | 0.9 | |
| | 10 | 0.0087 | 1.5 | |
| | 100 | 0.0357 | 6.0 | |
| | 1000 | 0.2782 | 47 | |
| H3L12 | 0 | 0.0065 | - | 5.0 |
| | 1 | 0.0078 | 1.2 | |
| | 10 | 0.0092 | 1.4 | |
| | 100 | 0.0369 | 5.7 | |
| | 1000 | 0.2622 | 41 | |
| H1L2 | 0 | 0.0034 | - | 2.6 |
| | 1 | 0.0036 | 1.1 | |
| | 10 | 0.0069 | 2.0 | |
| | 100 | 0.0326 | 9.5 | |
| | 1000 | 0.2832 | 83 | |

FIG. 2A

| Capture | pTau (pg/mL) | Ave AEB | S/B |
|---|---|---|---|
| H7L4 | 0 | 0.0491 | - |
| | 1 | 0.0487 | 1.0 |
| | 10 | 0.0433 | 0.9 |
| | 100 | 0.0436 | 0.9 |
| | 1000 | 0.0441 | 0.9 |
| H3L12 | 0 | 0.0660 | - |
| | 1 | 0.0669 | 1.0 |
| | 10 | 0.0640 | 1.0 |
| | 100 | 0.0660 | 1.0 |
| | 1000 | 0.0595 | 0.9 |
| H1L2 | 0 | 0.0364 | - |
| | 1 | 0.0344 | 0.9 |
| | 10 | 0.0318 | 0.9 |
| | 100 | 0.0302 | 0.8 |
| | 1000 | 0.0323 | 0.9 |

FIG. 2B

| Capture | pTau (pg/mL) | Ave AEB | S/B | LOD (pg/mL) |
|---|---|---|---|---|
| H7L4 | 0 | 0.0034 | - | 14.7 |
| | 1 | 0.0035 | 1.0 | |
| | 10 | 0.0045 | 1.3 | |
| | 100 | 0.0078 | 2.3 | |
| | 1000 | 0.0447 | 13 | |
| H3L12 | 0 | 0.0056 | - | 88.1 |
| | 1 | 0.0052 | 0.9 | |
| | 10 | 0.0046 | 0.8 | |
| | 100 | 0.0106 | 1.9 | |
| | 1000 | 0.0474 | 8.4 | |
| H1L2 | 0 | 0.0026 | - | 9.1 |
| | 1 | 0.0029 | 1.1 | |
| | 10 | 0.0036 | 1.4 | |
| | 100 | 0.0069 | 2.7 | |
| | 1000 | 0.0331 | 13 | |

FIG. 2C

| Capture | pTau (pg/mL) | Ave AEB | S/B |
|---|---|---|---|
| H7L4 | 0 | 0.0204 | - |
| | 1 | 0.0218 | 1.1 |
| | 10 | 0.0210 | 1.0 |
| | 100 | 0.0227 | 1.1 |
| | 1000 | 0.0247 | 1.2 |
| H3L12 | 0 | 0.0348 | - |
| | 1 | 0.0356 | 1.0 |
| | 10 | 0.0352 | 1.0 |
| | 100 | 0.0366 | 1.1 |
| | 1000 | 0.0347 | 1.0 |
| H1L2 | 0 | 0.0123 | - |
| | 1 | 0.0125 | 1.0 |
| | 10 | 0.0157 | 1.3 |
| | 100 | 0.0141 | 1.2 |
| | 1000 | 0.0157 | 1.3 |

FIG. 2D

Antibody 5

Normal skeletal muscle: no stain

| | QC_L1 | QC_L2 | QC_M | QC_H |
|---|---|---|---|---|
| Number of values | 3 | 3 | 2 | 2 |
| Coefficient of variation | 19.42% | 14.00% | 2.70% | 2.36% |

|  | CAL | s1 | s2 | s3 |
|---|---|---|---|---|
| Y Intercept | 1.68 | 1.38 | 1.45 | 1.46 |
| Slope | -0.99 | -0.89 | -0.92 | -0.94 |
| % Difference |  | 90% | 93% | 95% |

```
                              SEQUENCE LISTING

Sequence total quantity: 81
SEQ ID NO: 1           moltype = AA   length = 5
FEATURE                Location/Qualifiers
source                 1..5
                       mol_type = protein
                       organism = synthetic construct
SEQUENCE: 1
SQKVG                                                                    5

SEQ ID NO: 2           moltype = AA   length = 5
FEATURE                Location/Qualifiers
source                 1..5
                       mol_type = protein
                       organism = synthetic construct
SEQUENCE: 2
SYAMI                                                                    5

SEQ ID NO: 3           moltype = AA   length = 5
FEATURE                Location/Qualifiers
source                 1..5
                       mol_type = protein
                       organism = synthetic construct
SEQUENCE: 3
NYKVG                                                                    5

SEQ ID NO: 4           moltype = AA   length = 5
FEATURE                Location/Qualifiers
source                 1..5
                       mol_type = protein
                       organism = synthetic construct
SEQUENCE: 4
NYAMS                                                                    5

SEQ ID NO: 5           moltype = AA   length = 5
FEATURE                Location/Qualifiers
source                 1..5
                       mol_type = protein
                       organism = synthetic construct
```

```
SEQUENCE: 5
THAMT                                                                    5

SEQ ID NO: 6          moltype = AA  length = 16
FEATURE               Location/Qualifiers
source                1..16
                      mol_type = protein
                      organism = synthetic construct
SEQUENCE: 6
IINNYGSTYY ASWAKG                                                       16

SEQ ID NO: 7          moltype = AA  length = 16
FEATURE               Location/Qualifiers
source                1..16
                      mol_type = protein
                      organism = synthetic construct
SEQUENCE: 7
FISRSGITYY ASWAKG                                                       16

SEQ ID NO: 8          moltype = AA  length = 16
FEATURE               Location/Qualifiers
source                1..16
                      mol_type = protein
                      organism = synthetic construct
SEQUENCE: 8
IINYYSQTYY ASWAKG                                                       16

SEQ ID NO: 9          moltype = AA  length = 16
FEATURE               Location/Qualifiers
source                1..16
                      mol_type = protein
                      organism = synthetic construct
SEQUENCE: 9
VINPSGSAYY ATWVNG                                                       16

SEQ ID NO: 10         moltype = AA  length = 10
FEATURE               Location/Qualifiers
source                1..10
                      mol_type = protein
                      organism = synthetic construct
SEQUENCE: 10
DPDGSIVFDI                                                              10

SEQ ID NO: 11         moltype = AA  length = 16
FEATURE               Location/Qualifiers
source                1..16
                      mol_type = protein
                      organism = synthetic construct
SEQUENCE: 11
EFGAVGSDYY RDAFNL                                                       16

SEQ ID NO: 12         moltype = AA  length = 16
FEATURE               Location/Qualifiers
source                1..16
                      mol_type = protein
                      organism = synthetic construct
SEQUENCE: 12
EFGAVGSDYY RDALRL                                                       16

SEQ ID NO: 13         moltype = AA  length = 15
FEATURE               Location/Qualifiers
source                1..15
                      mol_type = protein
                      organism = synthetic construct
SEQUENCE: 13
DYITAGDYYM DAFDP                                                        15

SEQ ID NO: 14         moltype = AA  length = 13
FEATURE               Location/Qualifiers
source                1..13
                      mol_type = protein
                      organism = synthetic construct
SEQUENCE: 14
QSSQSVVYNN RLS                                                          13
```

```
SEQ ID NO: 15            moltype = AA   length = 11
FEATURE                  Location/Qualifiers
source                   1..11
                         mol_type = protein
                         organism = synthetic construct SEQUENCE: 15
QASESINSWL S                                                          11

SEQ ID NO: 16            moltype = AA   length = 11
FEATURE                  Location/Qualifiers
source                   1..11
                         mol_type = protein
                         organism = synthetic construct SEQUENCE: 16
QASQNIYSNL A                                                          11

SEQ ID NO: 17            moltype = AA   length = 13
FEATURE                  Location/Qualifiers
source                   1..13
                         mol_type = protein
                         organism = synthetic construct SEQUENCE: 17
QSSQSVYSNK RLA                                                        13

SEQ ID NO: 18            moltype = AA   length = 11
FEATURE                  Location/Qualifiers
source                   1..11
                         mol_type = protein
                         organism = synthetic construct SEQUENCE: 18
QASQSIGSNL A                                                          11

SEQ ID NO: 19            moltype = AA   length = 11
FEATURE                  Location/Qualifiers
source                   1..11
                         mol_type = protein
                         organism = synthetic construct SEQUENCE: 19
QASQSISNQL S                                                          11

SEQ ID NO: 20            moltype = AA   length = 7
FEATURE                  Location/Qualifiers
source                   1..7
                         mol_type = protein
                         organism = synthetic construct SEQUENCE: 20
GASTLAS                                                               7

SEQ ID NO: 21            moltype = AA   length = 7
FEATURE                  Location/Qualifiers
source                   1..7
                         mol_type = protein
                         organism = synthetic construct SEQUENCE: 21
RASTLAS                                                               7

SEQ ID NO: 22            moltype = AA   length = 7
FEATURE                  Location/Qualifiers
source                   1..7
                         mol_type = protein
                         organism = synthetic construct SEQUENCE: 22
GASNLAS                                                               7

SEQ ID NO: 23            moltype = AA   length = 7
FEATURE                  Location/Qualifiers
source                   1..7
                         mol_type = protein
                         organism = synthetic construct SEQUENCE: 23
GASTLES                                                               7

SEQ ID NO: 24            moltype = AA   length = 13
FEATURE                  Location/Qualifiers
source                   1..13
                         mol_type = protein
                         organism = synthetic construct
```

```
SEQUENCE: 24
LGSYDCSSGD CHA                                                          13

SEQ ID NO: 25          moltype = AA  length = 12
FEATURE                Location/Qualifiers
source                 1..12
                       mol_type = protein
                       organism = synthetic construct
SEQUENCE: 25
QSYYEEDGIG YA                                                           12

SEQ ID NO: 26          moltype = AA  length = 12
FEATURE                Location/Qualifiers
source                 1..12
                       mol_type = protein
                       organism = synthetic construct
SEQUENCE: 26
QGYDYSTAGA YP                                                           12

SEQ ID NO: 27          moltype = AA  length = 13
FEATURE                Location/Qualifiers
source                 1..13
                       mol_type = protein
                       organism = synthetic construct
SEQUENCE: 27
AGGYDCSTGD CWT                                                          13

SEQ ID NO: 28          moltype = AA  length = 12
FEATURE                Location/Qualifiers
source                 1..12
                       mol_type = protein
                       organism = synthetic construct
SEQUENCE: 28
QSYYEGSDIG YA                                                           12

SEQ ID NO: 29          moltype = AA  length = 12
FEATURE                Location/Qualifiers
source                 1..12
                       mol_type = protein
                       organism = synthetic construct
SEQUENCE: 29
QQGYNRDNVD NL                                                           12

SEQ ID NO: 30          moltype = AA  length = 134
FEATURE                Location/Qualifiers
source                 1..134
                       mol_type = protein
                       organism = synthetic construct
SEQUENCE: 30
METGLRWLLL VAVLKGVQCQ SLEESGGRLV TPGTPLTLTC TVSGFSLSSQ KVGWVRQAPG       60
KGLEWIGIIN NYGSTYYASW AKGRFTISKT STTVDLRITS LTAEDTATYF CARDPDGSIV      120
FDIWGPGTLV TVSL                                                        134

SEQ ID NO: 31          moltype = AA  length = 140
FEATURE                Location/Qualifiers
source                 1..140
                       mol_type = protein
                       organism = synthetic construct
SEQUENCE: 31
METGLRWLLL VAVLKGVQCQ SVEESGGRLV TPGTPLTLTC TVSGFSLSSY AMIWVRQAPG       60
KGLEWIGFIS RSGITYYASW AKGRFTISKT STTVDLKMTS LTTEDTATYF CAREFGAVGS      120
DYYRDAFNLW GPGTLVTVSS                                                  140

SEQ ID NO: 32          moltype = AA  length = 134
FEATURE                Location/Qualifiers
source                 1..134
                       mol_type = protein
                       organism = synthetic construct
SEQUENCE: 32
METGLRWLLL VAVLKGVQCQ SLEESGGRLV TPGTPLTLTC TVSGFSLNNY KVGWVRQAPG       60
KGLEWIGIIN YYSQTYYASW AKGRFTISKT STTVDLKLTS PTTEDTATYF CARDPDGSIV      120
FDIWGPGTLV TVSL                                                        134

SEQ ID NO: 33          moltype = AA  length = 140
FEATURE                Location/Qualifiers
source                 1..140
                       mol_type = protein
                       organism = synthetic construct
```

```
SEQUENCE: 33
METGLRWLLL VAVLKGVQCQ SVEESGGGLV TPGGTLTLTC TVSGFSLSNY AMSWVRQAPG    60
KGLEWIGFIS RSGITYYASW AKGRFTISKT STTVDLKITS PTTEDTAAYF CAREFGAVGS   120
DYYRDALRLW GPGTLVTVSS                                               140

SEQ ID NO: 34           moltype = AA  length = 139
FEATURE                 Location/Qualifiers
source                  1..139
                        mol_type = protein
                        organism = synthetic construct
SEQUENCE: 34
METGLRWLLL VAVLKGVQCQ SLEESGGRLV TPGTPLTLTC TVSGIDLSTH AMTWVRQAPG    60
KGLEWIGVIN PSGSAYYATW VNGRFTISKT STTVDLKITS PTTGDTAKYF CARDYITAGD   120
YYMDAFDPWG PGTLVTVSS                                                139

SEQ ID NO: 35           moltype = AA  length = 135
FEATURE                 Location/Qualifiers
source                  1..135
                        mol_type = protein
                        organism = synthetic construct
SEQUENCE: 35
MDTRAPTQLL GLLLLWLPGA TFAQVLTQTA SPVSAAVGGT VTINCQSSQS VVYNNRLSWF    60
QQKPGQPPKL LIYGASTLAS GVPSRFKGSG SGTQFTLTIS DVQCDDAATY YCLGSYDCSS   120
GDCHAFGGGT EVVVK                                                    135

SEQ ID NO: 36           moltype = AA  length = 133
FEATURE                 Location/Qualifiers
source                  1..133
                        mol_type = protein
                        organism = synthetic construct
SEQUENCE: 36
MDMRAPTQLL GLLLLWLPGA RCADIVMTQT PASVEAAVGG TVTINCQASE SINSWLSWYQ    60
QKPGQPPNLL IYRASTLASG VPSRFSGGGS GTEYTLTISD LECADAVTYY CQSYYEEDGI   120
GYAFGGGTEV VVE                                                      133

SEQ ID NO: 37           moltype = AA  length = 133
FEATURE                 Location/Qualifiers
source                  1..133
                        mol_type = protein
                        organism = synthetic construct
SEQUENCE: 37
MDMRAPTQLL GLLLLWLPGA RCADIVMTQT PSSVSAAVGG TVTINCQASQ NIYSNLAWYQ    60
QKPGQRPRLL IYGASNLASG VPSRFKGSRS GTEFTLTISD LECADAATYY CQGYDYSTAG   120
AYPFGGGTAV VVK                                                      133

SEQ ID NO: 38           moltype = AA  length = 135
FEATURE                 Location/Qualifiers
source                  1..135
                        mol_type = protein
                        organism = synthetic construct
SEQUENCE: 38
MDTRAPTQLL GLLLLWLPGA TFAQVLTQTA SPVSAAVGST VTINCQSSQS VYSNKRLAWF    60
QLKPGQPPKL LIYGASTLAS GVPSRFKGSG SGTQFTLTIS DVQCDDAATY YCAGGYDCST   120
GDCWTFGGGT EVVVT                                                    135

SEQ ID NO: 39           moltype = AA  length = 133
FEATURE                 Location/Qualifiers
source                  1..133
                        mol_type = protein
                        organism = synthetic construct
SEQUENCE: 39
MDMRAPTQLL GLLLLWLPGA RCADIVMTQT PSSVSAAVGG TVTIKCQASQ SIGSNLAWYQ    60
QKPGQPPKLL IYGASTLESG VPSRFKGSGS GTEYTLTISD LECADAATYY CQSYYEGSDI   120
GYAFGGGTEV VVE                                                      133

SEQ ID NO: 40           moltype = AA  length = 133
FEATURE                 Location/Qualifiers
source                  1..133
                        mol_type = protein
                        organism = synthetic construct
SEQUENCE: 40
MDTRAPTQLL GLLLLWLPGA RCADIVMTQT PASVSAAVGG TVTIKCQASQ SISNQLSWYQ    60
QKSGQPPKLL IYRASTLASG VPSRFKGSGS GTEFTLTISD LECADAATYY CQQGYNRDNV   120
DNLFGGGTEV VVK                                                      133
```

```
SEQ ID NO: 41            moltype = AA   length = 457
FEATURE                  Location/Qualifiers
source                   1..457
                         mol_type = protein
                         organism = synthetic construct
SEQUENCE: 41
METGLRWLLL VAVLKGVQCQ SLEESGGRLV TPGTPLTLTC TVSGFSLSSQ KVGWVRQAPG    60
KGLEWIGIIN NYGSTYYASW AKGRFTISKT STTVDLRITS LTAEDTATYF CARDPDGSIV   120
FDIWGPGTLV TVSLGQPKAP SVFPLAPCCG DTPSSTVTLG CLVKGYLPEP VTVTWNSGTL   180
TNGVRTFPSV RQSSGLYSLS SVVSVTSSSQ PVTCNVAHPA TNTKVDKTVA PSTCSKPTCP   240
PPELLGRSSV FIFPPKPKDT LMISRTPEVT CVVVDVSQDD PEVQFTWYIN NEQVRTARPP   300
LREQQFNSTI RVVSTLPIAH QDWLRGKEFK CKVHNKALPA PIEKTISKAR GQPLEPKVYT   360
MGPPREELSS RSVSLTCMIN GFYPSDISVE WEKNGKAEDN YKTTPAVLDS DGSYFLYSKL   420
SVPTSEWQRG DVFTCSVMHE ALHNYTQKS ISRSPGK                              457

SEQ ID NO: 42            moltype = AA   length = 239
FEATURE                  Location/Qualifiers
source                   1..239
                         mol_type = protein
                         organism = synthetic construct
SEQUENCE: 42
MDTRAPTQLL GLLLLWLPGA TFAQVLTQTA SPVSAAVGGT VTINCQSSQS VVYNNRLSWF    60
QQKPGQPPKL LIYGASTLAS GVPSRFKGSG SGTQFTLTIS DVQCDDAATY YCLGSYDCSS   120
GDCHAFGGGT EVVVKGDPVA PTVLIFPPAA DQVATGTVTI VCVANKYFPD VTVTWEVDGT   180
TQTTGIENSK TPQNSADCTY NLSSTLTLTS TQYNSHKEYT CKVTQGTTSV VQSFNRGDC    239

SEQ ID NO: 43            moltype = AA   length = 463
FEATURE                  Location/Qualifiers
source                   1..463
                         mol_type = protein
                         organism = synthetic construct
SEQUENCE: 43
METGLRWLLL VAVLKGVQCQ SVEESGGRLV TPGTPLTLTC TVSGFSLSSY AMIWVRQAPG    60
KGLEWIGFIS RSGITYYASW AKGRFTISKT STTVDLKMTS LTTEDTATYF CAREFGAVGS   120
DYYRDAFNLW GPGTLVTVSS GQPKAPSVFP LAPCCGDTPS STVTLGCLVK GYLPEPVTVT   180
WNSGTLTNGV RTFPSVRQSS GLYSLSSVVS VTSSSQPVTC NVAHPATNTK VDKTVAPSTC   240
SKPTCPPPEL LGRSSVFIFP PKPKDTLMIS RTPEVTCVVV DVSQDDPEVQ FTWYINNEQV   300
RTARPPLREQ QFNSTIRVVS TLPIAHQDWL RGKEFKCKVH NKALPAPIEK TISKARGQPL   360
EPKVYTMGPP REELSSRSVS LTCMINGFYP SDISVEWEKN GKAEDNYKTT PAVLDSDGSY   420
FLYSKLSVPT SEWQRGDVFT CSVMHEALHN HYTQKSISRS PGK                     463

SEQ ID NO: 44            moltype = AA   length = 237
FEATURE                  Location/Qualifiers
source                   1..237
                         mol_type = protein
                         organism = synthetic construct
SEQUENCE: 44
MDMRAPTQLL GLLLLWLPGA RCADIVMTQT PASVEAAVGG TVTINCQASE SINSWLSWYQ    60
QKPGQPPNLL IYRASTLASG VPSRFSGGGS GTEYTLTISD LECADAVTYY CQSYYEEDGI   120
GYAFGGGTEV VVEGDPVAPT VLIFPPAADQ VATGTVTIVC VANKYFPDVT VTWEVDGTTQ   180
TTGIENSKTP QNSADCTYNL SSTLTLTSTQ YNSHKEYTCK VTQGTTSVVQ SFNRGDC      237

SEQ ID NO: 45            moltype = AA   length = 237
FEATURE                  Location/Qualifiers
source                   1..237
                         mol_type = protein
                         organism = synthetic construct
SEQUENCE: 45
MDMRAPTQLL GLLLLWLPGA RCADIVMTQT PSSVSAAVGG TVTINCQASQ NIYSNLAWYQ    60
QKPGQRPRLL IYGASNLASG VPSRFKGSRS GTEFTLTISD LECADAATYY CQGYDYSTAG   120
AYPFGGGTAV VVKGDPVAPT VLIFPPAADQ VATGTVTIVC VANKYFPDVT VTWEVDGTTQ   180
TTGIENSKTP QNSADCTYNL SSTLTLTSTQ YNSHKEYTCK VTQGTTSVVQ SFNRGDC      237

SEQ ID NO: 46            moltype = AA   length = 457
FEATURE                  Location/Qualifiers
source                   1..457
                         mol_type = protein
                         organism = synthetic construct
SEQUENCE: 46
METGLRWLLL VAVLKGVQCQ SLEESGGRLV TPGTPLTLTC TVSGFSLNNY KVGWVRQAPG    60
KGLEWIGIIN YYSQTYYASW AKGRFTISKT STTVDLKLTS PTTEDTATYF CARDPDGSIV   120
FDIWGPGTLV TVSLGQPKAP SVFPLAPCCG DTPSSTVTLG CLVKGYLPEP VTVTWNSGTL   180
TNGVRTFPSV RQSSGLYSLS SVVSVTSSSQ PVTCNVAHPA TNTKVDKTVV PSTCSKPTCP   240
PPELLGRSSV FIFPPKPKDT LMISRTPEVT CVVVDVSQDD PEVQFTWYIN NEQVRTARPP   300
LREQQFNSTI RVVSTLPIAH QDWLRGKEFK CKVHNKALPA PIEKTISKAR GQPLEPKVYT   360
MGPPREELSS RSVSLTCMIN GFYPSDISVE WEKNGKAEDN YKTTPAVLDS DGSYFLYSKL   420
SVPTSEWQRG DVFTCSVMHE ALHNYTQKS ISRSPGK                              457
```

```
SEQ ID NO: 47            moltype = AA   length = 239
FEATURE                  Location/Qualifiers
source                   1..239
                         mol_type = protein
                         organism = synthetic construct
SEQUENCE: 47
MDTRAPTQLL GLLLLWLPGA TFAQVLTQTA SPVSAAVGST VTINCQSSQS VYSNKRLAWF  60
QLKPGQPPKL LIYGASTLAS GVPSRFKGSG SGTQFTLTIS DVQCDDAATY YCAGGYDCST 120
GDCWTFGGGT EVVVTGDPVA PTVLIFPPAA DQVATGTVTI VCVANKYFPD VTVTWEVDGT 180
TQTTGIENSK TPQNSADCTY NLSSTLTLTS TQYNSHKEYT CKVTQGTTSV VQSFNRGDC  239

SEQ ID NO: 48            moltype = AA   length = 463
FEATURE                  Location/Qualifiers
source                   1..463
                         mol_type = protein
                         organism = synthetic construct
SEQUENCE: 48
METGLRWLLL VAVLKGVQCQ SVEESGGGLV TPGGTLTLTC TVSGFSLSNY AMSWVRQAPG  60
KGLEWIGFIS RSGITYYASW AKGRFTISKT STTVDLKITS PTTEDTAAYF CAREFGAVGS 120
DYYRDALRLW GPGTLVTVSS GQPKAPSVFP LAPCCGDTPS STVTLGCLVK GYLPEPVTVT 180
WNSGTLTNGV RTFPSVRQSS GLYSLSSVVS VTSSSQPVTC NVAHPATNTK VDKTVAPSTC 240
SKPTCPPPEL LGRSSVFIFP PKPKDTLMIS RTPEVTCVVV DVSQDDPEVQ FTWYINNEQV 300
RTARPPLREQ QFNSTIRVVS TLPIAHQDWL RGKEFKCKVH NKALPAPIEK TISKARGQPL 360
EPKVYTMGPP REELSSRSVS LTCMINGFYP SDISVEWEKN GKAEDNYKTT PAVLDSDGSY 420
FLYSKLSVPT SEWQRGDVFT CSVMHEALHN HYTQKSISRS PGK                  463

SEQ ID NO: 49            moltype = AA   length = 237
FEATURE                  Location/Qualifiers
source                   1..237
                         mol_type = protein
                         organism = synthetic construct
SEQUENCE: 49
MDMRAPTQLL GLLLLWLPGA RCADIVMTQT PSSVSAAVGG TVTIKCQASQ SIGSNLAWYQ  60
QKPGQPPKLL IYGASTLESG VPSRFKGSGS GTEYTLTISD LECADAATYY CQSYYEGSDI 120
GYAFGGGTEV VVEGDPVAPT VLIFPPAADQ VATGTVTIVC VANKYFPDVT VTWEVDGTTQ 180
TTGIENSKTP QNSADCTYNL SSTLTLTSTQ YNSHKEYTCK VTQGTTSVVQ SFNRGDC    237

SEQ ID NO: 50            moltype = AA   length = 462
FEATURE                  Location/Qualifiers
source                   1..462
                         mol_type = protein
                         organism = synthetic construct
SEQUENCE: 50
METGLRWLLL VAVLKGVQCQ SLEESGGRLV TPGTPLTLTC TVSGIDLSTH AMTWVRQAPG  60
KGLEWIGVIN PSGSAYYATW VNGRFTISKT STTVDLKITS PTTGDTAKYF CARDYITAGD 120
YYMDAFDPWG PGTLVTVSSG QPKAPSVFPL APCCGDTPSS TVTLGCLVKG YLPEPVTVTW 180
NSGTLTNGVR TFPSVRQSSG LYSLSSVVSV TSSSQPVTCN VAHPATNTKV DKTVAPSTCS 240
KPTCPPPELL GRSSVFIFPP KPKDTLMISR TPEVTCVVVD VSQDDPEVQF TWYINNEQVR 300
TARPPLREQQ FNSTIRVVST LPIAHQDWLG KEFKCKVHN KALPAPIEKT ISKARGQPLE 360
PKVYTMGPPR EELSSRSVSL TCMINGFYPS DISVEWEKNG KAEDNYKTTP AVLDSDGSYF 420
LYSKLSVPTS EWQRGDVFTC SVMHEALHNH YTQKSISRSP GK                   462

SEQ ID NO: 51            moltype = AA   length = 237
FEATURE                  Location/Qualifiers
source                   1..237
                         mol_type = protein
                         organism = synthetic construct
SEQUENCE: 51
MDTRAPTQLL GLLLLWLPGA RCADIVMTQT PASVSAAVGG TVTIKCQASQ SISNQLSWYQ  60
QKSGQPPKLL IYRASTLASG VPSRFKGSGS GTEFTLTISD LECADAATYY CQQGYNRDNV 120
DNLFGGGTEV VVKGDPVAPT VLIFPPAADQ VATGTVTIVC VANKYFPDVT VTWEVDGTTQ 180
TTGIENSKTP QNSADCTYNL SSTLTLTSTQ YNSHKEYTCK VTQGTTSVVQ SFNRGDC    237

SEQ ID NO: 52            moltype = DNA   length = 402
FEATURE                  Location/Qualifiers
source                   1..402
                         mol_type = other DNA
                         organism = synthetic construct
SEQUENCE: 52
atggagactg ggctgcgctg gcttctcctg gtcgctgtgc tcaaaggtgt ccagtgtcag  60
tcgctcgagg agtccggggg tcgcctgggc acgccctgac actcacctgc acctcctgtg 120
acagtctctg gatttcccct cagtagccac aaagtgggct gggtccgcca ggctccaggg 180
aaggggctgg aatggatcgg aatcattaat aattatggta gcacatacta cgcgagctgg 240
gcgaaaggcc gattcaccat ctcgaaaacc tcgaccacag tggatctgag aatcaccagt 300
ctgacgaccg aggacacggc cacctatttc tgtgcccgtg atcctgatgg tagtattgtc 360
tttgacatct ggggcccagg caccccttgtc accgtctcct tg                  402
```

-continued

SEQ ID NO: 53           moltype = DNA   length = 420
FEATURE                 Location/Qualifiers
source                  1..420
                        mol_type = other DNA
                        organism = synthetic construct
SEQUENCE: 53
atggagactg ggctgcgctg gcttctcctg gtcgctgtgc tcaaaggtgt ccagtgtcag    60
tcggtggagg agtccggggg tcgcctggtc acgcctggga caccectgac actcacctgc   120
accgtctctg gattctccct cagtagctat gcaatgatct gggtccgcca ggctccaggg   180
aaggggctgg aatggatcgg attcattagt cgtagtggta tcacatacta cgcgagctgg   240
gcaaaaggcc gattcaccat ctccaaaacc tcgaccacgg tggatctgaa aatgaccagt   300
ctgacaaccg aggacacggc cacctatttc tgtgccagag aattcggtgc tgttggtagt   360
gattattata gggacgcctt taacttgtgg ggcccaggca ccctggtcac cgtctcctca   420

SEQ ID NO: 54           moltype = DNA   length = 402
FEATURE                 Location/Qualifiers
source                  1..402
                        mol_type = other DNA
                        organism = synthetic construct
SEQUENCE: 54
atggagactg ggctgcgctg gcttctcctg gtcgctgtgc tcaaaggtgt ccagtgtcag    60
tcgctggagg agtccggggg tcgcctggtc acgcctggga caccectgac actcacctgc   120
acagtctctg gattttccct aaataactac aaagtgggct gggtccgcca ggctccagga   180
aaggggctgg aatggatcgg aatcattaac tattatagtc agacatacta cgcgagctgg   240
gccaaaggcc gattcaccat ctcgaaaacc tcgaccacgg tggatctgaa gctcaccagt   300
ccgacaaccg aagacacggc cacctatttc tgtgcccgtg atcctgatgg tagtattgtc   360
tttgacatct ggggcccagg cacccttgtc accgtctcct tg                      402

SEQ ID NO: 55           moltype = DNA   length = 420
FEATURE                 Location/Qualifiers
source                  1..420
                        mol_type = other DNA
                        organism = synthetic construct
SEQUENCE: 55
atggagactg ggctgcgctg gcttctcctg gtcgctgtgc tcaaaggtgt ccagtgtcag    60
tcggtggagg agtccggagg aggcctggta acgcctggag aaccectgac actcacctgc   120
accgtctctg gattctccct cagtaactat gcaatgagct gggtccgcca ggctccaggg   180
aaggggctgg aatggatcgg attcattagt cgtagtggta ttacatacta cgcgagctgg   240
gcaaaaggcc gattcaccat ctccaaaacc tcgaccacgg tggatctgaa aatcaccagt   300
ccgacgaccg aggacacggc cgcctatttc tgtgccagag aattcggtgc tgttggtagt   360
gattattata gggacgcctt gaggttgtgg ggcccaggca ccctggtcac cgtctcctca   420

SEQ ID NO: 56           moltype = DNA   length = 417
FEATURE                 Location/Qualifiers
source                  1..417
                        mol_type = other DNA
                        organism = synthetic construct
SEQUENCE: 56
atggagactg ggctgcgctg gcttctcctg gtcgctgtgc tcaaaggtgt ccagtgtcag    60
tcgctggagg agtccggggg tcgcctggta acgcctggga caccectgac actcacctgc   120
acagtctctg gaatcgacct cagtacccat gcaatgacct gggtccgcca ggctccagga   180
aaggggctgg aatggatcgg agtcattaat cctagtggta gcgcatacta cgcgacctgg   240
gtgaatggcc gattcaccat ctccaaaacc tcgaccacgg tggatctgaa aatcaccagt   300
ccgacaaccg gggacacggc caagtatttc tgtgccagag attatattac tgcgggtgat   360
tattatatgg atgcttttga tccctggggc ccaggcaccc tggtcaccgt ctcctca      417

SEQ ID NO: 57           moltype = DNA   length = 405
FEATURE                 Location/Qualifiers
source                  1..405
                        mol_type = other DNA
                        organism = synthetic construct
SEQUENCE: 57
atggacacga gggcccccac tcagctgctg gggctcctgc tgctctggct cccaggtgcc    60
acatttgccc aagtgctgac ccagactgca tcccccgtgt ctgcggctgt ggaggcaca    120
gtcaccatca attgccagtc cagtcagagt gttgtatata caaccgctt atcctggttt    180
caacagaaac cagggcagcc tcccaagctc ctgatctatg gtgcatccac tctggcatct   240
ggggtcccat cgcggttcaa aggcagtgga tctgggacac agttcactct caccatcagc   300
gacgtgcagt gtgacgatgc tgccacttac tactgtcag gctcctatga ttgtagtagt   360
ggtgattgcc atgctttcgg cggagggacc gaggtggtgg tcaaa                   405

SEQ ID NO: 58           moltype = DNA   length = 399
FEATURE                 Location/Qualifiers
source                  1..399
                        mol_type = other DNA
                        organism = synthetic construct
SEQUENCE: 58
atggacatga gggcccccac tcagctgctg gggctcctac tgctctggct cccaggtgcc    60
agatgtgctg acattgtgat gacccagact ccagcctccg tggaggcagc tgtgggaggc   120

```
acagtcacca tcaattgcca agccagtgag agcattaata gttggttgtc ctggtatcag    180
cagaaaccag gcagcctcc caacctcctg atctacaggg catccactct ggcatctggg     240
gtcccatcgc ggttcagtgg cggtggatct gggacagagt acactctcac catcagcgac    300
ctggagtgtg ccgatgctgt cacttattac tgtcaaagct attatgagga ggatggtatt    360
ggttatgctt tcggcggagg gaccgagtg gtggtcaa                             399

SEQ ID NO: 59          moltype = DNA   length = 399
FEATURE                Location/Qualifiers
source                 1..399
                       mol_type = other DNA
                       organism = synthetic construct
SEQUENCE: 59
atggacatga gggcccccac tcagctgctg gggctcctgc tgctctggct cccaggtgcc    60
agatgtgctg acattgtgat gacccagact ccatcctccg tgtctgcagc tgtgggaggc    120
acagtcacca tcaattgcca ggccagtcag aacatttaca gcaatttagc ctggtatcag    180
cagaaaccag gcagcgtcc caggctcctg atctatggcg catccaatct ggcatctggg     240
gtcccatcgc ggttcaaagg cagtagatct gggacagagt tcactctcac catcagcgac    300
ctggagtgtg ccgatgctgc cacttactac tgtcaaggct atgattatag tactgctggt    360
gcctatcctt tcggcggagg gaccgcgtg gtggtcaaa                            399

SEQ ID NO: 60          moltype = DNA   length = 405
FEATURE                Location/Qualifiers
source                 1..405
                       mol_type = other DNA
                       organism = synthetic construct
SEQUENCE: 60
atggacacga gggcccccac tcagctgctg gggctcctgc tgctctggct cccaggtgcc    60
acatttgccc aagtgctgac ccagactgca tcgcccgtgt ctgcggctgt ggaagcaca    120
gtcaccatca attgccagtc cagtcagagc gtttatagta caagcgctt agcctggttt    180
cagctgaaac cagggcagcc tcccaagctc ctgatctatg gtgcatccac actggcatct   240
ggggtcccat cgcggattca aggcagtgga tctgggacac agttcactct caccatcagc   300
gacgtgcagt gtgacgatgc tgccacttac tactgtgcag gcggttatga ttgtagtact   360
ggtgattgtt ggactttcgg cggaggggacc gaggtggtgg tcaca                   405

SEQ ID NO: 61          moltype = DNA   length = 399
FEATURE                Location/Qualifiers
source                 1..399
                       mol_type = other DNA
                       organism = synthetic construct
SEQUENCE: 61
atggacatga gggcccccac tcagctgctg gggctcctgc tgctctggct cccaggtgcc    60
agatgtgctg acatcgtgat gacccagact ccatcctccg tgtctgcagc tgtgggaggc    120
acagtcacca tcaagtgcca ggccagtcag agcattggta gtaatttagc ctggtatcag   180
cagaaaccag gcagcctcc caagctcctg atctatggtg catccactct ggaatctggg    240
gtcccatcgc ggtttaaagg cagtggatct gggacagagt acactctcac catcagcgac   300
ctggagtgtg ccgatgctgc cacttactac tgtcaaagct attatgaggg tagtgatatt   360
ggttatgctt tcggcggagg gaccgagtg gtggtcaa                             399

SEQ ID NO: 62          moltype = DNA   length = 399
FEATURE                Location/Qualifiers
source                 1..399
                       mol_type = other DNA
                       organism = synthetic construct
SEQUENCE: 62
atggacacga gggcccccac tcagctgctg gggctcctgc tgctctggct cccaggtgcc    60
agatgtgctg acatcgtgat gacccagact ccagcctctg tgtctgcagc tgtgggaggc    120
acagtcacca tcaagtgcca ggccagtcag agcattagca accaactatc ctggtatcag   180
cagaaatcag gcagcctcc caagctcctg atctacaggg catctactct ggcatctggg    240
gtcccatcgc ggttcaaagg cagtggatct gggacagagt tcactctcac catcagcgac   300
ctggagtgtg ccgatgctgc cacttactac tgtcaacagg ttataatag ataatgtt      360
gataatctt tcggcggagg gaccgaggtg gtggtcaa                             399

SEQ ID NO: 63          moltype = DNA   length = 1374
FEATURE                Location/Qualifiers
source                 1..1374
                       mol_type = other DNA
                       organism = synthetic construct
SEQUENCE: 63
atggagactg gctgcgctg gcttctcctg tcgctgtgc tcaaaggtgt ccagtgtcag     60
tcgctggagg agtccggggg tcgcctggtc acgcctggga caccctgac actcacctgc   120
acagtctctg gattttccct cagtagccag aaagtgggc gggtccgcca ggctccaggg  180
aaggggctga atggatcgg aatcattaat aattatggta gcacatacta cgcgagctgg   240
gcgaaaggcc gattcaccat ctcgaaaacc tcgaccacag tggatctgag aatcaccagt   300
ctgacggccg aggacacggc caccttatttt tgtgcccgtg atcctgatgg tagtattgtc   360
tttgacatct ggggcccagg caccccttgtc accgtctcct ggggcaacc taaggctcca   420
tcagtcttcc cactggcccc ctgctgcggg gacacaccca gctccacggt gaccctgggc   480
tgcctggtca aaggctacct cccggagcca gtgaccgtga cctggaactc gggcacccc   540
accaatgggg tacgcacctt cccgtccgtc cggcagtcct caggcctcta ctcgctgagc   600
agcgtggtga cgtgacctc aagcagccag cccgtcacct gcaacgtggc ccacccagcc   660
```

```
accaacacca aagtggacaa gaccgttgcg ccctcgacat gcagcaagcc cacgtgccca    720
cccccctgaac tcctggggcg atcctctgtc ttcatcttcc ccccaaaacc caaggacacc    780
ctcatgatct cacgcacccc cgaggtcaca tgcgtggtgg tggacgtgag ccaggatgac    840
cccgaggtgc agttcacatg gtacataaac aacgagcagg tgcgcaccgc ccggccgccg    900
ctacgggagc agcagttcaa cagcacgatc cgcgtggtca gcaccctccc catcgcgcac    960
caggactggc tgaggggcaa ggagttcaag tgcaaagtcc acaacaaggc actcccggcc   1020
cccatcgaga aaaccatctc caaagccaga gggcagcccc tggagccgaa ggtctacacc   1080
atgggccctc cccggggagga gctgagcagc aggtcggtca gcctgacctg catgatcaac   1140
ggcttctacc cttccgacat ctcggtggag tgggagaaga acgggaaggc agaggacaac   1200
tacaagacca cgccggccgt gctggacagc gacggctcct acttcctcta cagcaagctc   1260
tcagtgccca cgagtgagtg gcagcggggc gacgtcttca cctgctccgt gatgcacgag   1320
gccttgcaca accactacac gcagaagtcc atctcccgct ctccgggtaa atga          1374

SEQ ID NO: 64        moltype = DNA  length = 1392
FEATURE              Location/Qualifiers
source               1..1392
                     mol_type = other DNA
                     organism = synthetic construct
SEQUENCE: 64
atggagactg ggctgcgctg gcttctcctg gtcgctgtgc tcaaaggtgt ccagtgtcag     60
tcggtggagg agtccggggg tcgcctggtc acgcctggga caccctgac actcacctgc    120
accgtctctg gatttcccct cagtagctat gcaatgatct gggtccgcca ggtccaggg    180
aaggggctgg aatggatcgg attcattagt cgtagtggta tcacatacta cgcgagctgg   240
gcaaaaggcc gattcaccat ctccaaaacc tcgaccacgg tggatctgaa aatgaccagt   300
ctgacaaccg aggacacggc cacctatttc tgtgccagag aattcggtgc tgttggtagt   360
gattattata gggacgcctt taacttgtgg ggcccaggca ccctggtcac cgtctcctca   420
gggcaaccta aggctccatc agtcttccca ctggccccct gctgcgggga cacacccagc   480
tccacggtga ccctgggctg cctggtcaaa ggctacctcc cggagccagt gaccgtgacc   540
tggaactcgg gcaccctcac caatgggta cgcaccttcc cgtccgtccg gcagtcctca   600
ggcctctact cgctgagcag cgtggtgagc tgacctcaa gcagccagcc cgtcacctgc   660
aacgtggccc acccagccac caacaccaaa gtggacaaga ccgttgcgcc ctcgacatgc   720
agcaagccca cgtgcccacc ccctgaactc ctggggcgat cctctgtctt catcttcccc   780
ccaaaaccca aggacaccct catgatctca cgcacccccg aggtcacatg cgtggtggtg   840
gacgtgagcc aggatgaccc cgaggtgcag ttcacatggt acataaacaa cgagcaggtg   900
cgcaccgccc ggccgccgct acgggagcag cagttcaaca gcacgatccg cgtggtcagc   960
accctcccca tcgcgcacca ggactggctg aggggcaagg agttcaagtg caaagtccac  1020
aacaaggcac tcccggcccc catcgagaaa accatctcca agccagagg gcagcccctg  1080
gagccgaagg tctacaccat gggcccctcc cggggaggagc tgagcagcag gtcggtcagc  1140
ctgacctgca tgatcaacgg cttctacccct tccgacatcct cggtggagtg ggagaagaac  1200
gggaaggcag aggacaacta caagaccacg ccggccgtgc tggacagcga cggctcctac  1260
ttcctctaca gcaagctctc agtgcccacg agtgagtggc agcgggggcga cgtcttcacc  1320
tgctccgtga tgcacgaggc cttgcacaac cactacacgc agaagtccat ctcccgctct  1380
ccgggtaaat ga                                                     1392

SEQ ID NO: 65        moltype = DNA  length = 1374
FEATURE              Location/Qualifiers
source               1..1374
                     mol_type = other DNA
                     organism = synthetic construct
SEQUENCE: 65
atggagactg ggctgcgctg gcttctcctg gtcgctgtgc tcaaaggtgt ccagtgtcag     60
tcgctggagg agtccggggg tcgcctggtc acgcctggga caccctgac actcacctgc    120
acagtctctg gattttccct aaataactac aaagtgggct gggtccgcca ggctccagga   180
aaggggctgg aatggatcgg aatcattaac tattatagtc agacatacta cgcgagctgg   240
gccaaaggcc gattcaccat ctcgaaaacc tcgaccacgg tggatctgaa atcaccagt    300
ccgacaaccg aagacacggc cacctatttc tgtgcccgtg atcctgatgg tagtattgtc   360
tttgacatct ggggccccagg caccctgtc accgtctcct ggggcaacc taaggctcca   420
tcagtcttcc cactggcccc ctgctgcggg gacacaccca gctccacggt gaccctgggc   480
tgcctggtca aaggctacct cccggagcca gtgaccgtga cctggaactc gggcaccctc   540
accaatgggg tacgcacctt cccgtccgtc cggcagtcct caggcctcta ctcgctgagc   600
agcgtggtga gcgtgacctc aagcagccag cccgtcacct gcaacgtggc cacccagcc   660
accaacacca aagtggacaa gaccgttgtg ccctcgacat gcagcaagcc cacgtgccca   720
cccccctgaac tcctggggcg atcctctgtc ttcatcttcc ccccaaaacc caaggacacc   780
ctcatgatct cacgcacccc cgaggtcaca tgcgtggtgg tggacgtgag ccaggatgac   840
cccgaggtgc agttcacatg gtacataaac aacgagcagg tgcgcaccgc ccggccgccg   900
ctacgggagc agcagttcaa cagcacgatc cgcgtggtca gcaccctccc catcgcgcac   960
caggactggc tgaggggcaa ggagttcaag tgcaaagtcc acaacaaggc actcccggcc  1020
cccatcgaga aaaccatctc caaagccaga gggcagcccc tggagccgaa ggtctacacc  1080
atgggccctc cccggggagga gctgagcagc aggtcggtca gcctgacctg catgatcaac  1140
ggcttctacc cttccgacat ctcggtggag tgggagaaga acgggaaggc agaggacaac  1200
tacaagacca cgccggccgt gctggacagc gacggctcct acttcctcta cagcaagctc  1260
tcagtgccca cgagtgagtg gcagcggggc gacgtcttca cctgctccgt gatgcacgag  1320
gccttgcaca accactacac gcagaagtcc atctcccgct ctccgggtaa atga         1374

SEQ ID NO: 66        moltype = DNA  length = 1392
FEATURE              Location/Qualifiers
source               1..1392
                     mol_type = other DNA
                     organism = synthetic construct
```

```
SEQUENCE: 66
atggagactg ggctgcgctg gcttctcctg gtcgctgtgc tcaaaggtgt ccagtgtcag    60
tcggtggagg agtccggagg aggcctggta acgcctggag aaccctgac actcacctgc    120
accgtctctg gattctccct cagtaactat gcaatgagct gggtccgcca ggctccaggg   180
aaggggctga atggatcgg attcattagt cgtagtggta ttacatacta cgcgagctgg    240
gcaaaaggcc gattcaccat ctccaaaacc tcgaccacgg tggatctgaa aatcaccagt    300
ccgacgaccg aggacacggc cgcctatttc tgtgccagag aattcggtgc tgttggtagt   360
gattattata gggacgcctt gaggttgtgg ggcccaggca ccctggtcac cgtctcctca   420
gggcaaccta aggctccatc agtcttccca ctggcccct gctgcgggga cacccagc     480
tccacgtga ccctgggctg cctggtcaaa ggctacctcc cggagccagt gaccgtgacc    540
tggaactcgg caccctcac caatgggta cgcaccttcc cgtccgtccg gcagtcctca    600
ggcctctact cgctgagcag cgtggtgagc gtgacctcaa gcagccagcc cgtcacctgc   660
aacgtggccc acccagccac caacaccaaa gtggacaaga ccgttgcgcc ctcgacatgc   720
agcaagccca cgtgcccacc ccctgaactc ctggggcgat cctctgtctt catcttcccc   780
ccaaaaccca aggacaccct catgatctca cgcacccccg aggtcacatg cgtggtggtg   840
gacgtgagcc aggatgaccc cgaggtgcag ttcacatggt acataaacaa cgagcaggtg   900
cgcaccgccc ggccgccgct acgggacgca cagttcaaca gcacgatccg cgtggtcagc   960
accctcccca tcgcgcacca ggactggctg aggggcaagg agttcaagtg caaagtccac  1020
aacaaggcac tccggccccc catcgagaaa accatctcca aagccagagg gcagcccctg  1080
gagccgaagg tctacaccat gggccctccc cgggaggagc tgagcagcag gtcggtcagc  1140
ctgacctgca tgatcaacgg cttctaccct tccgacatct cggtggagtg ggagaagaac  1200
gggaaggcag aggacaacta caagaccacg ccggccgtgc tggacagcga cggctccac   1260
ttcctctaca gcaagctctc agtgccacg agtgagtggc agcggggcga cgtcttcacc   1320
tgctccgtga tgcacgaggc cttgcacaac cactacacgc agaagtccat ctcccgctct  1380
ccgggtaaat ga                                                      1392

SEQ ID NO: 67            moltype = DNA  length = 1389
FEATURE                  Location/Qualifiers
source                   1..1389
                         mol_type = other DNA
                         organism = synthetic construct
SEQUENCE: 67
atggagactg ggctgcgctg gcttctcctg gtcgctgtgc tcaaaggtgt ccagtgtcag    60
tcgctggagg agtccggggg tcgcctggta acgcctggga caccctgac actcacctgc    120
acagtctctg gaatcgacct cagtacccat gcaatgacct gggtccgcca ggctccagga   180
aaggggctgg aatggatcgg agtcattaat cctagtggta gcgcatacta cgcgacctgg   240
gtgaatggcc gattcaccat ctccaaaacc tcgaccacgg tggatctgaa aatcaccagt   300
ccgacaaccg gggacacggc caagtatttc tgtgccagaa attatattac tgcgggtgat   360
tattatatgg atgcttttga tccctggggc ccaggcaccc tggtcaccgt ctcctcaggg   420
caacctaagg ctccatcagt cttcccactg gcccctgct gcgggacac acccagctcc    480
acggtgaccc tgggctgcct ggtcaaaggc tacctcccgg agccagtgac cgtgacctgg   540
aactcgggca ccctcaccaa tggggtacgc accttcccgt ccgtccggca gtcctcaggc   600
ctctactcgc tgagcagcgt ggtgagcgtg acctcaagca gccagcccgt cacctgcaac   660
gtggcccacc cagccaccaa caccaaagtg gacaagaccg ttgcgccctc gacatgcagc   720
aagcccacgt gcccaccccc tgaactcctg ggcgatcct ctgtcttcat cttccccca    780
aaacccaaga cacctcat gatctcacgc acccccgagg tcacatgcgt ggtggtggac    840
gtgagccagg atgaccccga ggtgcagttc acatggtaca taaacaacga gcaggtgcgc   900
accgcccgc cgccgctacg ggagcagcag ttcaacagca cgatccgcgt gtcagcacc    960
ctccccatcg cgcaccagga ctggctgagg gcaaggagt tcaagtgcaa agtccacaac   1020
aaggcactcc ggccccccat cgagaaaacc atctccaaag ccagagggca gcccctggag   1080
ccgaaggtct acaccatggg ccctccccgg gaggagctga gcagcaggtc ggtcagcctg   1140
acctgcatga tcaacggctt ctaccttcc gacatctcgg tggagtggga agaacggg     1200
aaggcagagg acaactacaa gaccacgccg gccgtgctgg acagcgacgg ctcctacttc   1260
ctctacagca agctctcagt gccacgagt gagtggcagc agggcgacgt cttcacctgc   1320
tccgtgatgc acgaggcctt gcacaaccac tacacgcaga agtccatctc ccgctctccg   1380
ggtaaatga                                                          1389

SEQ ID NO: 68            moltype = DNA  length = 720
FEATURE                  Location/Qualifiers
source                   1..720
                         mol_type = other DNA
                         organism = synthetic construct
SEQUENCE: 68
atggacacga gggcccccac tcagctgctg ggctcctgc tgctctggct cccaggtgcc    60
acatttgccc aagtgctgac ccagactgca tccccgtgt ctgcggctgt tggaggcaca   120
gtcaccatca attgccagtc cagtcagagt gttgtatata caaccgcctt atcctggttt   180
caacagaaac cagggcagcc tcccaagctc ctgatctatg gtgcatccac tctggcatct   240
ggggtcccat cgcggttcaa aggcagtgga tctgggacac agttcactct caccatcagc   300
gacgtgcagt gtgacgatgc tgccacttac tactgtctag gctcctatga ttgtagtagt   360
ggtgattgcc atgctttcgg cggagggacc gaggtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga gaacagtaaa acaccgcaga attctgcaga ttgtacctac   600
aacctcagca gcactctgac actgaccagc acacagtaca cagccacaa agtacacc    660
tgcaaggtga cccagggcac gacctcagtc gtccagagct caataggg tgactgttag   720
```

| SEQ ID NO: 69 | moltype = DNA length = 714 |
|---|---|
| FEATURE | Location/Qualifiers |
| source | 1..714 |
| | mol_type = other DNA |
| | organism = synthetic construct |

SEQUENCE: 69
```
atggacatga gggcccccac tcagctgctg gggctcctac tgctctggct cccaggtgcc   60
agatgtgctg acattgtgat gacccagact ccagcctccg tggaggcagc tgtgggaggc  120
acagtcacca tcaattgcca agccagtgag agcattaata gttggttgtc ctggtatcag  180
cagaaaccag gcagcctcc caacctcctg atctacaggg catccactct ggcatctggg  240
gtcccatcgc ggttcagtgg cggtggatct gggacagagt acactctcac catcagcgac  300
ctggagtgtg ccgatgctgt cacttattac tgtcaaagct attatgagga ggatggtatt  360
ggttatgctt tcggcggagg gaccgaggtg gtggtcaaag gtgatccagt tgcacctact  420
gtcctcatct tcccaccagc tgctgatcag gtgcaactg aacagtcac catcgtgtgt  480
gtggcgaata atactttcc cgatgtcacc gtcacctggg aggtggatgg caccaccccaa  540
acaactggca tcgagaacag taaaacaccg cagaattctg cagattgtac ctacaacctc  600
agcagcactc tgacactgac cagcacacag tacaacagcc acaaagagta cacctgcaag  660
gtgacccagg gcacgacctc agtcgtccag agcttcaata ggggtgactg ttag         714
```

| SEQ ID NO: 70 | moltype = DNA length = 714 |
|---|---|
| FEATURE | Location/Qualifiers |
| source | 1..714 |
| | mol_type = other DNA |
| | organism = synthetic construct |

SEQUENCE: 70
```
atggacatga gggcccccac tcagctgctg gggctcctgc tgctctggct cccaggtgcc   60
agatgtgctg acattgtgat gacccagact ccatcctccg tgtctgcagc tgtgggaggc  120
acagtcacca tcaattgcca ggccagtcag aacatttaca gcaatttagc ctggtatcag  180
cagaaaccag gcagcgtcc caggctcctg atctatggcg catccaatct ggcatctggg  240
gtcccatcgc ggttcaaagg cagtagatct gggacagagt tcactctcac catcagcgac  300
ctggagtgtg ccgatgctgc cacttactac tgtcaaggct atgattatag tactgctggt  360
gcctatcctt cggcggagg gaccgcggtg gtggtcaaag tgatccagt tgcacctact  420
gtcctcatct tcccaccagc tgctgatcag gtgcaactg aacagtcac catcgtgtgt  480
gtggcgaata atactttcc cgatgtcacc gtcacctggg aggtggatgg caccaccccaa  540
acaactggca tcgagaacag taaaacaccg cagaattctg cagattgtac ctacaacctc  600
agcagcactc tgacactgac cagcacacag tacaacagcc acaaagagta cacctgcaag  660
gtgacccagg gcacgacctc agtcgtccag agcttcaata ggggtgactg ttag         714
```

| SEQ ID NO: 71 | moltype = DNA length = 720 |
|---|---|
| FEATURE | Location/Qualifiers |
| source | 1..720 |
| | mol_type = other DNA |
| | organism = synthetic construct |

SEQUENCE: 71
```
atggacacga gggcccccac tcagctgctg gggctcctgc tgctctggct cccaggtgcc   60
acatttgccc aagtgctgac ccagactgca tcgcccgtgt ctgcggctgt gggaagcaca  120
gtcaccatca attgccagtc cagtcagagc gtttatagta acaagcgctt agcctggttt  180
cagctgaaac agggcagcc tcccaagctc ctgatctatg gtgcatccac actggcatct  240
ggggtcccat cgcgattcaa gggcagtgga tctgggacag agttcactct caccatcagc  300
gacgtgcagt gtgacgatgc tgccacttac tactgtgcag gcggttatga tttgtagtact  360
ggtgattgtt ggactttcgg cggagggacc gaggtggtgg tcacaggtga tccagttgca  420
cctactgtcc tcatcttccc accagctgct gatcaggtgg caactggaac agtcaccatc  480
gtgtgtgtgg cgaataaata ctttcccgat gtcaccgtca cctgggaggt ggatggcacc  540
acccaaacaa ctggcatcga gaacagtaaa acaccgcaga ttctgcaga ttgtacctac  600
aacctcagca gcactctgac actgaccagc acacagtaca acagccacaa agagtacacc  660
tgcaaggtga cccagggcac gacctcagtc gtccagagct tcaatagggg tgactgttag  720
```

| SEQ ID NO: 72 | moltype = DNA length = 714 |
|---|---|
| FEATURE | Location/Qualifiers |
| source | 1..714 |
| | mol_type = other DNA |
| | organism = synthetic construct |

SEQUENCE: 72
```
atggacatga gggcccccac tcagctgctg gggctcctgc tgctctggct cccaggtgcc   60
agatgtgctg acatcgtgat gacccagact ccatcctccg tgtctgcagc tgtgggaggc  120
acagtcacca tcaagtgcca ggccagtcag agcattggta gtaatttagc ctggtatcag  180
cagaaaccag gcagcctcc caagctcctg atctatggtg catccactct ggaatctggg  240
gtcccatcgc ggtttaaagg cagtggatct gggacagagt acactctcac catcagcgac  300
ctggagtgtg ccgatgctgc cacttactac tgtcaaagct attatgaggg tagtgatatt  360
ggttatgctt tcggcggagg gaccgaggtg gtggtcaaag gtgatccagt tgcacctact  420
gtcctcatct tcccaccagc tgctgatcag gtgcaactg aacagtcac catcgtgtgt  480
gtggcgaata atactttcc cgatgtcacc gtcacctggg aggtggatgg caccaccccaa  540
acaactggca tcgagaacag taaaacaccg cagaattctg cagattgtac ctacaacctc  600
agcagcactc tgacactgac cagcacacag tacaacagcc acaaagagta cacctgcaag  660
gtgacccagg gcacgacctc agtcgtccag agcttcaata ggggtgactg ttag         714
```

```
SEQ ID NO: 73          moltype = DNA  length = 714
FEATURE                Location/Qualifiers
source                 1..714
                       mol_type = other DNA
                       organism = synthetic construct
SEQUENCE: 73
atggacacga gggcccccac tcagctgctg gggctcctgc tgctctggct cccaggtgcc    60
agatgtgctg acatcgtgat gacccagact ccagcctctg tgtctgcagc tgtgggaggc   120
acagtcacca tcaagtgcca ggcagtcagt agcattagca accaactatc ctggtatcag   180
cagaaatcag ggcagcctcc caagctcctg atctacaggg catctactct ggcatctggg   240
gtcccatcgc ggttcaaagg cagtggatct gggacagagt tcactctcac catcagcgac   300
ctggagtgtg ccgatgctgc cacttactac tgtcaacagg gttataatag agataatgtt   360
gataatcttt tcggcggagg gaccgaggtg gtggtcaaag gtgatccagt tgcacctact   420
gtcctcatct tcccaccagc tgctgatcag gtggcaactg gaacagtcac catcgtgtgt   480
gtggcgaata atactttcc cgatgtcacc gtcacctggg aggtggatgg caccacccaa   540
acaactggca tcgagaacag taaaacaccg cagaattctg cagattgtac ctacaacctc   600
agcagcactc tgacactgac cagcacacag tacaacgcc acaaagagta cacctgcaag   660
gtgacccagg gcacgacctc agtcgtccag agcttcaata ggggtgactg ttag         714

SEQ ID NO: 74          moltype = AA  length = 17
FEATURE                Location/Qualifiers
source                 1..17
                       mol_type = protein
                       organism = synthetic construct
SITE                   9
                       note = Phosphorylated threonine
SEQUENCE: 74
RSRTPSLPTP PTREPKC                                                   17

SEQ ID NO: 75          moltype = AA  length = 17
FEATURE                Location/Qualifiers
source                 1..17
                       mol_type = protein
                       organism = synthetic construct
SITE                   6
                       note = Phosphorylated threonine
SEQUENCE: 75
TPSLPTPPTR EPKKVAC                                                   17

SEQ ID NO: 76          moltype = AA  length = 20
FEATURE                Location/Qualifiers
source                 1..20
                       mol_type = protein
                       organism = synthetic construct
SEQUENCE: 76
RSRTPSLPTP PTREPKKVAC                                                20

SEQ ID NO: 77          moltype = AA  length = 17
FEATURE                Location/Qualifiers
source                 1..17
                       mol_type = protein
                       organism = synthetic construct
SITE                   4
                       note = Phosphorylated threonine
SEQUENCE: 77
RSRTPSLPTP PTREPKC                                                   17

SEQ ID NO: 78          moltype = AA  length = 17
FEATURE                Location/Qualifiers
source                 1..17
                       mol_type = protein
                       organism = synthetic construct
SITE                   6
                       note = Phosphorylated serine
SEQUENCE: 78
RSRTPSLPTP PTREPKC                                                   17

SEQ ID NO: 79          moltype = AA  length = 20
FEATURE                Location/Qualifiers
source                 1..20
                       mol_type = protein
                       organism = synthetic construct
SITE                   12
                       note = Phosphorylated threonine
SEQUENCE: 79
RSRTPSLPTP PTREPKKVAC                                                20
```

```
SEQ ID NO: 80          moltype = AA  length = 16
FEATURE                Location/Qualifiers
source                 1..16
                       mol_type = protein
                       organism = synthetic construct
SITE                   7
                       note = Phosphorylated threonine
SEQUENCE: 80
KVAVVRTPPK SPSSAC                                                    16

SEQ ID NO: 81          moltype = AA  length = 16
FEATURE                Location/Qualifiers
source                 1..16
                       mol_type = protein
                       organism = synthetic construct
SEQUENCE: 81
KVAVVRTPPK SPSSAC                                                    16
```

PHOSPHO-TAU ANTIBODIES AND METHODS OF USE

CROSS-REFERENCE

This application is a continuation of International Application No.: PCT/US2022/042963 filed on Sep. 8, 2022, which claims the benefit of U.S. Provisional Patent Application No. 63/242,437 filed on Sep. 9, 2021, each of which is incorporated by reference in its entirety.

SEQUENCE LISTING

The instant application contains a sequence listing which has been submitted electronically in xml format and is hereby incorporated by reference in its entirety. Said xml copy, created on Mar. 6, 2024, is named 58484-705_301_SL.xml and is 94,094 bytes in size.

BACKGROUND

The discovery of biomarkers and screening techniques of Alzheimer's disease (AD) and other tauopathies is an ongoing area of development in which these tools may be applied to screening populations to determine which non-demented individuals are at greatest risk of developing AD dementia and also to assess disease progression in patients. Proteins that are reflective of AD pathology, including amyloid beta 42 (Aβ42), neurofilament light chain, and various tau isoforms have been detected by a variety of means. Abnormal or excessive phosphorylation of tau has been associated with transformation of pathologically normal tau molecules into paired-helical-filament (PHF) tau and neurofibrillary tangles (NFTs) indicative of various tauopathy pathologies.

SUMMARY

Tau is an important microtubule-associated protein, abundantly expressed in CNS neurons, and serves critical roles in normal cellular physiology. Tau has also been found to be dysregulated in Alzheimer's disease and other tauopathies. Six isoforms of tau protein are generated from the TAU gene by alternative splicing. The isoforms differ from each other by the presence or absence of two N-terminal inserts and a repeat termed R2. All six protein isoforms of tau are highly soluble under normal and healthy cellular conditions and are typically regulated by phosphorylation and dephosphorylation. Tau has been demonstrated to interact with microtubules and promote microtubule assembly. In neurons, tau promotes the formation of axonal microtubules and stabilizes them. Tau has additional roles in driving neurite outgrowth. Impaired interaction of tau with microtubules may be an important component in the pathology, development, and progression of tauopathies. Hyperphosphorylation of tau is a hallmark feature of AD and other tauopathies and the extent of hyperphosphorylation is often correlated with disease progression. Hyperphosphorylation of tau protein can result in the self-assembly of insoluble tangles of paired helical filaments and straight filaments of tau. These insoluble aggregates of tangles, termed neurofibrillary tangles (NFTs), are comprised of hyperphosphorylated tau and are considered to be pathological markers of tauopathies.

Phosphorylated tau (pTau), total tau, and Aβ42 each detected from the cerebrospinal fluid (CSF) and/or the blood are individual biomarkers for Alzheimer's disease and several other related tauopathies. CSF pTau is increased in individuals later confirmed to have AD both at the prodromal stages and the dementia stages compared to age- and gender-matched controls. CSF pTau levels exhibit a strong degree of correlation to the extent of cognitive impairment in individuals with AD. In fact, CSF pTau levels may be used with some degree of precision as a biomarker to predict progression from cognitively unimpaired, to mild cognitive impairment (MCI) and then to AD dementia. In terms of utility as a biomarker to predict even relatively early stages of AD progression, CSF pTau has been shown to be significantly increased in samples from individuals with preclinical AD. Changes in the extent of pTau phosphorylation have been demonstrated in both preclinical sporadic cases of AD and in early stages of autosomal-dominant AD. Blood levels of pTau, total tau, and Aβ$_{42}$ are generally lower than CSF levels when assayed within the same individual and may be utilized as informative biomarkers for AD and other related tauopathies if blood levels of these biomarkers can be assayed with sufficient specificity and precision.

Several sites of phosphorylation contributing to hyperphosphorylated tau which aggregates into NFTs have been identified. In the longest tau isoform, 79 potential serine or threonine phosphorylation sites are present and at least 30 of these sites have been identified as phosphorylated in NFT aggregates. A common site used to assay tau molecules for phosphorylation status is at threonine-181. CSF fluid contains an array of tau fragments at various abundances. Fragments of tau from the N-terminal region and from the middle region of tau polypeptides are considerably more abundant in CSF samples than C-terminal tau fragments. Plasma samples from individuals also contain tau polypeptides and tau polypeptide fragments, however they tend to be present at lower concentrations that in matched CSF samples. Being able to detect tau phosphorylation at particular amino acid residues relevant for disease pathology and progression is a critical component of diagnosis, disease staging, and as a metric to measure treatment efficacy for AD and other tauopathies. Detection and measurement of pTau levels at particular disease-relevant residues from plasma samples would aid greatly to the development of more sensitive and finely-tuned diagnosis, prognosis, and disease analysis for individuals who may be at risk for developing or are at early stages of AD or other tauopathies. Phosphorylation of tau at threonine 217 (pTau 217) is one such residue of particular interest in development new biomarkers and diagnostic assays. Alterations in pTau biomarker concentration in CSF and in plasma are thought to precede measurable behavioral or cognitive changes in AD and in other tauopathies. A development of new assays to enable a continuum of specific points and extents of tau phosphorylation of certain residues would undoubtedly aid in the clinically relevant medical diagnosis and treatment decisions. A comparison of results from new assays to results from existing assays can also yield further medically informative determinations. Results from plasma-based tau biomarker assays can be compared against matched CSF samples (detecting CSF pTau or CSF soluble AD) and also against positron emission tomography (PET) scans detecting an extent and locations of Aβ aggregates as metrics for their utility, especially for analysis at preclinical or early disease stages.

Provided herein are methods for detecting phosphorylated tau in a sample from an individual comprising: performing an immunoassay on the sample using an antibody or antibody fragment comprising a variable domain, heavy chain region (VH) and a variable domain, light chain region (VL), wherein the VH comprises an amino acid sequence at least about 90% identical to a sequence as set forth in any one of SEQ ID NOs: 30-34, and wherein the VL comprises an amino acid sequence at least about 90% identical to a sequence as set forth in any one of SEQ ID NOs: 35-40. Further provided herein are methods for detecting phosphorylated tau in a sample from an individual, wherein the phosphorylated tau is selected from the group consisting of pTau-181, pTau-212, pTau-217, pTau-231, pTau-214, and pTau-220. Further provided herein are methods for detecting phosphorylated tau in a sample from an individual, wherein the phosphorylated tau is pTau-217. Further provided herein are methods for detecting phosphorylated tau in a sample from an individual, wherein the phosphorylated tau is pTau-231. Further provided herein are methods for detecting phosphorylated tau in a sample from an individual, wherein the method detects pTau-217 and pTau-231. Further provided herein are methods for detecting phosphorylated tau in a sample from an individual, wherein the method detects pTau-212 and pTau-217. Further provided herein are methods for detecting phosphorylated tau in a sample from an individual, wherein the method detects pTau-212 and pTau-231. Further provided herein are methods for detecting phosphorylated tau in a sample from an individual, wherein the method detects pTau-181 and pTau-217. Further provided herein are methods for detecting phosphorylated tau in a sample from an individual, wherein the method detects pTau-181 and pTau-231. Further provided herein are methods for detecting phosphorylated tau in a sample from an individual, wherein the method detects pTau-181, pTau-217, and pTau-231. Further provided herein are methods for detecting phosphorylated tau in a sample from an individual, wherein the method detects pTau-212, pTau-217 and pTau-231. Further provided herein are methods for detecting phosphorylated tau in a sample from an individual, wherein the method detects pTau-217 and pTau-231 in a sample selected from the group consisting of a plasma sample and serum sample. Further provided herein are methods for detecting phosphorylated tau in a sample from an individual, wherein the method detects pTau-212 and pTau-217 in a sample selected from the group consisting of a plasma sample and serum sample. Further provided herein are methods for detecting phosphorylated tau in a sample from an individual, wherein the method detects pTau-212 and pTau-231 in a sample selected from the group consisting of a plasma sample and serum sample. Further provided herein are methods for detecting phosphorylated tau in a sample from an individual, wherein the method detects pTau-181 and pTau-217 in a sample selected from the group consisting of a plasma sample and serum sample. Further provided herein are methods for detecting phosphorylated tau in a sample from an individual, wherein the method detects pTau-181 and pTau-231 in a sample selected from the group consisting of a plasma sample and serum sample. Further provided herein are methods for detecting phosphorylated tau in a sample from an individual, wherein the method detects pTau-181, pTau-217, and pTau-231 in a sample selected from the group consisting of a plasma sample and serum sample. Further provided herein are methods for detecting phosphorylated tau in a sample from an individual, wherein the method detects pTau-212, pTau-217, and pTau-231 in a sample selected from the group consisting of a plasma sample and serum sample. Further provided herein are methods for detecting phosphorylated tau in a sample from an individual, wherein the VH comprises an amino acid sequence according to any one of SEQ ID NOs: 30-34. Further provided herein are methods for detecting phosphorylated tau in a sample from an individual, wherein the VL comprises an amino acid sequence according to any one of SEQ ID NOs: 35-40. Further provided herein are methods for detecting phosphorylated tau in a sample from an individual, wherein the VH comprises an amino acid sequence according to any one of SEQ ID NOs: 30-34, and wherein the VL comprises an amino acid sequence according to any one of SEQ ID NOs: 35-40. Further provided herein are methods for detecting phosphorylated tau in a sample from an individual, wherein the VH comprises an amino acid sequence at least about 90% identical to SEQ ID NO: 30, and wherein the VL comprises an amino acid sequence at least about 90% identical to SEQ ID NO: 35. Further provided herein are methods for detecting phosphorylated tau in a sample from an individual, wherein the VH comprises an amino acid sequence at least about 90% identical to SEQ ID NO: 31, and wherein the VL comprises an amino acid sequence at least about 90% identical to SEQ ID NO: 36. Further provided herein are methods for detecting phosphorylated tau in a sample from an individual, wherein the VH comprises an amino acid sequence at least about 90% identical to SEQ ID NO: 31, and wherein the VL comprises an amino acid sequence at least about 90% identical to SEQ ID NO: 37. Further provided herein are methods for detecting phosphorylated tau in a sample from an individual, wherein the VH comprises an amino acid sequence at least about 90% identical to SEQ ID NO: 32, and wherein the VL comprises an amino acid sequence at least about 90% identical to SEQ ID NO: 38. Further provided herein are methods for detecting phosphorylated tau in a sample from an individual, wherein the VH comprises an amino acid sequence at least about 90% identical to SEQ ID NO: 33, and wherein the VL comprises an amino acid sequence at least about 90% identical to SEQ ID NO: 39. Further provided herein are methods for detecting phosphorylated tau in a sample from an individual, wherein the VH comprises an amino acid sequence at least about 90% identical to SEQ ID NO: 34, and wherein the VL comprises an amino acid sequence at least about 90% identical to SEQ ID NO: 40. Further provided herein are methods for detecting phosphorylated tau in a sample from an individual, wherein the antibody or antibody fragment comprises an amino acid sequence at least about 90% identical to any one of SEQ ID NOs: 41-51. Further provided herein are methods for detecting phosphorylated tau in a sample from an individual, further comprising performing an assay on the sample to determine a level of a biomarker selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof. Further provided herein are methods for detecting phosphorylated tau in a sample from an individual, wherein the sample is selected from the group consisting of a blood sample, a plasma sample, a serum sample, and a cerebrospinal fluid (CSF) sample. Further provided herein are methods for detecting phosphorylated tau in a sample from an individual, further comprising establishing Alzheimer's disease in the individual based on detection of phosphorylated tau. Further provided herein are methods for detecting phosphorylated tau in a sample from an individual, further comprising establishing prognosis of the individual for developing Alzheimer's disease based on detection of phosphorylated tau. Further provided herein are methods for detecting phosphorylated tau in a sample from an individual, further determining the individual's age, genotype, or expression of a biomarker. Further provided herein are methods for detecting phosphorylated tau in a sample from an individual, wherein the biomarker is selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof. Further provided herein are methods for detecting phosphorylated tau in a sample from an individual, wherein the method has a specificity of at least about 80% for detecting phosphorylated tau. Further provided herein are methods for detecting phosphorylated tau in a sample from an individual, wherein the method has a specificity of at least about 85% for detecting phosphorylated tau. Further provided herein are methods for detecting phosphorylated tau in a sample from an individual, wherein the method has a specificity of at least about 90% for detecting phosphorylated tau. Further provided herein are methods for detecting phosphorylated tau in a sample from an individual, wherein the method has a sensitivity of at least about 80% for detecting phosphorylated tau. Further provided herein are methods for detecting phosphorylated tau in a sample from an individual, wherein the method has a sensitivity of at least about 85% for detecting phosphorylated tau. Further provided herein are methods for detecting phosphorylated tau in a sample from an individual, wherein the method has a sensitivity of at least about 90% for detecting phosphorylated tau. Further provided herein are methods for detecting phosphorylated tau in a sample from an individual, wherein the method is capable of detecting phosphorylated tau in the sample at a limit of detection of at least about 1.0 picogram per milliliter (pg/mL). Further provided herein are methods for detecting phosphorylated tau in a sample from an individual, wherein the method is capable of detecting phosphorylated tau in the sample at a limit of detection of at least about 1.5 picogram per milliliter (pg/mL). Further provided herein are methods for detecting phosphorylated tau in a sample from an individual, wherein the method is capable of detecting phosphorylated tau in the sample at a limit of detection of at least about 5 picogram per milliliter (pg/mL).

Also provided herein are, in certain embodiments, anti-tau antibodies comprising i) a heavy chain comprising variable heavy chain (VH) domain and ii) a light chain comprising a variable light chain (VL) domain, wherein the VH domain comprises HCDR1 sequence comprising a sequence selected from SEQ ID NOs: 1-5, HCDR2 sequence comprising a sequence selected from SEQ ID NOs: 6-9, and HCDR3 sequence comprising a sequence selected from SEQ ID NOs: 10-13, and VL domain comprises LCDR1 sequence comprising a sequence selected from SEQ ID NOs: 14-19, LCDR2 sequence comprising a sequence selected from SEQ ID NOs: 20-23, and LCDR3 sequence comprising a sequence selected from SEQ ID NOs: 24-29. In some embodiments, the HCDR1 sequence comprises SEQ ID NO: 1, the HCDR2 sequence comprises SEQ ID NO: 6, the HCDR3 sequence comprises SEQ ID NO: 10, the LCDR1 sequence comprises SEQ ID NO: 14, the LCDR2 sequence comprises SEQ ID NO: 20, and the LCDR3 sequence comprises SEQ ID NO: 24. In some embodiments, the HCDR1 sequence comprises SEQ ID NO: 2, the HCDR2 sequence comprises SEQ ID NO: 7, the HCDR3 sequence comprises SEQ ID NO: 11, the LCDR1 sequence comprises SEQ ID NO: 15, the LCDR2 sequence comprises SEQ ID NO: 21, and the LCDR3 sequence comprises SEQ ID NO: 25. In some embodiments, the HCDR1 sequence comprises SEQ ID NO: 2, the HCDR2 sequence comprises SEQ ID NO: 7, the HCDR3 sequence comprises SEQ ID NO: 11, the LCDR1 sequence comprises SEQ ID NO: 16, the LCDR2 sequence comprises SEQ ID NO: 22, and the LCDR3 sequence comprises SEQ ID NO: 26. In some embodiments, the HCDR1 sequence comprises SEQ ID NO: 3, the HCDR2 sequence comprises SEQ ID NO: 8, the HCDR3 sequence comprises SEQ ID NO: 10, the LCDR1 sequence comprises SEQ ID NO: 17, the LCDR2 sequence comprises SEQ ID NO: 20, and the LCDR3 sequence comprises SEQ ID NO: 27. In some embodiments, the HCDR1 sequence comprises SEQ ID NO: 4, the HCDR2 sequence comprises SEQ ID NO: 7, the HCDR3 sequence comprises SEQ ID NO: 12, the LCDR1 sequence comprises SEQ ID NO: 18, the LCDR2 sequence comprises SEQ ID NO: 23, and the LCDR3 sequence comprises SEQ ID NO: 28. In some embodiments, the HCDR1 sequence comprises SEQ ID NO: 5, the HCDR2 sequence comprises SEQ ID NO: 9, the HCDR3 sequence comprises SEQ ID NO: 13, the LCDR1 sequence comprises SEQ ID NO: 19, the LCDR2 sequence comprises SEQ ID NO: 21, and the LCDR3 sequence comprises SEQ ID NO: 29. Further provided herein are, in some embodiments, anti-tau antibodies comprising i) a heavy chain comprising variable heavy chain (VH) domain and ii) a light chain comprising a variable light chain (VL) domain, wherein the VH domain comprises at least 80%, at least 85%, at least 90%, at least 95% sequence identity to a sequence selected from SEQ ID NOs: 30-34. Further provided herein are, in some embodiments, anti-tau antibodies comprising i) a heavy chain comprising variable heavy chain (VH) domain and ii) a light chain comprising a variable light chain (VL) domain, wherein the VL domain comprises at least 80%, at least 85%, at least 90%, at least 95% sequence identity to a sequence selected from SEQ ID NOs: 35-40. In some embodiments, the anti-tau antibody described herein is a chimeric antibody or antigen binding fragment thereof. In some embodiments, the anti-tau antibody described herein comprises an IgG-scFv, nanobody, BiTE, diabody, DART, TandAb, scDiabody, scDiabody-CH3, triple body, miniantibody, minibody, TriBi minibody, scFv-CH3 KIH, Fab-scFv-Fc KIH, Fab-scFv, scFv-CH-CL-scFv, Fab', F(ab')2, F(ab')3, F(ab')2-scFv2, scFv, scFv-KIH, Fab-scFv-Fc, tetravalent HCAb, scDiabody-Fc, diabody-Fc, tandem scFv-Fc, or intrabody. In some embodiments, the anti-tau antibody described herein is an IgG1 antibody. In some embodiments, the anti-tau antibody described herein is an IgG2 antibody. In some embodiments, the anti-tau antibody described herein is an IgG4 antibody. Further provided herein are, in some embodiments, anti-tau antibodies comprising i) a heavy chain comprising variable heavy chain (VH) domain and ii) a light chain comprising a variable light chain (VL) domain, wherein the light chain is a kappa chain. Further provided herein are, in some embodiments, anti-tau antibodies comprising i) a heavy chain comprising variable heavy chain (VH) domain and ii) a light chain comprising a variable light chain (VL) domain, wherein the anti-tau antibody has a binding affinity to human tau of about 100 pM to about 3 nM. Provided herein are, in some embodiments, anti-tau antibodies comprising a VH domain that is encoded by a nucleic acid comprising at least 80%, at least 85%, at least 90%, at least 95% sequence identity to a sequence selected from SEQ ID NOs: 52-56. Provided herein are, in some embodiments, anti-tau antibodies comprising a VL domain that is encoded by a nucleic acid comprising at least 80%, at least 85%, at least 90%, at least 95% sequence identity to a sequence selected from SEQ ID NOs: 57-62. Provided herein are, in some embodiments, anti-tau antibodies comprising a VH domain that is encoded by a nucleic acid comprising at least 80%, at least 85%, at least 90%, at least 95% sequence identity to a sequence selected from SEQ ID NOs: 52-56 and a VL domain that is encoded by a nucleic acid comprising at least 80%, at least 85%, at least 90%, at least 95% sequence identity to a sequence selected from SEQ ID NOs: 57-62. Provided herein are, in some embodiments, anti-tau antibodies comprising a VH domain that is encoded by a nucleic acid comprising a sequence identical to SEQ ID NOs: 52-56. Provided herein are, in some embodiments, anti-tau antibodies comprising a VL domain that is encoded by a nucleic acid comprising a sequence identical to SEQ ID NOs: 57-62. Provided herein are, in some embodiments, anti-tau antibodies comprising a VH domain that is encoded by a nucleic acid comprising a sequence identical to SEQ ID NOs: 52-56 and a VL domain that is encoded by a nucleic acid comprising a sequence identical to SEQ ID NOs: 57-62.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 2A-2D depict data for Antibody 1, Antibody 2, Antibody 3, Antibody 4, Antibody 5, and Antibody 6 in the Simoa® assay.

DETAILED DESCRIPTION

Figure 1:
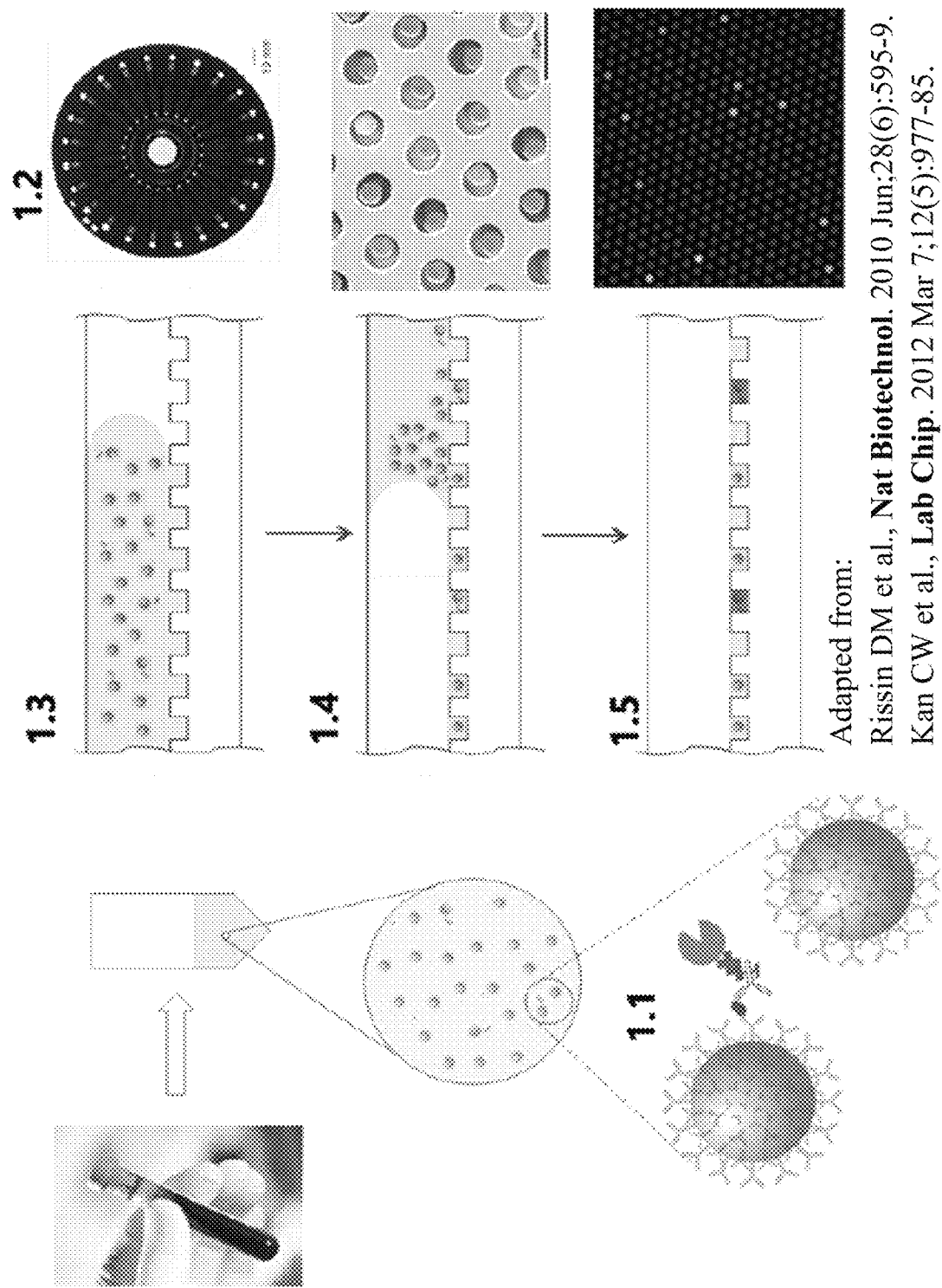
FIG. 1 depicts a schema of the single molecule array (Simoa®) method used herein for assaying tau antibodies described herein. After substrate is added to sample (sandwich ELISA on bead, 1.1), sample is added to Simoa® Disk (1.2). Beads are given time to settle into microarray wells on disk (one bead per well) (1.3). Then, sealing oil is used to remove excess beads to allow for imaging (1.4). Beads that have sandwich complex (positive beads) will fluoresce with the substrate and show up during imaging; beads without sandwich complex (negative) will still show up in imaging but will not fluoresce (1.5). The percentage of positive beads is converted to an AEB (average enzymes per bead) value.

Alzheimer's disease (AD) is a complex disease and effective treatment requires accurate diagnosis. Described herein are improved compositions and methods for detecting AD that comprises improved antibodies for use in diagnostic and/or prognostic assays.

Certain Terminologies

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The terms "individual," "patient," or "subject" are used interchangeably. None of the terms require or are limited to a situation characterized by the supervision (e.g., constant or intermittent) of a health care worker (e.g., a doctor, a registered nurse, a nurse practitioner, a physician's assistant, an orderly, or a hospice worker). Further, these terms refer to human or animal subjects.

The term "antibody" herein is used in the broadest sense and includes monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, and heteroconjugate antibodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a rabbit IgG1 constant region. The antibody can comprise a rabbit IgG4 constant region. An antibody includes, but is not limited to, full-length and native antibodies, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A monoclonal antibody can comprise a rabbit IgG1 constant region or a rabbit IgG4 constant region.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

The term "Fab" refers to a protein that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 Jan. 27(1):55-77 ("IMGT" numbering scheme); Honegger A and Plickthun A, "Yet another numbering scheme for immunoglobulin variable domains: an automatic modeling and analysis tool," J Mol Biol, 2001 Jun. 8; 309(3):657-70, ("Aho" numbering scheme); and Whitelegg N R and Rees A R, "WAM: an improved algorithm for modelling antibodies on the WEB," Protein Eng. 2000 Dec. 13(12):819-24 ("AbM" numbering scheme. In certain embodiments the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Unless defined otherwise, all technical and scientific terms used herein have the same meaning as commonly understood by one of ordinary skill in the art to which the methods and compositions described herein belong. Although any methods and materials similar or equivalent to those described herein can also be used in the practice or testing of the methods and compositions described herein, representative illustrative methods and materials are now described.

Tau Antibodies

Provided herein are antibodies that bind to tau. In some instances, the antibodies that bind to tau are monoclonal antibodies. In certain aspects, disclosed herein is an anti-tau antibody. In some instances, the anti-tau antibody specifically binds to mammalian tau. In some instances, the anti-tau antibody specifically binds to a human tau. In some instances, the anti-tau antibody specifically binds to an N-terminal portion of tau. In some instances, the anti-tau antibody specifically binds to an N-terminal portion of human tau. In some instances, the anti-tau antibody specifically binds to an portion of tau comprising protein domain P2. In some instances, the anti-tau antibody specifically binds to an portion of human tau comprising protein domain P2. In some instances, the anti-tau antibody specifically binds to an portion of tau comprising protein domain P1. In some instances, the anti-tau antibody specifically binds to an portion of human tau comprising protein domain P1. In some instances, the anti-tau antibody specifically binds to an portion of tau comprising protein domains P1 and P2. In some instances, the anti-tau antibody specifically binds to an portion of human tau comprising protein domains P1 and P2.

In some embodiments, the anti-tau antibody comprises i) a heavy chain comprising a variable heavy chain (VH) domain and ii) a light chain comprising a variable light chain (VL) domain. In some embodiments, VH domain comprises heavy chain CDR1 (HCDR1) sequence comprising a sequence selected from SEQ ID NOs: 1-5, heavy chain CDR2 (HCDR2) sequence comprising a sequence selected from SEQ ID NOs: 6-9, and heavy chain CDR3 (HCDR3) sequence comprising a sequence selected from SEQ ID NOs: 10-13. In some embodiments, VL domain comprises light chain CDR1 (LCDR1) sequence comprising a sequence selected from SEQ ID NOs: 14-19, light chain CDR2 (LCDR2) sequence comprising a sequence selected from SEQ ID NOs: 20-23, and light chain CDR3 (LCDR3) sequence comprising a sequence selected from SEQ ID NOs: 24-29.

In some embodiments, the VH region of the anti-tau antibody comprises HCDR1, HCDR2, and HCDR3 sequences selected from Table 1.

TABLE 1

| HCDR Amino Acid Sequences | |
|---|---|
| SEQ ID NO: | HCDR1 Sequence |
| 1 | SQKVG |
| 2 | SYAMI |
| 3 | NYKVG |
| 4 | NYAMS |
| 5 | THAMT |
| SEQ ID NO: | HCDR2 Sequence |
| 6 | IINNYGSTYYASWAKG |
| 7 | FISRSGITYYASWAKG |
| 8 | IINYYSQTYYASWAKG |
| 9 | VINPSGSAYYATWVNG |
| SEQ ID NO: | HCDR3 Sequence |
| 10 | DPDGSIVFDI |
| 11 | EFGAVGSDYYRDAFNL |
| 12 | EFGAVGSDYYRDALRL |
| 13 | DYITAGDYYMDAFDP |

In some embodiments, the VH region comprises HCDR1 sequence comprising SEQ ID NO: 1; HCDR2 sequence comprising SEQ ID NO: 6; and HCDR3 sequence comprising SEQ ID NO: 10. In some embodiments, the VH region comprises HCDR1 sequence comprising SEQ ID NO: 2; HCDR2 sequence comprising SEQ ID NO: 7; and HCDR3 sequence comprising SEQ ID NO: 11. In some embodiments, the VH region comprises HCDR1 sequence comprising SEQ ID NO: 3; HCDR2 sequence comprising SEQ ID NO: 8; and HCDR3 sequence comprising SEQ ID NO: 10. In some embodiments, the VH region comprises HCDR1 sequence comprising SEQ ID NO: 4; HCDR2 sequence comprising SEQ ID NO: 7; and HCDR3 sequence comprising SEQ ID NO: 12. In some embodiments, the VH region comprises HCDR1 sequence comprising SEQ ID NO: 5; HCDR2 sequence comprising SEQ ID NO: 9; and HCDR3 sequence comprising SEQ ID NO: 13.

In some embodiments, the VL region of the anti-tau antibody comprises LCDR1, LCDR2, and LCDR3 sequences selected from Table 2.

TABLE 2

| LCDR Amino Acid Sequences | |
|---|---|
| SEQ ID NO: | LCDR1 Sequence |
| 14 | QSSQSVVYNNRLS |
| 15 | QASESINSWLS |
| 16 | QASQNIYSNLA |
| 17 | QSSQSVYSNKRLA |
| 18 | QASQSIGSNLA |
| 19 | QASQSISNQLS |
| SEQ ID NO: | LCDR2 Sequence |
| 20 | GASTLAS |
| 21 | RASTLAS |
| 22 | GASNLAS |
| 23 | GASTLES |
| SEQ ID NO: | LCDR3 Sequence |
| 24 | LGSYDCSSGDCHA |
| 25 | QSYYEEDGIGYA |
| 26 | QGYDYSTAGAYP |
| 27 | AGGYDCSTGDCWT |
| 28 | QSYYEGSDIGYA |
| 29 | QQGYNRDNVDNL |

In some embodiments, the VL region comprises LCDR1 sequence comprising SEQ ID NO: 14; LCDR2 sequence comprising SEQ ID NO: 20; and LCDR3 sequence comprising SEQ ID NO: 24. In some embodiments, the VL region comprises LCDR1 sequence comprising SEQ ID NO: 15; LCDR2 sequence comprising SEQ ID NO: 21; and LCDR3 sequence comprising SEQ ID NO: 25. In some embodiments, the VL region comprises LCDR1 sequence comprising SEQ ID NO: 16; LCDR2 sequence comprising SEQ ID NO: 22; and LCDR3 sequence comprising SEQ ID NO: 26. In some embodiments, the VL region comprises LCDR1 sequence comprising SEQ ID NO: 17; LCDR2 sequence comprising SEQ ID NO: 20; and LCDR3 sequence comprising SEQ ID NO: 27. In some embodiments, the VL region comprises LCDR1 sequence comprising SEQ ID NO: 18; LCDR2 sequence comprising SEQ ID NO: 23; and LCDR3 sequence comprising SEQ ID NO: 28. In some embodiments, the VL region comprises LCDR1 sequence comprising SEQ ID NO: 19; LCDR2 sequence comprising SEQ ID NO: 21; and LCDR3 sequence comprising SEQ ID NO: 29.

In some embodiments, the anti-tau antibody is an antigen binding fragment thereof. In some embodiments, the anti-tau antibody is a chimeric antibody or antigen binding fragment thereof. In some embodiments, the anti-tau antibody comprises an IgG-scFv, nanobody, mini-antibody, minibody, scFv-CH3 KIH, Fab-scFv-Fc KIH, Fab-scFv, scFv-CH-CL-scFv, Fab', F(ab')2, F(ab')3, F(ab')2-scFv2, scFv, scFv-KIH, Fab-scFv-Fc, or intrabody. In some embodiments, the anti-tau antibody comprises a bispecific antibody. In some embodiments, the anti-tau antibody comprises a multispecific antibody. In some embodiments, the anti-tau antibody is an IgG1 antibody. In some embodiments, the anti-tau antibody is an IgG2 antibody. In some embodiments, the anti-tau antibody is an IgG4 antibody. In some embodiments, the anti-tau antibody comprises a light chain wherein the light chain is a kappa chain.

In some embodiments, the anti-tau antibody has a binding affinity to human tau of about 100 pM to about 3 nM. In some embodiments, the anti-tau antibody has a binding affinity to human tau of about 100 pM to 300 pM. In some embodiments, the anti-tau antibody has a binding affinity to human tau of about 100 pM to 500 pM. In some embodiments, the anti-tau antibody has a binding affinity to human tau of about 100 pM to 800 pM. In some embodiments, the anti-tau antibody has a binding affinity to human tau of about 300 pM to 600 pM. In some embodiments, the anti-tau antibody has a binding affinity to human tau of about 300 pM to 900 pM. In some embodiments, the anti-tau antibody has a binding affinity to human tau of about 400 pM to 1 nM. In some embodiments, the anti-tau antibody has a binding affinity to human tau of about 500 pM to 1.5 nM. In some embodiments, the anti-tau antibody has a binding affinity to human tau of about 500 pM to 2 nM. In some embodiments, the anti-tau antibody has a binding affinity to human tau of about 600 pM to 3 nM. In some embodiments, the anti-tau antibody has a binding affinity to human tau of about 100 pM to about 3 nM.

In some embodiments, the anti-tau antibody has a binding affinity to phosphorylated human tau of about 100 pM to 300 pM. In some embodiments, the anti-tau antibody has a binding affinity to phosphorylated human tau of about 100 pM to 500 pM. In some embodiments, the anti-tau antibody has a binding affinity to phosphorylated human tau of about 100 pM to 800 pM. In some embodiments, the anti-tau antibody has a binding affinity to phosphorylated human tau of about 300 pM to 600 pM. In some embodiments, the anti-tau antibody has a binding affinity to phosphorylated human tau of about 300 pM to 900 pM. In some embodiments, the anti-tau antibody has a binding affinity to phosphorylated human tau of about 400 pM to 1 nM. In some embodiments, the anti-tau antibody has a binding affinity to phosphorylated human tau of about 500 pM to 1.5 nM. In some embodiments, the anti-tau antibody has a binding affinity to phosphorylated human tau of about 500 pM to 2 nM. In some embodiments, the anti-tau antibody has a binding affinity to phosphorylated human tau of about 600 pM to 3 nM.

Described herein are antibodies comprising a sequence of any sequence set forth in Table 3 or Table 4.

TABLE 3

Variable Domain, Heavy Chain

| Name | SEQ ID NO: | Amino Acid Sequence |
| --- | --- | --- |
| Antibody 1 Variable Domain, Heavy Chain | 30 | METGLRWLLLVAVLKGVQCQSLEESGGRLVTPGTPLTLT CTVSGFSLSSQKVGWVRQAPGKGLEWIGIINNYGSTYYAS WAKGRFTISKTSTTVDLRITSLTAEDTATYFCARDPDGSIV FDIWGPGTLVTVSL |
| Antibody 2 and Antibody 3 Variable Domain, Heavy Chain | 31 | METGLRWLLLVAVLKGVQCQSVEESGGRLVTPGTPLTLT CTVSGFSLSSYAMIWVRQAPGKGLEWIGFISRSGITYYASW AKGRFTISKTSTTVDLKMTSLTTEDTATYFCAREFGAVGS DYYRDAFNLWGPGTLVTVSS |
| Antibody 4 Variable Domain, Heavy Chain | 32 | METGLRWLLLVAVLKGVQCQSLEESGGRLVTPGTPLTLT CTVSGFSLNNYKVGWVRQAPGKGLEWIGIINYYSQTYYA SWAKGRFTISKTSTTVDLKLTSPTTEDTATYFCARDPDGS IVFDIWGPGTLVTVSL |
| Antibody 5 Variable Domain, Heavy Chain | 33 | METGLRWLLLVAVLKGVQCQSVEESGGGLVTPGGTLTLT CTVSGFSLSNYAMSWVRQAPGKGLEWIGFISRSGITYYAS WAKGRFTISKTSTTVDLKITSPTTEDTAAYFCAREFGAVGS DYYRDALRLWGPGTLVTVSS |
| Antibody 6 Variable Domain, Heavy Chain | 34 | METGLRWLLLVAVLKGVQCQSLEESGGRLVTPGTPLTLT CTVSGIDLSTHAMTWVRQAPGKGLEWIGVINPSGSAYYA TWVNGRFTISKTSTTVDLKITSPTTGDTAKYFCARDYITA GDYYMDAFDPWGPGTLVTVSS |

TABLE 4

Variable Domain, Light Chain

| Name | SEQ ID NO: | Amino Acid Sequence |
|---|---|---|
| Antibody 1 Variable Domain, Light Chain | 35 | MDTRAPTQLLGLLLLWLPGATFAQVLTQTASPVSAAVG GTVTINCQSSQSVVYNNRLSWFQQKPGQPPKLLIYGAST LASGVPSRFKGSGSGTQFTLTISDVQCDDAATYYCLGSY DCSSGDCHAFGGGTEVVVK |
| Antibody 2 Variable Domain, Light Chain | 36 | MDMRAPTQLLGLLLLWLPGARCADIVMTQTPASVEAA VGGTVTINCQASESINSWLSWYQQKPGQPPNLLIYRAST LASGVPSRFSGGGSGTEYTLTISDLECADAVTYYCQSYY EEDGIGYAFGGGTEVVVE |
| Antibody 3 Variable Domain, Light Chain | 37 | MDMRAPTQLLGLLLLWLPGARCADIVMTQTPSSVSAA VGGTVTINCQASQNIYSNLAWYQQKPGQRPRLLIYGAS NLASGVPSRFKGSRSGTEFTLTISDLECADAATYYCQGY DYSTAGAYPFGGGTAVVVK |
| Antibody 4 Variable Domain, Light Chain | 38 | MDTRAPTQLLGLLLLWLPGATFAQVLTQTASPVSAAV GSTVTINCQSSQSVYSNKRLAWFQLKPGQPPKLLIYGAS TLASGVPSRFKGSGSGTQFTLTISDVQCDDAATYYCAGG YDCSTGDCWTFGGGTEVVVT |
| Antibody 5 Variable Domain, Light Chain | 39 | MDMRAPTQLLGLLLLWLPGARCADIVMTQTPSSVSAA VGGTVTIKCQASQSIGSNLAWYQQKPGQPPKLLIYGAS TLESGVPSRFKGSGSGTEYTLTISDLECADAATYYCQSY YEGSDIGYAFGGGTEVVVE |
| Antibody 6 Variable Domain, Light Chain | 40 | MDTRAPTQLLGLLLLWLPGARCADIVMTQTPASVSAA VGGTVTIKCQASQSISNQLSWYQQKSGQPPKLLIYRAS TLASGVPSRFKGSGSGTEFTLTISDLECADAATYYCQQ GYNRDNVDNLFGGGTEVVVK |

In some embodiments, the variable domain, heavy chain region (VH) comprises an amino acid sequence that has at least 70% sequence identity to the amino acid sequence according to any one of SEQ ID NOs: 30-34. In some embodiments, the VH comprises an amino acid sequence that has at least 80% sequence identity to the amino acid sequence according to any one of SEQ ID NOs: 30-34. In some embodiments, the VH comprises an amino acid sequence that has at least 85% sequence identity to the amino acid sequence according to any one of SEQ ID NOs: 30-34. In some embodiments, the VH comprises an amino acid sequence that has at least 90% sequence identity to the amino acid sequence according to any one of SEQ ID NOs: 30-34. In some embodiments, the VH comprises an amino acid sequence that has at least 91% sequence identity to the amino acid sequence according to any one of SEQ ID NOs: 30-34. In some embodiments, the VH comprises an amino acid sequence that has at least 92% sequence identity to the amino acid sequence according to any one of SEQ ID NOs: 30-34. In some embodiments, the VH comprises an amino acid sequence that has at least 93% sequence identity to the amino acid sequence according to any one of SEQ ID NOs: 30-34. In some embodiments, the VH comprises an amino acid sequence that has at least 94% sequence identity to the amino acid sequence according to any one of SEQ ID NOs: 30-34. In some embodiments, the VH comprises an amino acid sequence that has at least 95% sequence identity to the amino acid sequence according to any one of SEQ ID NOs: 30-34. In some embodiments, the VH comprises an amino acid sequence that has at least 96% sequence identity to the amino acid sequence according to any one of SEQ ID NOs: 30-34. In some embodiments, the VH comprises an amino acid sequence that has at least 97% sequence identity to the amino acid sequence according to any one of SEQ ID NOs: 30-34. In some embodiments, the VH comprises an amino acid sequence that has at least 98% sequence identity to the amino acid sequence according to any one of SEQ ID NOs: 30-34. In some embodiments, the VH comprises an amino acid sequence that has at least 99% sequence identity to the amino acid sequence according to any one of SEQ ID NOs: 30-34. In some embodiments, the VH comprises an amino acid sequence according to any one of SEQ ID NOs: 30-34.

In some embodiments, the VH comprises an amino acid sequence of at least 50 consecutive amino acid residues of any one of SEQ ID NOs: 30-34. In some embodiments, the VH comprises an amino acid sequence of at least 60 consecutive amino acid residues of any one of SEQ ID NOs: 30-34. In some embodiments, the VH comprises an amino acid sequence of at least 70 consecutive amino acid residues of any one of SEQ ID NOs: 30-34. In some embodiments, the VH comprises an amino acid sequence of at least 80 consecutive amino acid residues of any one of SEQ ID NOs: 30-34. In some embodiments, the VH comprises an amino acid sequence of at least 90 consecutive amino acid residues of any one of SEQ ID NOs: 30-34. In some embodiments, the VH comprises an amino acid sequence of at least 100 consecutive amino acid residues of any one of SEQ ID NOs: 30-34. In some embodiments, the VH comprises an amino acid sequence of at least 105 consecutive amino acid residues of any one of SEQ ID NOs: 30-34. In some embodiments, the VH comprises an amino acid sequence of at least 110 consecutive amino acid residues of any one of SEQ ID NOs: 30-34. In some embodiments, the VH comprises an amino acid sequence of at least 115 consecutive amino acid residues of any one of SEQ ID NOs: 30-34. In some embodiments, the VH comprises an amino acid sequence of at least 120 consecutive amino acid residues of any one of SEQ ID NOs: 30-34.

In some embodiments, the VH comprises an amino acid sequence of at least 50 consecutive amino acid residues of any one of SEQ ID NOs: 30-34, and has at least 80% sequence identity to the at least 50 consecutive amino acid residues of any one of SEQ ID NOs: 30-34. In some embodiments, the VH comprises an amino acid sequence of at least 60 consecutive amino acid residues of any one of SEQ ID NOs: 30-34, and has at least 80% sequence identity to the at least 60 consecutive amino acid residues of any one of SEQ ID NOs: 30-34. In some embodiments, the VH comprises an amino acid sequence of at least 70 consecutive amino acid residues of any one of SEQ ID NOs: 30-34, and has at least 80% sequence identity to the at least 70 consecutive amino acid residues of any one of SEQ ID NOs: 30-34. In some embodiments, the VH comprises an amino acid sequence of at least 80 consecutive amino acid residues of any one of SEQ ID NOs: 30-34, and has at least 80% sequence identity to the at least 80 consecutive amino acid residues of any one of SEQ ID NOs: 30-34. In some embodiments, the VH comprises an amino acid sequence of at least 90 consecutive amino acid residues of any one of SEQ ID NOs: 30-34, and has at least 80% sequence identity to the at least 90 consecutive amino acid residues of any one of SEQ ID NOs: 30-34. In some embodiments, the VH comprises an amino acid sequence of at least 100 consecutive amino acid residues of any one of SEQ ID NOs: 30-34, and has at least 80% sequence identity to the at least 100 consecutive amino acid residues of any one of SEQ ID NOs: 30-34. In some embodiments, the VH comprises an amino acid sequence of at least 105 consecutive amino acid residues of any one of SEQ ID NOs: 30-34, and has at least 80% sequence identity to the at least 105 consecutive amino acid residues of any one of SEQ ID NOs: 30-34. In some embodiments, the VH comprises an amino acid sequence of at least 110 consecutive amino acid residues of any one of SEQ ID NOs: 30-34, and has at least 80% sequence identity to the at least 110 consecutive amino acid residues of any one of SEQ ID NOs: 30-34. In some embodiments, the VH comprises an amino acid sequence of at least 115 consecutive amino acid residues of any one of SEQ ID NOs: 30-34, and has at least 80% sequence identity to the at least 115 consecutive amino acid residues of any one of SEQ ID NOs: 30-34. In some embodiments, the VH comprises an amino acid sequence of at least 120 consecutive amino acid residues of any one of SEQ ID NOs: 30-34, and has at least 80% sequence identity to the at least 120 consecutive amino acid residues of any one of SEQ ID NOs: 30-34.

In some embodiments, the VH comprises an amino acid sequence of at least 50 consecutive amino acid residues of any one of SEQ ID NOs: 30-34, and has at least 90% sequence identity to the at least 50 consecutive amino acid residues of any one of SEQ ID NOs: 30-34. In some embodiments, the VH comprises an amino acid sequence of at least 60 consecutive amino acid residues of any one of SEQ ID NOs: 30-34, and has at least 90% sequence identity to the at least 60 consecutive amino acid residues of any one of SEQ ID NOs: 30-34. In some embodiments, the VH comprises an amino acid sequence of at least 70 consecutive amino acid residues of any one of SEQ ID NOs: 30-34, and has at least 90% sequence identity to the at least 70 consecutive amino acid residues of any one of SEQ ID NOs: 30-34. In some embodiments, the VH comprises an amino acid sequence of at least 80 consecutive amino acid residues of any one of SEQ ID NOs: 30-34, and has at least 90% sequence identity to the at least 80 consecutive amino acid residues of any one of SEQ ID NOs: 30-34. In some embodiments, the VH comprises an amino acid sequence of at least 90 consecutive amino acid residues of any one of SEQ ID NOs: 30-34, and has at least 90% sequence identity to the at least 90 consecutive amino acid residues of any one of SEQ ID NOs: 30-34. In some embodiments, the VH comprises an amino acid sequence of at least 100 consecutive amino acid residues of any one of SEQ ID NOs: 30-34, and has at least 90% sequence identity to the at least 100 consecutive amino acid residues of any one of SEQ ID NOs: 30-34. In some embodiments, the VH comprises an amino acid sequence of at least 105 consecutive amino acid residues of any one of SEQ ID NOs: 30-34, and has at least 90% sequence identity to the at least 105 consecutive amino acid residues of any one of SEQ ID NOs: 30-34. In some embodiments, the VH comprises an amino acid sequence of at least 110 consecutive amino acid residues of any one of SEQ ID NOs: 30-34, and has at least 90% sequence identity to the at least 110 consecutive amino acid residues of any one of SEQ ID NOs: 30-34. In some embodiments, the VH comprises an amino acid sequence of at least 115 consecutive amino acid residues of any one of SEQ ID NOs: 30-34, and has at least 90% sequence identity to the at least 115 consecutive amino acid residues of any one of SEQ ID NOs: 30-34. In some embodiments, the VH comprises an amino acid sequence of at least 120 consecutive amino acid residues of any one of SEQ ID NOs: 30-34, and has at least 90% sequence identity to the at least 120 consecutive amino acid residues of any one of SEQ ID NOs: 30-34.

In some embodiments, the VH comprises an amino acid sequence of at least 50 consecutive amino acid residues of any one of SEQ ID NOs: 30-34, and has at least 95% sequence identity to the at least 50 consecutive amino acid residues of any one of SEQ ID NOs: 30-34. In some embodiments, the VH comprises an amino acid sequence of at least 60 consecutive amino acid residues of any one of SEQ ID NOs: 30-34, and has at least 95% sequence identity to the at least 60 consecutive amino acid residues of any one of SEQ ID NOs: 30-34. In some embodiments, the VH comprises an amino acid sequence of at least 70 consecutive amino acid residues of any one of SEQ ID NOs: 30-34, and has at least 95% sequence identity to the at least 70 consecutive amino acid residues of any one of SEQ ID NOs: 30-34. In some embodiments, the VH comprises an amino acid sequence of at least 80 consecutive amino acid residues of any one of SEQ ID NOs: 30-34, and has at least 95% sequence identity to the at least 80 consecutive amino acid residues of any one of SEQ ID NOs: 30-34. In some embodiments, the VH comprises an amino acid sequence of at least 90 consecutive amino acid residues of any one of SEQ ID NOs: 30-34, and has at least 95% sequence identity to the at least 90 consecutive amino acid residues of any one of SEQ ID NOs: 30-34. In some embodiments, the VH comprises an amino acid sequence of at least 100 consecutive amino acid residues of any one of SEQ ID NOs: 30-34, and has at least 95% sequence identity to the at least 100 consecutive amino acid residues of any one of SEQ ID NOs: 30-34. In some embodiments, the VH comprises an amino acid sequence of at least 105 consecutive amino acid residues of any one of SEQ ID NOs: 30-34, and has at least 95% sequence identity to the at least 105 consecutive amino acid residues of any one of SEQ ID NOs: 30-34. In some embodiments, the VH comprises an amino acid sequence of at least 110 consecutive amino acid residues of any one of SEQ ID NOs: 30-34, and has at least 95% sequence identity to the at least 110 consecutive amino acid residues of any one of SEQ ID NOs: 30-34. In some embodiments, the VH comprises an amino acid sequence of at least 115 consecutive amino acid residues of any one of SEQ ID NOs: 30-34, and has at least 95% sequence identity to the at least 115 consecutive amino acid residues of any one of SEQ ID NOs: 30-34. In some embodiments, the VH comprises an amino acid sequence of at least 120 consecutive amino acid residues of any one of SEQ ID NOs: 30-34, and has at least 95% sequence identity to the at least 120 consecutive amino acid residues of any one of SEQ ID NOs: 30-34.

In some embodiments, the VH comprises an amino acid sequence of at least 100 consecutive amino acid residues of any one of SEQ ID NOs: 30-34, and has at least 99% sequence identity to the at least 100 consecutive amino acid residues of any one of SEQ ID NOs: 30-34. In some embodiments, the VH comprises an amino acid sequence of at least 105 consecutive amino acid residues of any one of SEQ ID NOs: 30-34, and has at least 99% sequence identity to the at least 105 consecutive amino acid residues of any one of SEQ ID NOs: 30-34. In some embodiments, the VH comprises an amino acid sequence of at least 110 consecutive amino acid residues of any one of SEQ ID NOs: 30-34, and has at least 99% sequence identity to the at least 110 consecutive amino acid residues of any one of SEQ ID NOs: 30-34. In some embodiments, the VH comprises an amino acid sequence of at least 115 consecutive amino acid residues of any one of SEQ ID NOs: 30-34, and has at least 99% sequence identity to the at least 115 consecutive amino acid residues of any one of SEQ ID NOs: 30-34. In some embodiments, the VH comprises an amino acid sequence of at least 120 consecutive amino acid residues of any one of SEQ ID NOs: 30-34, and has at least 99% sequence identity to the at least 120 consecutive amino acid residues of any one of SEQ ID NOs: 30-34.

In some embodiments, the variable domain, light chain region (VL) comprises an amino acid sequence that has at least 70% sequence identity to the amino acid sequence according to any one of SEQ ID NOs: 35-40. In some embodiments, the VL comprises an amino acid sequence that has at least 80% sequence identity to the amino acid sequence according to any one of SEQ ID NOs: 35-40. In some embodiments, the VL comprises an amino acid sequence that has at least 85% sequence identity to the amino acid sequence according to any one of SEQ ID NOs: 35-40. In some embodiments, the VL comprises an amino acid sequence that has at least 90% sequence identity to the amino acid sequence according to any one of SEQ ID NOs: 35-40. In some embodiments, the VL comprises an amino acid sequence that has at least 91% sequence identity to the amino acid sequence according to any one of SEQ ID NOs: 35-40. In some embodiments, the VL comprises an amino acid sequence that has at least 92% sequence identity to the amino acid sequence according to any one of SEQ ID NOs: 35-40. In some embodiments, the VL comprises an amino acid sequence that has at least 93% sequence identity to the amino acid sequence according to any one of SEQ ID NOs: 35-40. In some embodiments, the VL comprises an amino acid sequence that has at least 94% sequence identity to the amino acid sequence according to any one of SEQ ID NOs: 35-40. In some embodiments, the VL comprises an amino acid sequence that has at least 95% sequence identity to the amino acid sequence according to any one of SEQ ID NOs: 35-40. In some embodiments, the VL comprises an amino acid sequence that has at least 96% sequence identity to the amino acid sequence according to any one of SEQ ID NOs: 35-40. In some embodiments, the VL comprises an amino acid sequence that has at least 97% sequence identity to the amino acid sequence according to any one of SEQ ID NOs: 35-40. In some embodiments, the VL comprises an amino acid sequence that has at least 98% sequence identity to the amino acid sequence according to any one of SEQ ID NOs: 35-40. In some embodiments, the VL comprises an amino acid sequence that has at least 99% sequence identity to the amino acid sequence according to any one of SEQ ID NOs: 35-40. In some embodiments, the VL comprises an amino acid sequence according to any one of SEQ ID NOs: 35-40.

In some embodiments, the VL comprises an amino acid sequence of at least 50 consecutive amino acid residues of any one of SEQ ID NOs: 35-40. In some embodiments, the VL comprises an amino acid sequence of at least 60 consecutive amino acid residues of any one of SEQ ID NOs: 35-40. In some embodiments, the VL comprises an amino acid sequence of at least 70 consecutive amino acid residues of any one of SEQ ID NOs: 35-40. In some embodiments, the VL comprises an amino acid sequence of at least 80 consecutive amino acid residues of any one of SEQ ID NOs: 35-40. In some embodiments, the VL comprises an amino acid sequence of at least 90 consecutive amino acid residues of any one of SEQ ID NOs: 35-40. In some embodiments, the VL comprises an amino acid sequence of at least 100 consecutive amino acid residues of any one of SEQ ID NOs: 35-40. In some embodiments, the VL comprises an amino acid sequence of at least 105 consecutive amino acid residues of any one of SEQ ID NOs: 35-40.

In some embodiments, the VL comprises an amino acid sequence of at least 50 consecutive amino acid residues of any one of SEQ ID NOs: 35-40, and has at least 80% sequence identity to the at least 50 consecutive amino acid residues of any one of SEQ ID NOs: 35-40. In some embodiments, the VL comprises an amino acid sequence of at least 60 consecutive amino acid residues of any one of SEQ ID NOs: 35-40, and has at least 80% sequence identity to the at least 60 consecutive amino acid residues of any one of SEQ ID NOs: 35-40. In some embodiments, the VL comprises an amino acid sequence of at least 70 consecutive amino acid residues of any one of SEQ ID NOs: 35-40, and has at least 80% sequence identity to the at least 70 consecutive amino acid residues of any one of SEQ ID NOs: 35-40. In some embodiments, the VL comprises an amino acid sequence of at least 80 consecutive amino acid residues of any one of SEQ ID NOs: 35-40, and has at least 80% sequence identity to the at least 80 consecutive amino acid residues of any one of SEQ ID NOs: 35-40. In some embodiments, the VL comprises an amino acid sequence of at least 90 consecutive amino acid residues of any one of SEQ ID NOs: 35-40, and has at least 80% sequence identity to the at least 90 consecutive amino acid residues of any one of SEQ ID NOs: 35-40. In some embodiments, the VL comprises an amino acid sequence of at least 100 consecutive amino acid residues of any one of SEQ ID NOs: 35-40, and has at least 80% sequence identity to the at least 100 consecutive amino acid residues of any one of SEQ ID NOs: 35-40. In some embodiments, the VL comprises an amino acid sequence of at least 105 consecutive amino acid residues of any one of SEQ ID NOs: 35-40, and has at least 80% sequence identity to the at least 105 consecutive amino acid residues of any one of SEQ ID NOs: 35-40.

In some embodiments, the VL comprises an amino acid sequence of at least 50 consecutive amino acid residues of any one of SEQ ID NOs: 35-40, and has at least 90% sequence identity to the at least 50 consecutive amino acid residues of any one of SEQ ID NOs: 35-40. In some embodiments, the VL comprises an amino acid sequence of at least 60 consecutive amino acid residues of any one of SEQ ID NOs: 35-40, and has at least 90% sequence identity to the at least 60 consecutive amino acid residues of any one of SEQ ID NOs: 35-40. In some embodiments, the VL comprises an amino acid sequence of at least 70 consecutive amino acid residues of any one of SEQ ID NOs: 35-40, and has at least 90% sequence identity to the at least 70 consecutive amino acid residues of any one of SEQ ID NOs: 35-40. In some embodiments, the VL comprises an amino acid sequence of at least 80 consecutive amino acid residues of any one of SEQ ID NOs: 35-40, and has at least 90% sequence identity to the at least 80 consecutive amino acid residues of any one of SEQ ID NOs: 35-40. In some embodiments, the VL comprises an amino acid sequence of at least 90 consecutive amino acid residues of any one of SEQ ID NOs: 35-40, and has at least 90% sequence identity to the at least 90 consecutive amino acid residues of any one of SEQ ID NOs: 35-40. In some embodiments, the VL comprises an amino acid sequence of at least 100 consecutive amino acid residues of any one of SEQ ID NOs: 35-40, and has at least 90% sequence identity to the at least 100 consecutive amino acid residues of any one of SEQ ID NOs: 35-40. In some embodiments, the VL comprises an amino acid sequence of at least 105 consecutive amino acid residues of any one of SEQ ID NOs: 35-40, and has at least 90% sequence identity to the at least 105 consecutive amino acid residues of any one of SEQ ID NOs: 35-40.

In some embodiments, the VL comprises an amino acid sequence of at least 50 consecutive amino acid residues of any one of SEQ ID NOs: 35-40, and has at least 95% sequence identity to the at least 50 consecutive amino acid residues of any one of SEQ ID NOs: 35-40. In some embodiments, the VL comprises an amino acid sequence of at least 60 consecutive amino acid residues of any one of SEQ ID NOs: 35-40, and has at least 95% sequence identity to the at least 60 consecutive amino acid residues of any one of SEQ ID NOs: 35-40. In some embodiments, the VL comprises an amino acid sequence of at least 70 consecutive amino acid residues of any one of SEQ ID NOs: 35-40, and has at least 95% sequence identity to the at least 70 consecutive amino acid residues of any one of SEQ ID NOs: 35-40. In some embodiments, the VL comprises an amino acid sequence of at least 80 consecutive amino acid residues of any one of SEQ ID NOs: 35-40, and has at least 95% sequence identity to the at least 80 consecutive amino acid residues of any one of SEQ ID NOs: 35-40. In some embodiments, the VL comprises an amino acid sequence of at least 90 consecutive amino acid residues of any one of SEQ ID NOs: 35-40, and has at least 95% sequence identity to the at least 90 consecutive amino acid residues of any one of SEQ ID NOs: 35-40. In some embodiments, the VL comprises an amino acid sequence of at least 100 consecutive amino acid residues of any one of SEQ ID NOs: 35-40, and has at least 95% sequence identity to the at least 100 consecutive amino acid residues of any one of SEQ ID NOs: 35-40. In some embodiments, the VL comprises an amino acid sequence of at least 105 consecutive amino acid residues of any one of SEQ ID NOs: 35-40, and has at least 95% sequence identity to the at least 105 consecutive amino acid residues of any one of SEQ ID NOs: 35-40. In some embodiments, the VL comprises an amino acid sequence of at least 100 consecutive amino acid residues of any one of SEQ ID NOs: 35-40, and has at least 99% sequence identity to the at least 100 consecutive amino acid residues of any one of SEQ ID NOs: 35-40. In some embodiments, the VL comprises an amino acid sequence of at least 105 consecutive amino acid residues of any one of SEQ ID NOs: 35-40, and has at least 99% sequence identity to the at least 105 consecutive amino acid residues of any one of SEQ ID NOs: 35-40.

In some embodiments, the VH comprises an amino acid sequence that has at least 70% sequence identity to the amino acid sequence according to any one of SEQ ID NOs: 30-34; and the VL comprises an amino acid sequence that has at least 70% sequence identity to the amino acid sequence according to any one of SEQ ID NOs: 35-40. In some embodiments, the VH comprises an amino acid sequence that has at least 80% sequence identity to the amino acid sequence according to any one of SEQ ID NOs: 30-34; and the VL comprises an amino acid sequence that has at least 80% sequence identity to the amino acid sequence according to any one of SEQ ID NOs: 35-40. In some embodiments, the VH comprises an amino acid sequence that has at least 85% sequence identity to the amino acid sequence according to any one of SEQ ID NOs: 30-34; and the VL comprises an amino acid sequence that has at least 85% sequence identity to the amino acid sequence according to any one of SEQ ID NOs: 35-40. In some embodiments, the VH comprises an amino acid sequence that has at least 90% sequence identity to the amino acid sequence according to any one of SEQ ID NOs: 30-34; and the VL comprises an amino acid sequence that has at least 90% sequence identity to the amino acid sequence according to any one of SEQ ID NOs: 35-40. In some embodiments, the VH comprises an amino acid sequence that has at least 91% sequence identity to the amino acid sequence according to any one of SEQ ID NOs: 30-34; and the VL comprises an amino acid sequence that has at least 91% sequence identity to the amino acid sequence according to any one of SEQ ID NOs: 35-40. In some embodiments, the VH comprises an amino acid sequence that has at least 92% sequence identity to the amino acid sequence according to any one of SEQ ID NOs: 30-34; and the VL comprises an amino acid sequence that has at least 92% sequence identity to the amino acid sequence according to any one of SEQ ID NOs: 35-40. In some embodiments, the VH comprises an amino acid sequence that has at least 93% sequence identity to the amino acid sequence according to any one of SEQ ID NOs: 30-34; and the VL comprises an amino acid sequence that has at least 93% sequence identity to the amino acid sequence according to any one of SEQ ID NOs: 35-40. In some embodiments, the VH comprises an amino acid sequence that has at least 94% sequence identity to the amino acid sequence according to any one of SEQ ID NOs: 30-34; and the VL comprises an amino acid sequence that has at least 94% sequence identity to the amino acid sequence according to any one of SEQ ID NOs: 35-40. In some embodiments, the VH comprises an amino acid sequence that has at least 95% sequence identity to the amino acid sequence according to any one of SEQ ID NOs: 30-34; and the VL comprises an amino acid sequence that has at least 95% sequence identity to the amino acid sequence according to any one of SEQ ID NOs: 35-40. In some embodiments, the VH comprises an amino acid sequence that has at least 96% sequence identity to the amino acid sequence according to any one of SEQ ID NOs: 30-34; and the VL comprises an amino acid sequence that has at least 96% sequence identity to the amino acid sequence according to any one of SEQ ID NOs: 35-40. In some embodiments, the VH comprises an amino acid sequence that has at least 97% sequence identity to the amino acid sequence according to any one of SEQ ID NOs: 30-34; and the VL comprises an amino acid sequence that has at least 97% sequence identity to the amino acid sequence according to any one of SEQ ID NOs: 35-40. In some embodiments, the VH comprises an amino acid sequence that has at least 98% sequence identity to the amino acid sequence according to any one of SEQ ID NOs: 30-34; and the VL comprises an amino acid sequence that has at least 98% sequence identity to the amino acid sequence according to any one of SEQ ID NOs: 35-40. In some embodiments, the VH comprises an amino acid sequence that has at least 99% sequence identity to the amino acid sequence according to any one of SEQ ID NOs: 30-34; and the VL comprises an amino acid sequence that has at least 99% sequence identity to the amino acid sequence according to any one of SEQ ID NOs: 35-40.

In some embodiments, the VH comprises an amino acid sequence that has at least 70% sequence identity to the amino acid sequence according to SEQ ID NO: 30; and the VL comprises an amino acid sequence that has at least 70% sequence identity to the amino acid sequence according to SEQ ID NO: 35. In some embodiments, the VH comprises an amino acid sequence that has at least 80% sequence identity to the amino acid sequence according to SEQ ID NO: 30; and the VL comprises an amino acid sequence that has at least 80% sequence identity to the amino acid sequence according to SEQ ID NO: 35. In some embodiments, the VH comprises an amino acid sequence that has at least 85% sequence identity to the amino acid sequence according to SEQ ID NO: 30; and the VL comprises an amino acid sequence that has at least 85% sequence identity to the amino acid sequence according to SEQ ID NO: 35. In some embodiments, the VH comprises an amino acid sequence that has at least 90% sequence identity to the amino acid sequence according to SEQ ID NO: 30; and the VL comprises an amino acid sequence that has at least 90% sequence identity to the amino acid sequence according to SEQ ID NO: 35. In some embodiments, the VH comprises an amino acid sequence that has at least 91% sequence identity to the amino acid sequence according to SEQ ID NO: 30; and the VL comprises an amino acid sequence that has at least 91% sequence identity to the amino acid sequence according to SEQ ID NO: 35. In some embodiments, the VH comprises an amino acid sequence that has at least 92% sequence identity to the amino acid sequence according to SEQ ID NO: 30; and the VL comprises an amino acid sequence that has at least 92% sequence identity to the amino acid sequence according to SEQ ID NO: 35. In some embodiments, the VH comprises an amino acid sequence that has at least 93% sequence identity to the amino acid sequence according to SEQ ID NO: 30; and the VL comprises an amino acid sequence that has at least 93% sequence identity to the amino acid sequence according to SEQ ID NO: 35. In some embodiments, the VH comprises an amino acid sequence that has at least 94% sequence identity to the amino acid sequence according to SEQ ID NO: 30; and the VL comprises an amino acid sequence that has at least 94% sequence identity to the amino acid sequence according to SEQ ID NO: 35. In some embodiments, the VH comprises an amino acid sequence that has at least 95% sequence identity to the amino acid sequence according to SEQ ID NO: 30; and the VL comprises an amino acid sequence that has at least 95% sequence identity to the amino acid sequence according to SEQ ID NO: 35. In some embodiments, the VH comprises an amino acid sequence that has at least 96% sequence identity to the amino acid sequence according to SEQ ID NO: 30; and the VL comprises an amino acid sequence that has at least 96% sequence identity to the amino acid sequence according to SEQ ID NO: 35. In some embodiments, the VH comprises an amino acid sequence that has at least 97% sequence identity to the amino acid sequence according to SEQ ID NO: 30; and the VL comprises an amino acid sequence that has at least 97% sequence identity to the amino acid sequence according to SEQ ID NO: 35. In some embodiments, the VH comprises an amino acid sequence that has at least 98% sequence identity to the amino acid sequence according to SEQ ID NO: 30; and the VL comprises an amino acid sequence that has at least 98% sequence identity to the amino acid sequence according to SEQ ID NO: 35. In some embodiments, the VH comprises an amino acid sequence that has at least 99% sequence identity to the amino acid sequence according to SEQ ID NO: 30; and the VL comprises an amino acid sequence that has at least 99% sequence identity to the amino acid sequence according to SEQ ID NO: 35.

In some embodiments, the VH comprises an amino acid sequence that has at least 70% sequence identity to the amino acid sequence according to SEQ ID NO: 31; and the VL comprises an amino acid sequence that has at least 70% sequence identity to the amino acid sequence according to SEQ ID NO: 36. In some embodiments, the VH comprises an amino acid sequence that has at least 80% sequence identity to the amino acid sequence according to SEQ ID NO: 31; and the VL comprises an amino acid sequence that has at least 80% sequence identity to the amino acid sequence according to SEQ ID NO: 36. In some embodiments, the VH comprises an amino acid sequence that has at least 85% sequence identity to the amino acid sequence according to SEQ ID NO: 31; and the VL comprises an amino acid sequence that has at least 85% sequence identity to the amino acid sequence according to SEQ ID NO: 36. In some embodiments, the VH comprises an amino acid sequence that has at least 90% sequence identity to the amino acid sequence according to SEQ ID NO: 31; and the VL comprises an amino acid sequence that has at least 90% sequence identity to the amino acid sequence according to SEQ ID NO: 36. In some embodiments, the VH comprises an amino acid sequence that has at least 91% sequence identity to the amino acid sequence according to SEQ ID NO: 31; and the VL comprises an amino acid sequence that has at least 91% sequence identity to the amino acid sequence according to SEQ ID NO: 36. In some embodiments, the VH comprises an amino acid sequence that has at least 92% sequence identity to the amino acid sequence according to SEQ ID NO: 31; and the VL comprises an amino acid sequence that has at least 92% sequence identity to the amino acid sequence according to SEQ ID NO: 36. In some embodiments, the VH comprises an amino acid sequence that has at least 93% sequence identity to the amino acid sequence according to SEQ ID NO: 31; and the VL comprises an amino acid sequence that has at least 93% sequence identity to the amino acid sequence according to SEQ ID NO: 36. In some embodiments, the VH comprises an amino acid sequence that has at least 94% sequence identity to the amino acid sequence according to SEQ ID NO: 31; and the VL comprises an amino acid sequence that has at least 94% sequence identity to the amino acid sequence according to SEQ ID NO: 36. In some embodiments, the VH comprises an amino acid sequence that has at least 95% sequence identity to the amino acid sequence according to SEQ ID NO: 31; and the VL comprises an amino acid sequence that has at least 95% sequence identity to the amino acid sequence according to SEQ ID NO: 36. In some embodiments, the VH comprises an amino acid sequence that has at least 96% sequence identity to the amino acid sequence according to SEQ ID NO: 31; and the VL comprises an amino acid sequence that has at least 96% sequence identity to the amino acid sequence according to SEQ ID NO: 36. In some embodiments, the VH comprises an amino acid sequence that has at least 97% sequence identity to the amino acid sequence according to SEQ ID NO: 31; and the VL comprises an amino acid sequence that has at least 97% sequence identity to the amino acid sequence according to SEQ ID NO: 36. In some embodiments, the VH comprises an amino acid sequence that has at least 98% sequence identity to the amino acid sequence according to SEQ ID NO: 31; and the VL comprises an amino acid sequence that has at least 98% sequence identity to the amino acid sequence according to SEQ ID NO: 36. In some embodiments, the VH comprises an amino acid sequence that has at least 99% sequence identity to the amino acid sequence according to SEQ ID NO: 31; and the VL comprises an amino acid sequence that has at least 99% sequence identity to the amino acid sequence according to SEQ ID NO: 36.

In some embodiments, the VH comprises an amino acid sequence that has at least 70% sequence identity to the amino acid sequence according to SEQ ID NO: 31; and the VL comprises an amino acid sequence that has at least 70% sequence identity to the amino acid sequence according to SEQ ID NO: 37. In some embodiments, the VH comprises an amino acid sequence that has at least 80% sequence identity to the amino acid sequence according to SEQ ID NO: 31; and the VL comprises an amino acid sequence that has at least 80% sequence identity to the amino acid sequence according to SEQ ID NO: 37. In some embodiments, the VH comprises an amino acid sequence that has at least 85% sequence identity to the amino acid sequence according to SEQ ID NO: 31; and the VL comprises an amino acid sequence that has at least 85% sequence identity to the amino acid sequence according to SEQ ID NO: 37. In some embodiments, the VH comprises an amino acid sequence that has at least 90% sequence identity to the amino acid sequence according to SEQ ID NO: 31; and the VL comprises an amino acid sequence that has at least 90% sequence identity to the amino acid sequence according to SEQ ID NO: 37. In some embodiments, the VH comprises an amino acid sequence that has at least 91% sequence identity to the amino acid sequence according to SEQ ID NO: 31; and the VL comprises an amino acid sequence that has at least 91% sequence identity to the amino acid sequence according to SEQ ID NO: 37. In some embodiments, the VH comprises an amino acid sequence that has at least 92% sequence identity to the amino acid sequence according to SEQ ID NO: 31; and the VL comprises an amino acid sequence that has at least 92% sequence identity to the amino acid sequence according to SEQ ID NO: 37. In some embodiments, the VH comprises an amino acid sequence that has at least 93% sequence identity to the amino acid sequence according to SEQ ID NO: 31; and the VL comprises an amino acid sequence that has at least 93% sequence identity to the amino acid sequence according to SEQ ID NO: 37. In some embodiments, the VH comprises an amino acid sequence that has at least 94% sequence identity to the amino acid sequence according to SEQ ID NO: 31; and the VL comprises an amino acid sequence that has at least 94% sequence identity to the amino acid sequence according to SEQ ID NO: 37. In some embodiments, the VH comprises an amino acid sequence that has at least 95% sequence identity to the amino acid sequence according to SEQ ID NO: 31; and the VL comprises an amino acid sequence that has at least 95% sequence identity to the amino acid sequence according to SEQ ID NO: 37. In some embodiments, the VH comprises an amino acid sequence that has at least 96% sequence identity to the amino acid sequence according to SEQ ID NO: 31; and the VL comprises an amino acid sequence that has at least 96% sequence identity to the amino acid sequence according to SEQ ID NO: 37. In some embodiments, the VH comprises an amino acid sequence that has at least 97% sequence identity to the amino acid sequence according to SEQ ID NO: 31; and the VL comprises an amino acid sequence that has at least 97% sequence identity to the amino acid sequence according to SEQ ID NO: 37. In some embodiments, the VH comprises an amino acid sequence that has at least 98% sequence identity to the amino acid sequence according to SEQ ID NO: 31; and the VL comprises an amino acid sequence that has at least 98% sequence identity to the amino acid sequence according to SEQ ID NO: 37. In some embodiments, the VH comprises an amino acid sequence that has at least 99% sequence identity to the amino acid sequence according to SEQ ID NO: 31; and the VL comprises an amino acid sequence that has at least 99% sequence identity to the amino acid sequence according to SEQ ID NO: 37.

In some embodiments, the VH comprises an amino acid sequence that has at least 70% sequence identity to the amino acid sequence according to SEQ ID NO: 32; and the VL comprises an amino acid sequence that has at least 70% sequence identity to the amino acid sequence according to SEQ ID NO: 38. In some embodiments, the VH comprises an amino acid sequence that has at least 80% sequence identity to the amino acid sequence according to SEQ ID NO: 32; and the VL comprises an amino acid sequence that has at least 80% sequence identity to the amino acid sequence according to SEQ ID NO: 38. In some embodiments, the VH comprises an amino acid sequence that has at least 85% sequence identity to the amino acid sequence according to SEQ ID NO: 32; and the VL comprises an amino acid sequence that has at least 85% sequence identity to the amino acid sequence according to SEQ ID NO: 38. In some embodiments, the VH comprises an amino acid sequence that has at least 90% sequence identity to the amino acid sequence according to SEQ ID NO: 32; and the VL comprises an amino acid sequence that has at least 90% sequence identity to the amino acid sequence according to SEQ ID NO: 38. In some embodiments, the VH comprises an amino acid sequence that has at least 91% sequence identity to the amino acid sequence according to SEQ ID NO: 32; and the VL comprises an amino acid sequence that has at least 91% sequence identity to the amino acid sequence according to SEQ ID NO: 38. In some embodiments, the VH comprises an amino acid sequence that has at least 92% sequence identity to the amino acid sequence according to SEQ ID NO: 32; and the VL comprises an amino acid sequence that has at least 92% sequence identity to the amino acid sequence according to SEQ ID NO: 38. In some embodiments, the VH comprises an amino acid sequence that has at least 93% sequence identity to the amino acid sequence according to SEQ ID NO: 32; and the VL comprises an amino acid sequence that has at least 93% sequence identity to the amino acid sequence according to SEQ ID NO: 38. In some embodiments, the VH comprises an amino acid sequence that has at least 94% sequence identity to the amino acid sequence according to SEQ ID NO: 32; and the VL comprises an amino acid sequence that has at least 94% sequence identity to the amino acid sequence according to SEQ ID NO: 38. In some embodiments, the VH comprises an amino acid sequence that has at least 95% sequence identity to the amino acid sequence according to SEQ ID NO: 32; and the VL comprises an amino acid sequence that has at least 95% sequence identity to the amino acid sequence according to SEQ ID NO: 38. In some embodiments, the VH comprises an amino acid sequence that has at least 96% sequence identity to the amino acid sequence according to SEQ ID NO: 32; and the VL comprises an amino acid sequence that has at least 96% sequence identity to the amino acid sequence according to SEQ ID NO: 38. In some embodiments, the VH comprises an amino acid sequence that has at least 97% sequence identity to the amino acid sequence according to SEQ ID NO: 32; and the VL comprises an amino acid sequence that has at least 97% sequence identity to the amino acid sequence according to SEQ ID NO: 38. In some embodiments, the VH comprises an amino acid sequence that has at least 98% sequence identity to the amino acid sequence according to SEQ ID NO: 32; and the VL comprises an amino acid sequence that has at least 98% sequence identity to the amino acid sequence according to SEQ ID NO: 38. In some embodiments, the VH comprises an amino acid sequence that has at least 99% sequence identity to the amino acid sequence according to SEQ ID NO: 32; and the VL comprises an amino acid sequence that has at least 99% sequence identity to the amino acid sequence according to SEQ ID NO: 38.

In some embodiments, the VH comprises an amino acid sequence that has at least 70% sequence identity to the amino acid sequence according to SEQ ID NO: 33; and the VL comprises an amino acid sequence that has at least 70% sequence identity to the amino acid sequence according to SEQ ID NO: 39. In some embodiments, the VH comprises an amino acid sequence that has at least 80% sequence identity to the amino acid sequence according to SEQ ID NO: 33; and the VL comprises an amino acid sequence that has at least 80% sequence identity to the amino acid sequence according to SEQ ID NO: 39. In some embodiments, the VH comprises an amino acid sequence that has at least 85% sequence identity to the amino acid sequence according to SEQ ID NO: 33; and the VL comprises an amino acid sequence that has at least 85% sequence identity to the amino acid sequence according to SEQ ID NO: 39. In some embodiments, the VH comprises an amino acid sequence that has at least 90% sequence identity to the amino acid sequence according to SEQ ID NO: 33; and the VL comprises an amino acid sequence that has at least 90% sequence identity to the amino acid sequence according to SEQ ID NO: 39. In some embodiments, the VH comprises an amino acid sequence that has at least 91% sequence identity to the amino acid sequence according to SEQ ID NO: 33; and the VL comprises an amino acid sequence that has at least 91% sequence identity to the amino acid sequence according to SEQ ID NO: 39. In some embodiments, the VH comprises an amino acid sequence that has at least 92% sequence identity to the amino acid sequence according to SEQ ID NO: 33; and the VL comprises an amino acid sequence that has at least 92% sequence identity to the amino acid sequence according to SEQ ID NO: 39. In some embodiments, the VH comprises an amino acid sequence that has at least 93% sequence identity to the amino acid sequence according to SEQ ID NO: 33; and the VL comprises an amino acid sequence that has at least 93% sequence identity to the amino acid sequence according to SEQ ID NO: 39. In some embodiments, the VH comprises an amino acid sequence that has at least 94% sequence identity to the amino acid sequence according to SEQ ID NO: 33; and the VL comprises an amino acid sequence that has at least 94% sequence identity to the amino acid sequence according to SEQ ID NO: 39. In some embodiments, the VH comprises an amino acid sequence that has at least 95% sequence identity to the amino acid sequence according to SEQ ID NO: 33; and the VL comprises an amino acid sequence that has at least 95% sequence identity to the amino acid sequence according to SEQ ID NO: 39. In some embodiments, the VH comprises an amino acid sequence that has at least 96% sequence identity to the amino acid sequence according to SEQ ID NO: 33; and the VL comprises an amino acid sequence that has at least 96% sequence identity to the amino acid sequence according to SEQ ID NO: 39. In some embodiments, the VH comprises an amino acid sequence that has at least 97% sequence identity to the amino acid sequence according to SEQ ID NO: 33; and the VL comprises an amino acid sequence that has at least 97% sequence identity to the amino acid sequence according to SEQ ID NO: 39. In some embodiments, the VH comprises an amino acid sequence that has at least 98% sequence identity to the amino acid sequence according to SEQ ID NO: 33; and the VL comprises an amino acid sequence that has at least 98% sequence identity to the amino acid sequence according to SEQ ID NO: 39. In some embodiments, the VH comprises an amino acid sequence that has at least 99% sequence identity to the amino acid sequence according to SEQ ID NO: 33; and the VL comprises an amino acid sequence that has at least 99% sequence identity to the amino acid sequence according to SEQ ID NO: 39.

In some embodiments, the VH comprises an amino acid sequence that has at least 70% sequence identity to the amino acid sequence according to SEQ ID NO: 34; and the VL comprises an amino acid sequence that has at least 70% sequence identity to the amino acid sequence according to SEQ ID NO: 40. In some embodiments, the VH comprises an amino acid sequence that has at least 80% sequence identity to the amino acid sequence according to SEQ ID NO: 34; and the VL comprises an amino acid sequence that has at least 80% sequence identity to the amino acid sequence according to SEQ ID NO: 40. In some embodiments, the VH comprises an amino acid sequence that has at least 85% sequence identity to the amino acid sequence according to SEQ ID NO: 34; and the VL comprises an amino acid sequence that has at least 85% sequence identity to the amino acid sequence according to SEQ ID NO: 40. In some embodiments, the VH comprises an amino acid sequence that has at least 90% sequence identity to the amino acid sequence according to SEQ ID NO: 34; and the VL comprises an amino acid sequence that has at least 90% sequence identity to the amino acid sequence according to SEQ ID NO: 40. In some embodiments, the VH comprises an amino acid sequence that has at least 91% sequence identity to the amino acid sequence according to SEQ ID NO: 34; and the VL comprises an amino acid sequence that has at least 91% sequence identity to the amino acid sequence according to SEQ ID NO: 40. In some embodiments, the VH comprises an amino acid sequence that has at least 92% sequence identity to the amino acid sequence according to SEQ ID NO: 34; and the VL comprises an amino acid sequence that has at least 92% sequence identity to the amino acid sequence according to SEQ ID NO: 40. In some embodiments, the VH comprises an amino acid sequence that has at least 93% sequence identity to the amino acid sequence according to SEQ ID NO: 34; and the VL comprises an amino acid sequence that has at least 93% sequence identity to the amino acid sequence according to SEQ ID NO: 40. In some embodiments, the VH comprises an amino acid sequence that has at least 94% sequence identity to the amino acid sequence according to SEQ ID NO: 34; and the VL comprises an amino acid sequence that has at least 94% sequence identity to the amino acid sequence according to SEQ ID NO: 40. In some embodiments, the VH comprises an amino acid sequence that has at least 95% sequence identity to the amino acid sequence according to SEQ ID NO: 34; and the VL comprises an amino acid sequence that has at least 95% sequence identity to the amino acid sequence according to SEQ ID NO: 40. In some embodiments, the VH comprises an amino acid sequence that has at least 96% sequence identity to the amino acid sequence according to SEQ ID NO: 34; and the VL comprises an amino acid sequence that has at least 96% sequence identity to the amino acid sequence according to SEQ ID NO: 40. In some embodiments, the VH comprises an amino acid sequence that has at least 97% sequence identity to the amino acid sequence according to SEQ ID NO: 34; and the VL comprises an amino acid sequence that has at least 97% sequence identity to the amino acid sequence according to SEQ ID NO: 40. In some embodiments, the VH comprises an amino acid sequence that has at least 98% sequence identity to the amino acid sequence according to SEQ ID NO: 34; and the VL comprises an amino acid sequence that has at least 98% sequence identity to the amino acid sequence according to SEQ ID NO: 40. In some embodiments, the VH comprises an amino acid sequence that has at least 99% sequence identity to the amino acid sequence according to SEQ ID NO: 34; and the VL comprises an amino acid sequence that has at least 99% sequence identity to the amino acid sequence according to SEQ ID NO: 40.

Described herein, in some embodiments, are antibodies or antibody fragments comprising a heavy chain sequence at least about 90% identical to a sequence as set forth in any one of SEQ ID NOs: 41, 43, 46, 48, and 50. In some instances, the antibodies or antibody fragments comprise a heavy chain sequence at least or about 70%, 80%, 85%, 90%, 91%, 92%, 93%, 94%, 95%, 96%, 97%, 98%, 99%, or 100% sequence identity to any one of SEQ ID NOs: 41, 43, 46, 48, and 50.

Described herein, in some embodiments, are antibodies or antibody fragments comprising a light chain sequence at least about 90% identical to a sequence as set forth in any one of SEQ ID NOs: 42, 44, 45, 47, 49, and 51. In some instances, the antibodies or antibody fragments comprise a light chain sequence at least or about 70%, 80%, 85%, 90%, 91%, 92%, 93%, 94%, 95%, 96%, 97%, 98%, 99%, or 100% sequence identity to any one of SEQ ID NOs: 42, 44, 45, 47, 49, and 51.

Described herein, in some embodiments, are antibodies or antibody fragments comprising a heavy chain sequence at least about 90% identical to a sequence as set forth in any one of SEQ ID NOs: 41, 43, 46, 48, and 50 and a light chain sequence at least about 90% identical to a sequence as set forth in any one of SEQ ID NOs: 42, 44, 45, 47, 49, and 51. In some instances, the antibodies or antibody fragments comprise a heavy chain sequence at least or about 70%, 80%, 85%, 90%, 91%, 92%, 93%, 94%, 95%, 96%, 97%, 98%, 99%, or 100% sequence identity to any one of SEQ ID NOs: 41, 43, 46, 48, and 50 and a light chain sequence at least or about 70%, 80%, 85%, 90%, 91%, 92%, 93%, 94%, 95%, 96%, 97%, 98%, 99%, or 100% sequence identity to any one of SEQ ID NOs: 42, 44, 45, 47, 49, and 51.

TABLE 5

Heavy Chain and Light Chain Sequences

| Name | SEQ ID NO: | Amino Acid Sequence |
|---|---|---|
| Antibody 1 Heavy Chain | 41 | METGLRWLLLLVAVLKGVQCQSLEESGGRLVTPGTPLTLTCTVSG FSLSSQKVGWVRQAPGKGLEWIGIINNYGSTYYASWAKGRFTIS KTSTTVDLRITSLTAEDTATYFCARDPDGSIVFDIWGPGTLVTVSL GQPKAPSVFPLAPCCGDTPSSTVTLGCLVKGYLPEPVTVTWNSG TLTNGVRTFPSVRQSSGLYSLSSVVSVTSSSQPVTCNVAHPATNT KVDKTVAPSTCSKPTCPPPELLGRSSVFIFPPKPKDTLMISRTPEV TCVVVDVSQDDPEVQFTWYINNEQVRTARPPLREQQFNSTIRVV STLPIAHQDWLRGKEFKCKVHNKALPAPIEKTISKARGQPLEPKV YTMGPPREELSSRSVSLTCMINGFYPSDISVEWEKNGKAEDNYK TTPAVLDSDGSYFLYSKLSVPTSEWQRGDVFTCSVMHEALHNH YTQKSISRSPGK |
| Antibody 1 Light Chain | 42 | MDTRAPTQLLGLLLLWLPGATFAQVLTQTASPVSAAVGGTVTI NCQSSQSVVYNNRLSWFQQKPGQPPKLLIYGASTLASGVPSRF KGSGSGTQFTLTISDVQCDDAATYYCLGSYDCSSGDCHAFGGG TEVVVKGDPVAPTVLIFPPAADQVATGTVTIVCVANKYFPDVT VTWEVDGTTQTTGIENSKTPQNSADCTYNLSSTLTLTSTQYNSH KEYTCKVTQGTTSVVQSFNRGDC |
| Antibody 2 and Antibody 3 Heavy Chain | 43 | METGLRWLLLLVAVLKGVQCQSVEESGGRLVTPGTPLTLTCTVSG FSLSSYAMIWVRQAPGKGLEWIGFISRSGITYYASWAKGRFTISK TSTTVDLKMTSLTTEDTATYFCAREFGAVGSDYYRDAFNLWGP GTLVTVSSGQPKAPSVFPLAPCCGDTPSSTVTLGCLVKGYLPEPV TVTWNSGTLTNGVRTFPSVRQSSGLYSLSSVVSVTSSSQPVTCNV AHPATNTKVDKTVAPSTCSKPTCPPPELLGRSSVFIFPPKPKDTL MISRTPEVTCVVVDVSQDDPEVQFTWYINNEQVRTARPPLREQQ FNSTIRVVSTLPIAHQDWLRGKEFKCKVHNKALPAPIEKTISKAR GQPLEPKVYTMGPPREELSSRSVSLTCMINGFYPSDISVEWEKNG KAEDNYKTTPAVLDSDGSYFLYSKLSVPTSEWQRGDVFTCSVM HEALHNHYTQKSISRSPGK |

TABLE 5-continued

Heavy Chain and Light Chain Sequences

| Name | SEQ ID NO: | Amino Acid Sequence |
|---|---|---|
| Antibody 2 Light Chain | 44 | MDMRAPTQLLGLLLLWLPGARCADIVMTQTPASVEAAVGGTV TINCQASESINSWLSWYQQKPGQPPNLLIYRASTLASGVPSRFSG GGSGTEYTLTISDLECADAVTYYCQSYYEEDGIGYAFGGGTEVV VEGDPVAPTVLIFPPAADQVATGTVTIVCVANKYFPDVTVTWE VDGTTQTTGIENSKTPQNSADCTYNLSSTLTLTSTQYNSHKEYT CKVTQGTTSVVQSFNRGDC |
| Antibody 3 Light Chain | 45 | MDMRAPTQLLGLLLLWLPGARCADIVMTQTPSSVSAAVGGTVT INCQASQNIYSNLAWYQQKPGQRPRLLIYGASNLASGVPSRFKG SRSGTEFTLTISDLECADAATYYCQGYDYSTAGAYPFGGGTAVV VKGDPVAPTVLIFPPAADQVATGTVTIVCVANKYFPDVTVTWEV DGTTQTTGIENSKTPQNSADCTYNLSSTLTLTSTQYNSHKEYTCK VTQGTTSVVQSFNRGDC |
| Antibody 4 Heavy Chain | 46 | METGLRWLLLVAVLKGVQCQSLEESGGRLVTPGTPLTLTCTVS GFSLNNYKVGWVRQAPGKGLEWIGIINYYSQTYYASWAKGRF TISKTSTTVDLKLTSPTTEDTATYFCARDPDGSIVFDIWGPGTLV TVSLGQPKAPSVFPLAPCCGDTPSSTVTLGCLVKGYLPEPVTVT WNSGTLTNGVRTFPSVRQSSGLYSLSSVVSVTSSSQPVTCNVAH PATNTKVDKTVVPSTCSKPTCPPPELLGRSSVFIFPPKPKDTLMI SRTPEVTCVVVDVSQDDPEVQFTWYINNEQVRTARPPLREQQF NSTIRVVSTLPIAHQDWLRGKEFKCKVHNKALPAPIEKTISKAR GQPLEPKVYTMGPPREELSSRSVSLTCMINGFYPSDISVEWEKN GKAEDNYKTTPAVLDSDGSYFLYSKLSVPTSEWQRGDVFTCSV MHEALHNHYTQKSISRSPGK |
| Antibody 4 Light Chain | 47 | MDTRAPTQLLGLLLLWLPGATFAQVLTQTASPVSAAVGSTVTIN CQSSQSVYSNKRLAWFQLKPGQPPKLLIYGASTLASGVPSRFKG SGSGTQFTLTISDVQCDDAATYYCAGGYDCSTGDCWTFGGGTE VVVTGDPVAPTVLIFPPAADQVATGTVTIVCVANKYFPDVTVT WEVDGTTQTTGIENSKTPQNSADCTYNLSSTLTLTSTQYNSHKE YTCKVTQGTTSVVQSFNRGDC |
| Antibody 5 Heavy Chain | 48 | METGLRWLLLVAVLKGVQCQSVEESGGGLVTPGGTLTLTCTVS GFSLSNYAMSWVRQAPGKGLEWIGFISRSGITYYASWAKGRFT ISKTSTTVDLKITSPTTEDTAAYFCAREFGAVGSDYYRDALRLW GPGTLVTVSSGQPKAPSVFPLAPCCGDTPSSTVTLGCLVKGYLP EPVTVTWNSGTLTNGVRTFPSVRQSSGLYSLSSVVSVTSSSQPVT CNVAHPATNTKVDKTVAPSTCSKPTCPPPELLGRSSVFIFPPKPK DTLMISRTPEVTCVVVDVSQDDPEVQFTWYINNEQVRTARPPL REQQFNSTIRVVSTLPIAHQDWLRGKEFKCKVHNKALPAPIEKT ISKARGQPLEPKVYTMGPPREELSSRSVSLTCMINGFYPSDISVE WEKNGKAEDNYKTTPAVLDSDGSYFLYSKLSVPTSEWQRGDV FTCSVMHEALHNHYTQKSISRSPGK |
| Antibody 5 Light Chain | 49 | MDMRAPTQLLGLLLLWLPGARCADIVMTQTPSSVSAAVGGTVT IKCQASQSIGSNLAWYQQKPGQPPKLLIYGASTLESGVPSRFKGS GSGTEYTLTISDLECADAATYYCQSYYEGSDIGYAFGGGTEVV EGDPVAPTVLIFPPAADQVATGTVTIVCVANKYFPDVTVTWEVD GTTQTTGIENSKTPQNSADCTYNLSSTLTLTSTQYNSHKEYTCKV TQGTTSVVQSFNRGDC |
| Antibody 6 Heavy Chain | 50 | METGLRWLLLVAVLKGVQCQSLEESGGRLVTPGTPLTLTCTVS GIDLSTHAMTWVRQAPGKGLEWIGVINPSGSAYYATWVNGRF TISKTSTTVDLKITSPTTGDTAKYFCARDYITAGDYYMDAFDPW GPGTLVTVSSGQPKAPSVFPLAPCCGDTPSSTVTLGCLVKGYLP EPVTVTWNSGTLTNGVRTFPSVRQSSGLYSLSSVVSVTSSSQPV TCNVAHPATNTKVDKTVAPSTCSKPTCPPPELLGRSSVFIFPPKP KDTLMISRTPEVTCVVVDVSQDDPEVQFTWYINNEQVRTARPP LREQQFNSTIRVVSTLPIAHQDWLRGKEFKCKVHNKALPAPIEK TISKARGQPLEPKVYTMGPPREELSSRSVSLTCMINGFYPSDISV EWEKNGKAEDNYKTTPAVLDSDGSYFLYSKLSVPTSEWQRGD VFTCSVMHEALHNHYTQKSISRSPGK |
| Antibody 6 Light Chain | 51 | MDTRAPTQLLGLLLLWLPGARCADIVMTQTPASVSAAVGGTV TIKCQASQSISNQLSWYQQKSGQPPKLLIYRASTLASGVPSRFK GSGSGTEFTLTISDLECADAATYYCQQGYNRDNVDNLFGGGT EVVVKGDPVAPTVLIFPPAADQVATGTVTIVCVANKYFPDVTV TWEVDGTTQTTGIENSKTPQNSADCTYNLSSTLTLTSTQYNSH KEYTCKVTQGTTSVVQSFNRGDC |

In some embodiments, the anti-tau antibody comprises a VH domain that is encoded by a nucleic acid comprising at least 80%, at least 85%, at least 90%, at least 95% sequence identity to a sequence selected from SEQ ID NOs: 52-56. In some embodiments, the anti-tau antibody comprises a VL domain that is encoded by a nucleic acid comprising at least 80%, at least 85%, at least 90%, at least 95% sequence identity to a sequence selected from SEQ ID NOs: 57-62. Nucleic acid sequences for VH domains for anti-tau-tau antibodies described here are listed in Table 6 and nucleic acid sequences for VL domains for anti-tau-tau antibodies described here are listed in Table 7. In some embodiments, the anti-tau-tau antibody comprises a VH domain that is encoded by a nucleic acid comprising at least 90% sequence identity to SEQ ID NO: 52. In some embodiments, the anti-tau-tau antibody comprises a VH domain that is encoded by a nucleic acid comprising at least 90% sequence identity to SEQ ID NO: 53. In some embodiments, the anti-tau-tau antibody comprises a VH domain that is encoded by a nucleic acid comprising at least 90% sequence identity to SEQ ID NO: 54. In some embodiments, the anti-tau-tau antibody comprises a VH domain that is encoded by a nucleic acid comprising at least 90% sequence identity to SEQ ID NO: 55. In some embodiments, the anti-tau-tau antibody comprises a VH domain that is encoded by a nucleic acid comprising at least 90% sequence identity to SEQ ID NO: 56. In some embodiments, the anti-tau-tau antibody comprises a VL domain that is encoded by a nucleic acid comprising at least 90% sequence identity to SEQ ID NO: 57. In some embodiments, the anti-tau-tau antibody comprises a VL domain that is encoded by a nucleic acid comprising at least 90% sequence identity to SEQ ID NO: 58. In some embodiments, the anti-tau antibody comprises a VL domain that is encoded by a nucleic acid comprising at least 90% sequence identity to SEQ ID NO: 59. In some embodiments, the anti-tau antibody comprises a VL domain that is encoded by a nucleic acid comprising at least 90% sequence identity to SEQ ID NO: 60. In some embodiments, the anti-tau antibody comprises a VL domain that is encoded by a nucleic acid comprising at least 90% sequence identity to SEQ ID NO: 61. In some embodiments, the anti-tau antibody comprises a VL domain that is encoded by a nucleic acid comprising at least 90% sequence identity to SEQ ID NO: 62. In some embodiments, the anti-tau antibody comprises a VH domain that is encoded by a nucleic acid comprising at least 90% sequence identity to SEQ ID NO: 52 and a VL domain that is encoded by a nucleic acid comprising at least 90% sequence identity to SEQ ID NO: 57. In some embodiments, the anti-tau antibody comprises a VH domain that is encoded by a nucleic acid comprising at least 90% sequence identity to SEQ ID NO: 53 and a VL domain that is encoded by a nucleic acid comprising at least 90% sequence identity to SEQ ID NO: 58. In some embodiments, the anti-tau antibody comprises a VH domain that is encoded by a nucleic acid comprising at least 90% sequence identity to SEQ ID NO: 53 and a VL domain that is encoded by a nucleic acid comprising at least 90% sequence identity to SEQ ID NO: 59. In some embodiments, the anti-tau antibody comprises a VH domain that is encoded by a nucleic acid comprising at least 90% sequence identity to SEQ ID NO: 54 and a VL domain that is encoded by a nucleic acid comprising at least 90% sequence identity to SEQ ID NO: 60. In some embodiments, the anti-tau antibody comprises a VH domain that is encoded by a nucleic acid comprising at least 90% sequence identity to SEQ ID NO: 55 and a VL domain that is encoded by a nucleic acid comprising at least 90% sequence identity to SEQ ID NO: 61. In some embodiments, the anti-tau antibody comprises a VH domain that is encoded by a nucleic acid comprising at least 90% sequence identity to SEQ ID NO: 563 and a VL domain that is encoded by a nucleic acid comprising at least 90% sequence identity to SEQ ID NO: 62. In some embodiments, the anti-tau antibody comprises a VH domain that is encoded by a nucleic acid comprising a sequence identical to SEQ ID NO: 52. In some embodiments, the anti-tau antibody comprises a VH domain that is encoded by a nucleic acid comprising a sequence identical to SEQ ID NO: 53. In some embodiments, the anti-tau antibody comprises a VH domain that is encoded by a nucleic acid comprising a sequence identical to SEQ ID NO: 54. In some embodiments, the anti-tau antibody comprises a VH domain that is encoded by a nucleic acid comprising a sequence identical to SEQ ID NO: 55. In some embodiments, the anti-tau antibody comprises a VH domain that is encoded by a nucleic acid comprising a sequence identical to SEQ ID NO: 56. In some embodiments, the anti-tau antibody comprises a VL domain that is encoded by a nucleic acid comprising a sequence identical to SEQ ID NO: 57. In some embodiments, the anti-tau antibody comprises a VL domain that is encoded by a nucleic acid comprising a sequence identical to SEQ ID NO: 58. In some embodiments, the anti-tau antibody comprises a VL domain that is encoded by a nucleic acid comprising a sequence identical to SEQ ID NO: 59. In some embodiments, the anti-tau antibody comprises a VL domain that is encoded by a nucleic acid comprising a sequence identical to SEQ ID NO: 60. In some embodiments, the anti-tau antibody comprises a VL domain that is encoded by a nucleic acid comprising a sequence identical to SEQ ID NO: 61. In some embodiments, the anti-tau antibody comprises a VL domain that is encoded by a nucleic acid comprising a sequence identical to SEQ ID NO: 62. In some embodiments, the anti-tau antibody comprises a VH domain that is encoded by a nucleic acid comprising a sequence identical to SEQ ID NO: 52 and a VL domain that is encoded by a nucleic acid comprising a sequence identical to SEQ ID NO: 57. In some embodiments, the anti-tau antibody comprises a VH domain that is encoded by a nucleic acid comprising a sequence identical to SEQ ID NO: 53 and a VL domain that is encoded by a nucleic acid comprising a sequence identical to SEQ ID NO: 58. In some embodiments, the anti-tau antibody comprises a VH domain that is encoded by a nucleic acid comprising a sequence identical to SEQ ID NO: 53 and a VL domain that is encoded by a nucleic acid comprising a sequence identical to SEQ ID NO: 59. In some embodiments, the anti-tau antibody comprises a VH domain that is encoded by a nucleic acid comprising a sequence identical to SEQ ID NO: 54 and a VL domain that is encoded by a nucleic acid comprising a sequence identical to SEQ ID NO: 60. In some embodiments, the anti-tau antibody comprises a VH domain that is encoded by a nucleic acid comprising a sequence identical to SEQ ID NO: 55 and a VL domain that is encoded by a nucleic acid comprising a sequence identical to SEQ ID NO: 61. In some embodiments, the anti-tau antibody comprises a VH domain that is encoded by a nucleic acid comprising a sequence identical to SEQ ID NO: 56 and a VL domain that is encoded by a nucleic acid comprising a sequence identical to SEQ ID NO: 62.

TABLE 6

Nucleic acid sequences encoding VH domains

| SEQ ID NO: | Nucleic acid sequences encoding VH domains |
|---|---|
| 52 | ATGGAGACTGGGCTGCGCTGGCTTCTCCTGGTCGCTGTGCTCAAAGG<br>TGTCCAGTGTCAGTCGCTGGAGGAGTCCGGGGGTCGCCTGGTCACG<br>CCTGGGACACCCCTGACACTCACCTGCACAGTCTCTGGATTTTCCCT<br>CAGTAGCCAGAAAGTGGGCTGGGTCCGCCAGGCTCCAGGGAAGGGG<br>CTGGAATGGATCGGAATCATTAATAATTATGGTAGCACATACTACGC<br>GAGCTGGGCGAAAGGCCGATTCACCATCTCGAAAACCTCGACCACA<br>GTGGATCTGAGAATCACCAGTCTGACGGCCGAGGACACGGCCACCT<br>ATTTCTGTGCCCGTGATCCTGATGGTAGTATTGTCTTTGACATCTGGG<br>GCCCAGGCACCCTTGTCACCGTCTCCTTG |
| 53 | ATGGAGACTGGGCTGCGCTGGCTTCTCCTGGTCGCTGTGCTCAAAGG<br>TGTCCAGTGTCAGTCGGTGGAGGAGTCCGGGGGTCGCCTGGTCACG<br>CCTGGGACACCCCTGACACTCACCTGCACCGTCTCTGGATTCTCCCTC<br>AGTAGCTATGCAATGATCTGGGTCCGCCAGGCTCCAGGGAAGGGGC<br>TGGAATGGATCGGATTCATTAGTCGTAGTGGTATCACATACTACGCG<br>AGCTGGGCAAAAGGCCGATTCACCATCTCCAAAACCTCGACCACGG<br>TGGATCTGAAAATGACCAGTCTGACAACCGAGGACACGGCCACCTA<br>TTTCTGTGCCAGAGAATTCGGTGCTGTTGGTAGTGATTATTATAGGG<br>ACGCCTTTAACTTGTGGGGCCCAGGCACCCTGGTCACCGTCTCCTCA |
| 54 | ATGGAGACTGGGCTGCGCTGGCTTCTCCTGGTCGCTGTGCTCAAAGG<br>TGTCCAGTGTCAGTCGCTGGAGGAGTCCGGGGGTCGCCTGGTCACG<br>CCTGGGACACCCCTGACACTCACCTGCACAGTCTCTGGATTTTCCCT<br>AAATAACTACAAAGTGGGCTGGGTCCGCCAGGCTCCAGGAAAGGG<br>GCTGGAATGGATCGGAATCATTAACTATTATAGTCAGACATACTAC<br>GCGAGCTGGGCAAAGGCCGATTCACCATCTCGAAAACCTCGACC<br>ACGGTGGATCTGAAGCTCACCAGTCCGACAACCGAAGACACGGCC<br>ACCTATTTCTGTGCCCGTGATCCTGATGGTAGTATTGTCTTTGACAT<br>CTGGGGCCCAGGCACCCTTGTCACCGTCTCCTTG |
| 55 | ATGGAGACTGGGCTGCGCTGGCTTCTCCTGGTCGCTGTGCTCAAAGG<br>TGTCCAGTGTCAGTCGGTGGAGGAGTCCGAGGAGGCCTGGTAACG<br>CCTGGAGGAACCCTGACACTCACCTGCACCGTCTCTGGATTCTCCCT<br>CAGTAACTATGCAATGAGCTGGGTCCGCCAGGCTCCAGGGAAGGGG<br>CTGGAATGGATCGGATTCATTAGTCGTAGTGGTATTACATACTACGC<br>GAGCTGGGCAAAAGGCCGATTCACCATCTCCAAAACCTCGACCACG<br>GTGGATCTGAAAATCACCAGTCCGACGACCGAGGACACGGCCGCCT<br>ATTTCTGTGCCAGAGAATTCGGTGCTGTTGGTAGTGATTATTATAGG<br>GACGCCTTGAGGTTGTGGGGCCCAGGCACCCTGGTCACCGTCTCCT<br>CA |
| 56 | ATGGAGACTGGGCTGCGCTGGCTTCTCCTGGTCGCTGTGCTCAAAGG<br>TGTCCAGTGTCAGTCGCTGGAGGAGTCCGGGGGTCGCCTGGTAACG<br>CCTGGGACACCCCTGACACTCACCTGCACAGTCTCTGGAATCGACCT<br>CAGTACCCATGCAATGACCTGGGTCCGCCAGGCTCCAGGAAAGGGG<br>CTGGAATGGATCGGAGTCATTAATCCTAGTGGTAGCGCATACTACG<br>CGACCTGGGTGAATGGCCGATTCACCATCTCCAAAACCTCGACCACG<br>GTGGATCTGAAAATCACCAGTCCGACAACCGGGACACGGCCAAGT<br>ATTTCTGTGCCAGAGATTATATTACTGCGGGTGATTATTATATGGAT<br>GCTTTTGATCCCTGGGGCCCAGGCACCCTGGTCACCGTCTCCTCA |

TABLE 7

Nucleic acid sequences encoding VL domains

| SEQ ID NO: | Nucleic acid sequences encoding VL domains |
|---|---|
| 57 | ATGGACACGAGGGCCCCCACTCAGCTGCTGGGGCTCCTGCTGCTC<br>TGGCTCCCAGGTGCCACATTTGCCCAAGTGCTGACCCAGACTGCA<br>TCCCCCGTGTCTGCGGCTGTTGGAGGCACAGTCACCATCAATTGC<br>CAGTCCAGTCAGAGTGTTGTATATAACAACCGCTTATCCTGGTTT<br>CAACAGAAACCAGGGCAGCCTCCCAAGCTCCTGATCTATGGTGCA<br>TCCACTCTGGCATCTGGGGTCCCATCGCGGTTCAAAGGCAGTGGA<br>TCTGGGACACAGTTCACTCTCACCATCAGCGACGTGCAGTGTGAC<br>GATGCTGCCACTTACTACTGTCTAGGCTCCTATGATTGTAGTAGT<br>GGTGATTGCCATGCTTTCGGCGGAGGGACCGAGGTGGTGGTCAAA |
| 58 | ATGGACATGAGGGCCCCCACTCAGCTGCTGGGGCTCCTACTGCTC<br>TGGCTCCCAGGTGCCAGATGTGCTGACATTGTGATGACCCAGACT<br>CCAGCCTCCGTGGAGGCAGCTGTGGGAGGCACAGTCACCATCAA<br>TTGCCAAGCCAGTGAGAGCATTAATAGTTGGTTGTCCTGGTATCA |

TABLE 7-continued

Nucleic acid sequences encoding VL domains

| SEQ ID NO: | Nucleic acid sequences encoding VL domains |
|---|---|
| | GCAGAAACCAGGGCAGCCTCCCAACCTCCTGATCTACAGGGCATC<br>CACTCTGGCATCTGGGGTCCCATCGCGGTTCAGTGGCGGTGGATC<br>TGGGACAGAGTACACTCTCACCATCAGCGACCTGGAGTGTGCCGA<br>TGCTGTCACTTATTACTGTCAAAGCTATTATGAGGAGGATGGTAT<br>TGGTTATGCTTTCGGCGGAGGGACCGAGGTGGTGGTCGAA |
| 59 | ATGGACATGAGGGCCCCCACTCAGCTGCTGGGGCTCCTGCTGCTCTG<br>GCTCCCAGGTGCCAGATGTGCTGACATTGTGATGACCCAGACTCCAT<br>CCTCCGTGTCTGCAGCTGTGGGAGGCACAGTCACCATCAATTGCCAG<br>GCCAGTCAGAACATTTACAGCAATTTAGCCTGGTATCAGCAGAAAC<br>CAGGGCAGCGTCCCAGGCTCCTGATCTATGGCGCATCCAATCTGGCA<br>TCTGGGGTCCCATCGCGGTTCAAAGGCAGTAGATCTGGGACAGAGTT<br>CACTCTCACCATCAGCGACCTGGAGTGTGCCGATGCTGCCACTTACT<br>ACTGTCAAGGCTATGATTATAGTACTGCTGGTGCCTATCCTTTCGGC<br>GGAGGGACCGCGGTGGTGGTCAAA |
| 60 | ATGGACACGAGGGCCCCCACTCAGCTGCTGGGGCTCCTGCTGCTCTG<br>GCTCCCAGGTGCCACATTTGCCCAAGTGCTGACCCAGACTGCATCGC<br>CCGTGTCTGCGGCTGTGGGAAGCACAGTCACCATCAATTGCCAGTCC<br>AGTCAGAGCGTTTATAGTAACAAGCGCTTAGCCTGGTTTCAGCTGAA<br>ACCAGGGCAGCCTCCCAAGCTCCTGATCTATGGTGCATCCACACTGG<br>CATCTGGGGTCCCATCGCGATTCAAGGGCAGTGGATCTGGGACACAG<br>TTCACTCTCACCATCAGCGACGTGCAGTGTGACGATGCTGCCACTTA<br>CTACTGTGCAGGCGGTTATGATTGTAGTACTGGTGATTGTTGGACTTT<br>CGGCGGAGGGACCGAGGTGGTGGTCACA |
| 61 | ATGGACATGAGGGCCCCCACTCAGCTGCTGGGGCTCCTGCTGCTC<br>TGGCTCCCAGGTGCCAGATGTGCTGACATCGTGATGACCCAGACT<br>CCATCCTCCGTGTCTGCAGCTGTGGGAGGCACAGTCACCATCAAG<br>TGCCAGGCCAGTCAGAGCATTGGTAGTAATTTAGCCTGGTATCAG<br>CAGAAACCAGGGCAGCCTCCCAAGCTCCTGATCTATGGTGCATCC<br>ACTCTGGAATCTGGGGTCCCATCGCGGTTTAAAGGCAGTGGATCT<br>GGGACAGAGTACACTCTCACCATCAGCGACCTGGAGTGTGCCGAT<br>GCTGCCACTTACTACTGTCAAAGCTATTATGAGGGTAGTGATATT<br>GGTTATGCTTTCGGCGGAGGGACCGAGGTGGTGGTCGAA |
| 62 | ATGGACACGAGGGCCCCCACTCAGCTGCTGGGGCTCCTGCTGCTC<br>TGGCTCCCAGGTGCCAGATGTGCTGACATCGTGATGACCCAGACT<br>CCAGCCTCTGTGTCTGCAGCTGTGGGAGGCACAGTCACCATCAAG<br>TGCCAGGCCAGTCAGAGCATTAGCAACCAACTATCCTGGTATCAG<br>CAGAAATCAGGGCAGCCTCCCAAGCTCCTGATCTACAGGGCATCT<br>ACTCTGGCATCTGGGGTCCCATCGCGGTTCAAAGGCAGTGGATCT<br>GGGACAGAGTTCACTCTCACCATCAGCGACCTGGAGTGTGCCGAT<br>GCTGCCACTTACTACTGTCAACAGGGTTATAATAGAGATAATGTT<br>GATAATCTTTTCGGCGGAGGGACCGAGGTGGTGGTCAAA |

In some embodiments, the anti-tau antibody comprises a heavy chain that is encoded by a nucleic acid comprising a sequence identical to a sequence selected from SEQ ID NOs: 63-67. In some embodiments, the anti-tau antibody comprises a light chain that is encoded by a nucleic acid comprising a sequence identical to a sequence selected from SEQ ID NOs: 68-73. Nucleic acid sequences for heavy chains for anti-tau antibodies described here are listed in Table 8 and nucleic acid sequences for light chains for anti-tau antibodies described here are listed in Table 9. Nucleic acid sequences listed in Table 8 and Table 9 may be used in the process of in vitro production of antibodies described herein. In some embodiments, the anti-tau antibody comprises a heavy chain that is encoded by a nucleic acid comprising a sequence identical to SEQ ID NO: 63. In some embodiments, the anti-tau antibody comprises a heavy chain that is encoded by a nucleic acid comprising a sequence identical to SEQ ID NO: 64. In some embodiments, the anti-tau antibody comprises a heavy chain that is encoded by a nucleic acid comprising a sequence identical to SEQ ID NO: 65. In some embodiments, the anti-tau antibody comprises a heavy chain that is encoded by a nucleic acid comprising a sequence identical to SEQ ID NO: 66. In some embodiments, the anti-tau antibody comprises a heavy chain that is encoded by a nucleic acid comprising a sequence identical to SEQ ID NO: 67. In some embodiments, the anti-tau antibody comprises a light chain that is encoded by a nucleic acid comprising a sequence identical to SEQ ID NO: 68. In some embodiments, the anti-tau antibody comprises a light chain that is encoded by a nucleic acid comprising a sequence identical to SEQ ID NO: 69. In some embodiments, the anti-tau antibody comprises a light chain that is encoded by a nucleic acid comprising a sequence identical to SEQ ID NO: 70. In some embodiments, the anti-tau antibody comprises a light chain that is encoded by a nucleic acid comprising a sequence identical to SEQ ID NO: 71. In some embodiments, the anti-tau antibody comprises a light chain that is encoded by a nucleic acid comprising a sequence identical to SEQ ID NO: 72. In some embodiments, the anti-tau antibody comprises a light chain that is encoded by a nucleic acid comprising a sequence identical to SEQ ID NO: 73. In some embodiments, the anti-tau antibody comprises a heavy chain that is encoded by a nucleic acid comprising a sequence identical to SEQ ID NO: 63 and a light chain that is encoded by a nucleic acid comprising a sequence identical to SEQ ID NO: 68. In some embodiments, the anti-tau antibody comprises a heavy chain that is encoded by a nucleic acid comprising a sequence identical to SEQ ID NO: 64 and a light chain that is encoded by a nucleic acid comprising a sequence identical to SEQ ID NO: 69. In some embodiments, the anti-tau antibody comprises a heavy chain that is encoded by a nucleic acid comprising a sequence identical to SEQ ID NO: 64 and a light chain that is encoded by a nucleic acid comprising a sequence identical to SEQ ID NO: 70. In some embodiments, the anti-tau antibody comprises a heavy chain that is encoded by a nucleic acid comprising a sequence identical to SEQ ID NO: 65 and a light chain that is encoded by a nucleic acid comprising a sequence identical to SEQ ID NO: 71. In some embodiments, the anti-tau antibody comprises a heavy chain that is encoded by a nucleic acid comprising a sequence identical to SEQ ID NO: 66 and a light chain that is encoded by a nucleic acid comprising a sequence identical to SEQ ID NO: 72. In some embodiments, the anti-tau antibody comprises a heavy chain that is encoded by a nucleic acid comprising a sequence identical to SEQ ID NO: 67 and a light chain that is encoded by a nucleic acid comprising a sequence identical to SEQ ID NO: 73.

TABLE 8

Nucleic acid sequences encoding heavy chains

| SEQ ID NO: | Nucleic acid sequences encoding heavy chains |
|---|---|
| 63 | ATGGAGACTGGGCTGCGCTGGCTTCTCCTGGTCGCTGTGCTCAAAGGTG
TCCAGTGTCAGTCGCTGGAGGAGTCCGGGGGTCGCCTGGTCACGCCTGG
GACACCCCTGACACTCACCTGCACAGTCTCTGGATTTTCCCTCAGTAGC
CAGAAAGTGGGCTGGGTCCGCCAGGCTCCAGGGAAGGGGCTGGAATGG
ATCGGAATCATTAATAATTATGGTAGCACATACTACGCGAGCTGGGCG
AAAGGCCGATTCACCATCTCGAAAACCTCGACCACAGTGGATCTGAGA
ATCACCAGTCTGACGGCCGAGGACACGGCCACCTATTTCTGTGCCCGTG
ATCCTGATGGTAGTATTGTCTTTGACATCTGGGGCCCAGGCACCCTTGTC
ACCGTCTCCTTGGGGCAACCTAAGGCTCCATCAGTCTTCCCACTGGCCC
CCTGCTGCGGGACACACCCAGCTCCACGGTGACCCTGGGCTGCCTGGT
CAAAGGCTACCTCCCGGAGCCAGTGACCGTGACCTGGAACTCGGGCAC
CCTCACCAATGGGGTACGCACCTTCCCGTCCGTCCGGCAGTCCTCAGGC
CTCTACTCGCTGAGCAGCGTGGTGAGCGTGACCTCAAGCAGCCAGCCC
GTCACCTGCAACGTGGCCCACCCAGCCACCAACACCAAAGTGGACAAG
ACCGTTGCGCCCTCGACATGCAGCAAGCCCACGTGCCCACCCCCTGAA
CTCCTGGGGCGATCCTCTGTCTTCATCTTCCCCCCAAAACCCAAGGACA
CCCTCATGATCTCACGCACCCCCGAGGTCACATGCGTGGTGGTGGACG
TGAGCCAGGATGACCCCGAGGTGCAGTTCACATGGTACATAAACAAC
GAGCAGGTGCGCACCGCCCGGCCGCCGCTACGGGAGCAGCAGTTCAAC
AGCACGATCCGCGTGGTCAGCACCCTCCCCATCGCGCACCAGGACTGG
CTGAGGGGCAAGGAGTTCAAGTGCAAAGTCCACAACAAGGCACTCCC
GGCCCCCATCGAGAAAACCATCTCCAAAGCCAGAGGGCAGCCCCTGG
AGCCGAAGGTCTACACCATGGGCCCTCCCCGGGAGGAGCTGAGCAGC
AGGTCGGTCAGCCTGACCTGCATGATCAACGGCTTCTACCCTTCCGAC
ATCTCGGTGGAGTGGGAGAAGAACGGGAAGGCAGAGGACAACTACAA
GACCACGCCGGCCGTGCTGGACAGCGACGGCTCCTACTTCCTCTACAG
CAAGCTCTCAGTGCCCACGAGTGAGTGGCAGCGGGGCGACGTCTTCAC
CTGCTCCGTGATGCACGAGGCCTTGCACAACCACTACACGCAGAAGTC
CATCTCCCGCTCTCCGGGTAAATGA |
| 64 | ATGGAGACTGGGCTGCGCTGGCTTCTCCTGGTCGCTGTGCTCAAAGG
TGTCCAGTGTCAGTCGGTGGAGGAGTCCGGGGGTCGCCTGGTCACGC
CTGGGACACCCCTGACACTCACCTGCACCGTCTCTGGATTCTCCCTC
AGTAGCTATGCAATGATCTGGGTCCGCCAGGCTCCAGGGAAGGGGC
TGGAATGGATCGGATTCATTAGTCGTAGTGGTATCACATACTACGCG
AGCTGGGCAAAAGGCCGATTCACCATCTCCAAAACCTCGACCACGG
TGGATCTGAAAATGACCAGTCTGACAACCGAGGACACGGCCACCTA
TTTCTGTGCCAGAGAATTCGGTGCTGTTGGTAGTGATTATTATAGGGA
CGCCTTTAACTTGTGGGGCCCAGGCACCCTGGTCACCGTCTCCTCAGG
GCAACCTAAGGCTCCATCAGTCTTCCCACTGGCCCCCTGCTGCGGGA
CACACCCAGCTCCACGGTGACCCTGGGCTGCCTGGTCAAAGGCTACCT
CCCGGAGCCAGTGACCGTGACCTGGAACTCGGGCACCCTCACCAATGG
GGTACGCACCTTCCCGTCCGTCCGGCAGTCCTCAGGCCTCTACTCGCTG
AGCAGCGTGGTGAGCGTGACCTCAAGCAGCCAGCCCGTCACCTGCAAC
GTGGCCCACCCAGCCACCAACACCAAAGTGGACAAGACCGTTGCGCCC
TCGACATGCAGCAAGCCCACGTGCCCACCCCCTGAACTCCTGGGGCGA
TCCTCTGTCTTCATCTTCCCCCCAAAACCCAAGGACACCCTCATGATCT
CACGCACCCCCGAGGTCACATGCGTGGTGGTGGACGTGAGCCAGGAT
GACCCCGAGGTGCAGTTCACATGGTACATAAACAACGAGCAGGTGCG
CACCGCCCGGCCGCCGCTACGGGAGCAGCAGTTCAACAGCACGATCC
GCGTGGTCAGCACCCTCCCCATCGCGCACCAGGACTGGCTGAGGGGC
AAGGAGTTCAAGTGCAAAGTCCACAACAAGGCACTCCCGGCCCCCAT
CGAGAAAACCATCTCCAAAGCCAGAGGGCAGCCCCTGGAGCCGAAG
GTCTACACCATGGGCCCTCCCCGGGAGGAGCTGAGCAGCAGGTCGGT
CAGCCTGACCTGCATGATCAACGGCTTCTACCCTTCCGACATCTCGGT
GGAGTGGGAGAAGAACGGGAAGGCAGAGGACAACTACAAGACCACG
CCGGCCGTGCTGGACAGCGACGGCTCCTACTTCCTCTACAGCAAGCTC |

TABLE 8-continued

Nucleic acid sequences encoding heavy chains

| SEQ ID NO: | Nucleic acid sequences encoding heavy chains |
|---|---|
| | TCAGTGCCCACGAGTGAGTGGCAGCGGGGCGACGTCTTCACCTGCTCC<br>GTGATGCACGAGGCCTTGCACAACCACTACACGCAGAAGTCCATCTC<br>CCGCTCTCCGGGTAAATGA |
| 65 | ATGGAGACTGGGCTGCGCTGGCTTCTCCTGGTCGCTGTGCTCAAAGG<br>TGTCCAGTGTCAGTCGCTGGAGGAGTCCGGGGGTCGCCTGGTCACG<br>CCTGGGACACCCCTGACACTCACCTGCACAGTCTCTGGATTTTCCCT<br>AAATAACTACAAAGTGGGCTGGGTCCGCCAGGCTCCAGGAAAGGG<br>GCTGGAATGGATCGGAATCATTAACTATTATAGTCAGACATACTAC<br>GCGAGCTGGGCCAAAGGCCGATTCACCATCTCGAAAACCTCGACC<br>ACGGTGGATCTGAAGCTCACCAGTCCGACAACCGAAGACACGGCC<br>ACCTATTTCTGTGCCCGTGATCCTGATGGTAGTATTGTCTTTGACAT<br>CTGGGGCCCAGGCACCCTTGTCACCGTCTCCTTGGGGCAACCTAAGG<br>CTCCATCAGTCTTCCCACTGGCCCCTGCTGCGGGACACACCCAGC<br>TCCACGGTGACCCTGGGCTGCCTGGTCAAAGGCTACCTCCCGGAGCC<br>AGTGACCGTGACCTGGAACTCGGGCACCCTCACCAATGGGGTACGCA<br>CCTTCCCGTCCGGCAGTCCTCAGGCCTCTACTCGCTGAGCAGCG<br>TGGTGAGCGTGACCTCAAGCAGCCAGCCCGTCACCTGCAACGTGGCC<br>CACCCAGCCACCAACACCAAAGTGGACAAGACCGTTGTGCCCTCGAC<br>ATGCAGCAAGCCCACGTGCCCACCCCCTGAACTCCTGGGGCGATCCT<br>CTGTCTTCATCTTCCCCCCAAAACCCAAGGACACCCTCATGATCTCAC<br>GCACCCCCGAGGTCACATGCGTGGTGGTGGACGTGAGCCAGGATGAC<br>CCCGAGGTGCAGTTCACATGGTACATAAACAACGAGCAGGTGCGCAC<br>CGCCCGGCCGCCGCTACGGGAGCAGCAGTTCAACAGCACGATCCGCG<br>TGGTCAGCACCCTCCCCATCGCGCACCAGGACTGGCTGAGGGGCAAG<br>GAGTTCAAGTGCAAAGTCCACAACAAGGCACTCCCGGCCCCCATCGA<br>GAAAACCATCTCCAAAGCCAGAGGGCAGCCCCTGGAGCCGAAGGTCT<br>ACACCATGGGCCCTCCCCGGGAGGAGCTGAGCAGCAGGTCGGTCAGC<br>CTGACCTGCATGATCAACGGCTTCTACCCTTCCGACATCTCGGTGGAG<br>TGGGAGAAGAACGGGAAGGCAGAGGACAACTACAAGACCACGCCGG<br>CCGTGCTGGACAGCGACGGCTCCTACTTCCTCTACAGCAAGCTCTCAG<br>TGCCCACGAGTGAGTGGCAGCGGGGCGACGTCTTCACCTGCTCCGTGA<br>TGCACGAGGCCTTGCACAACCACTACACGCAGAAGTCCATCTCCCGCT<br>CTCCGGGTAAATGA |
| 66 | ATGGAGACTGGGCTGCGCTGGCTTCTCCTGGTCGCTGTGCTCAAAGG<br>TGTCCAGTGTCAGTCGGTGGAGGAGTCCGGAGGAGGCCTGGTAACG<br>CCTGGAGGAACCCTGACACTCACCTGCACCGTCTCTGGATTCTCCCT<br>CAGTAACTATGCAATGAGCTGGGTCCGCCAGGCTCCAGGGAAGGGG<br>CTGGAATGGATCGGATTCATTAGTCGTAGTGGTATTACATACTACGC<br>GAGCTGGGCAAAAGGCCGATTCACCATCTCCAAAACCTCGACCACG<br>GTGGATCTGAAAATCACCAGTCCGACGACCGAGGACACGGCCGCCT<br>ATTTCTGTGCCAGAGAATTCGGTGCTGTTGGTAGTGATTATTATAGG<br>GACGCCTTGAGGTTGTGGGGCCCAGGCACCCTGGTCACCGTCTCCTC<br>AGGGCAACCTAAGGCTCCATCAGTCTTCCCACTGGCCCCTGCTGCG<br>GGGACACACCCAGCTCCACGGTGACCCTGGGCTGCCTGGTCAAAGG<br>CTACCTCCCGGAGCCAGTGACCGTGACCTGGAACTCGGGCACCCTCA<br>CCAATGGGGTACGCACCTTCCCGTCCGGCAGTCCTCAGGCCTC<br>TACTCGCTGAGCAGCGTGGTGAGCGTGACCTCAAGCAGCCAGCCCGT<br>CACCTGCAACGTGGCCCACCCAGCCACCAACACCAAAGTGGACAAGA<br>CCGTTGCGCCCTCGACATGCAGCAAGCCCACGTGCCCACCCCCTGAAC<br>TCCTGGGGCGATCCTCTGTCTTCATCTTCCCCCCAAAACCCAAGGACA<br>CCCTCATGATCTCACGCACCCCCGAGGTCACATGCGTGGTGGTGGACG<br>TGAGCCAGGATGACCCCGAGGTGCAGTTCACATGGTACATAAACAAC<br>GAGCAGGTGCGCACCGCCCGGCCGCCGCTACGGGAGCAGCAGTTCAA<br>CAGCACGATCCGCGTGGTCAGCACCCTCCCCATCGCGCACCAGGACTG<br>GCTGAGGGGCAAGGAGTTCAAGTGCAAAGTCCACAACAAGGCACTCC<br>CGGCCCCCATCGAGAAAACCATCTCCAAAGCCAGAGGGCAGCCCCTG<br>GAGCCGAAGGTCTACACCATGGGCCCTCCCCGGGAGGAGCTGAGCAG<br>CAGGTCGGTCAGCCTGACCTGCATGATCAACGGCTTCTACCCTTCCGA<br>CATCTCGGTGGAGTGGGAGAAGAACGGGAAGGCAGAGGACAACTAC<br>AAGACCACGCCGGCCGTGCTGGACAGCGACGGCTCCTACTTCCTCTA<br>CAGCAAGCTCTCAGTGCCCACGAGTGAGTGGCAGCGGGGCGACGTC<br>TTCACCTGCTCCGTGATGCACGAGGCCTTGCACAACCACTACACGCA<br>GAAGTCCATCTCCCGCTCTCCGGGTAAATGA |
| 67 | ATGGAGACTGGGCTGCGCTGGCTTCTCCTGGTCGCTGTGCTCAAAGG<br>TGTCCAGTGTCAGTCGCTGGAGGAGTCCGGGGGTCGCCTGGTAACG<br>CCTGGGACACCCCTGACACTCACCTGCACAGTCTCTGGAATCGACCT<br>CAGTACCCATGCAATGACCTGGGTCCGCCAGGCTCCAGGAAAGGGG<br>CTGGAATGGATCGGAGTCATTAATCCTAGTGGTAGCGCATACTACG<br>CGACCTGGGTGAATGGCCGATTCACCATCTCCAAAACCTCGACCACG<br>GTGGATCTGAAAATCACCAGTCCGACAACCGGGACACGGCCAAGT<br>ATTTCTGTGCCAGAGATTATATTACTGCGGGTGATTATTATATGGAT |

TABLE 8-continued

Nucleic acid sequences encoding heavy chains

| SEQ ID NO: | Nucleic acid sequences encoding heavy chains |
|---|---|
| | GCTTTTGATCCCTGGGGCCCAGGCACCCTGGTCACCGTCTCCTCAGG<br>GCAACCTAAGGCTCCATCAGTCTTCCCACTGGCCCCCTGCTGCGGGG<br>ACACACCCAGCTCCACGGTGACCCTGGGCTGCCTGGTCAAAGGCTAC<br>CTCCCGGAGCCAGTGACCGTGACCTGGAACTCGGGCACCCTCACCAA<br>TGGGGTACGCACCTTCCCGTCCGTCCGGCAGTCCTCAGGCCTCTACTC<br>GCTGAGCAGCGTGGTGAGCGTGACCTCAAGCAGCCAGCCCGTCACCT<br>GCAACGTGGCCCACCCAGCCACCAACACCAAAGTGGACAAGACCGTT<br>GCGCCCTCGACATGCAGCAAGCCCACGTGCCCACCCCCTGAACTCCT<br>GGGGCGATCCTCTGTCTTCATCTTCCCCCCAAAACCCAAGGACACCC<br>TCATGATCTCACGCACCCCCGAGGTCACATGCGTGGTGGTGGACGTG<br>AGCCAGGATGACCCCGAGGTGCAGTTCACATGGTACATAAACAACG<br>AGCAGGTGCGCACCGCCCGGCCGCCGCTACGGGAGCAGCAGTTCAA<br>CAGCACGATCCGCGTGGTCAGCACCCTCCCCATCGCGCACCAGGACT<br>GGCTGAGGGGCAAGGAGTTCAAGTGCAAAGTCCACAACAAGGCACT<br>CCCCGGCCCCCATCGAGAAAACCATCTCCAAAGCCAGAGGGCAGCCC<br>CTGGAGCCGAAGGTCTACACCATGGGCCTCTCCCGGGAGGAGCTGA<br>GCAGCAGGTCGGTCAGCCTGACCTGCATGATCAACGGCTTCTACCC<br>TTCCGACATCTCGGTGGAGTGGGAGAAGAACGGGAAGGCAGAGGA<br>CAACTACAAGACCACGGCCGGCCGTGCTGGACAGCGACGGCTCCTA<br>CTTCCTCTACAGCAAGCTCTCAGTGCCCACGAGTGAGTGGCAGCGG<br>GGCGACGTCTTCACCTGCTCCGTGATGCACGAGGCCTTGCACAACC<br>ACTACACGCAGAAGTCCATCTCCCGCTCTCCGGGTAAATGA |

TABLE 9

Nucleic acid sequences encoding light chains

| SEQ ID NO: | Nucleic acid sequences encoding light chains |
|---|---|
| 68 | ATGGACACGAGGGCCCCCACTCAGCTGCTGGGGCTCCTGCTGCTCTG<br>GCTCCCAGGTGCCACATTTGCCCAAGTGCTGACCCAGACTGCATCCC<br>CCGTGTCTGCGGCTGTTGGAGGCACAGTCACCATCAATTGCCAGTCC<br>AGTCAGAGTGTTGTATATAACAACCGCTTATCCTGGTTTCAACAGAA<br>ACCAGGGCAGCCTCCCAAGCTCCTGATCTATGGTGCATCCACTCTGG<br>CATCTGGGGTCCCATCGCGGTTCAAAGGCAGTGGATCTGGGACACA<br>GTTCACTCTCACCATCAGCGACGTGCAGTGTGACGATGCTGCCACTT<br>ACTACTGTCTAGGCTCCTATGATTGTAGTAGTGGTGATTGCCATGCT<br>TTCGGCGGAGGGACCGAGGTGGTGGTCAAAGGTGATCCAGTTGCAC<br>CTACTGTCCTCATCTTCCCACCAGCTGCTGATCAGGTGGCAACTGGA<br>ACAGTCACCATCGTGTGTGTGGCGAATAAATACTTTCCCGATGTCAC<br>CGTCACCTGGGAGGTGGATGGCACCACCCAAACAACTGGCATCGAG<br>AACAGTAAAACACCGCAGAATTCTGCAGATTGTACCTACAACCTCA<br>GCAGCACTCTGACACTGACCAGCACACAGTACAACAGCCACAAAG<br>AGTACACCTGCAAGGTGACCCAGGGCACGACCTCAGTCGTCCAGAG<br>CTTCAATAGGGGTGACTGTTAG |
| 69 | ATGGACATGAGGGCCCCCACTCAGCTGCTGGGGCTCCTACTGCTCTG<br>GCTCCCAGGTGCCAGATGTGCTGACATTGTGATGACCCAGACTCCAG<br>CCTCCGTGGAGGCAGCTGTGGGAGGCACAGTCACCATCAATTGCCAA<br>GCCAGTGAGAGCATTAATAGTTGGTTGTCCTGGTATCAGCAGAAACC<br>AGGGCAGCCTCCCAACCTCCTGATCTACAGGGCATCCACTCTGGCAT<br>CTGGGGTCCCATCGCGGTTCAGTGGCGGTGGATCTGGGACAGAGTAC<br>ACTCTCACCATCAGCGACCTGGAGTGTGCCGATGCTGTCACTTATTA<br>CTGTCAAAGCTATTATGAGGAGGATGGTATTGGTTATGCTTTCGGCG<br>GAGGGACCGAGGTGGTGGTCGAAGGTGATCCAGTTGCACCTACTGT<br>CCTCATCTTCCCACCAGCTGCTGATCAGGTGGCAACTGGAACAGTCA<br>CCATCGTGTGTGTGGCGAATAAATACTTTCCCGATGTCACCGTCACC<br>TGGGAGGTGGATGGCACCACCCAAACAACTGGCATCGAGAACAGTA<br>AAACACCGCAGAATTCTGCAGATTGTACCTACAACCTCAGCAGCACT<br>CTGACACTGACCAGCACACAGTACAACAGCCACAAAGAGTACACCT<br>GCAAGGTGACCCAGGGCACGACCTCAGTCGTCCAGAGCTTCAATAG<br>GGGTGACTGTTAG |
| 70 | ATGGACATGAGGGCCCCCACTCAGCTGCTGGGGCTCCTGCTGCTCTG<br>GCTCCCAGGTGCCAGATGTGCTGACATTGTGATGACCCAGACTCCAT<br>CCTCCGTGTCTGCAGCTGTGGGAGGCACAGTCACCATCAATTGCCAG<br>GCCAGTCAGAACATTTACAGCAATTTAGCCTGGTATCAGCAGAAACC<br>AGGGCAGCGTCCCAGGCTCCTGATCTATGGCGCATCCAATCTGGCAT<br>CTGGGGTCCCATCGCGGTTCAAAGGCAGTAGATCTGGGACAGAGTT<br>CACTCTCACCATCAGCGACCTGGAGTGTGCCGATGCTGCCACTTACT |

TABLE 9-continued

Nucleic acid sequences encoding light chains

| SEQ ID NO: | Nucleic acid sequences encoding light chains |
|---|---|
| | ACTGTCAAGGCTATGATTATAGTACTGCTGGTGCCTATCCTTTCGGC<br>GGAGGGACCGCGGTGGTGGTCAAAGGTGATCCAGTTGCACCTACTG<br>TCCTCATCTTCCCACCAGCTGCTGATCAGGTGGCAACTGGAACAGTC<br>ACCATCGTGTGTGTGGCGAATAAATACTTTCCCGATGTCACCGTCAC<br>CTGGGAGGTGGATGGCACCACCCAAACAACTGGCATCGAGAACAG<br>TAAAACACCGCAGAATTCTGCAGATTGTACCTACAACCTCAGCAGC<br>ACTCTGACACTGACCAGCACACAGTACAACAGCCACAAAGAGTAC<br>ACCTGCAAGGTGACCCAGGGCACGACCTCAGTCGTCCAGAGCTTCA<br>ATAGGGGTGACTGTTAG |
| 71 | ATGGACACGAGGGCCCCCACTCAGCTGCTGGGGCTCCTGCTGCTCTG<br>GCTCCCAGGTGCCACATTTGCCCAAGTGCTGACCCAGACTGCATCGC<br>CCGTGTCTGCGGCTGTGGGAAGCACAGTCACCATCAATTGCCAGTCC<br>AGTCAGAGCGTTTATAGTAACAAGCGCTTAGCCTGGTTTCAGCTGAA<br>ACCAGGGCAGCCTCCCAAGCTCCTGATCTATGGTGCATCCACACTGG<br>CATCTGGGGTCCCATCGCGATTCAAGGGCAGTGGATCTGGGACACAG<br>TTCACTCTCACCATCAGCGACGTGCAGTGTGACGATGCTGCCACTTA<br>CTACTGTGCAGGCGGTTATGATTGTAGTACTGGTGATTGTTGGACTTT<br>CGGCGGAGGGACCGAGGTGGTGGTCACAGGTGATCCAGTTGCACCT<br>ACTGTCCTCATCTTCCCACCAGCTGCTGATCAGGTGGCAACTGGAAC<br>AGTCACCATCGTGTGTGTGGCGAATAAATACTTTCCCGATGTCACCG<br>TCACCTGGGAGGTGGATGGCACCACCCAAACAACTGGCATCGAGAA<br>CAGTAAAACACCGCAGAATTCTGCAGATTGTACCTACAACCTCAGCA<br>GCACTCTGACACTGACCAGCACACAGTACAACAGCCACAAAGAGTA<br>CACCTGCAAGGTGACCCAGGGCACGACCTCAGTCGTCCAGAGCTTC<br>AATAGGGGTGACTGTTAG |
| 72 | ATGGACATGAGGGCCCCCACTCAGCTGCTGGGGCTCCTGCTGCTCTG<br>GCTCCCAGGTGCCAGATGTGCTGACATCGTGATGACCCAGACTCCAT<br>CCTCCGTGTCTGCAGCTGTGGGAGGCACAGTCACCATCAAGTGCCAG<br>GCCAGTCAGAGCATTGGTAGTAATTTAGCCTGGTATCAGCAGAAACC<br>AGGGCAGCCTCCCAAGCTCCTGATCTATGGTCATCCACTCTGGAAT<br>CTGGGGTCCCATCGCGGTTTAAAGGCAGTGGATCTGGGACAGAGTA<br>CACTCTCACCATCAGCGACCTGGAGTGTGCCGATGCTGCCACTTACT<br>ACTGTCAAAGCTATTATGAGGGTAGTGATATTGGTTATGCTTTCGGC<br>GGAGGGACCGAGGTGGTGGTCGAAGGTGATCCAGTTGCACCTACTG<br>TCCTCATCTTCCCACCAGCTGCTGATCAGGTGGCAACTGGAACAGTC<br>ACCATCGTGTGTGTGGCGAATAAATACTTTCCCGATGTCACCGTCAC<br>CTGGGAGGTGGATGGCACCACCCAAACAACTGGCATCGAGAACAGT<br>AAAACACCGCAGAATTCTGCAGATTGTACCTACAACCTCAGCAGCA<br>CTCTGACACTGACCAGCACACAGTACAACAGCCACAAAGAGTACAC<br>CTGCAAGGTGACCCAGGGCACGACCTCAGTCGTCCAGAGCTTCAAT<br>AGGGGTGACTGTTAG |
| 73 | ATGGACACGAGGGCCCCCACTCAGCTGCTGGGGCTCCTGCTGCTCTG<br>GCTCCCAGGTGCCAGATGTGCTGACATCGTGATGACCCAGACTCCAG<br>CCTCTGTGTCTGCAGCTGTGGGAGGCACAGTCACCATCAAGTGCCAG<br>GCCAGTCAGAGCATTAGCAACCAACTATCCTGGTATCAGCAGAAAT<br>CAGGGCAGCCTCCCAAGCTCCTGATCTACAGGGCATCTACTCTGGCA<br>TCTGGGGTCCCATCGCGGTTCAAAGGCAGTGGATCTGGGACAGAGTT<br>CACTCTCACCATCAGCGACCTGGAGTGTGCCGATGCTGCCACTTACT<br>ACTGTCAACAGGGTTATAATAGAGATAATGTTGATAATCTTTTCGGC<br>GGAGGGACCGAGGTGGTGGTCAAAGGTGATCCAGTTGCACCTACTG<br>TCCTCATCTTCCCACCAGCTGCTGATCAGGTGGCAACTGGAACAGTC<br>ACCATCGTGTGTGTGGCGAATAAATACTTTCCCGATGTCACCGTCAC<br>CTGGGAGGTGGATGGCACCACCCAAACAACTGGCATCGAGAACAGT<br>AAAACACCGCAGAATTCTGCAGATTGTACCTACAACCTCAGCAGCA<br>CTCTGACACTGACCAGCACACAGTACAACAGCCACAAAGAGTACAC<br>CTGCAAGGTGACCCAGGGCACGACCTCAGTCGTCCAGAGCTTCAAT<br>AGGGGTGACTGTTAG |

Methods of the Disclosure

Disclosed herein are methods for detecting phosphorylated tau in a sample from an individual using antibodies described herein. In some embodiments, the phosphorylated tau is selected from the group consisting of pTau-212, pTau-217, pTau-231, pTau-214, and pTau-220. In some embodiments, methods for detecting phosphorylated tau in a sample from an individual using antibodies described herein comprise improved specificity and sensitivity.

Described herein are methods for detecting phosphorylated tau in a sample from an individual comprising: performing an assay on the sample using an antibody or antibody fragment that binds to phosphorylated tau. Described herein are methods for detecting phosphorylated tau in a sample from an individual comprising: performing an immunoassay on the sample using an antibody or antibody fragment that binds to phosphorylated tau. In some embodiments, the phosphorylated tau is selected from the group consisting of pTau-212, pTau-217, pTau-231, pTau-214, pTau-220, and pTau-181. In some embodiments, the phosphorylated tau is selected from the group consisting of pTau-212, pTau-217, pTau-231, pTau-214, and pTau-220. In some embodiments, the phosphorylated tau is pTau-217. In some embodiments, the phosphorylated tau is pTau-231. In some embodiments, the phosphorylated tau is pTau-181. In some embodiments, the phosphorylated tau is pTau-212. In some embodiments, the phosphorylated tau is pTau-217. In some embodiments, the phosphorylated tau is pTau-214. In some embodiments, the phosphorylated tau is pTau-220. In some embodiments, the phosphorylated tau is pTau-181 and pTau-217. In some embodiments, the phosphorylated tau is pTau-181 and pTau-231. In some embodiments, the phosphorylated tau is pTau-217 and pTau-231. In some embodiments, the phosphorylated tau is pTau-181, pTau-217, and pTau-231.

Further described herein are methods for detecting phosphorylated tau in a sample from an individual comprising: performing an assay on the sample using an antibody or antibody fragment that binds to multiple phosphorylated tau proteins. In some embodiments, the methods detects pTau-217 and pTau-231. In some embodiments, the methods detects pTau-212 and pTau-217. In some embodiments, the methods detects pTau-212 and pTau-231. In some embodiments, the methods detects pTau-212, pTau-217 and pTau-231.

Described herein are methods for detecting phosphorylated tau in a sample from an individual, wherein the method detects pTau-217 and pTau-231 in a sample selected from the group consisting of a plasma sample and serum sample. In some embodiments, the methods detect pTau-212 and pTau-217 in a sample selected from the group consisting of a plasma sample and serum sample. In some embodiments, the methods detect pTau-212 and pTau-231 in a sample selected from the group consisting of a plasma sample and serum sample. In some embodiments, the methods detect pTau-212, pTau-217, and pTau-231 in a sample selected from the group consisting of a plasma sample and serum sample.

Methods as described herein can comprise performing an assay on a sample, wherein the sample is selected from the group consisting of a plasma sample and serum sample. In some instances, the sample is a blood sample. In some instances, the sample is a cerebrospinal fluid sample. The sample can be a blood sample obtained by a venous blood draw. The sample can be a blood sample obtained from a finger prick blood draw. The sample can be obtained by a health care provider or by the subject. The method can comprise obtaining a sample from a subject. In some cases, the sample is obtained from the subject during a visit to the clinic or the hospital.

Further described herein, in some embodiments, are methods to determine a level of a biomarker selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof. In some instances, the biomarker is Aβ42. In some instances, the biomarker is Aβ40. In some instances, the biomarker is Aβ42 and Aβ40. In some instances, the biomarker is APOE. In some instances, the biomarker is selected from the group consisting of APOE2, APOE3, and APOE4. In some instances, the biomarker is APOE4.

In some embodiments, methods for detecting phosphorylated tau in a sample comprise an immunoassay or a ligand assay using the antibodies or antibody fragments described herein. In some cases, the assay is selected from the group consisting of enzyme-linked immunosorbent assay (ELISA), a colorimetric immunoassay, a homogeneous immunoassay, a non-optical immunoassay, a fluorescence immunoassay, a chemiluminescence immunoassay, an electro-chemiluminescence immunoassay, a fluorescence resonance energy transfer (FRET) immunoassay, a time resolved fluorescence immunoassay, a lateral flow immunoassay, a microspot immunoassay, a surface plasmon resonance assay, a ligand assay, a clotting assay, a chromatography assay, and immunocapture coupled with mass spectrometry. In some cases, the assay comprises an immunoassay. In some cases, the assay is selected from the group consisting of a Western blot, enzyme-linked immunosorbent assays (ELISA), and chromatography. In some cases, the immunoassays are single-plexed. In some cases, the immunoassays are multi-plexed.

Methods as described herein can comprise a plurality of immunoassays using the antibodies or antibody fragments described herein. In some cases, the plurality of immunoassays are the same immunoassay (e.g., four or more ELISA assays). When the plurality of immunoassays are the same immunoassay, each of the plurality of immunoassays can detect a different phosphorylated tau. When the plurality of immunoassays are the same immunoassay, each of the plurality of immunoassays can be performed in the same reaction chamber or a different reaction chamber. A reaction chamber can be any suitable space for performing an immunoassay. Examples of reaction chambers include, but are not limited to, a well in a microplate, an Eppendorf tube, or a droplet.

In some cases, the plurality of immunoassays are different immunoassays. When the plurality of immunoassays are different immunoassays, each of the plurality of immunoassays can detect a different phosphorylated tau. When the plurality of immunoassays are different immunoassays, each of the plurality of immunoassays can be performed in the same reaction chamber or a different reaction chamber.

In some cases, the assay comprises a non-immunoassay. In some cases, the assay is selected from the group consisting of High Performance Liquid Chromatography (HPLC), High Performance Liquid Chromatography Mass spectrometry (HPLC-MS), Gas Chromatography Mass Spectrometry (GC-MS), Liquid Chromatography Mass spectrometry (LC-MS), Liquid Chromatography Tandem Mass spectrometry (LC-MS/MS), immunohistochemistry (IHC), polymerase chain reaction (PCR), quantitative PCR (qPCR), and combinations thereof.

Methods as described herein using the antibodies described herein may be used for establishing Alzheimer's disease in the individual based on detection of phosphorylated tau. In some embodiments, Alzheimer's disease in the individual is established if pTau-212, pTau-217, pTau-231, pTau-214, pTau-220, or combinations thereof is detected in the sample from the individual.

Methods as described herein using the antibodies described herein may be used for prognosis of the individual for developing Alzheimer's disease based on detection of phosphorylated tau. In some embodiments, prognosis of the individual for developing Alzheimer's disease is determined if pTau-212, pTau-217, pTau-231, pTau-214, pTau-220, or combinations thereof is detected in the sample from the individual.

Methods as described herein using the antibodies described herein may be used accurately and specifically establish Alzheimer's disease (AD) in an individual as compared to a disease or disorder or neurologically and cognitively unimpaired condition, selected from the group consisting of a non-Alzheimer's disease (AD) neurodegenerative disease, a AD-negative non-AD neurodegenerative disease, a AD-positive non-AD neurodegenerative diseases, behavioral variant of frontotemporal dementia (BvFTD), primary progressive aphasia (PPA), vascular dementia (VaD), Parkinson's disease (PD), PD with dementia (PDD), multiple system atrophy (MSA), progressive supranuclear palsy (PSP), corticobasal syndrome (CBS), A3-negative cognitively impaired or unimpaired controls and combinations thereof. In some embodiments, the methods as described herein using the antibodies described herein comprise an improved accuracy or specificity of at least or about 70%, 80%, 90%, 95%, 99%, or more at establishing AD as compared to a disease or disorder or neurologically and cognitively unimpaired condition.

Methods as described herein using the antibodies described herein may be used accurately and specifically establish Alzheimer's disease (AD) in an individual as compared to a neuropathological examination or clinical diagnosis. In some embodiments, the methods as described herein using the antibodies described herein comprise an improved accuracy or specificity of at least or about 70%, 80%, 90%, 95%, 99%, or more at establishing AD as compared to a neuropathological examination or clinical diagnosis. In some embodiments, the neuropathological examination or clinical diagnosis comprises neurological tests, mental exams, or brain imaging (e.g. MRI, CT, or PET scans).

Methods as described herein using the antibodies described herein may be capable of detecting phosphorylated tau in the sample at a low limit of detection. In some embodiments, the methods as described herein using the antibodies described herein are capable of detecting phosphorylated tau in the sample at a limit of detection of at least about 1.5 picogram per milliliter (pg/mL). In some embodiments, the methods as described herein using the antibodies described herein are capable of detecting phosphorylated tau in the sample at a limit of detection of at least about 5 picogram per milliliter (pg/mL). In some embodiments, the methods as described herein using the antibodies described herein are capable of detecting phosphorylated tau in the sample at a limit of detection in a range of about 0.5 pg/mL to about 10 µg/mL, about 1 µg/mL to about 8 µg/mL, about 1.5 pg/mL to about 7 µg/mL, about 2 µg/mL to about 6 µg/mL, or about 3 µg/mL to about 5 µg/mL.

Production of Tau Antibodies

In some embodiments, antibodies or antibody fragments described herein are produced using any method known in the art to be useful for the synthesis of antibodies or antibody fragments, in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., E. coli and B. subtilis) transformed with recombinant bacteriophage DNA, plasmid DNA or cosmid DNA expression vectors containing an antibody or its binding fragment coding sequences; yeast (e.g., Saccharomyces Pichia) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan and, 1993, Science 260:926-932; and Morgan and Anderson, 1993, Ann. Rev. Biochem. 62:191-217; May 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-*Thermus*, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli* bacilli.

Exemplary prokaryotic host cells include, but are not limited to, BL21, Machi™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. *Schizosaccharomyces* (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVScl.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PCC 7942.

NUMBERED EMBODIMENTS

Numbered embodiment 1 comprises a method for detecting phosphorylated tau in a sample from an individual comprising: performing an immunoassay on the sample using an antibody or antibody fragment comprising a variable domain, heavy chain region (VH) and a variable domain, light chain region (VL), wherein the VH comprises an amino acid sequence at least about 90% identical to a sequence as set forth in any one of SEQ ID NOs: 30-34, and wherein the VL comprises an amino acid sequence at least about 90% identical to a sequence as set forth in any one of SEQ ID NOs: 35-40. Numbered embodiment 2 comprises the method of numbered embodiment 1, wherein the phosphorylated tau is selected from the group consisting of pTau-181, pTau-212, pTau-217, pTau-231, pTau-214, and pTau-220. Numbered embodiment 3 comprises the method of numbered embodiments 1-2, wherein the phosphorylated tau is pTau-217. Numbered embodiment 4 comprises the method of numbered embodiments 1-2, wherein the phosphorylated tau is pTau-231. Numbered embodiment 5 comprises the method of numbered embodiment 2, wherein the method detects pTau-217 and pTau-231. Numbered embodiment 6 comprises the method of numbered embodiment 2, wherein the method detects pTau-212 and pTau-217. Numbered embodiment 7 comprises the method of numbered embodiment 2, wherein the method detects pTau-212 and pTau-231. Numbered embodiment 8 comprises the method of numbered embodiment 2, wherein the method detects pTau-181 and pTau-217. Numbered embodiment 9 comprises the method of numbered embodiment 2, wherein the method detects pTau-181 and pTau-231. Numbered embodiment 10 comprises the method of numbered embodiment 2, wherein the method detects pTau-181, pTau-217 and pTau-231. Numbered embodiment 11 comprises the method of numbered embodiment 2, wherein the method detects pTau-212, pTau-217 and pTau-231. Numbered embodiment 12 comprises the method of numbered embodiment 5, wherein the method detects pTau-217 and pTau-231 in a sample selected from the group consisting of a plasma sample and serum sample. Numbered embodiment 13 comprises the method of numbered embodiment 6, wherein the method detects pTau-212 and pTau-217 in a sample selected from the group consisting of a plasma sample and serum sample. Numbered embodiment 14 comprises the method of numbered embodiment 7, wherein the method detects pTau-212 and pTau-231 in a sample selected from the group consisting of a plasma sample and serum sample. Numbered embodiment 15 comprises the method of numbered embodiment 11, wherein the method detects pTau-181 and pTau-217 in a sample selected from the group consisting of a plasma sample and serum sample. Numbered embodiment 16 comprises the method of numbered embodiment 11, wherein the method detects pTau-181 and pTau-231 in a sample selected from the group consisting of a plasma sample and serum sample. Numbered embodiment 17 comprises the method of numbered embodiment 11, wherein the method detects pTau-181, pTau-217, and pTau-231 in a sample selected from the group consisting of a plasma sample and serum sample. Numbered embodiment 18 comprises the method of numbered embodiment 11, wherein the method detects pTau-212, pTau-217, and pTau-231 in a sample selected from the group consisting of a plasma sample and serum sample. Numbered embodiment 19 comprises the method of numbered embodiments 1-18, wherein the VH comprises an amino acid sequence according to any one of SEQ ID NOs: 30-34. Numbered embodiment 20 comprises the method of numbered embodiments 1-19, wherein the VL comprises an amino acid sequence according to any one of SEQ ID NOs: 35-40. Numbered embodiment 21 comprises the method of numbered embodiments 1-20, wherein the VH comprises an amino acid sequence according to any one of SEQ ID NOs: 30-34, and wherein the VL comprises an amino acid sequence according to any one of SEQ ID NOs: 35-40. Numbered embodiment 22 comprises the method of numbered embodiments 1-21, wherein the VH comprises an amino acid sequence at least about 90% identical to SEQ ID NO: 30, and wherein the VL comprises an amino acid sequence at least about 90% identical to SEQ ID NO: 35. Numbered embodiment 23 comprises the method of numbered embodiments 1-21, wherein the VH comprises an amino acid sequence at least about 90% identical to SEQ ID NO: 31, and wherein the VL comprises an amino acid sequence at least about 90% identical to SEQ ID NO: 36. Numbered embodiment 24 comprises the method of numbered embodiments 1-21, wherein the VH comprises an amino acid sequence at least about 90% identical to SEQ ID NO: 31, and wherein the VL comprises an amino acid sequence at least about 90% identical to SEQ ID NO: 37. Numbered embodiment 25 comprises the method of numbered embodiments 1-21, wherein the VH comprises an amino acid sequence at least about 90% identical to SEQ ID NO: 32, and wherein the VL comprises an amino acid sequence at least about 90% identical to SEQ ID NO: 38. Numbered embodiment 26 comprises the method of numbered embodiments 1-21, wherein the VH comprises an amino acid sequence at least about 90% identical to SEQ ID NO: 33, and wherein the VL comprises an amino acid sequence at least about 90% identical to SEQ ID NO: 39. Numbered embodiment 27 comprises the method of numbered embodiments 1-21, wherein the VH comprises an amino acid sequence at least about 90% identical to SEQ ID NO: 34, and wherein the VL comprises an amino acid sequence at least about 90% identical to SEQ ID NO: 40. Numbered embodiment 28 comprises the method of numbered embodiments 1-27, wherein the antibody or antibody fragment comprises an amino acid sequence at least about 90% identical to any one of SEQ ID NOs: 41-51. Numbered embodiment 29 comprises the method of numbered embodiments 1-28, further comprising performing an assay on the sample to determine a level of a biomarker selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof. Numbered embodiment 30 comprises the method of numbered embodiments 1-29, wherein the sample is selected from the group consisting of a blood sample, a plasma sample, a serum sample, and a cerebrospinal fluid (CSF) sample. Numbered embodiment 31 comprises the method of numbered embodiments 1-30, further comprising establishing Alzheimer's disease in the individual based on detection of phosphorylated tau. Numbered embodiment 32 comprises the method of numbered embodiments 1-31, further comprising establishing prognosis of the individual for developing Alzheimer's disease based on detection of phosphorylated tau. Numbered embodiment 33 comprises the method of numbered embodiment 32, further determining the individual's age, genotype, or expression of a biomarker. Numbered embodiment 34 comprises the method of numbered embodiment 33, wherein the biomarker is selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof. Numbered embodiment 35 comprises the method of numbered embodiments 1-34, wherein the method has a specificity of at least about 80% for detecting phosphorylated tau. Numbered embodiment 36 comprises the method of numbered embodiments 1-34, wherein the method has a specificity of at least about 85% for detecting phosphorylated tau. Numbered embodiment 37 comprises the method of numbered embodiments 1-34, wherein the method has a specificity of at least about 90% for detecting phosphorylated tau. Numbered embodiment 38 comprises the method of numbered embodiments 1-37, wherein the method has a sensitivity of at least about 80% for detecting phosphorylated tau. Numbered embodiment 39 comprises the method of numbered embodiments 1-37, wherein the method has a sensitivity of at least about 85% for detecting phosphorylated tau. Numbered embodiment 40 comprises the method of numbered embodiments 1-37, wherein the method has a sensitivity of at least about 90% for detecting phosphorylated tau. Numbered embodiment 41 comprises the method of numbered embodiments 1-40, wherein the method is capable of detecting phosphorylated tau in the sample at a limit of detection of at least about 1.0 picogram per milliliter (pg/mL). Numbered embodiment 42 comprises the method of numbered embodiments 1-40, wherein the method is capable of detecting phosphorylated tau in the sample at a limit of detection of at least about 1.5 picogram per milliliter (pg/mL). Numbered embodiment 43 comprises the method of numbered embodiments 1-40, wherein the method is capable of detecting phosphorylated tau in the sample at a limit of detection of at least about 5 picogram per milliliter (pg/mL).

Numbered embodiment 44 comprises an anti-tau antibody comprising i) a heavy chain comprising variable heavy chain (VH) domain and ii) a light chain comprising a variable light chain (VL) domain, wherein the VH domain comprises HCDR1 sequence comprising a sequence selected from SEQ ID NOs: 1-5, HCDR2 sequence comprising a sequence selected from SEQ ID NOs: 6-9, and HCDR3 sequence comprising a sequence selected from SEQ ID NOs: 10-13, and VL domain comprises LCDR1 sequence comprising a sequence selected from SEQ ID NOs: 14-19, LCDR2 sequence comprising a sequence selected from SEQ ID NOs: 20-23, and LCDR3 sequence comprising a sequence selected from SEQ ID NOs: 24-29. Numbered embodiment 45 comprises the anti-tau antibody of numbered embodiment 44, wherein the HCDR1 sequence comprises SEQ ID NO: 1, HCDR2 sequence comprises SEQ ID NO: 6, HCDR3 sequence comprises SEQ ID NO: 10, LCDR1 sequence comprises SEQ ID NO: 14, LCDR2 sequence comprises SEQ ID NO: 20, and LCDR3 sequence comprises SEQ ID NO: 24. Numbered embodiment 46 comprises the anti-tau antibody of numbered embodiment 44, wherein the HCDR1 sequence comprises SEQ ID NO: 2, HCDR2 sequence comprises SEQ ID NO: 7, HCDR3 sequence comprises SEQ ID NO: 11, LCDR1 sequence comprises SEQ ID NO: 15, LCDR2 sequence comprises SEQ ID NO: 21, and LCDR3 sequence comprises SEQ ID NO: 25. Numbered embodiment 47 comprises the anti-tau antibody of numbered embodiment 44, wherein the HCDR1 sequence comprises SEQ ID NO: 2, HCDR2 sequence comprises SEQ ID NO: 7, HCDR3 sequence comprises SEQ ID NO: 11, LCDR1 sequence comprises SEQ ID NO: 16, LCDR2 sequence comprises SEQ ID NO: 22, and LCDR3 sequence comprises SEQ ID NO: 26. Numbered embodiment 48 comprises the anti-tau antibody of numbered embodiment 44, wherein the HCDR1 sequence comprises SEQ ID NO: 3, HCDR2 sequence comprises SEQ ID NO: 8, HCDR3 sequence comprises SEQ ID NO: 10, LCDR1 sequence comprises SEQ ID NO: 17, LCDR2 sequence comprises SEQ ID NO: 20, and LCDR3 sequence comprises SEQ ID NO: 27. Numbered embodiment 49 comprises the anti-tau antibody of numbered embodiment 44, wherein the HCDR1 sequence comprises SEQ ID NO: 4, HCDR2 sequence comprises SEQ ID NO: 7, HCDR3 sequence comprises SEQ ID NO: 12, LCDR1 sequence comprises SEQ ID NO: 18, LCDR2 sequence comprises SEQ ID NO: 23, and LCDR3 sequence comprises SEQ ID NO: 28. Numbered embodiment 50 comprises the anti-tau antibody of numbered embodiment 44, wherein the HCDR1 sequence comprises SEQ ID NO: 5, HCDR2 sequence comprises SEQ ID NO: 9, HCDR3 sequence comprises SEQ ID NO: 13, LCDR1 sequence comprises SEQ ID NO: 19, LCDR2 sequence comprises SEQ ID NO: 21, and LCDR3 sequence comprises SEQ ID NO: 29. Numbered embodiment 51 comprises the anti-tau antibody of numbered embodiment 44, wherein the VH domain comprises at least 80%, at least 85%, at least 90%, at least 95% sequence identity to a sequence selected from SEQ ID NOs: 30-34. Numbered embodiment 52 comprises the anti-tau antibody of numbered embodiment 44, wherein the VL domain comprises at least 80%, at least 85%, at least 90%, at least 95% sequence identity to a sequence selected from SEQ ID NOs: 35-40.

Numbered embodiment 53 comprises the anti-tau antibody of numbered embodiments 44-52, wherein the anti-tau antibody is a chimeric antibody or antigen binding fragment thereof. Numbered embodiment 54 comprises the anti-tau antibody of numbered embodiments 44-53, wherein the anti-tau antibody comprises an IgG-scFv, nanobody, BiTE, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, Fab', F(ab')2, F(ab')3, F(ab')2-scFv2, scFv, scFv-KIH, Fab-scFv-Fc, tetravalent HCAb, scDiabody-Fc, diabody-Fc, tandem scFv-Fc, or intrabody. Numbered embodiment 55 comprises the anti-tau antibody of numbered embodiments 44-54, wherein the anti-tau antibody is an IgG1 antibody. Numbered embodiment 56 comprises the anti-tau antibody of numbered embodiments 44-55, wherein the anti-tau antibody is an IgG2 antibody. Numbered embodiment 57 comprises the anti-tau antibody of numbered embodiments 44-56, wherein the anti-tau antibody is an IgG4 antibody. Numbered embodiment 58 comprises the anti-tau antibody of numbered embodiments 44-57, wherein the light chain is a kappa chain. Numbered embodiment 59 comprises the anti-tau antibody of numbered embodiments 44-58, wherein the anti-tau antibody has a binding affinity to human tau of about 100 pM to about 3 nM. Numbered embodiment 60 comprises the anti-tau antibody of numbered embodiments 44-59, wherein the anti-tau antibody comprises a VH domain that is encoded by a nucleic acid comprising at least 80%, at least 85%, at least 90%, at least 95% sequence identity to a sequence selected from SEQ ID NOs: 52-56. Numbered embodiment 61 comprises the anti-tau antibody of numbered embodiments 44-60, wherein the anti-tau antibody comprises a VL domain that is encoded by a nucleic acid comprising at least 80%, at least 85%, at least 90%, at least 95% sequence identity to a sequence selected from SEQ ID NOs: 57-62. Numbered embodiment 62 comprises the anti-tau antibody of numbered embodiments 44-61, wherein the anti-tau antibody comprises a VH domain that is encoded by a nucleic acid comprising at least 80%, at least 85%, at least 90%, at least 95% sequence identity to a sequence selected from SEQ ID NOs: 52-56 and a VL domain that is encoded by a nucleic acid comprising at least 80%, at least 85%, at least 90%, at least 95% sequence identity to a sequence selected from SEQ ID NOs: 57-62. Numbered embodiment 63 comprises the anti-tau antibody of numbered embodiments 44-62, wherein the anti-tau antibody comprises a VH domain that is encoded by a nucleic acid comprising a sequence identical to SEQ ID NOs: 52-56. Numbered embodiment 64 comprises the anti-tau antibody of numbered embodiments 44-63, wherein the anti-tau antibody comprises a VL domain that is encoded by a nucleic acid comprising a sequence identical to SEQ ID NOs: 57-62. Numbered embodiment 65 comprises the anti-tau antibody of numbered embodiments 44-64 wherein the anti-tau antibody comprises a VH domain that is encoded by a nucleic acid comprising a sequence identical to SEQ ID NOs: 52-56 and a VL domain that is encoded by a nucleic acid comprising a sequence identical to SEQ ID NOs: 57-62.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Tau Antibody Screening

Tau antibodies that detect phosphorylated Tau were assayed in the Simoa® bead assay using a 2-step or 3-step protocol assay according to manufacturer's instructions. See FIG. 1.

The antibodies tested were Antibody 1, Antibody 2, Antibody 3, Antibody 4, Antibody 5, and Antibody 6. The capture results can be seen in FIGS. 2A-2D. FIG. 2A is data from an 2-step protocol assay in which all capture antibodies were tested against Tau-12 detector (detects Tau at the N-terminus). The data demonstrates all captures had similar results with improved sensitivity seen with Antibody 6. FIG. 2B is data from an 2-step protocol assay in which all capture antibodies were tested against HT7-BT2 detectors (detects Tau in the mid-domain region). Both biotinylated antibodies were used. Data shows about a 10-fold increase in background compared to Tau-12 detector. No signal at 1000 µg/mL for any capture was detected. FIG. 2C is data from an 3-step protocol assay in which all capture antibodies were tested against Tau-12 detector. The data demonstrates reduced sensitivity compared to the 2-step protocol and improved sensitivity seen with Antibody 6. FIG. 2D is data from an 3-step protocol assay in which all capture antibodies were tested against HT7-BT2 detectors. Both biotinylated antibodies were used. Data shows about a 10-fold increase in background compared to Tau-12 detector. Based on the results, the 2-step protocol was then further optimized for sensitivity.

Example 2. Pharmacokinetics of Tau Antibodies

Antibodies were tested for pharmacokinetic profile.
The antigen information for the antibodies is seen in Table 10.

TABLE 10

| Description | Antigen Name | SEQ ID NO: | Sequence |
|---|---|---|---|
| pT217a | WZN-1A | 74 | RSRTPSLP(PT)PPTREPKC |
| pT217b | WZN-1B | 75 | TPSLP(PT)PPTREPKKVAC |
| T217 | WZN-1C | 76 | RSRTPSLPTPPTREPKKVAC |
| pT212 | WZN-1D | 77 | RSR(pT)PSLPTPPTREPKC |
| pS214 | WZN-1E | 78 | RSRTP(pS)LPTPPTREPKC |
| pT220 | WZN-1F | 79 | RSRTPSLPTPP(PT)REPKKVAC |
| pT231 | WZN-1G | 80 | KVAVVR(PT)PPKSPSSAC |
| T231 | WZN-1H | 81 | KVAVVRTPPKSPSSAC |

Figure 3:
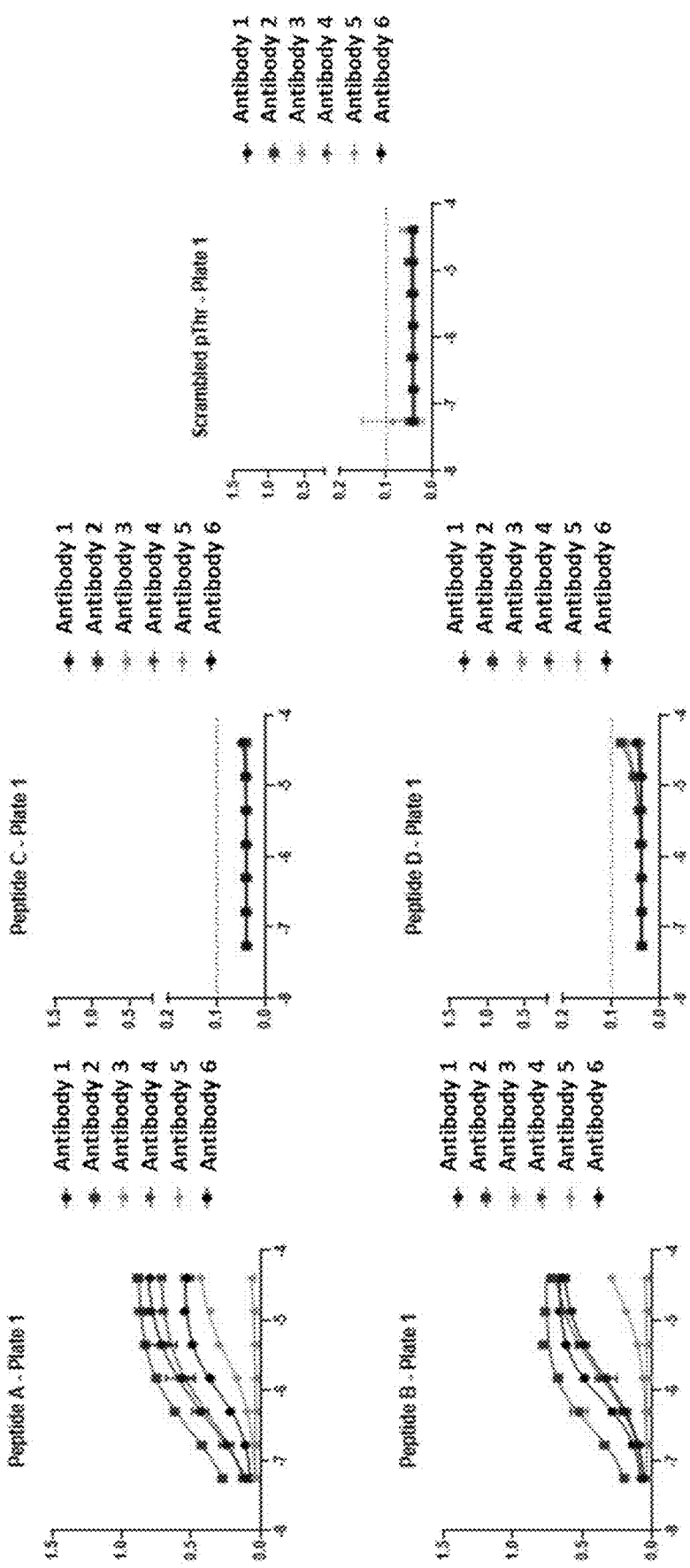
FIG. 3 depict ELISA data.
Figure 4A:
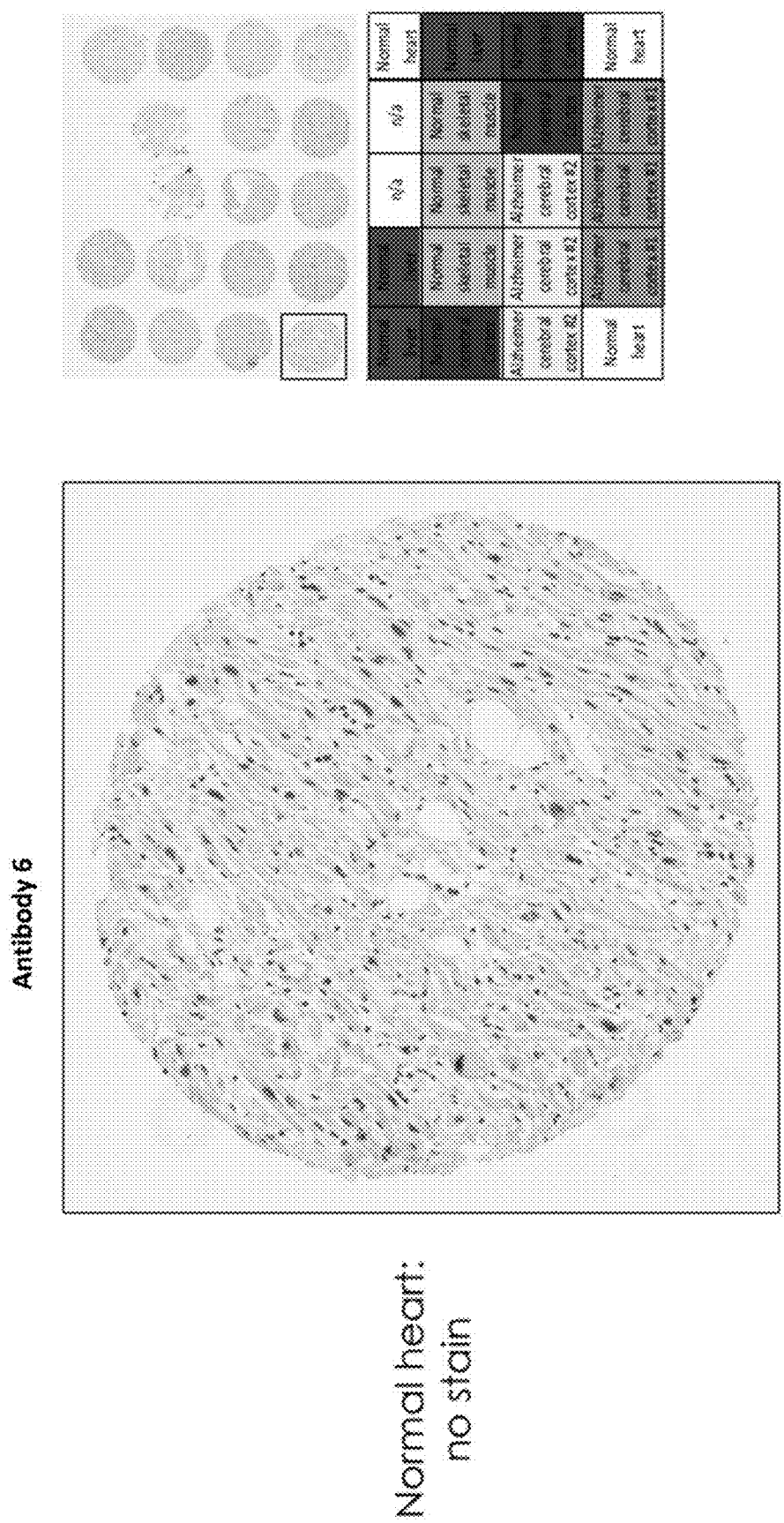
FIGS. 4A-4G depict data for immunohistochemistry staining of Antibody 6.
Figure 4B:
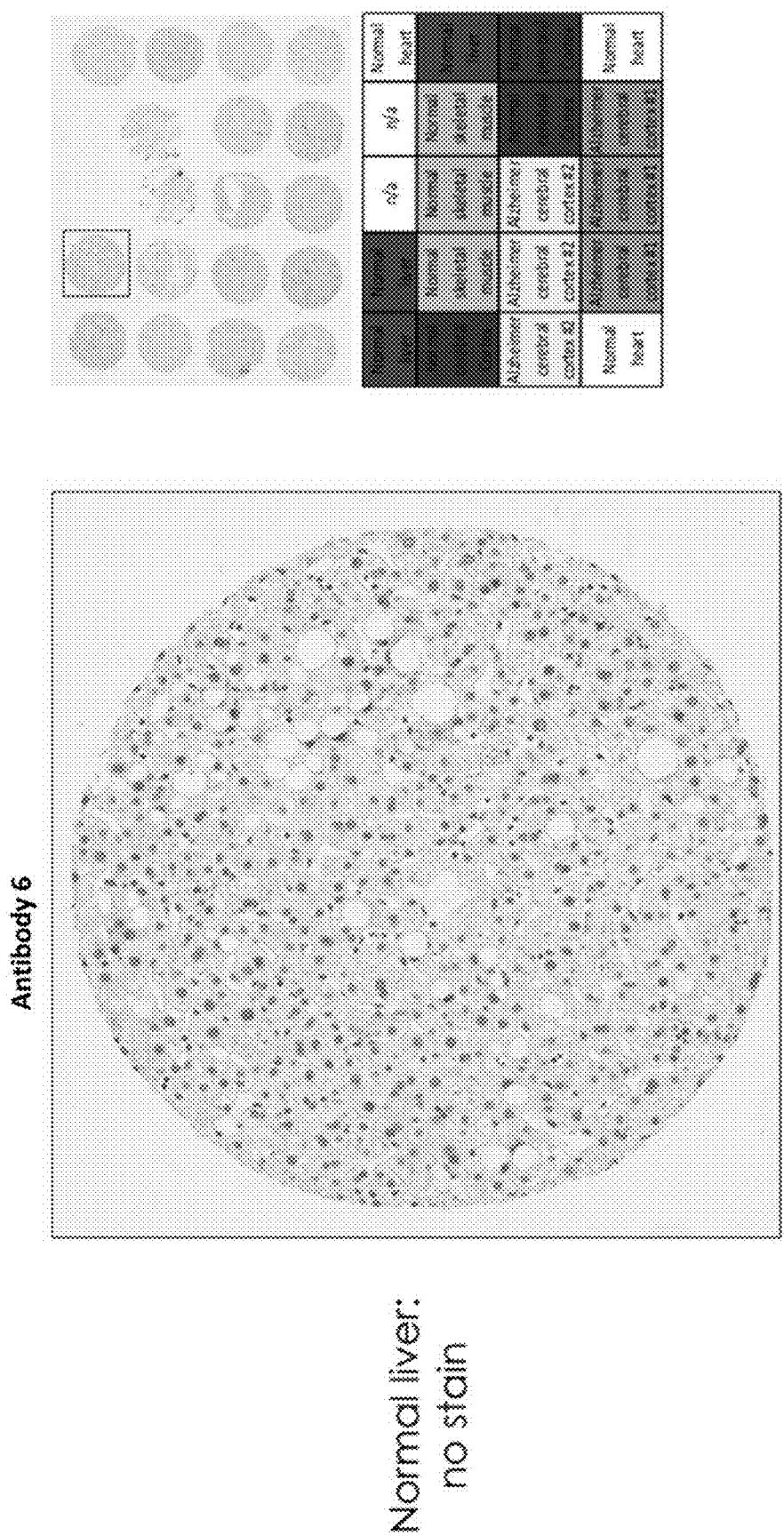
Figure 4C:
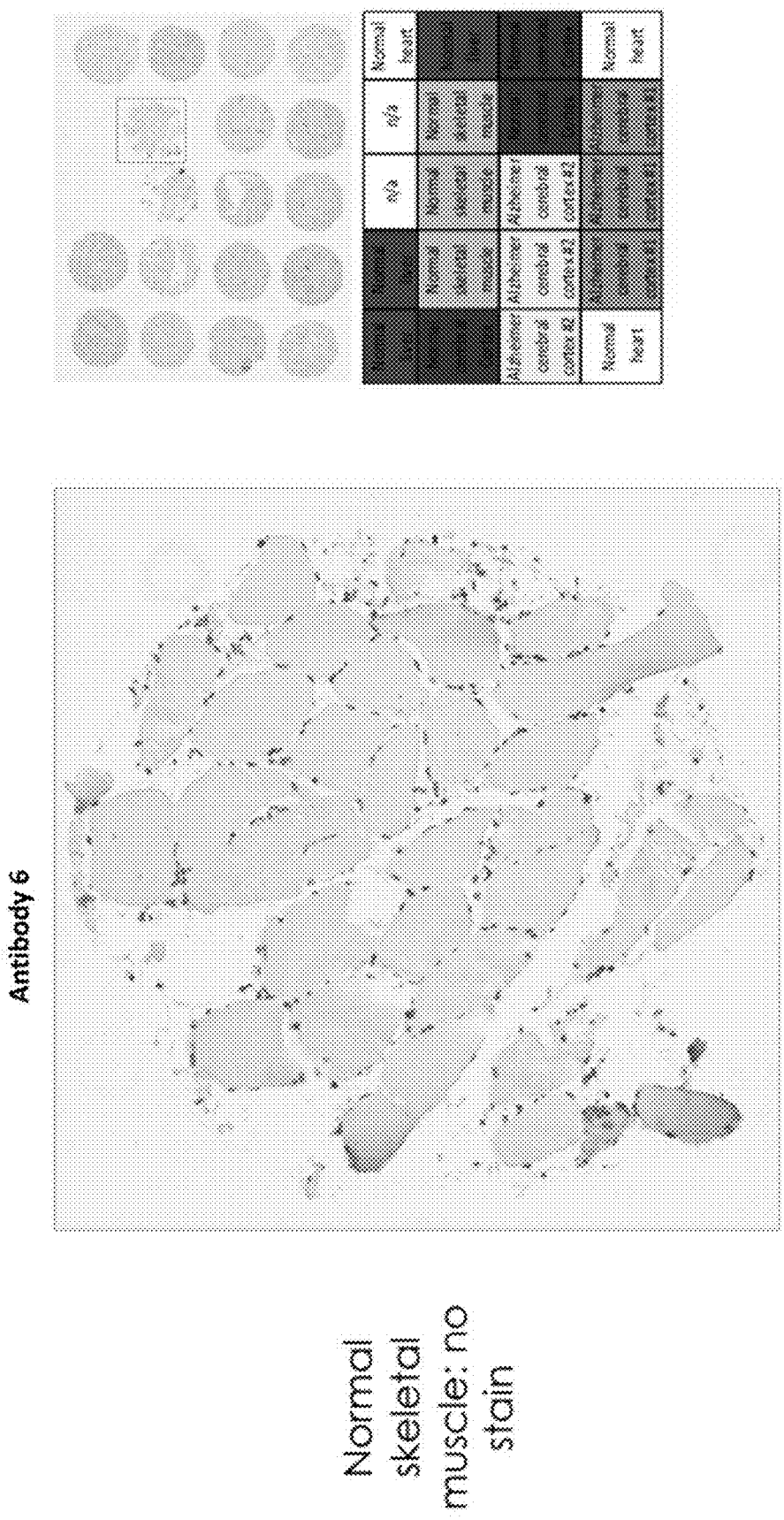
Figure 4D:
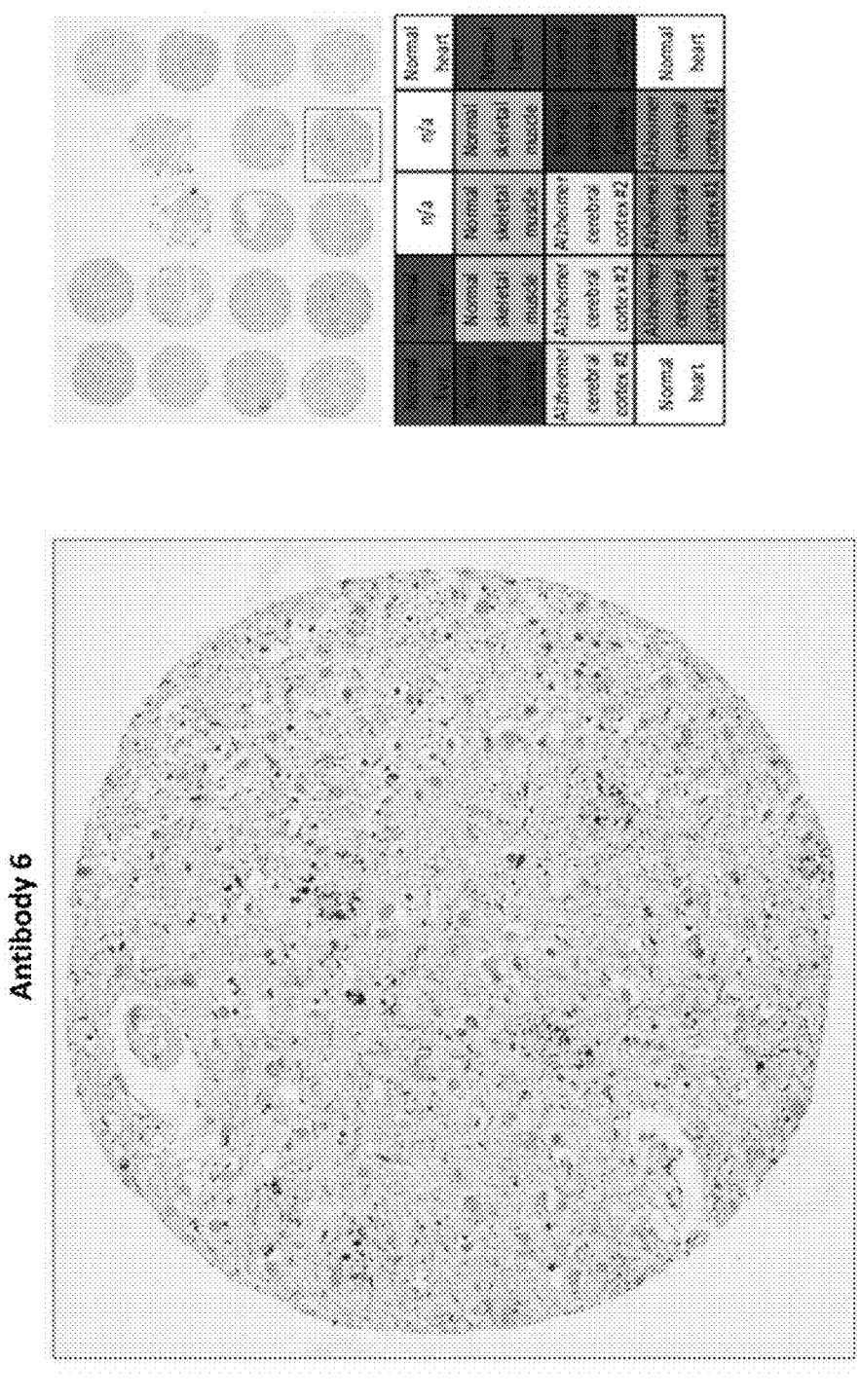
Figure 4E:
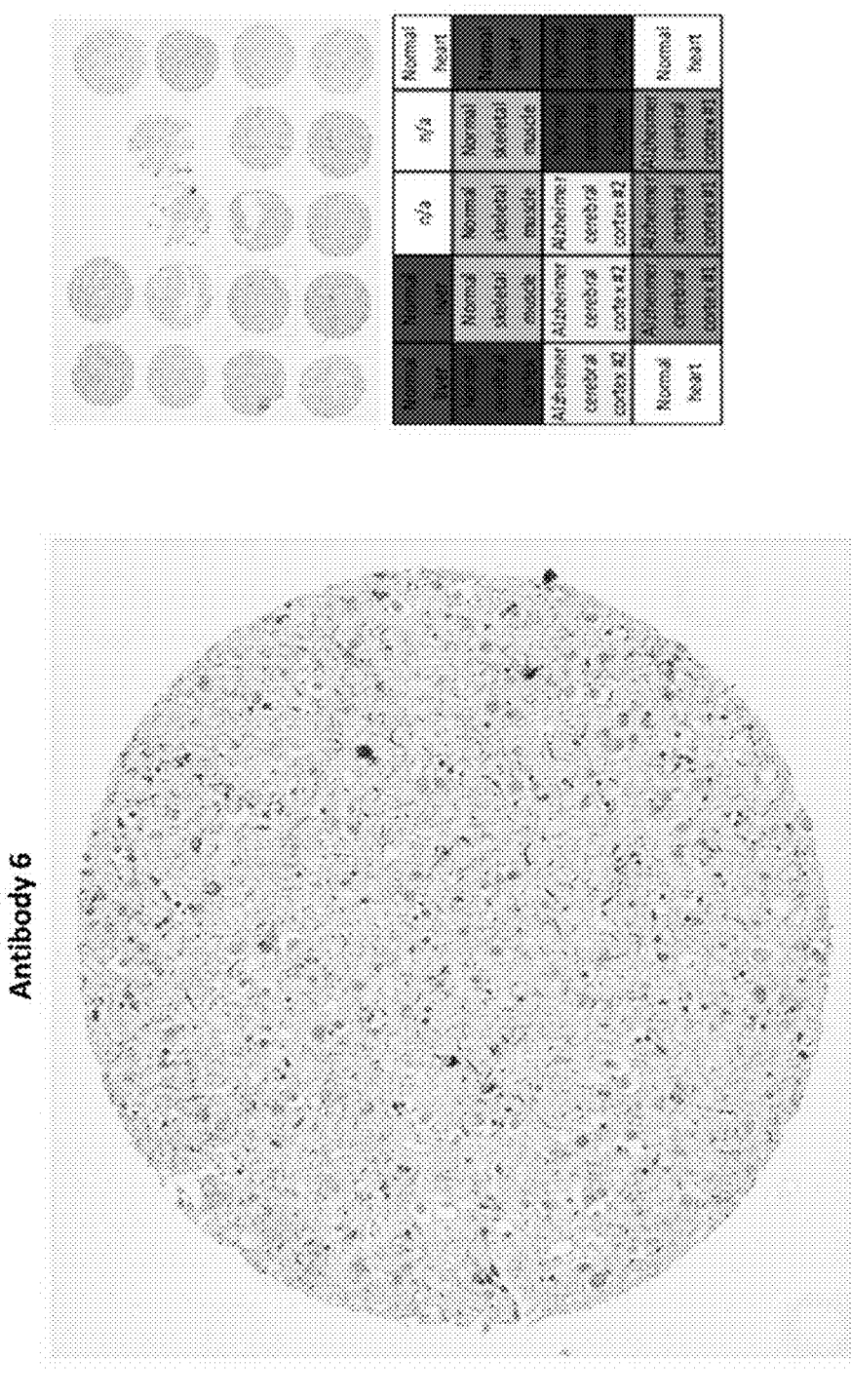
Figure 4F:
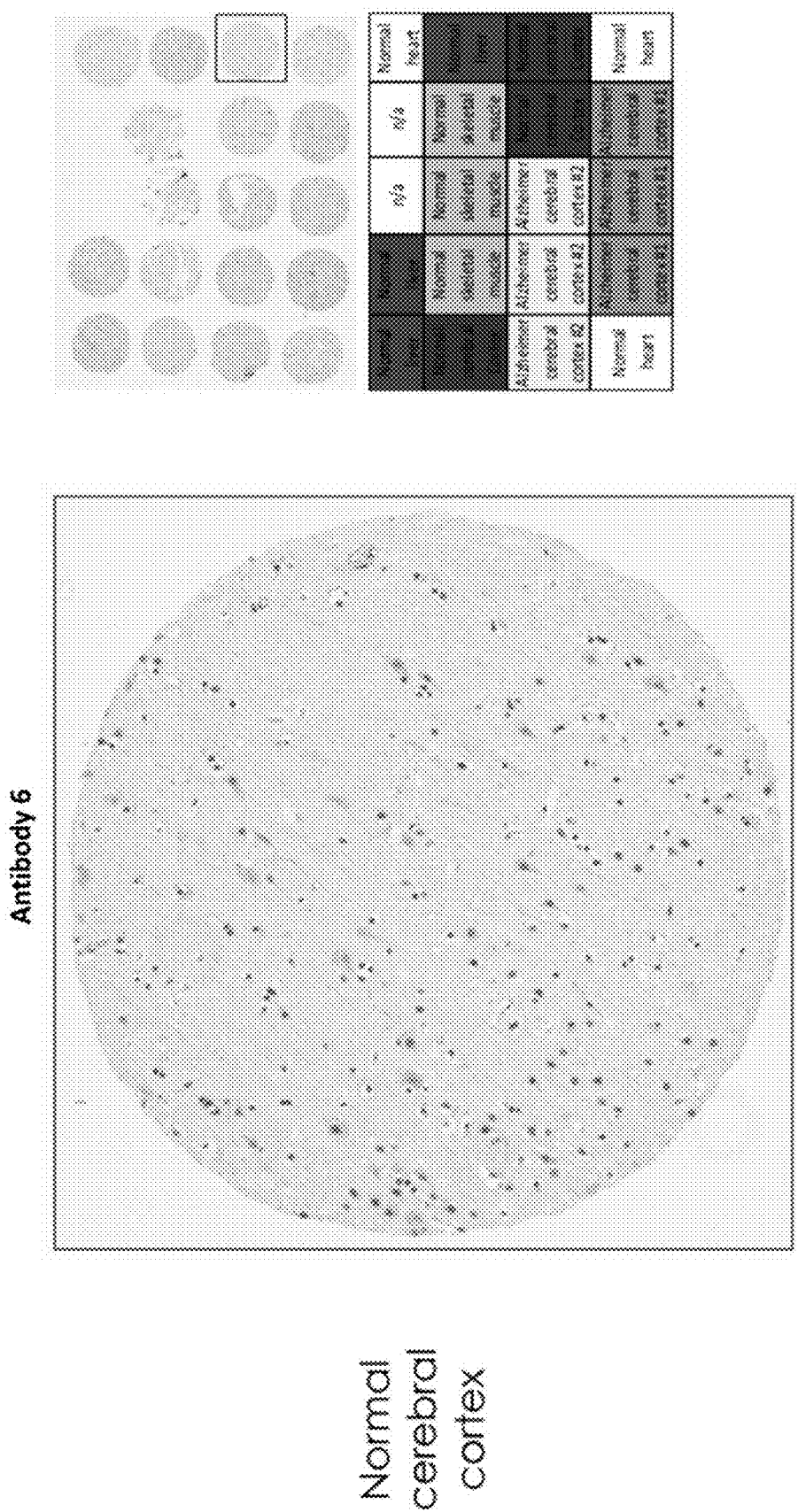
Figure 4G:
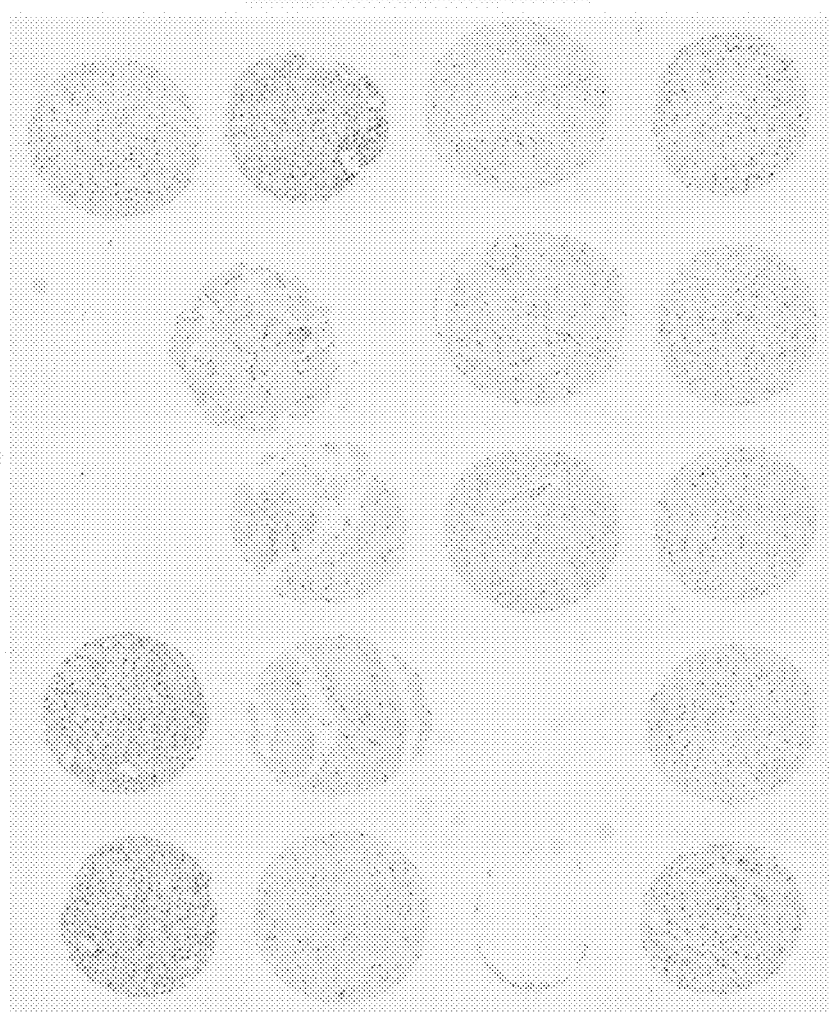
Figure 5A:
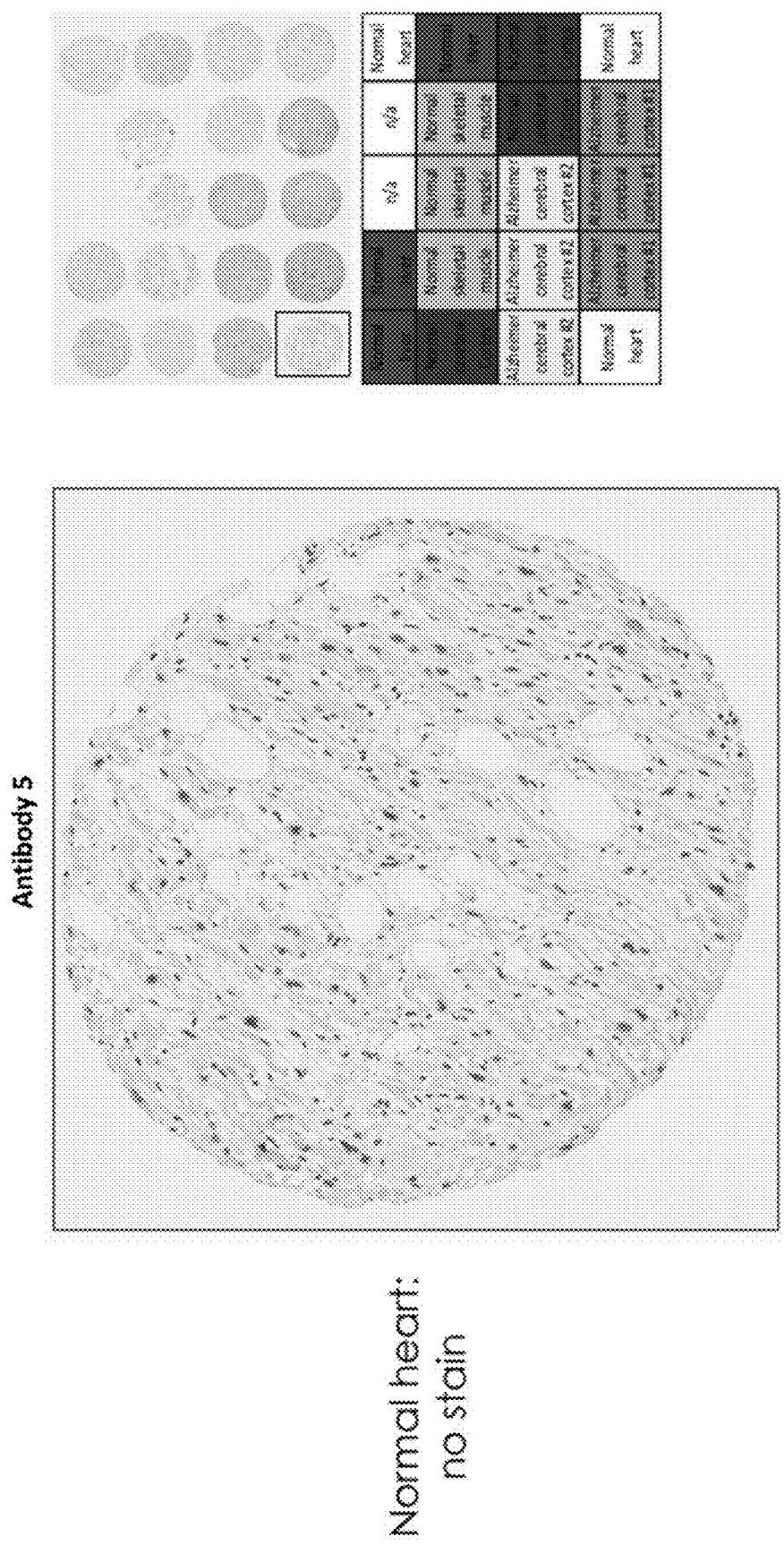
FIGS. 5A-5G depict data for immunohistochemistry staining of Antibody 5.
Figure 5B:
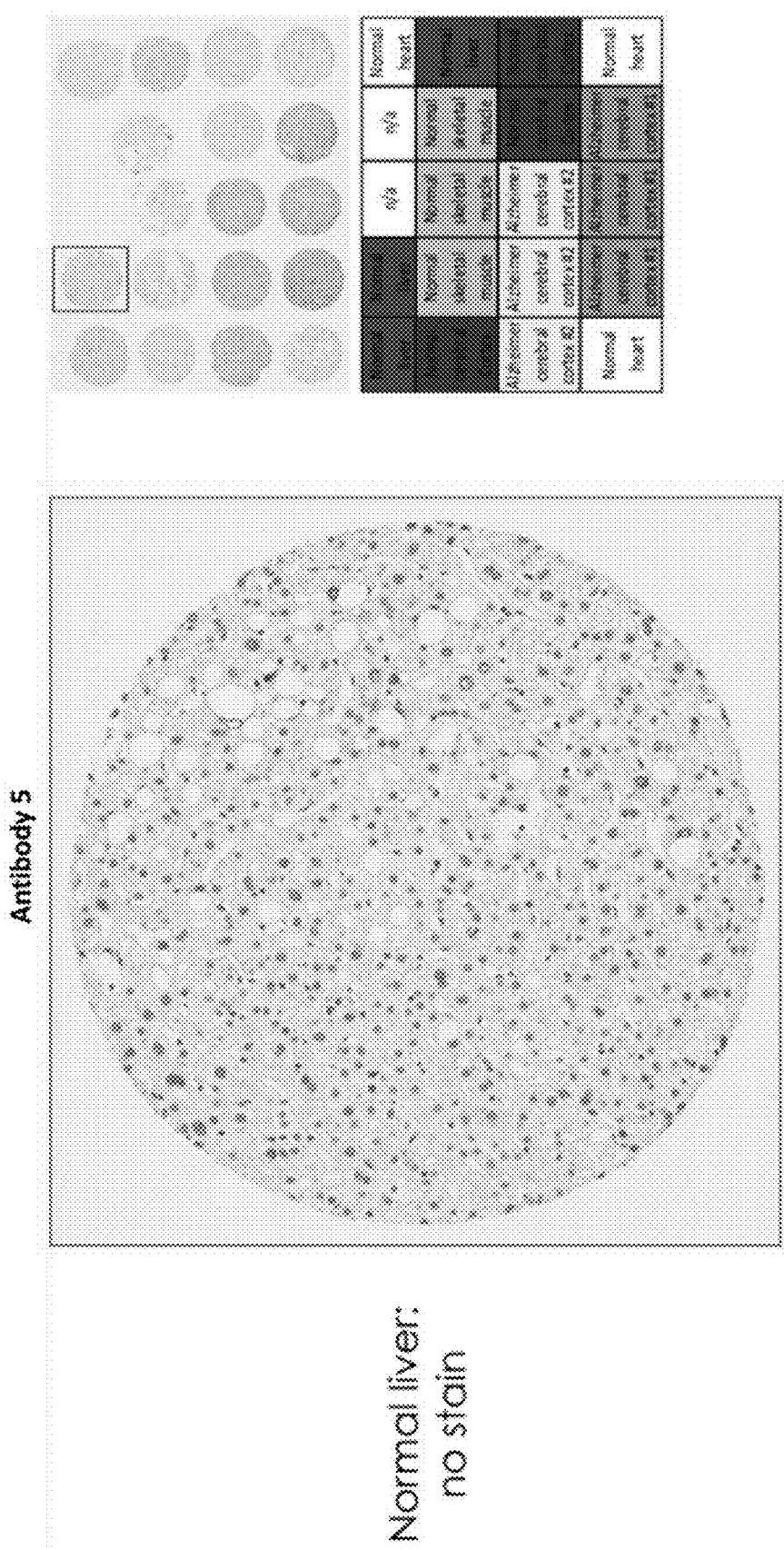
Figure 5C:
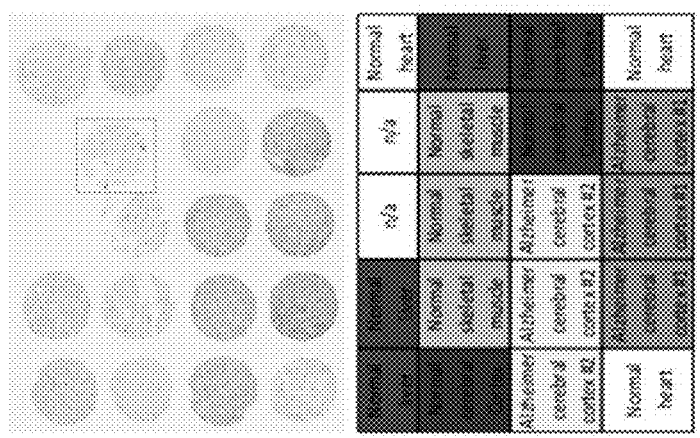
Figure 5C:
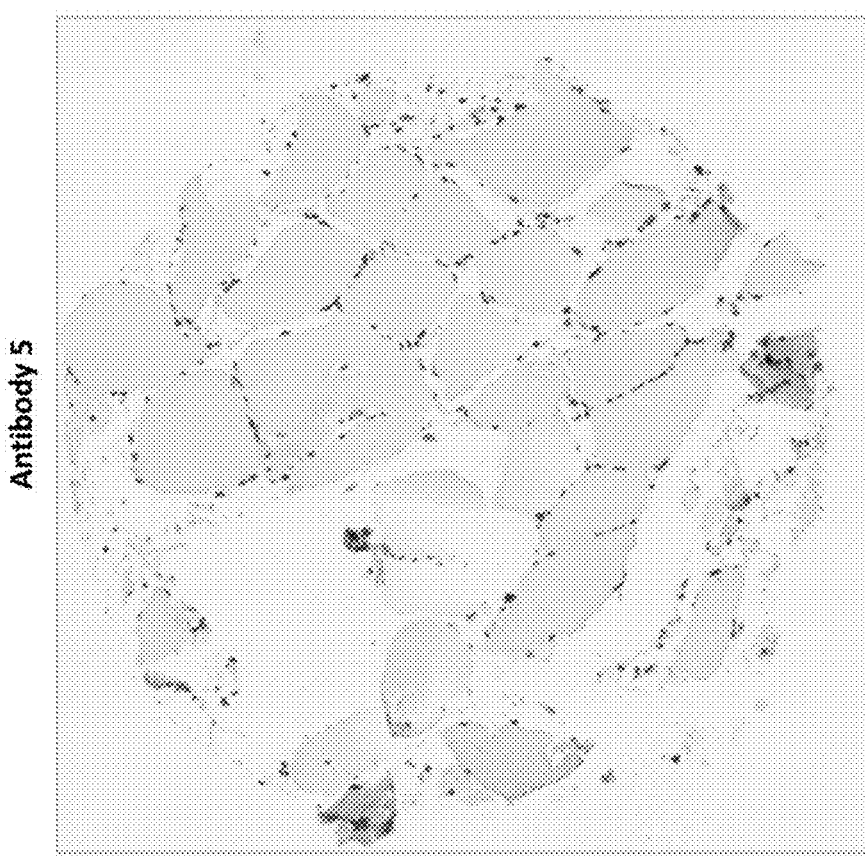
Figure 5D:
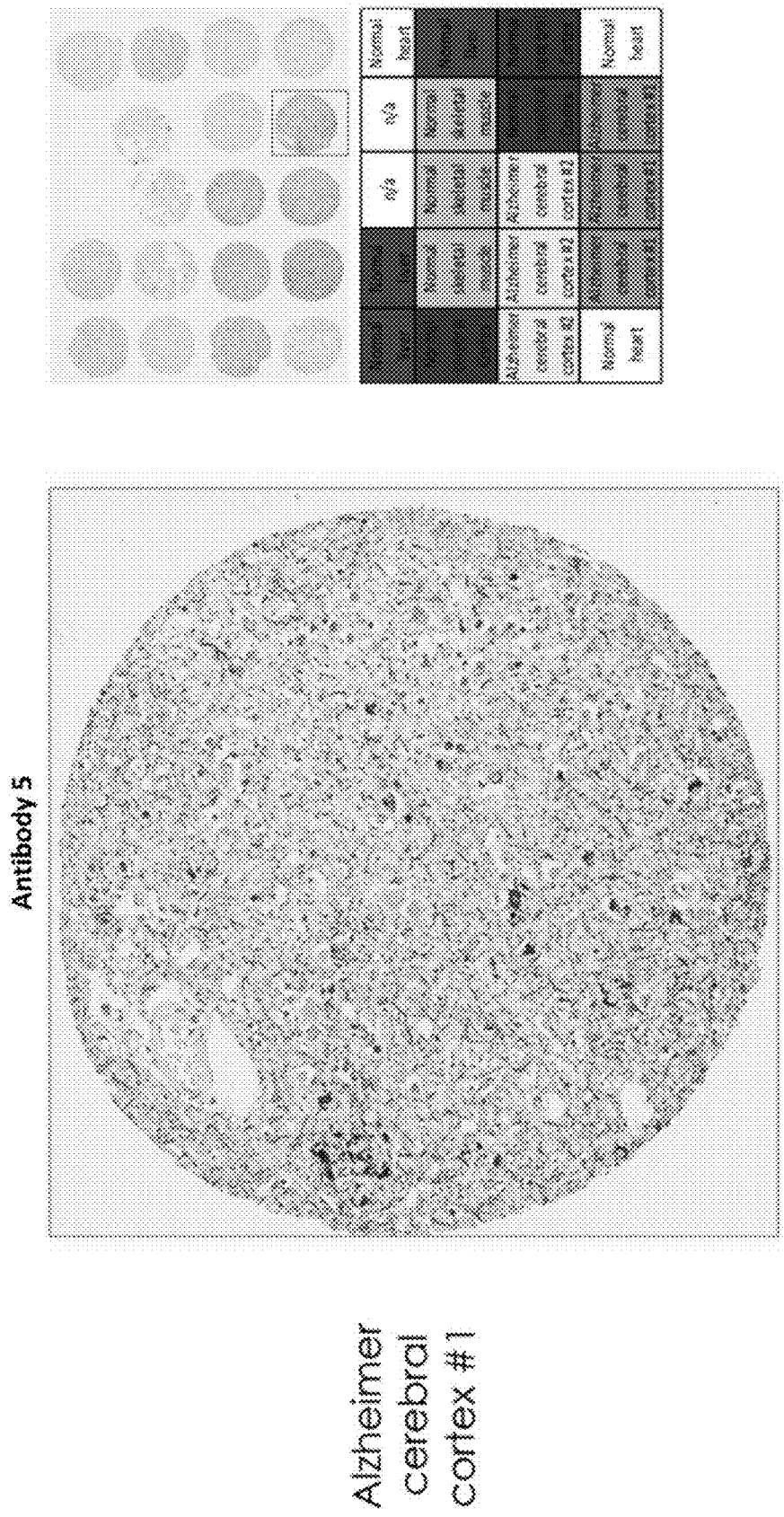
Figure 5E:
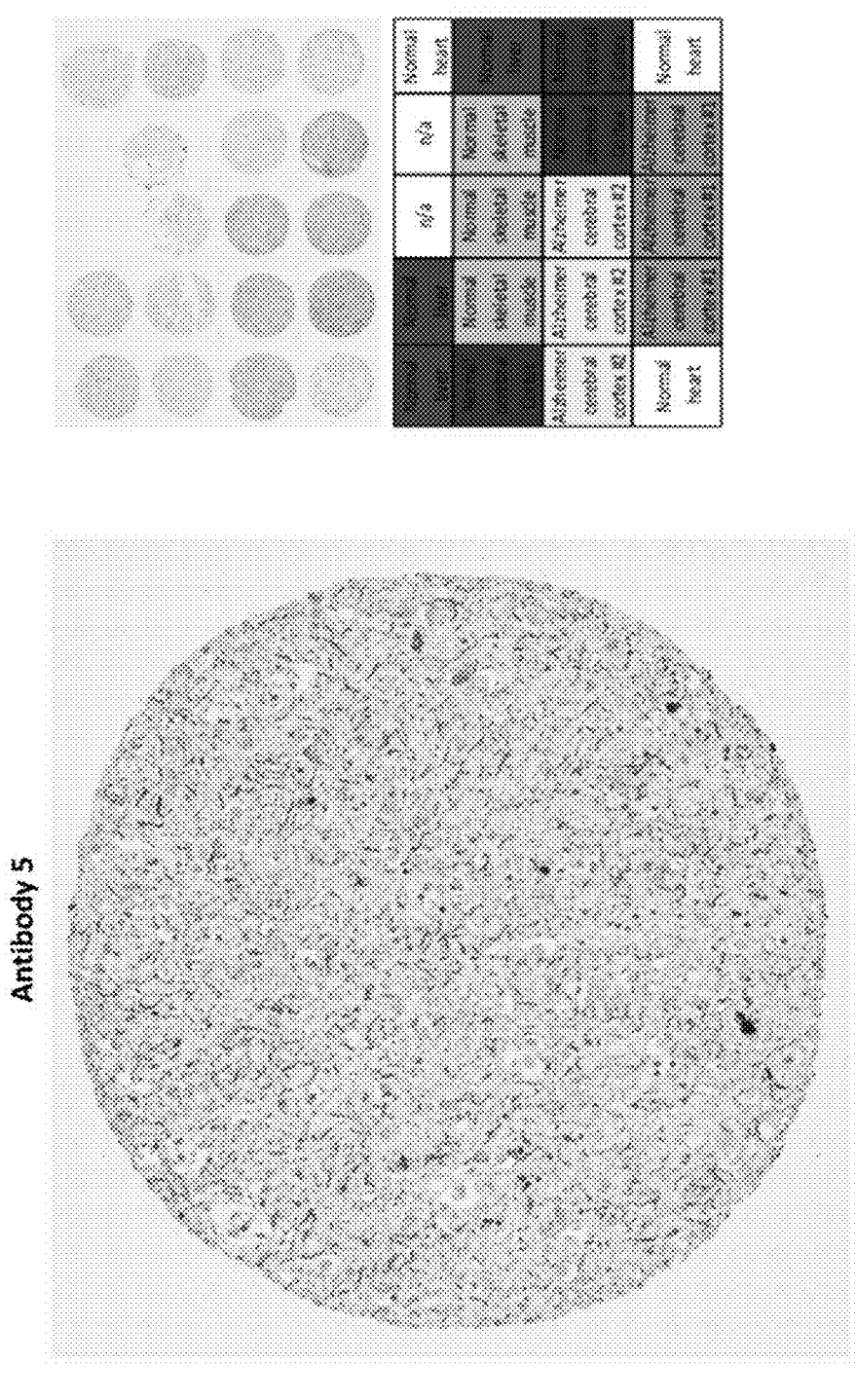
Figure 5F:
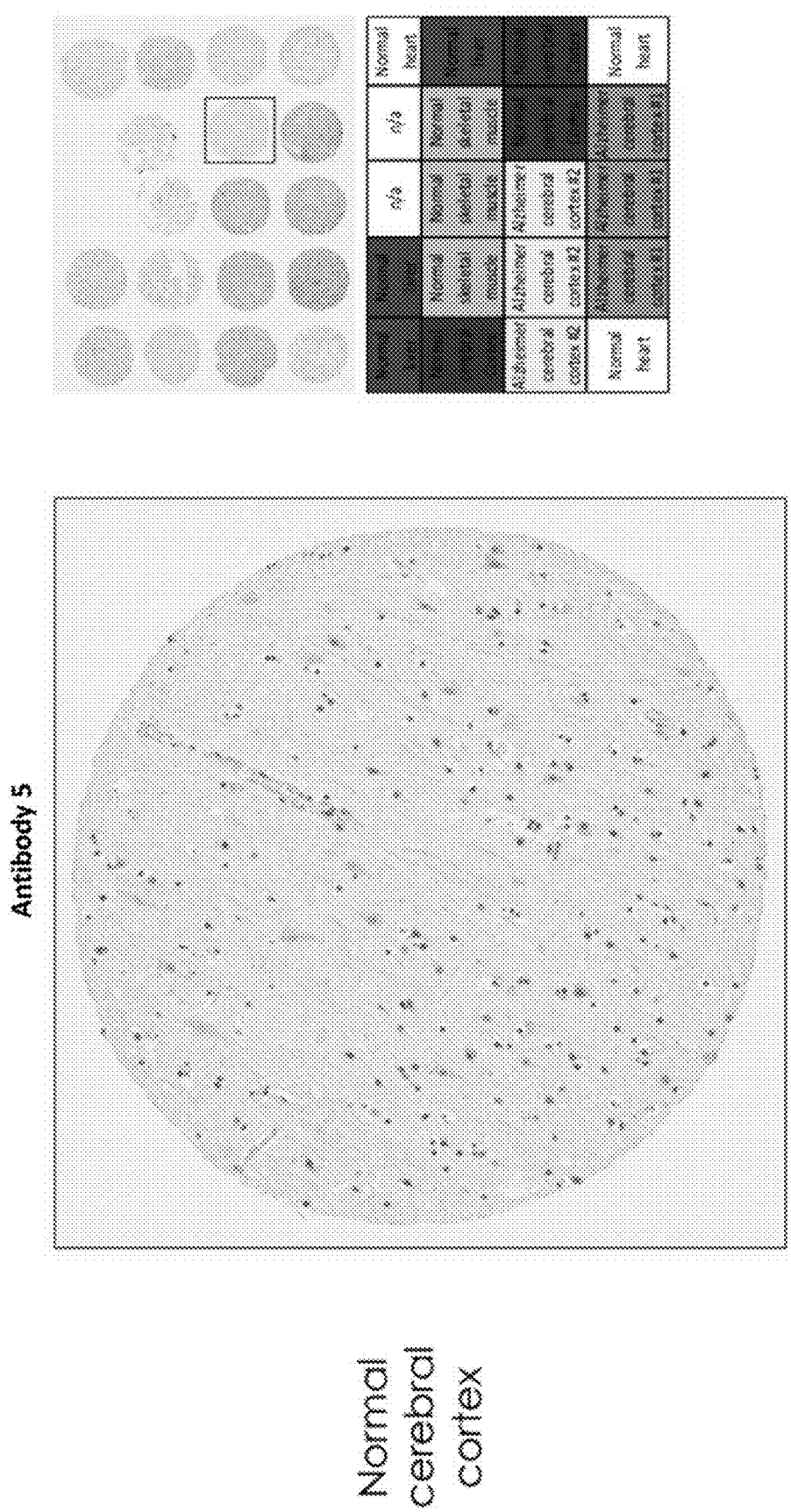
Figure 5G:
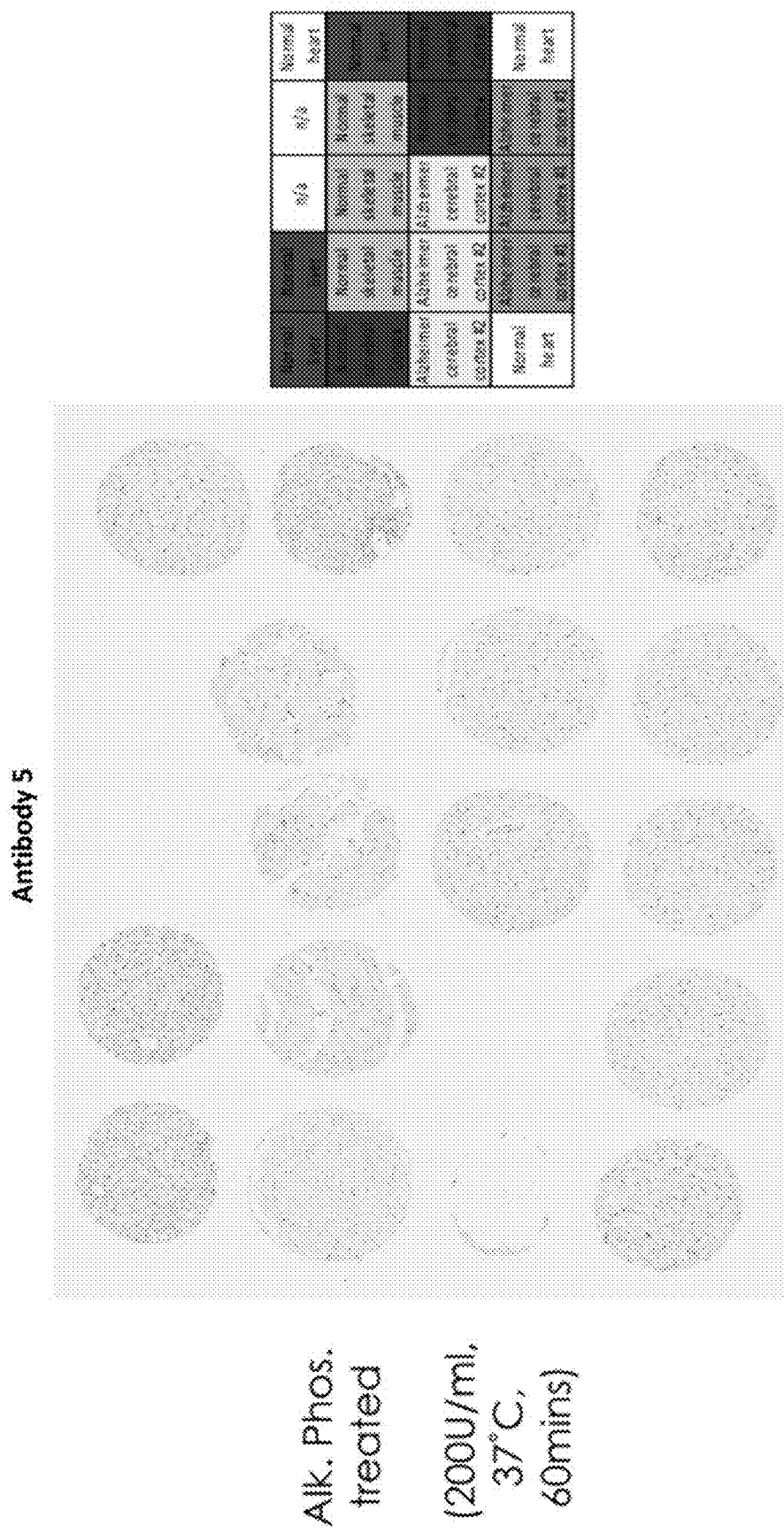
Figure 6A:
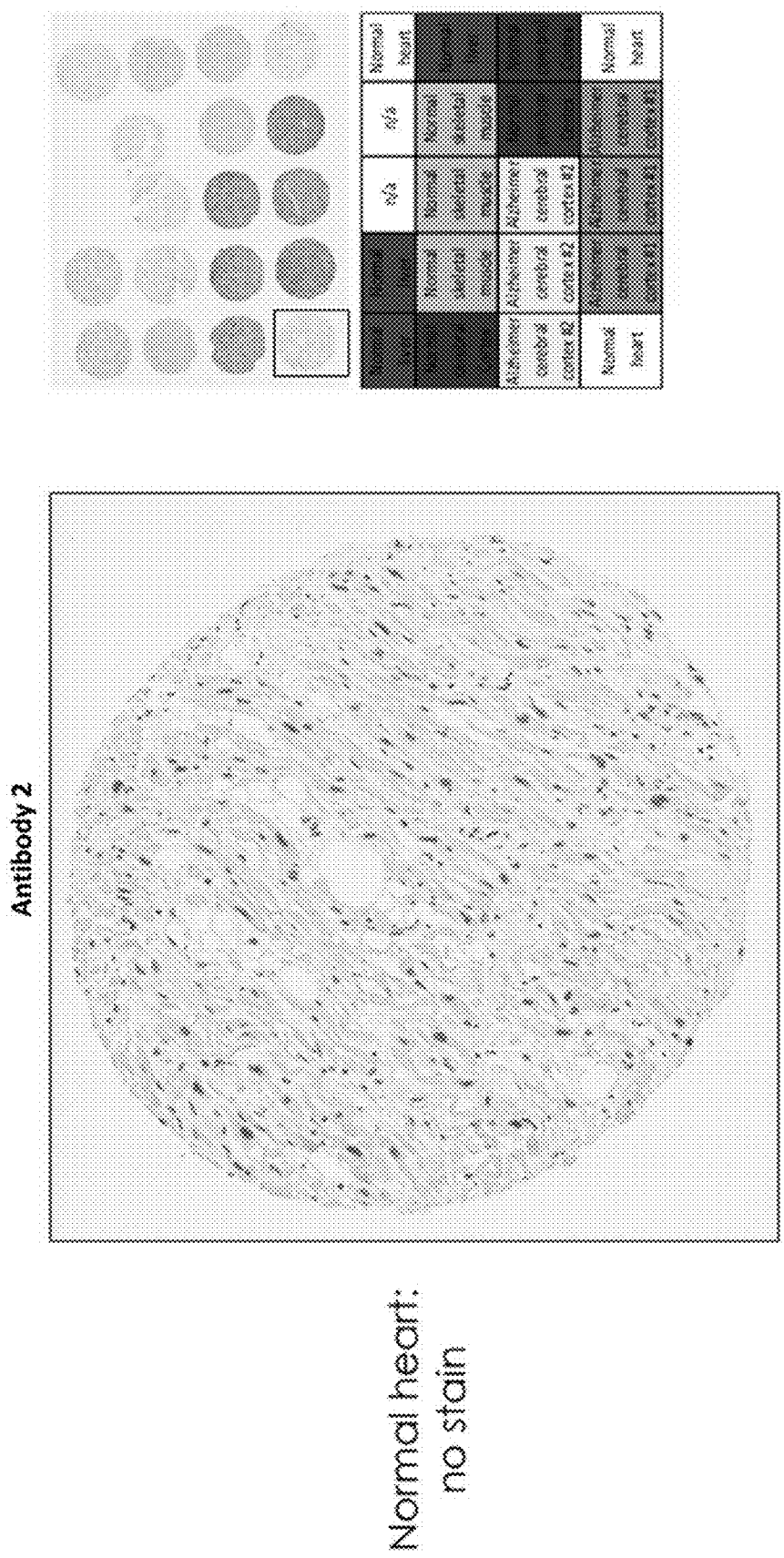
FIGS. 6A-6G depict data for immunohistochemistry staining of Antibody 2.
Figure 6B:
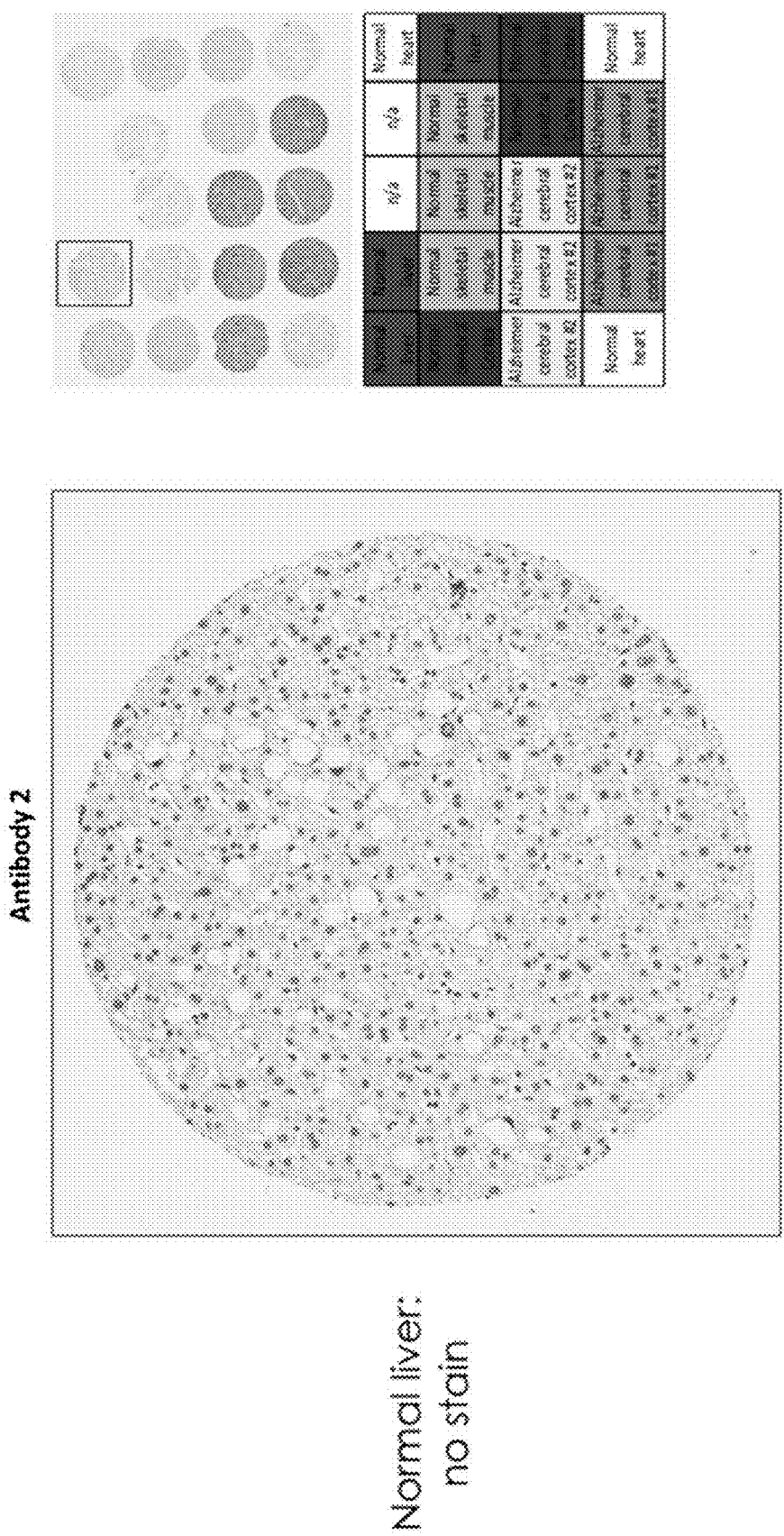
Figure 6C:
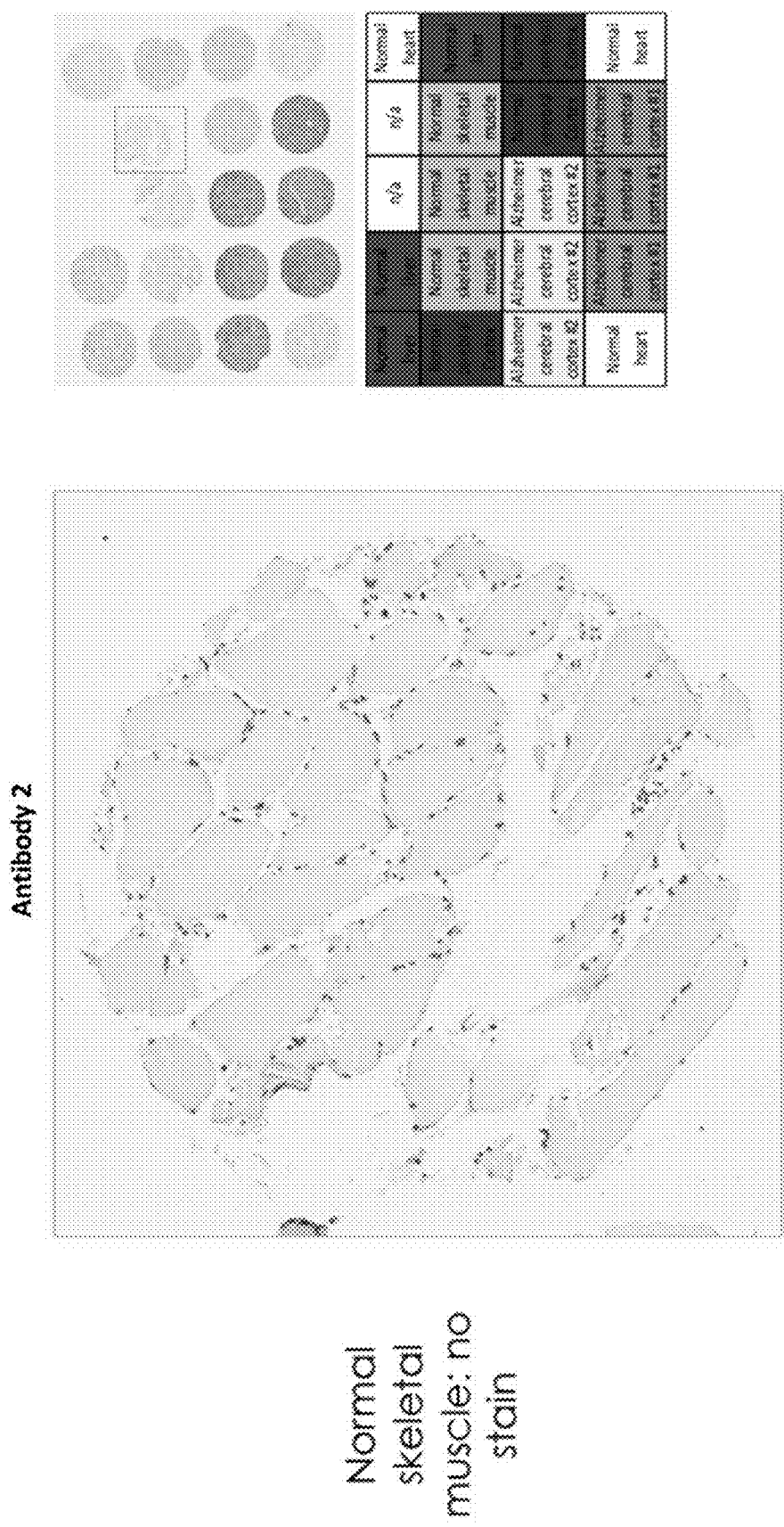
Figure 6D:
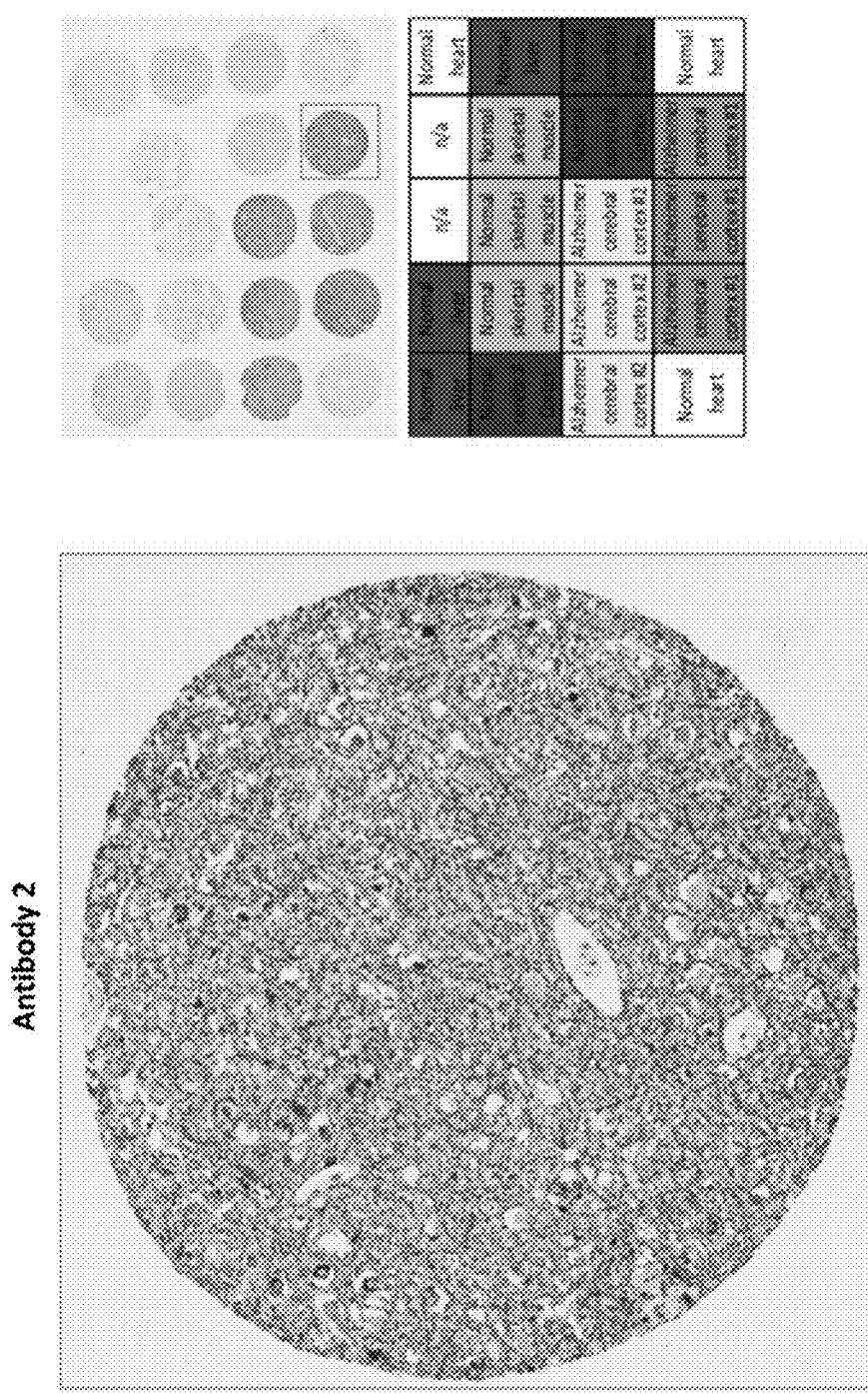
Figure 6E:
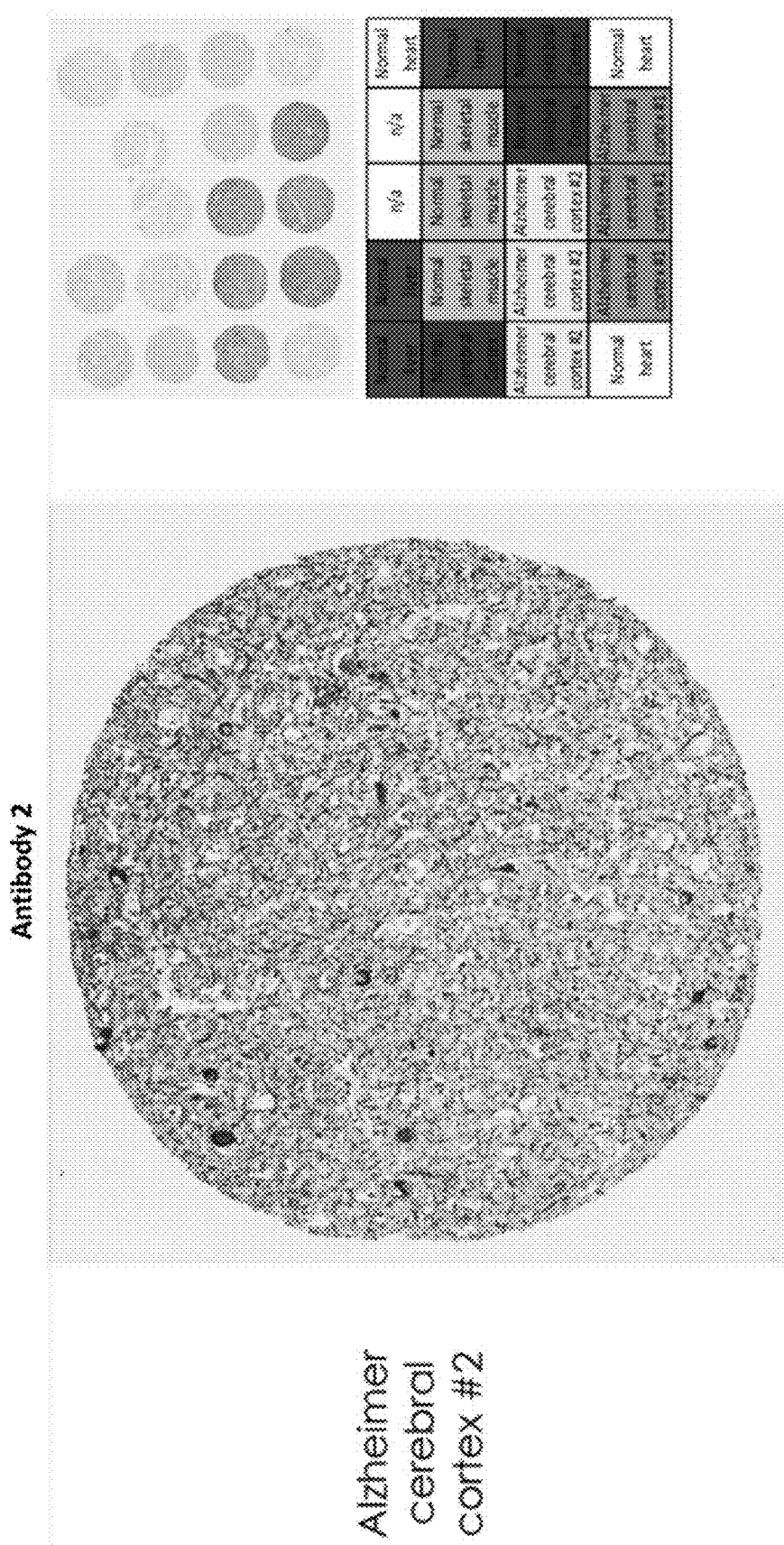
Figure 6F:
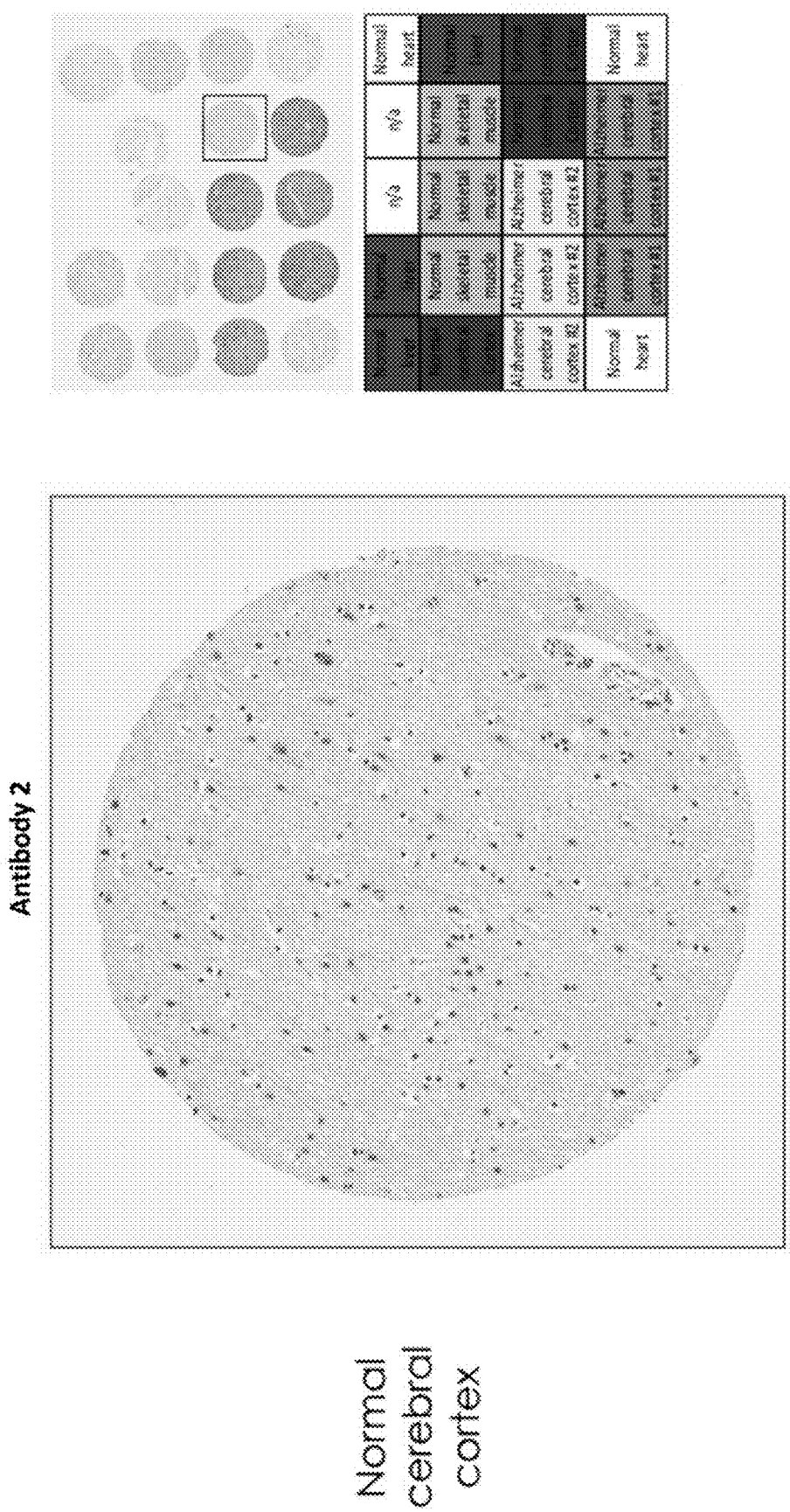
Figure 6G:
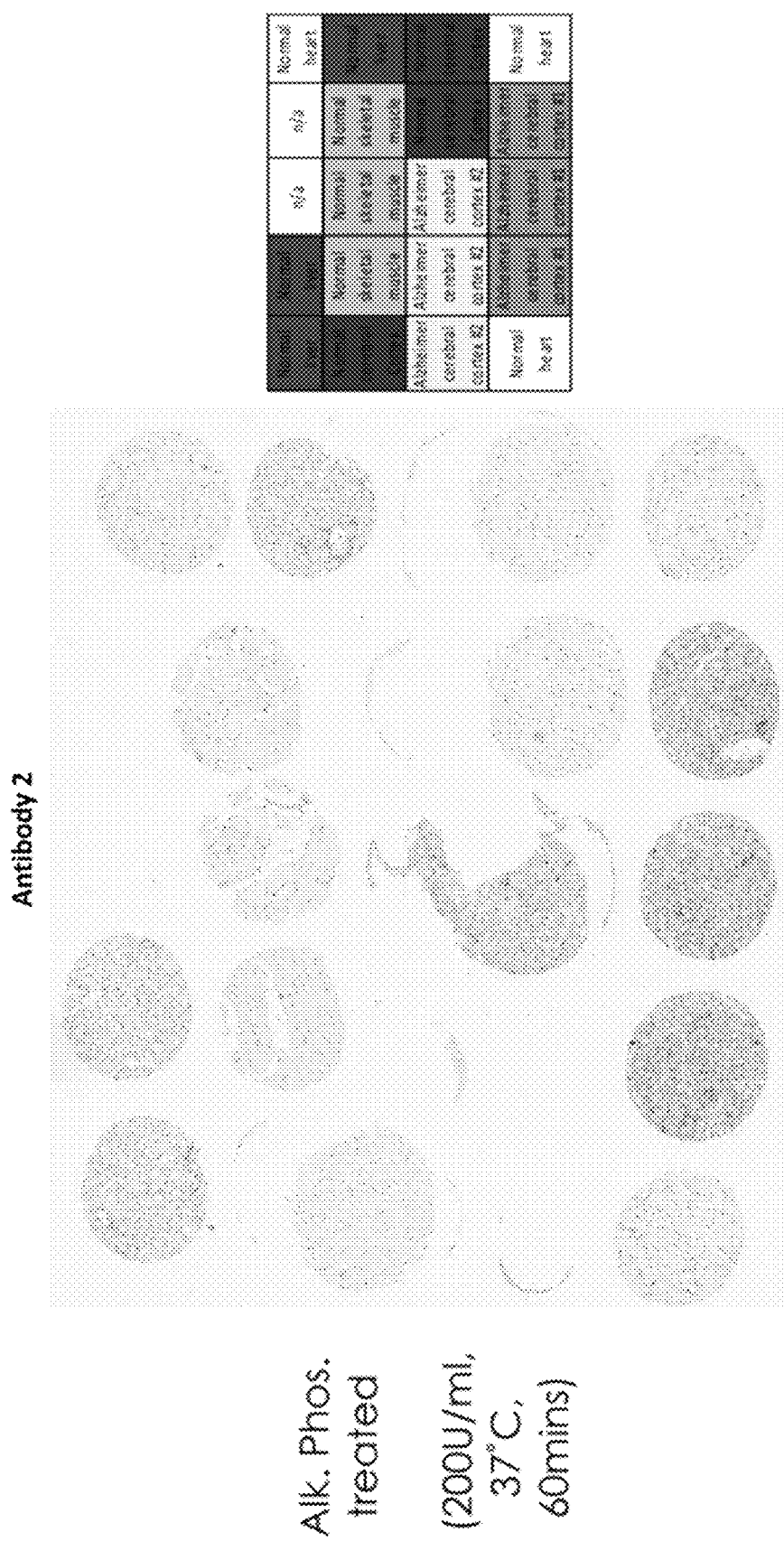

Antibodies were generated and purified. The antibodies were assayed using a standard indirect ELISA protocol. Briefly, peptide antigens corresponding to SEQ ID NOs: 74-81 were diluted to 1 µg/ml in PBS and plated onto a Greiner Bio One Microlon 96 well plate. Peptide antigens were produced by the manufacturer Abcam. WZN-1A and WZN-1B served as targets. WZN-1C, WZN-1D, WZN-1E, WZN-1F, WZN-1G, and WZN-1H served as negative controls. In the peptide antigen sequences, a phosphorylated residue is indicated by (pT) for phosphorylated threonine or (pS) for phosphorylated serine. After blocking with 1% BSA in PBS pH 7.4, antibodies were serially diluted 1 to 4 with an initial concentration of 1 µg/ml. After incubation, unbound antibodies were washed off with 1×TBST and HRP labeled goat anti-rabbit secondary antibody was applied according to the manufacturer's instructions. Subsequently, unbound secondary antibody was washed off with 1×TBST and 3,3'5,5'-tetramethylbenzidine (TMB) was applied for 5 minutes at room temperature and plates were read at 650 nm. Data is seen in FIG. 3. FIG. 3 shows screening data of the different monoclonal antibodies to varying peptide concentrations.

Example 3. Tau Antibodies for Immunohistochemistry

Tau antibodies described herein were tested in immunohistochemistry assays.

Briefly, all antibodies were optimised using a range of concentrations (0.01-3.00 µg/ml) and stained using a Leica Bond RX automated IHC platform: ER1 antigen retrieval (sodium citrate, pH 6) 20 mins at 100° C.; primary antibody 15 minutes at RT; IVD grade Leica Polymer Refine HRP detection 8 minutes at room temperature; DAB chromogen 10 minutes at room temperature, and finally hematoxylin counterstain 5 minutes at room temperature. Antibodies that passed basic IHC staining went on to undergo IHC staining following alkaline phosphatase (AP) treatment (200 U/ml, 37° C. for 60 minutes). A vehicle-only control (buffer containing no AP) was also employed. Positive antigen control tissues were FFPE normal human cerebral cortex and cerebral cortex from an Alzheimer patient. Negative antigen control tissues were FFPE normal human liver, skeletal muscle and heart muscle. All tissues were collated into a tissue micro array to streamline the IHC staining process. Negative reagent (detection system only) controls were employed and shown to be negative. Benchmark antibodies stained alongside the test antibodies were rabbit monoclonal [EPR22524-95] to Tau (ab254256, Abcam plc) and rabbit monoclonal [EPR1884(2)] to Tau (phospho S214) (ab170892, Abcam plc).

The benchmark antibodies demonstrated that the antibodies exhibited negative staining in the negative control tissue and positive staining in the positive control tissue (data not shown). Data for the Tau antibodies is seen in FIGS. 4A-4G (Antibody 6), FIGS. 5A-5G (Antibody 5), and FIGS. 6A-6G (Antibody 2). Antibody 5 and Antibody 6 demonstrated similar data as benchmark antibodies in that negative staining was observed in negative control tissues that included normal heart, normal liver, and normal skeletal muscle, and normal cerebral cortex and positive staining was observed in positive control tissues that included Alzheimer cerebral cortex. Antibodies 1-4 did not exhibit similar data as benchmark antibodies.

Example 4. Detection of Tau Peptides Using Tau Antibodies

Figure 7:
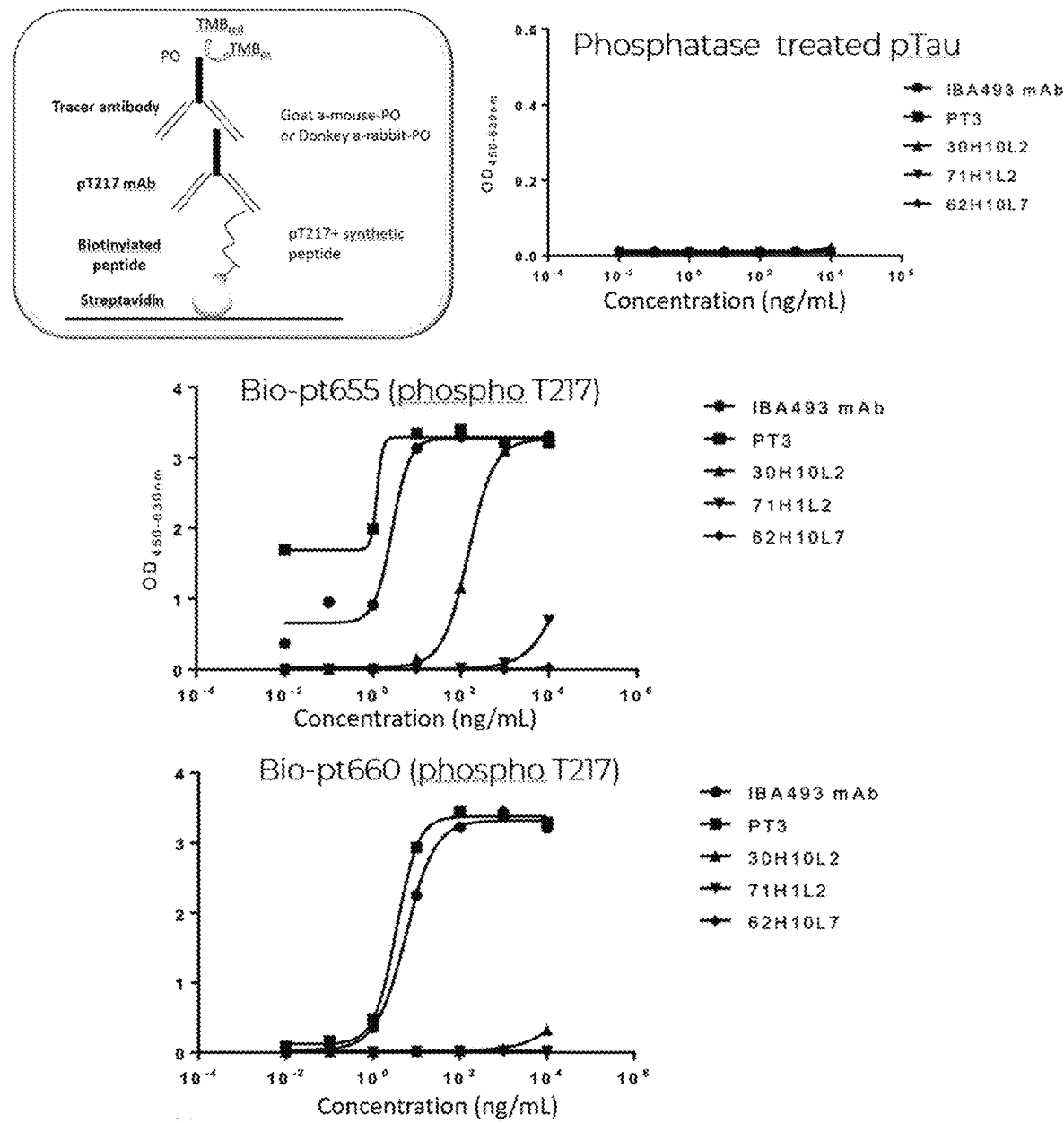
FIG. 7 depicts a diagram of an indirect ELISA assay and graphs of ELISA data assaying antibody binding to pTau-217 peptides.

Tau antibodies described herein that detect phosphorylated Tau were tested in ELISA assays. Tau antibodies were first tested for pTau 217 reactivity by indirect ELISA. FIG. 7 displays a diagram depicting the indirect ELISA assay format utilized. Briefly, streptavidin beads were bound to a plate and biotinylated peptide was added to the plates under conditions allowing for biotin-streptavidin binding. The biotinylated peptide was a synthetic peptide comprising a portion of Tau and possessing a phosphorylated threonine residue at position 217 (pT217). This was the target peptide. After binding of the synthetic peptide to the plate by the formation of the biotin-streptavidin complex, Tau antibodies were added to the plates under conditions allowing for antibody-target peptide binding. After binding, plates were washed to remove any unbound antibody and plates then had a secondary antibody, or a tracer antibody, added (either goat anti-mouse antibody conjugated to peroxidase or donkey anti-rabbit antibody conjugated to peroxidase) directed to the species from which the Tau antibodies were derived. After binding, plates were washed to remove any unbound tracer antibody and plates next had TMB ELISA Peroxidase chromogenic substrate (3, 3', 5, 5'-Tetramethylbenzidine) added to visualize antibody reactivity in indirect ELISA experiments. Antibody sample binding was quantitated using an ELISA microplate reader.

As shown in FIG. 7, five antibodies were tested for an ability to detect phosphorylated Tau using this indirect ELISA technique. IBA493 mAb corresponds to a rabbit anti-Tau antibody capable of binding to Tau phosphorylated at threonine residue 217 (pTau 217) (Eli Lilly and Company). PT3 corresponds to a mouse anti-phospho (T212/T217) Tau selective antibody (Janssen Biotech Inc.). 30H10L2 corresponds to Antibody 2 described herein. 71H1L2 corresponds to Antibody 6 described herein. 62H10L7 corresponds to Antibody 5 described herein. All five antibodies were assayed for reactivity with pTau 217 in two separate ELISA instruments at the following concentrations: $10^{-2}$, $10^{-1}$, $10^{-0}$, $10^{1}$, $10^{2}$, $10^{3}$, and $10^{4}$ ng/mL per plate. As can been seen in the Bio-pt655 (phospho T217) and Bio-pt660 (phospho T217) graphs, both IBA493 mAb and PT3 demonstrated a robust, concentration-dependent level reactivity to pTau 217. Antibody 2 demonstrated a more modest concentration-dependent level reactivity to pTau 217 revealed at $10^4$ ng/mL per plate. Antibody 5 and Antibody 6 did not demonstrate reactivity to pTau 217 in these assays. A graph in FIG. 7 showing the results of this ELISA assay using the five test antibodies on phosphatase-treated pTau demonstrated the specificity of antibodies IBA493 mAb, PT3, and Antibody 2 in detecting phosphorylated Tau.

Tau antibodies described herein that detect phosphorylated Tau were tested in Simoa®-based assays. FIGS. 8-24 display results Simoa® assays designed to sensitive tests for Tau reactivity to antibodies described herein. In some aspects, Simoa®-based assays can be approximately 1000× more sensitivity at detecting a given analyte when compared to detection of the same analyte in an indirect ELISA assay. This elevated sensitivity of Simoa®-based assays allows for the development and use of biomarkers that previously could not have generated a detectable signal using a traditional assay such as indirect ELISA. The elevated sensitivity of Simoa®-based assays when compared to conventional immunoassays such as indirect ELISA is due to the fact that the Simoa® method is capable of detecting single target molecules whereas conventional immunoassays typically require large reaction volume and millions of fluorophores, or millions of antibody-conjugated enzymes reacted to a color-producing substrate, before an optical signal can be detected. For Simoa®-based assays, average enzyme per bead (AEB) denotes raw signal output.

Figure 8:
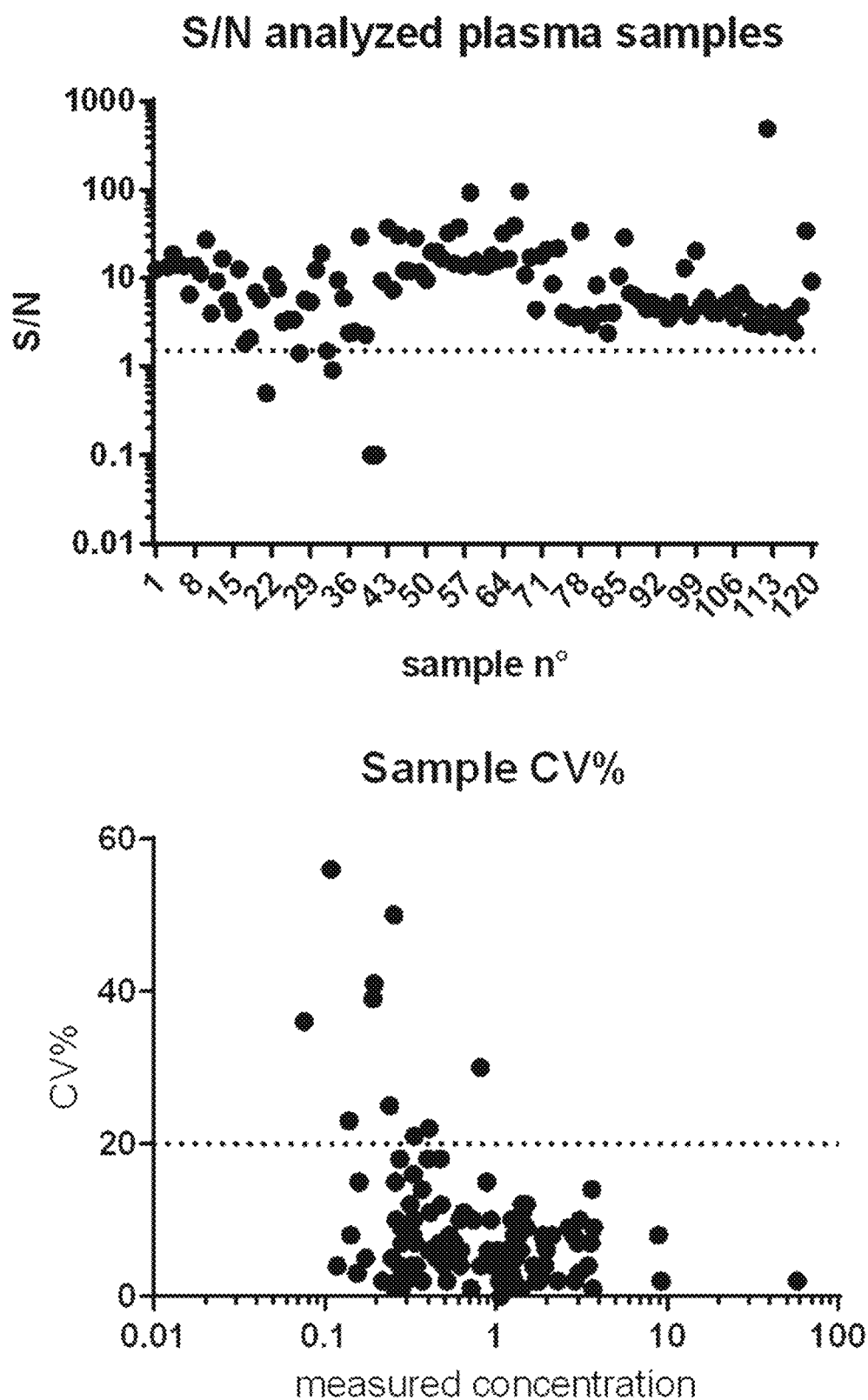
FIG. 8 depicts a graph of signal/noise (S/N) analysis of ELISA assay for Antibody 2 binding to a pTau-217 peptide for 120 clinic samples derived from plasma and a graph of a coefficient of variation (CV %) for ELISA assay for Antibody 2 binding to a pTau-217 peptide for 120 clinic samples derived from plasma.

In FIG. 8, Antibody 2, as described herein and is capable of detecting pTau 217, was used in a Simoa®-based assay to detect a level of an analyte per plasma sample derived from an individual. Signal-to-noise (S/N) ratio was determined by Simoa® for each sample and plotted in a graph. 120 plasma samples were taken from individuals and assayed. The graphed S/N ratio indicated that all tested samples apart from one yielded a signal within the expected concentration range. When plasma samples were diluted 1:3 and then assayed again, only 3 of the 120 samples yielded a result below measurement of a blank control and only 5 samples registered a measurement of S/N 1.5, which was determined to be the limit of detection (LOD). In FIG. 8, with each of the 120 plasma samples assayed, a calculation was made to determine the coefficient of variation (CV %) for each sample and the results were graphed against measured concentration. 10 of the 120 samples yielded a CV % greater than 20 and from this analysis, the estimated analytical lower limit of quantitation (LLOQ) was determined to be 0.08 pg/mL. This LLOQ value represents the lowest amount of an analyte (Tau phosphorylated at T217) that can be quantitatively determined with an acceptable level of precision. These results in FIG. 8 indicated the sensitivity of the Simoa® method to detect Tau phosphorylated at T217 using Antibody 2.

Figure 9:
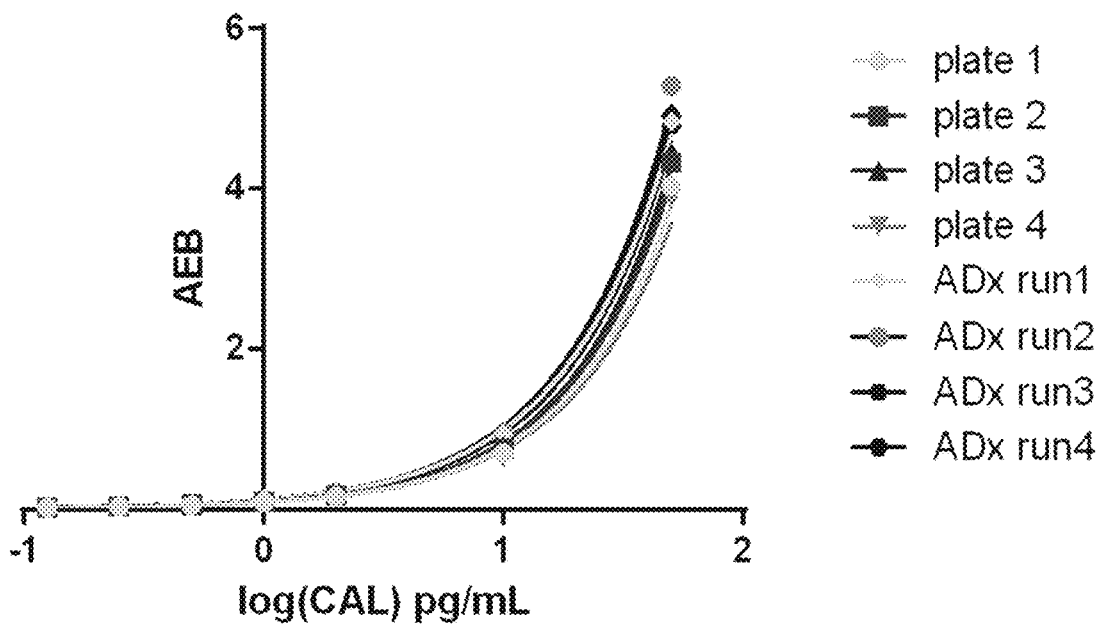
FIG. 9 depicts graphs of calibration curves (Cal curves) for a Simoa®-based pTau-217 assay using Antibody 2 on groups (plates) designated QTx of clinical samples derived from cerebrospinal fluid (68 CSF samples) and plasma (120 plasma samples) compared to the assay using ADx p204 antibody.
Figure 9:
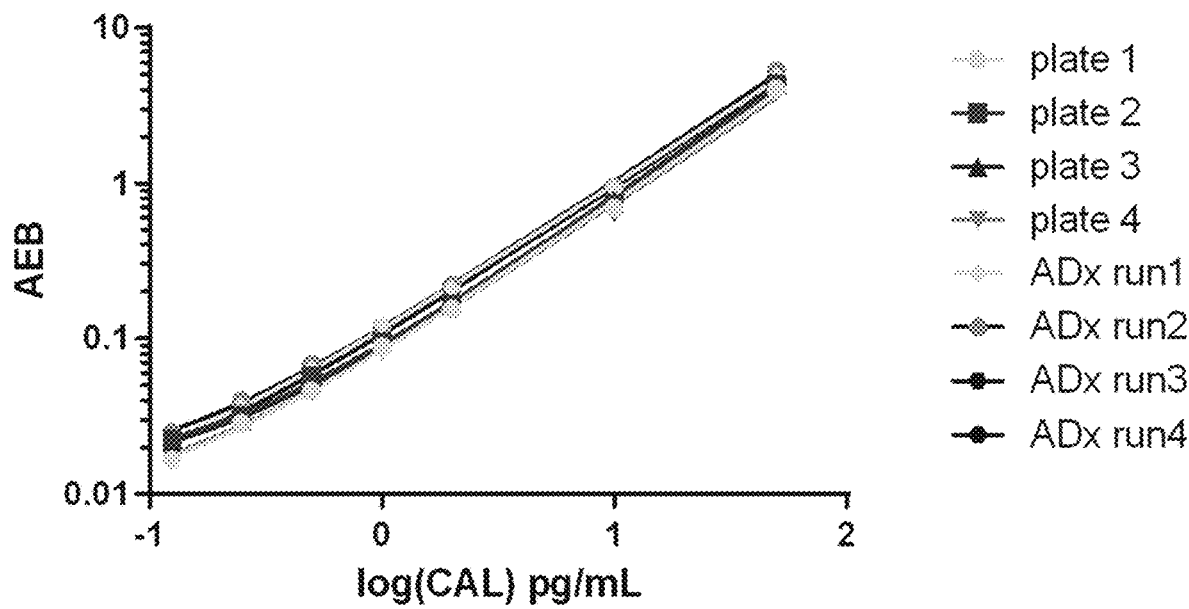

In FIG. 9, calibration curves were generated for the Simoa® pTau-217 assay and graphed [AEB vs log(CAL) pg/mL] using 68 CSF samples and 120 plasma samples separated into 4 plates using Antibody 2 and 4 plates using ADx Neuroscience antibody ADx204. In another graph from this assay performed on a separate instrument [AEB vs log(CAL) pg/mL] with AEB plotted on a log scale demonstrated the fit of the data can enable accurate analyte quantitation calculations when measuring samples.

Figure 10:
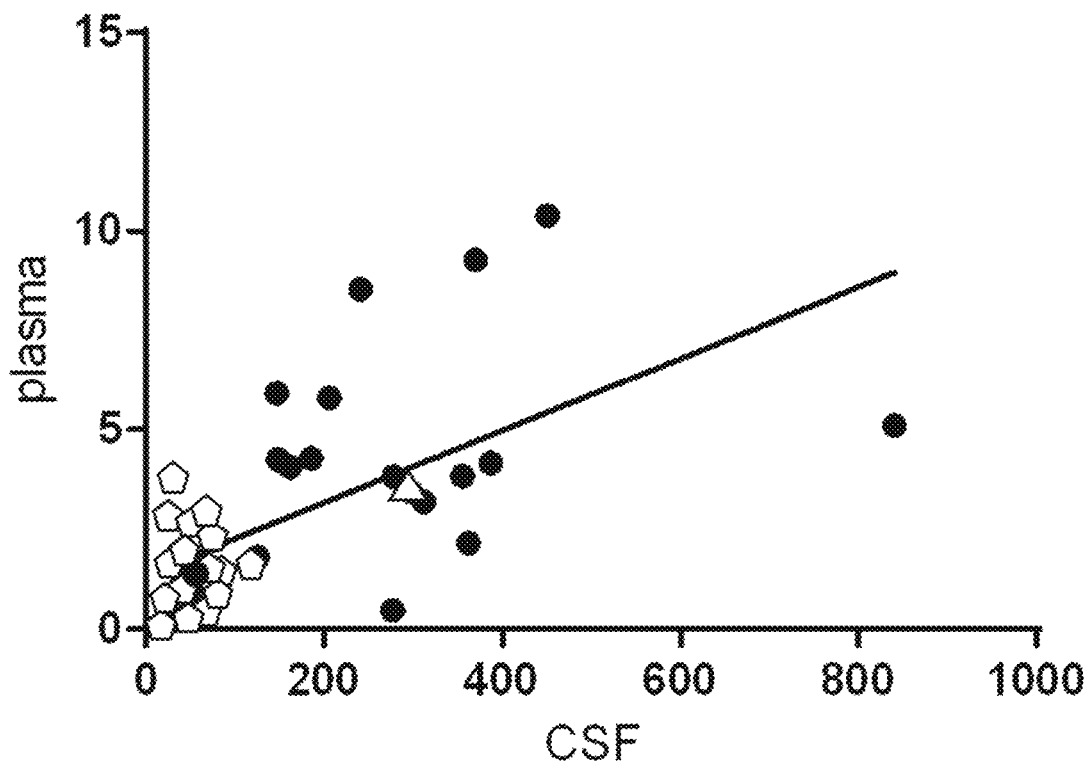
FIG. 10 depicts a graph of Simoa®-based pTau assay-217 results using Antibody 2 in matched samples from the sample individual derived from either plasma (Y-axis) or CSF (X-axis) and statistical analysis of correlated results in individual with a clinical diagnosis of either non-Alzheimer's disease, an uncertain diagnosis, or Alzheimer's disease.

In FIG. 10, 38 paired CSF and EDTA plasma samples were measured with the Simoa® pTau-217 assay using Antibody 2. This assay is also named as ALZpath Dx. Results were graphed and samples were indicated with their clinical diagnosis (non-AD, uncertain, or AD). These results, and the statistical analysis thereof, indicated a strong correlation between CSF and plasma pTau levels as measured with the Simoa® pTau-217 assay using Antibody 2 (R value ~0.7 and P value for two-tailed T test <0.0001 between non-AD and AD).

Figure 11:
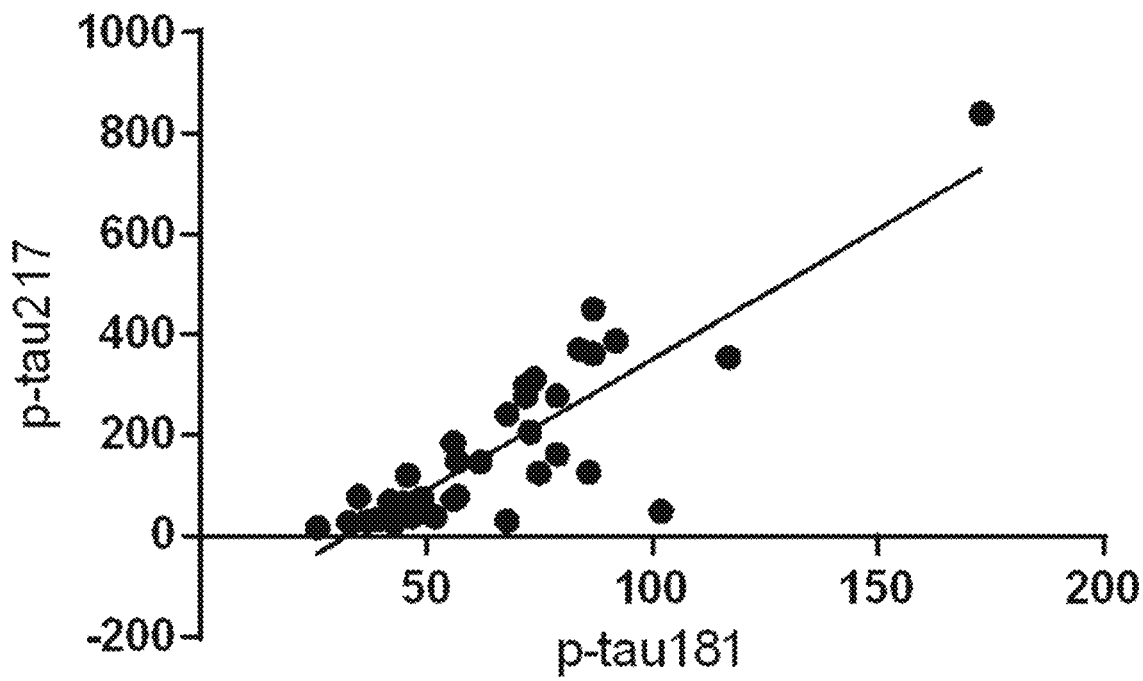
FIG. 11 depicts a graph of Simoa®-based pTau assay-217 results using Antibody 2 per sample vs Simoa®-based pTau assay-181 results using Antibody 2 per sample and statistical analysis of correlated results.

In FIG. 11, 42 CSF samples were measured with the Simoa® pTau-217 assay using Antibody 2 and a Simoa® pTau-181 assay using a pTau-181 antibody from Quanterix® (Quanterix® Corp., Item number 103714) and plotted against each other. This demonstrated that the Simoa® pTau-217 assay using Antibody 2 showed the expected relationship with an analyte implicated in AD detected in CSF (pTau-181). Statistical analysis indicated an R value ~0.8 and P value for two-tailed T test <0.0001.

Figure 12:
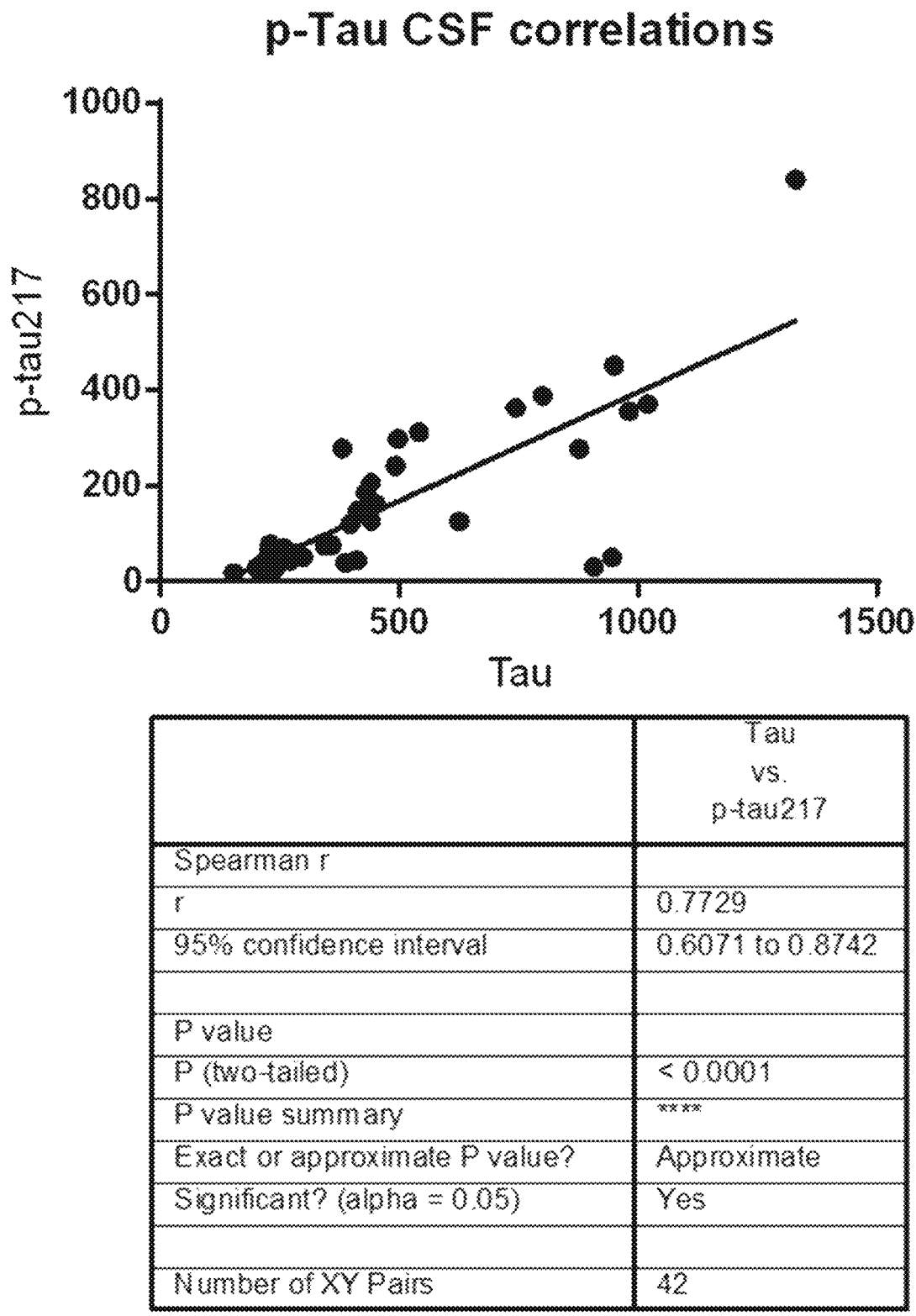
FIG. 12 depicts a graph of Simoa®-based pTau assay-217 results using Antibody 2 per sample vs Simoa®-based Tau assay results using Innotest pTau 181 antibody per sample and statistical analysis of correlated results.

In FIG. 12, 42 CSF samples were measured with the Simoa® pTau-217 assay using Antibody 2 and a Simoa® pTau assay using Innotest pTau-181 antibody and plotted against each other. This demonstrated that the Simoa® pTau-217 assay using Antibody 2 showed the expected relationship with an analyte implicated in AD detected in CSF (pTau). Statistical analysis indicated an R value ~0.77 and P value for two-tailed T test <0.0001.

Figure 13:
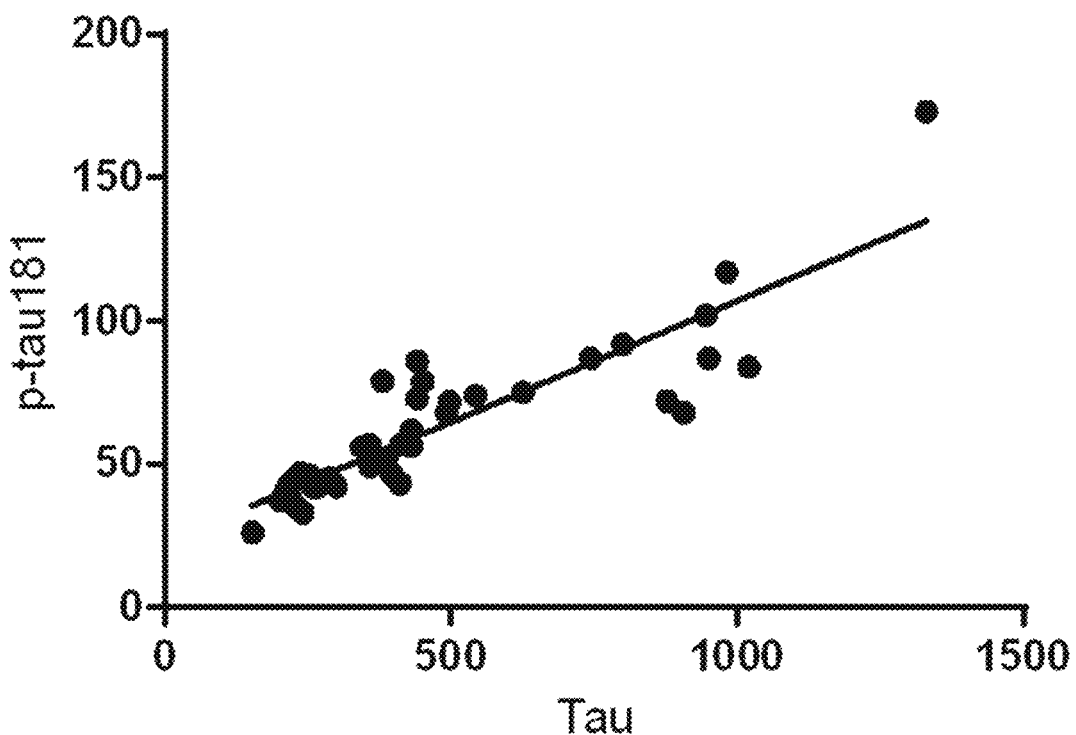
FIG. 13 depicts a graph of Simoa®-based pTau assay results using Antibody 2 as a capture antibody, antibody ADx p204 as a detector antibody and a peptide as calibrator and statistical analysis of correlated results.

In FIG. 13, 42 CSF samples were measured with a Simoa® HD-X assay using Antibody 2 as a capture antibody, ADx204 antibody as a detector, and a peptide as calibrator. This demonstrated that the Simoa® assays using known AD biomarkers showed the expected relationship. Statistical analysis indicated an R value ~0.9 and P value for two-tailed T test <0.0001.

Figure 14:
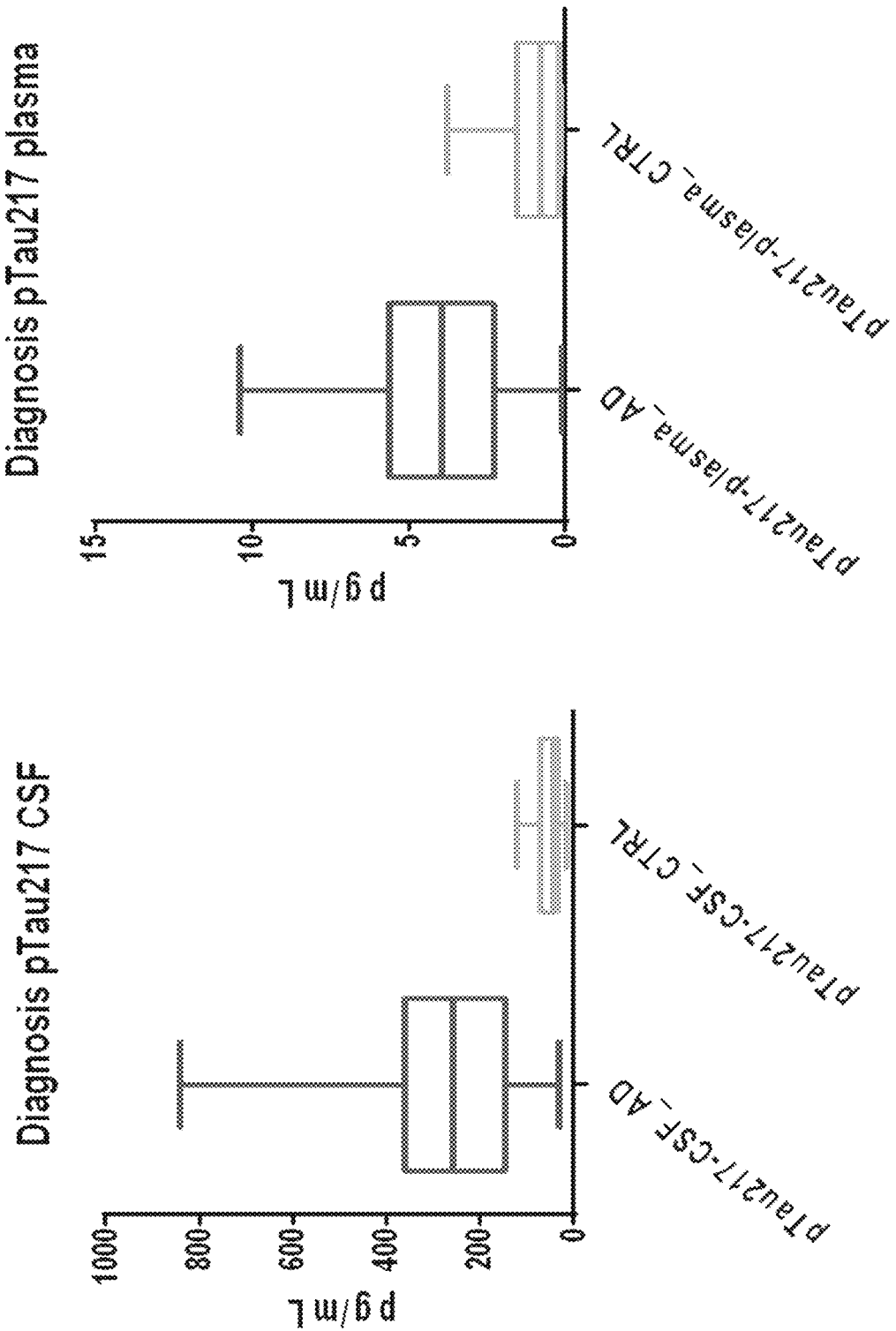
FIG. 14 depicts a graph of Simoa®-based pTau assay-217 results using Antibody 2 grouping together samples from individuals with a clinical diagnosis of Alzheimer's disease and samples from control individuals derived from either CSF or plasma.

In FIG. 14, CSF samples and plasma samples were measured with the Simoa® pTau-217 assay using Antibody 2 and graphed in separate graphs. Clinical diagnosis of AD, or control with no AD diagnosis, was used as the classifier for each sample. Analysis of the graphed results indicated a significant difference between samples derived from individuals with a clinical AD diagnosis vs controls for both CSF samples and plasma samples. Area under the curve (AUC) calculation was 0.94 for CSF samples and 0.86 for plasma samples. These results indicated that the Simoa® pTau-217 assay using Antibody 2 was able to differentiate AD cases in CSF and plasma.

Figure 15:
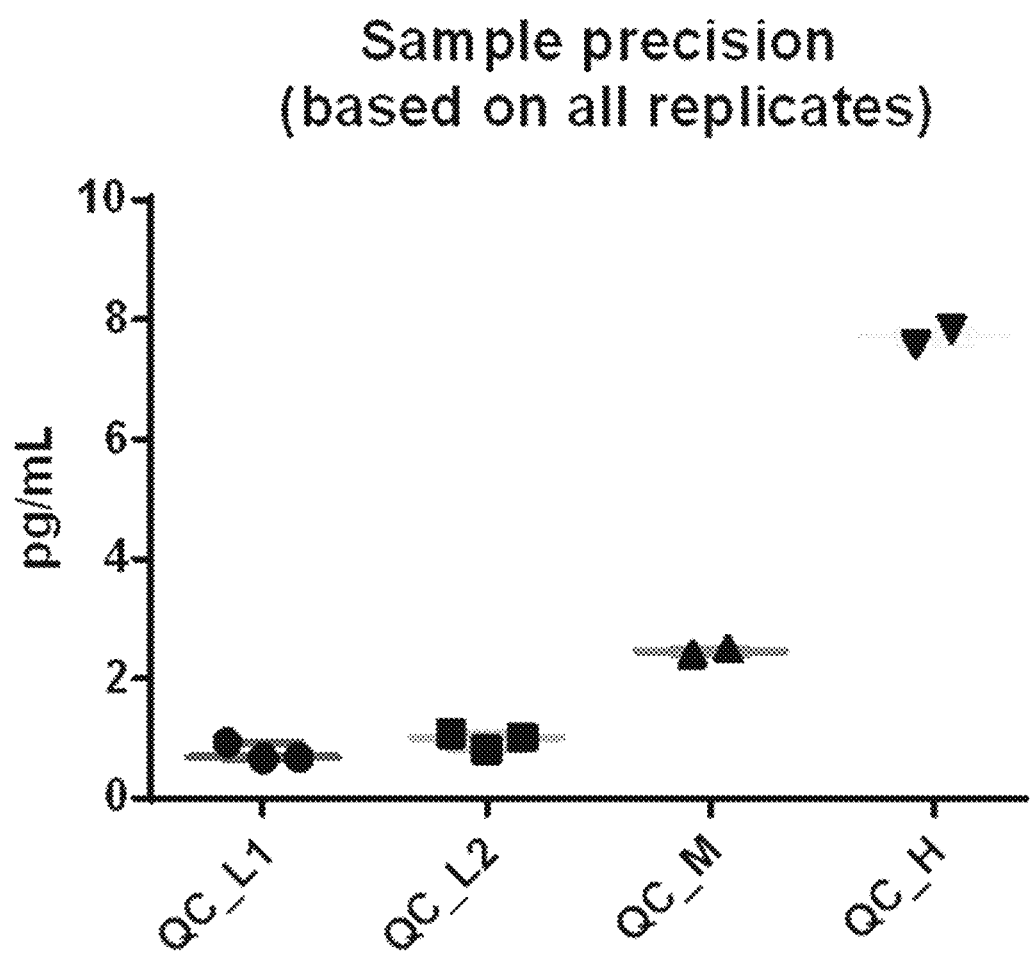
FIG. 15 depicts a graph of Simoa®-based pTau assay-217 results using Antibody 2 on various concentrations of EDTA plasma samples and a chart of listing coefficient of variation for each sample concentration to illustrate the precision of the assay.

In FIG. 15, 4 EDTA plasma samples with high pTau levels serve as quality controls (labelled QC_L1, QC_L2, QC_M, and QC_H) were measured with the Simoa® pTau-217 assay using Antibody 2 in duplicate test and pTau levels were calculated. Plotting the results from repeated testing demonstrated the precision and reproducibility of the Simoa® pTau-217 assay using Antibody 2.

Figure 16:
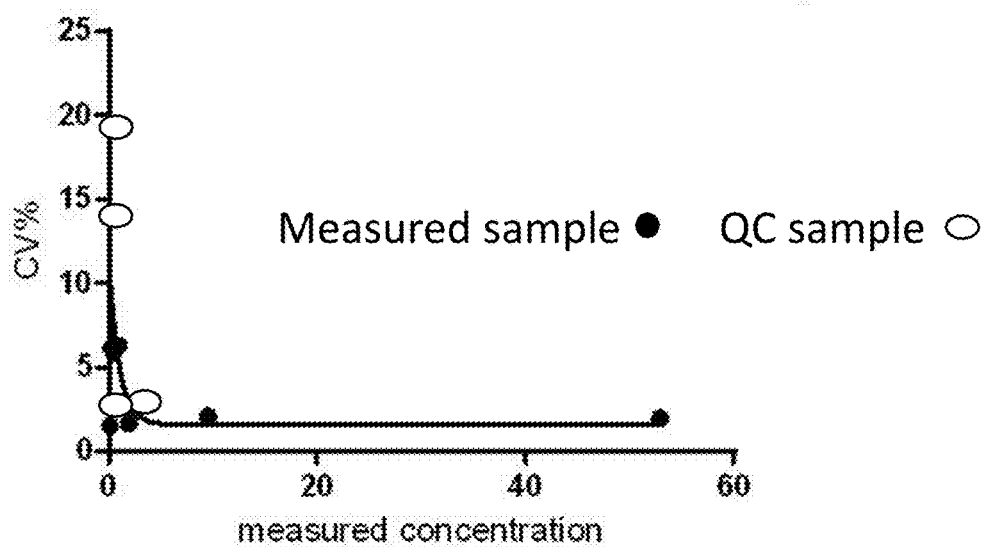
FIG. 16 depicts graphs of Simoa®-based pTau assay-217 results using Antibody 2 graphed as coefficient of variation (CV %) vs measured concentration.
Figure 16:
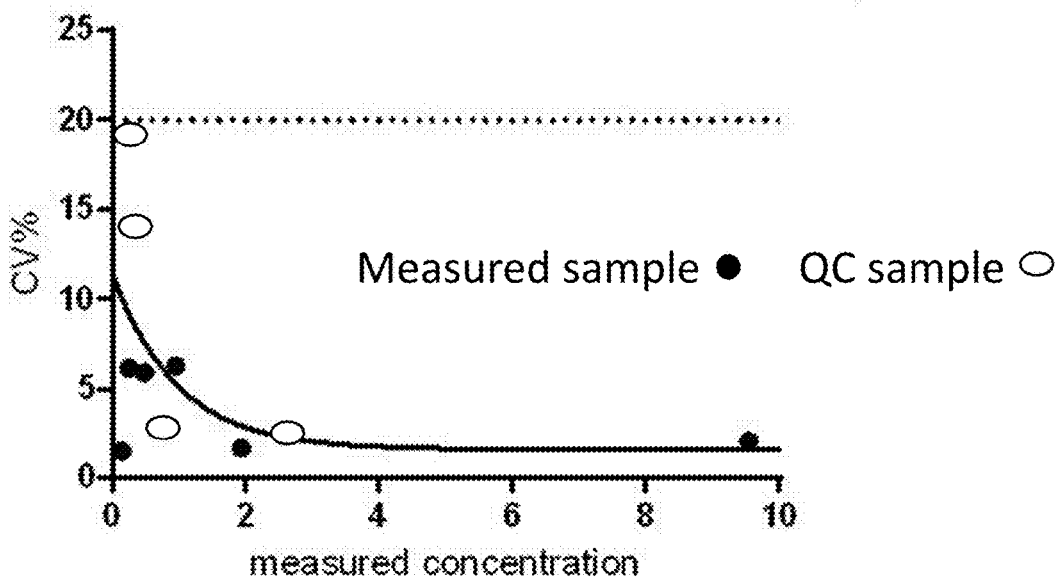

In FIG. 16, control samples from FIG. 15 and additional measured samples were measured with the Simoa® pTau-217 assay using Antibody 2 and plotted in two separate experiments to generate precision profiles. The precision profiles are based on measured sample concentration and inter-run CV % of the 4 QC samples. From this experiment, a functional LLOQ of pTau-217 in this assay was determined to be 0.26 pg/mL.

Figure 17:
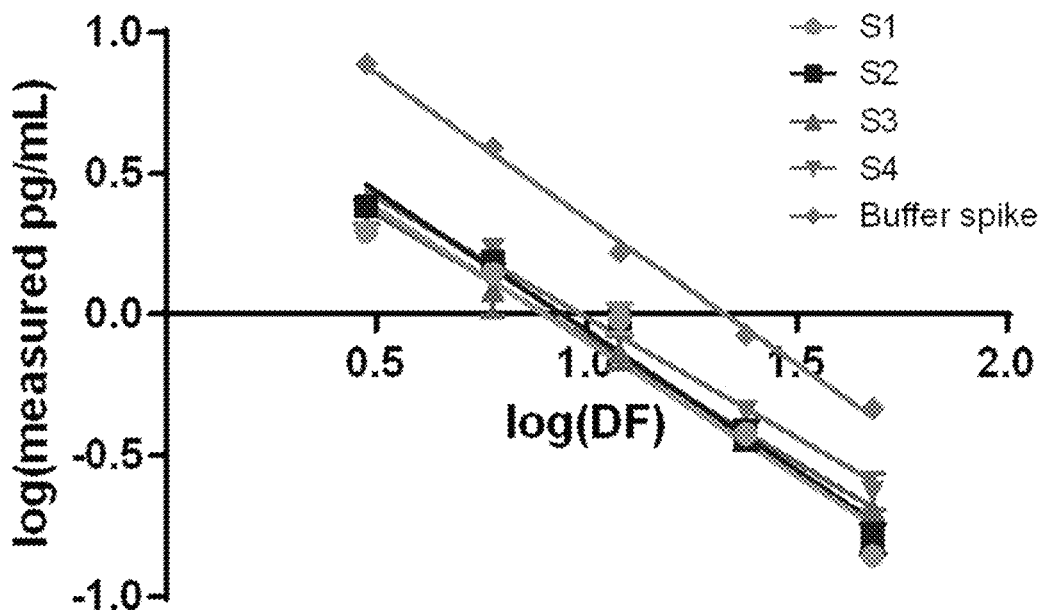
FIG. 17 depicts a graph of Simoa®-based pTau assay-217 results using Antibody 2 and statistical analysis of parallelism with determines whether actual samples containing high endogenous analyte concentrations provide a similar degree of detection in a standard curve after dilutions.

In FIG. 17, parallelism was assessed in the Simoa® pTau-217 assay using Antibody 2. A determination of parallelism is also important in that it shows if a signal is specific. Parallelism determines whether actual samples containing high endogenous analyte concentrations provide the same degree of detection in the assay in a standard curve after dilutions. This can represent differences in antibody binding affinity to endogenous analyte and a standard or calibration analyte. This can ensure that recombinant standards parallel native recognition of the endogenous analyte. In this experiment, 4 plasma samples, each from different donors, with relatively high concentration of detected pTau-217 and a spiked dilution buffer (sample 5) were diluted with a factor of 2 in 5 steps, starting at a dilution of 3×. The concentrations dropped below LLOD from dilution factor 12× onwards for all 4 plasma samples. In a graph of log (measured pg/mL) vs log [dilution factor (DF)] plasma measurements over spike measurements demonstrated linearity in detection along the various dilutions. 3 out of the 4 plasma samples were determined to fall within the accepted range of parallelism, with Sample 4 falling just outside of the accepted range. The accepted range of parallelism is <15%. These results demonstrated that the Simoa® pTau-217 assay using Antibody 2 on plasma samples yielded consistent and precise calculations of pTau-217 levels across various concentrations thus demonstrated its utility as a biomarker assay.

Figure 18:
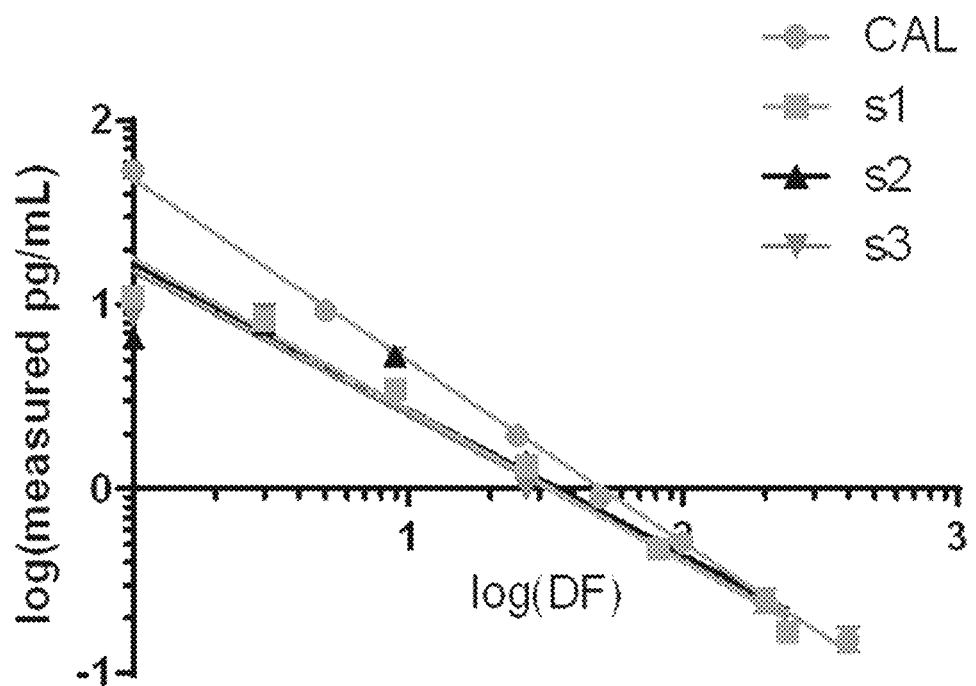
FIG. 18 depicts a graph of Simoa®-based pTau assay-217 results using Antibody 2 and statistical analysis of linearity with determines whether sample matrices spiked with detection analyte above an upper limit of detect can still provide reliable quantification after dilution within standard curve ranges for four samples plus a buffer spike.
Figure 19:
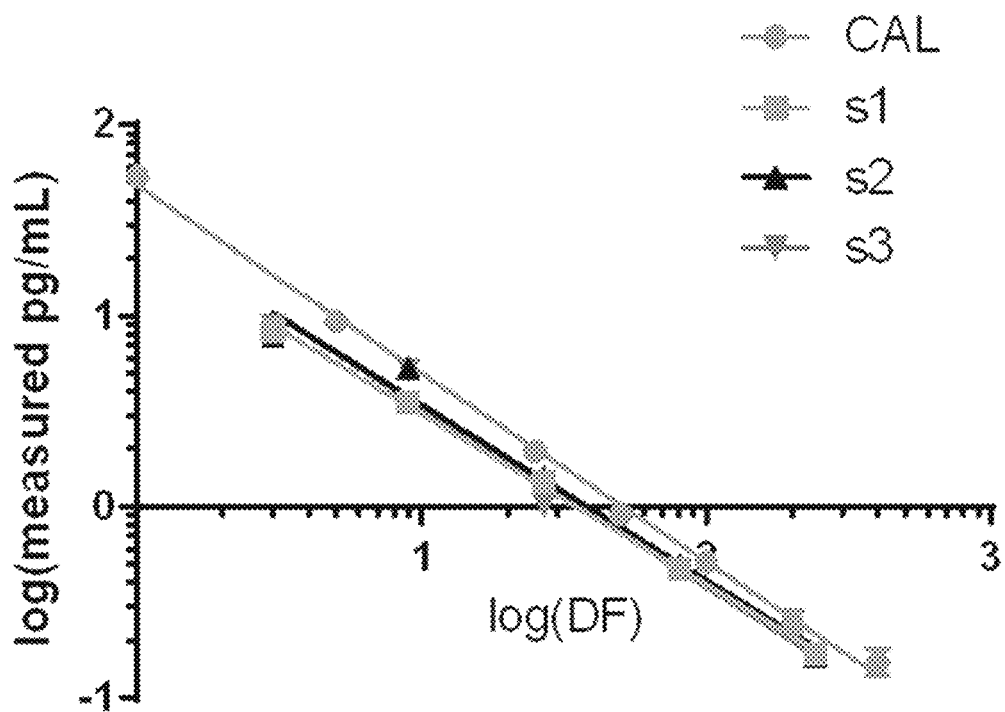
FIG. 19 depicts a graph of Simoa®-based pTau assay-217 results using Antibody 2 and statistical analysis of linearity with determines whether sample matrices spiked with detection analyte above an upper limit of detect can still provide reliable quantification after dilution within standard curve ranges for three samples plus a calibration sample.

In FIGS. 18-19, dilution linearity using the Simoa® pTau-217 assay using Antibody 2 was performed to demonstrate that a sample with a spike concentration about the upper limit of quantification (ULOQ) can be diluted to a concentration within the working range while still yielding a reliable assay result. In FIG. 18, three spiked samples (s1, s2, and s3) and the Calibration sample were assayed and plotted as log(measured pg/mL) vs log (DF) to determine dilution linearity. In FIG. 19, three spiked samples (s1, s2, and s3) and the Calibration sample were assayed and plotted as log(measured pg/mL) vs log (DF) to determine dilution linearity with the highest spike point omitted from s1, s2, and s3 since it was out of the calibration range of 50 μg/mL.

Figure 20:
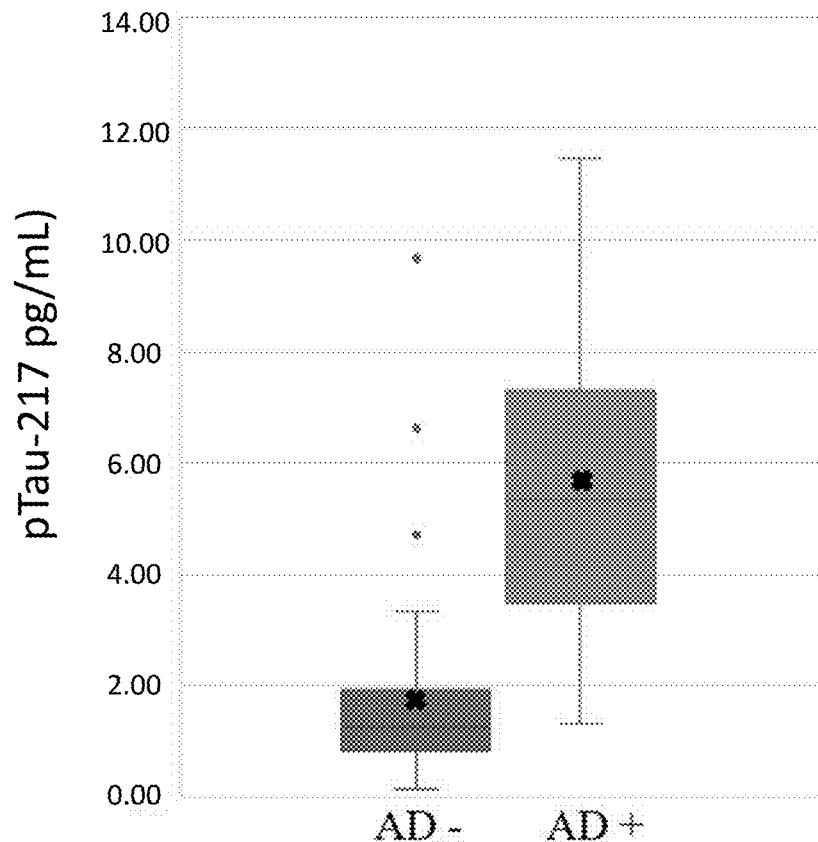
FIG. 20 depicts a graph of Simoa®-based pTau assay-217 results using Antibody 2 in a clinical validation of a memory clinic cohort and a graph of receiver-operating characteristic (ROC) analysis graphed against pTau-217 assay sensitivity.
Figure 20:
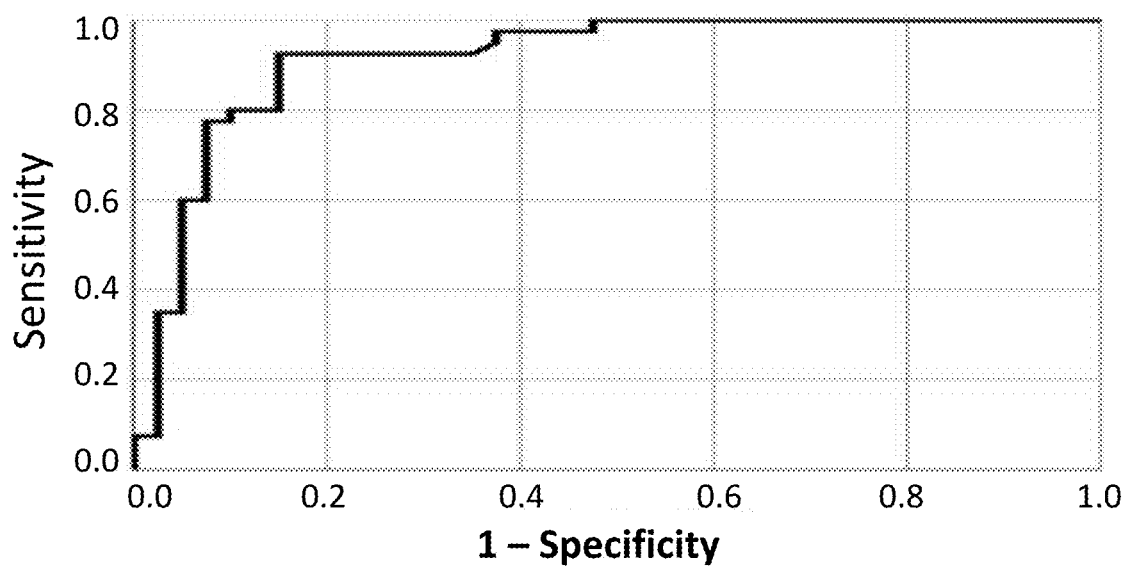

In FIG. 20, the Simoa® pTau-217 assay using Antibody 2 was used to assess samples taken from a memory clinic cohort. Plasma samples were measured and graphed for calculated pTau217 concentrations. Clinical diagnosis of AD was used as the classifier. AUC was calculated at 0.916 indicating success in distinguishing AD+ from AD− within this cohort with the Simoa® pTau-217 assay using Antibody 2. Also in FIG. 20, a receiver operating characteristic (ROC) curve was plotted to illustrate the diagnostic ability of this binary classifier (AD+ or AD−) system as it is possible that the discrimination threshold between classifiers is varied.

Figure 21:
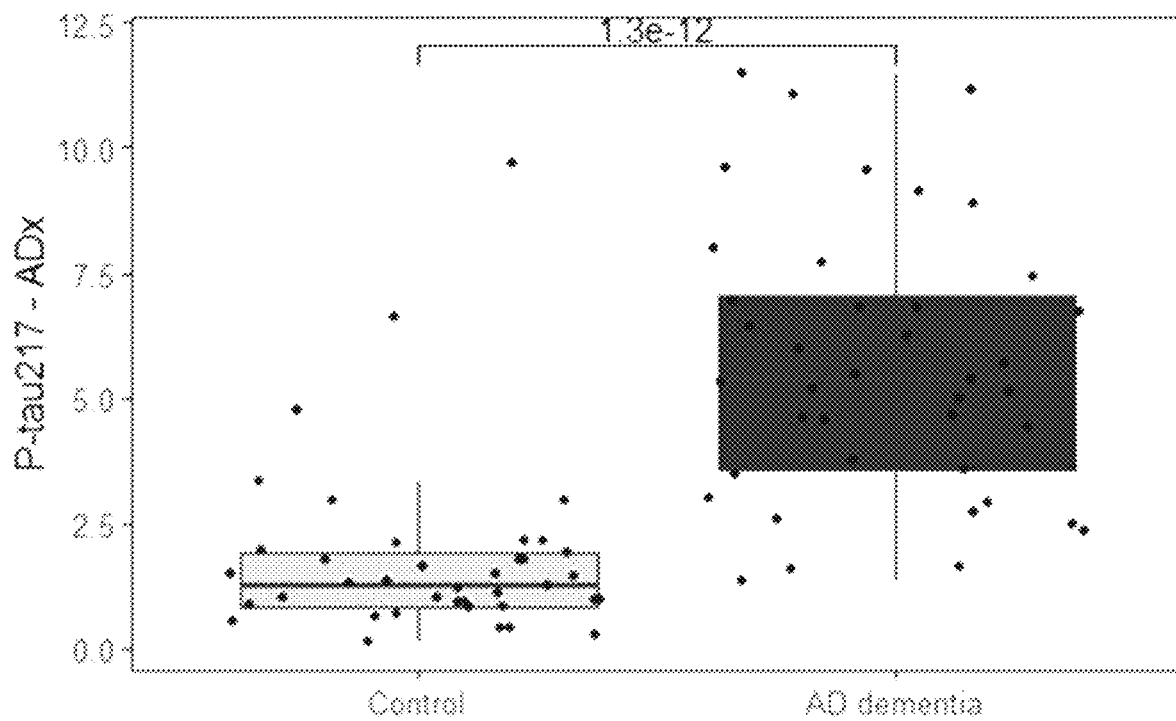
FIG. 21 depicts a graph of Simoa®-based pTau assay-217 results using Antibody 2 on groups from Control and AD dementia individuals.
Figure 22:
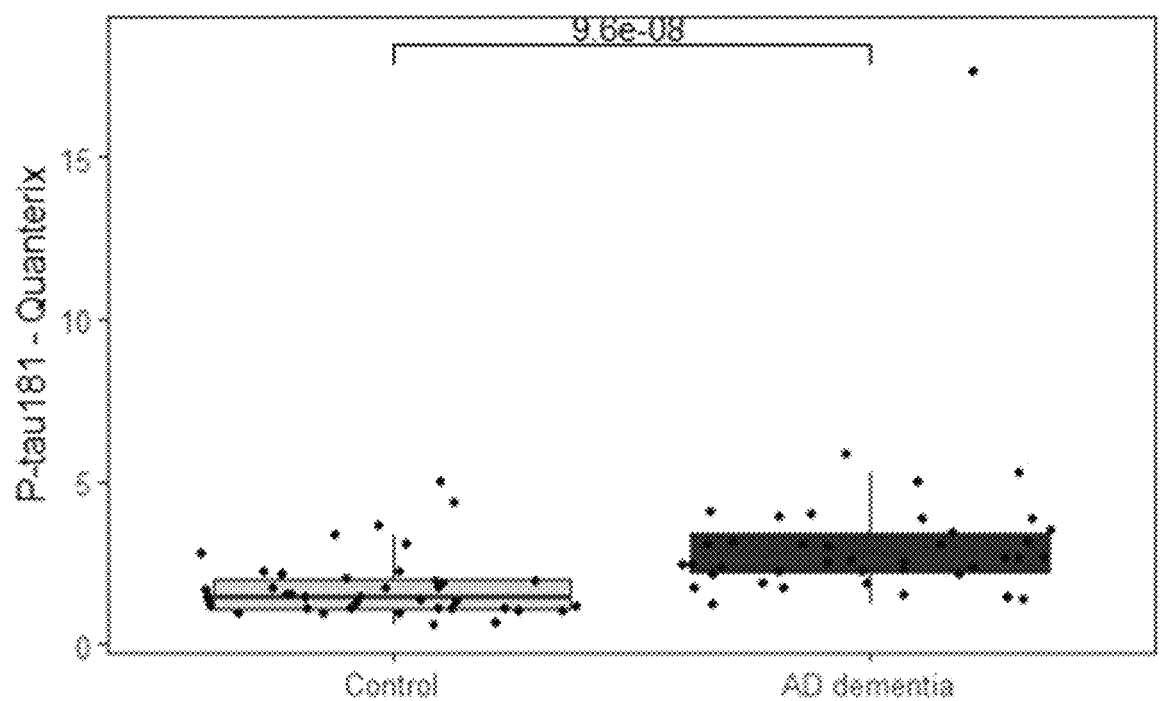
FIG. 22 depicts a graph of Simoa®-based pTau assay-181 results using an antibody from Quanterix® on groups from Control and AD dementia individuals and a chart of sample stratification.

In FIG. 21-22, clinical performance of the Simoa® pTau-217 assay using Antibody 2 was compared to a Simoa® pTau-181 assays using antibody P-tau181—Quanterix®. In FIG. 21, Antibody 2 was able to distinguish assayed plasma samples from taken from AD dementia individuals vs Controls (P value $1.3e^{-12}$ for Antibody 2). In FIG. 22, the commercially available P-tau181—Quanterix® Simoa® assay (Quanterix® Corp., Item number 103714) was also able to distinguish assayed plasma samples from taken from AD dementia individuals vs Controls (P value $9.6e^{-08}$). Data from the individuals from which the samples were derived for data from FIGS. 21-22 is listed in FIG. 22.

Figure 23:
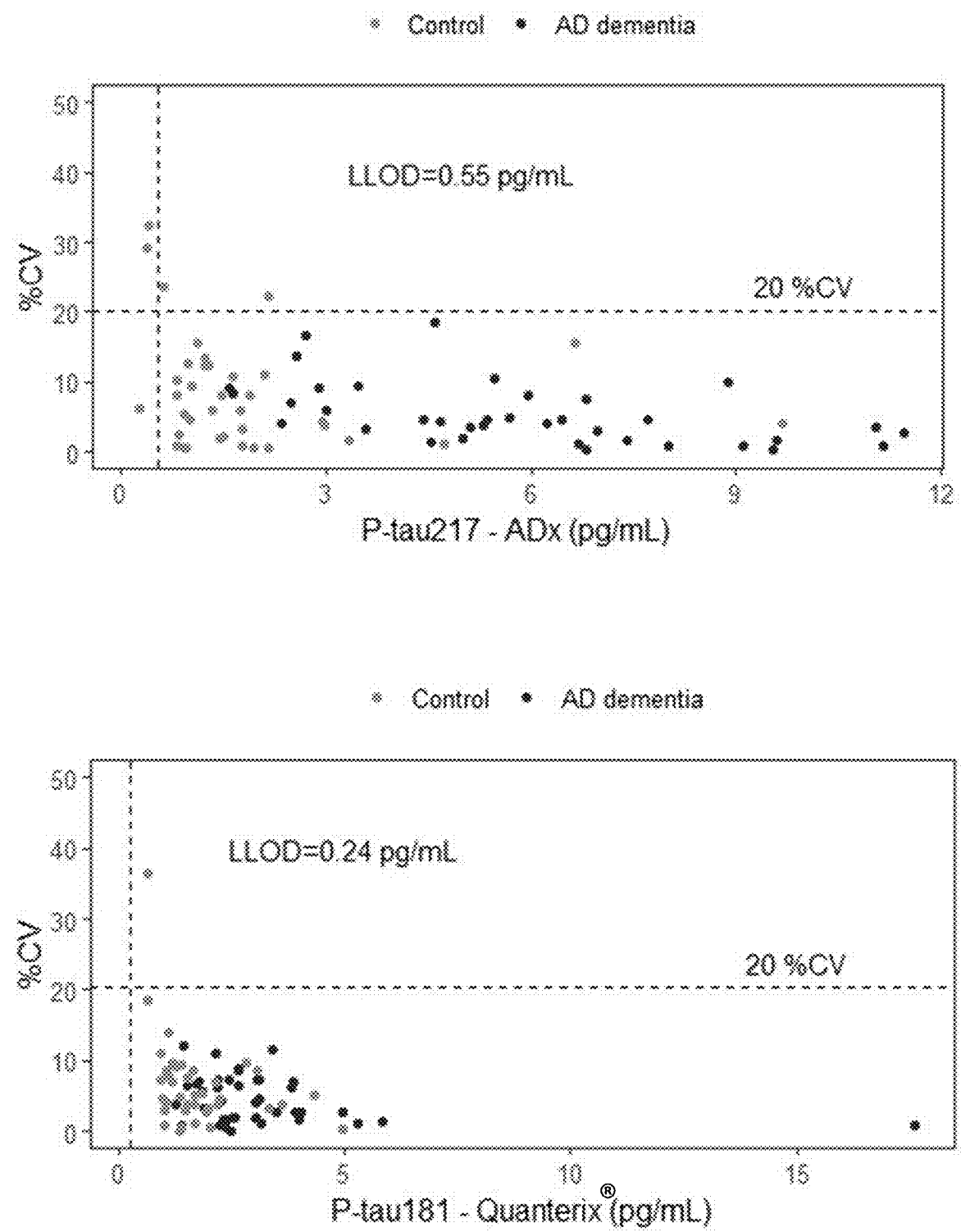
FIG. 23 depicts graphs of Simoa®-based pTau assay-217 results using Antibody 2, and Simoa®-based pTau assay-181 results using an antibody from Quanterix® showing precision plots with calculated coefficient of variation.

In FIG. 23 precision plots were generated for the Simoa® assay using P-tau217 Antibody 2 and P-tau181—Quanterix® antibody (Quanterix® Corp., Item number 103714). Calculated LLODs were 0.55 pg/mL and 0.24 pg/mL, respectively. Concentrations were not back calculated and LLOD values are accordingly not back calculated.

Figure 24:
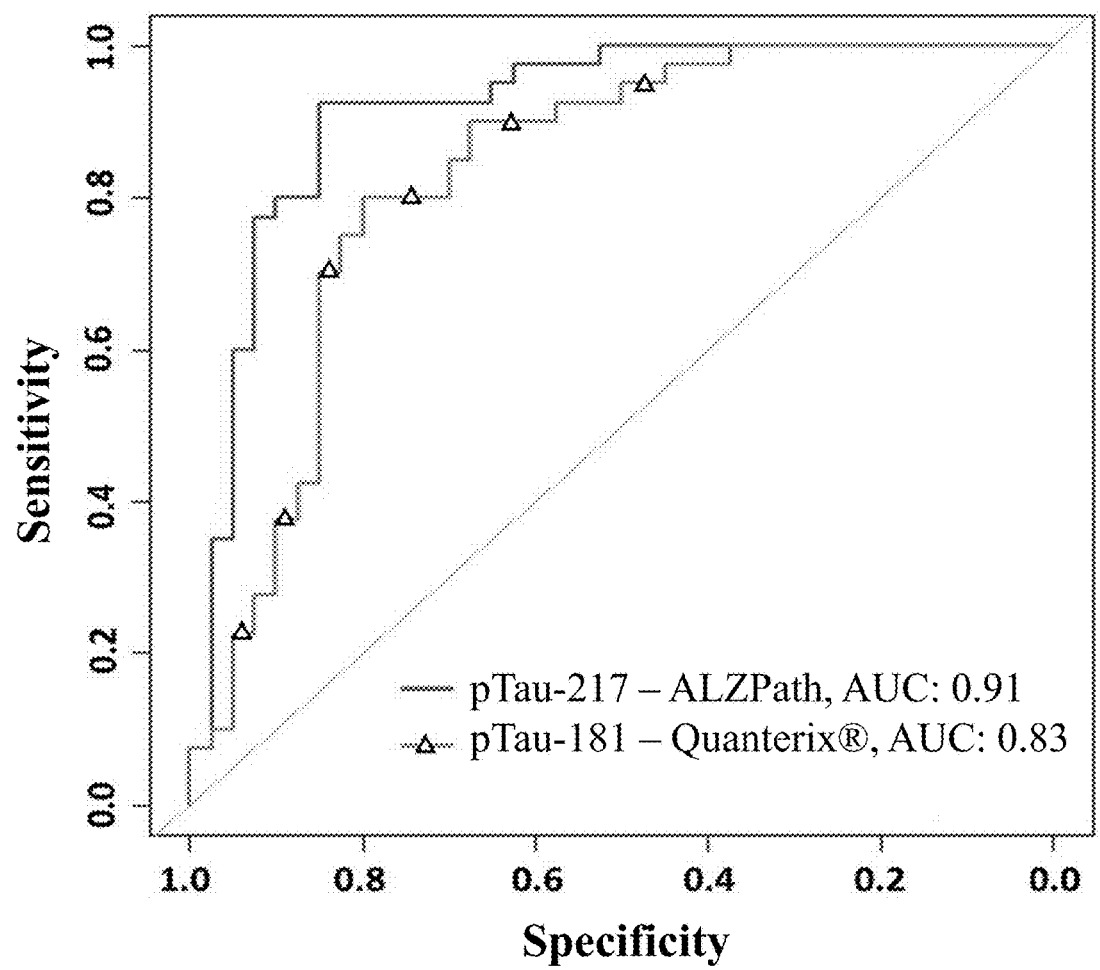
FIG. 24 depicts a graph of clinical performance of various pTau Simoa®-based assays comparing sensitivity and specificity and a chart with a statistical analysis of results.

In FIG. 24 ROC curves were plotted for the P-tau181—Quanterix® antibody (Quanterix® Corp., Item number 103714) and P-tau217 Antibody 2. Analysis of the data indicated that P-tau217 Antibody 2 exhibited superior sensitivity and specificity when comparing to the Simoa® assay using the P-tau181—Quanterix® antibody in differentiating AD-dementia from controls. The diagnostic accuracy of Antibody 2 for AD dementia in this Simoa® method is 92.5% when tested on plasma samples. The diagnostic specificity of Antibody 2 for AD dementia in this Simoa® method is 85% when tested on plasma samples.

Figure 25:
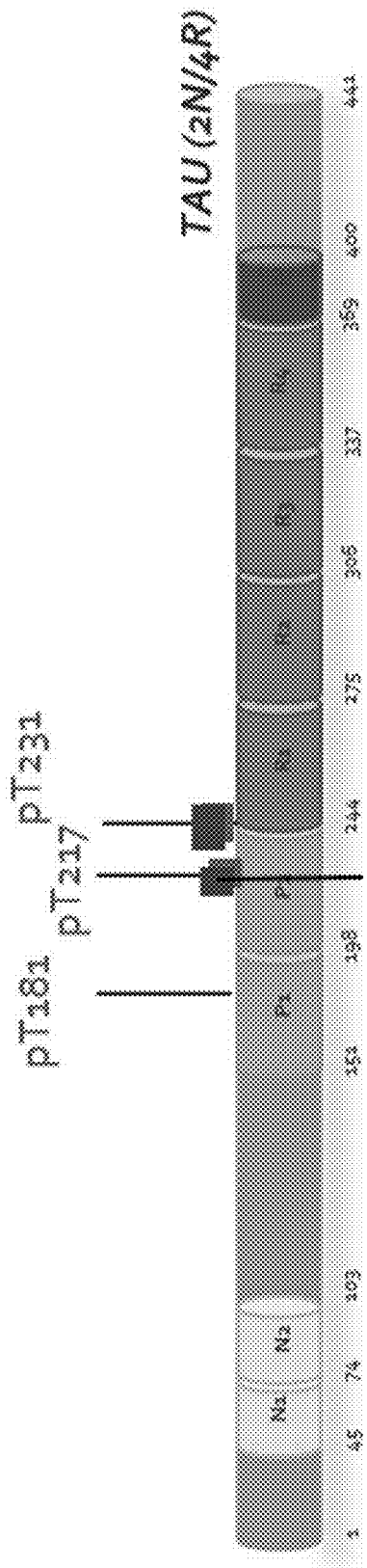
FIG. 25 depicts a schematic diagram of Tau indicating the relative location of various protein domains and the locations of threonine residues which can be assayed for phosphorylation status using methods disclosed herein.

In FIG. 25 a schematic diagram of Tau polypeptide indicating the relative location of various protein domains and the locations of threonine residues which can be assayed for phosphorylation status using methods disclosed herein is depicted. The location of pT217 within the P2 domain of Tau is indicated. pT181 resides within the P1 domain and pT231 resides near the border between the P2 and R1 domains.

Figure 26:
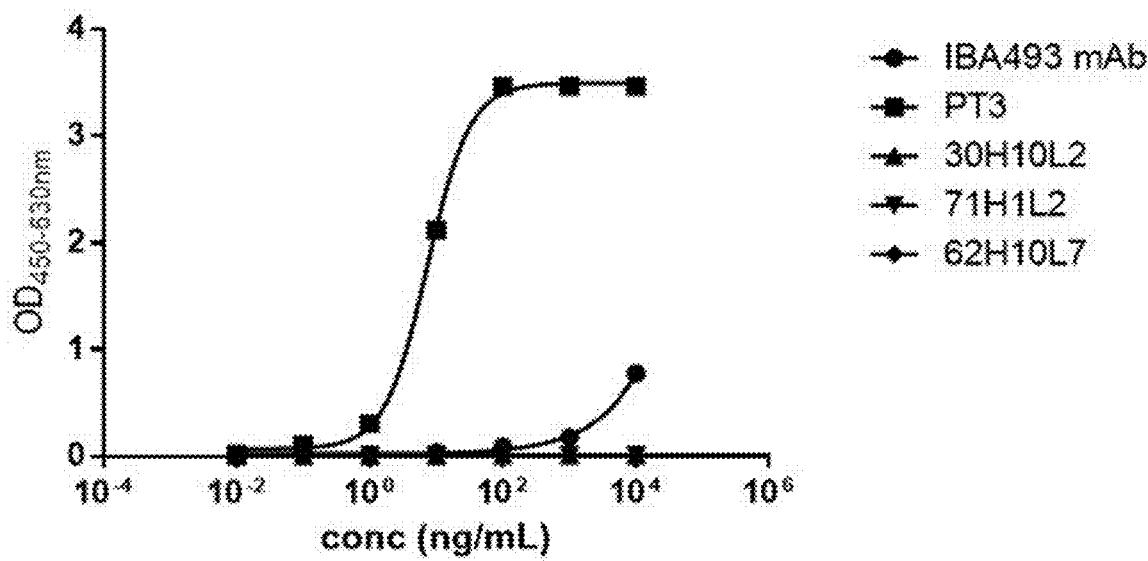
FIG. 26 depicts graphs of reactivity to a Tau fragment with non-phosphorylated T217 (Bio-pt654) and full length Tau (Tau441) in indirect ELISA for various antibodies.
Figure 26:
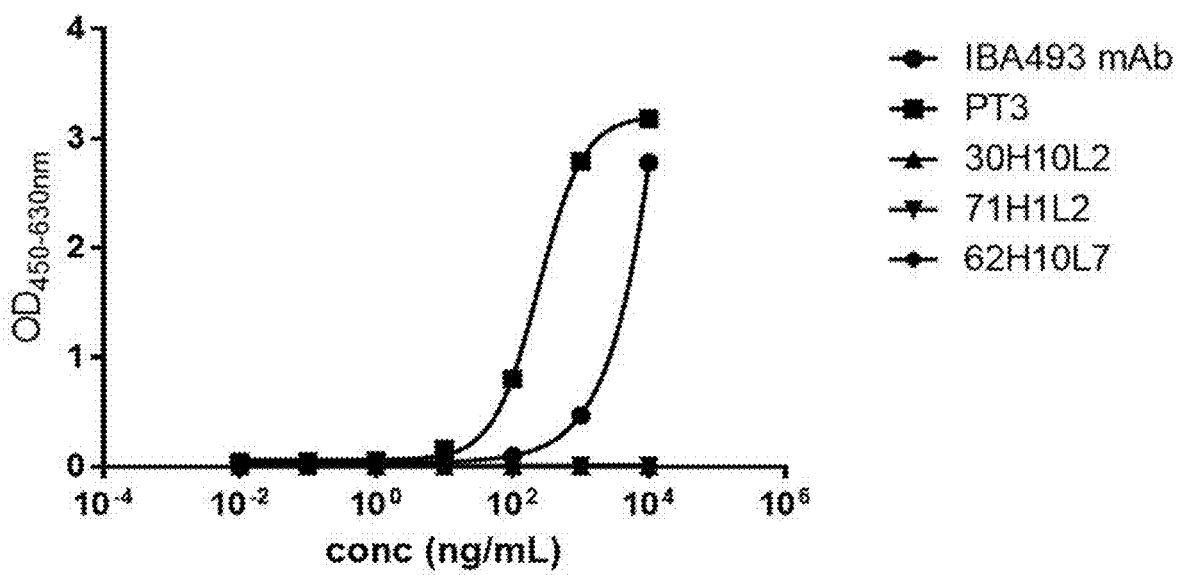

In FIG. 26 various Tau antibodies were assayed using indirect ELISA and extent of reactivity to a Tau fragment with non-phosphorylated T217 (Bio-pt654) and full length Tau (Tau441) were graphed. IBA493 mAB and PT3 displayed concentration dependent reactivity to both Bio-pt654 and Tau441. Antibody 2, 5, and 6 described herein do not display any reactivity to either Bio-pt654 or Tau441 in this assaying demonstrating precision and specificity in pTau-217 detection for Antibodies 2, 5, and 6.

Figure 27:
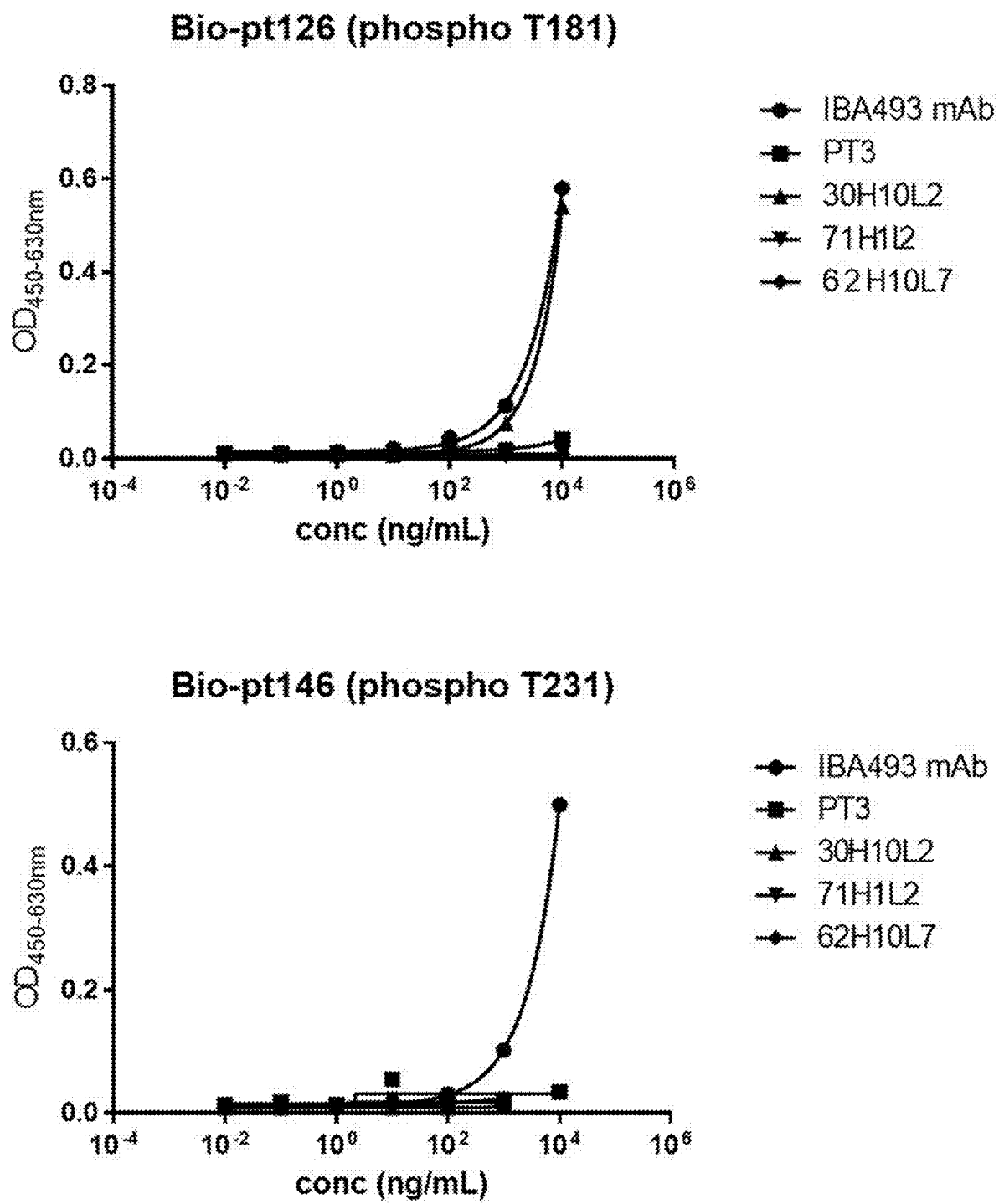
FIG. 27 depicts graphs of reactivity to Tau fragments with phosphorylated T181 (Bio-pt126) and phosphorylated T231 (Bio-pt146) in indirect ELISA for various antibodies.

In FIG. 27 various Tau antibodies were assayed using indirect ELISA and extent of reactivity to a Tau fragment with phosphorylated T181 (Bio-pt126) and phosphorylated T231 (Bio-pt146) were graphed. IBA493 mAB and Antibody 2 described herein displayed concentration dependent reactivity to Bio-pt126. IBA493 mAB was the only antibody of those tested displaying concentration dependent reactivity to Bio-pt146. This demonstrates that IBA493 mAB, PT3, and Antibody 2 described herein were each distinguishable based on which analytes each antibody interacted with via indirect ELISA. IBA493 mAB interacts with pTau-217, non-phospho T217, full length Tau, pTau-181, and pTau-231. PT3 interacts with pTau-217, non-phospho T217, and full length Tau. Antibody 2 interacts with pTau-217 and pTau-181. IBA493 mAB's interaction with non-phospho T217 was also shown to be considerably less than PT3's interaction with non-phospho T217.

Figure 28:
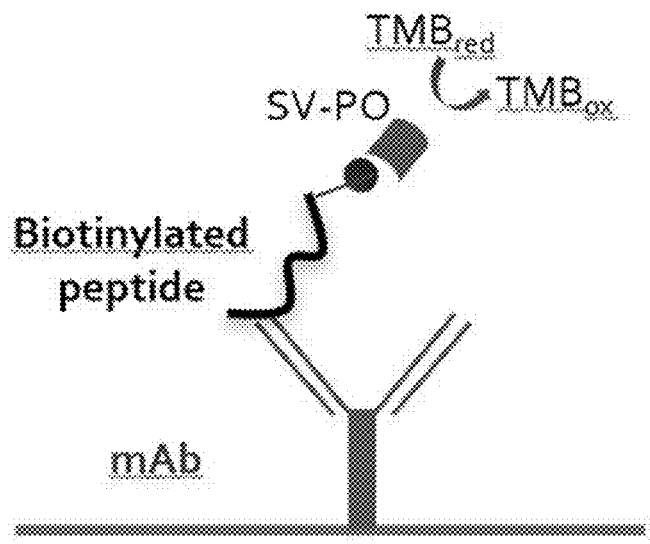
FIG. 28 depicts a diagram of an assay utilizing a pTau217 monoclonal antibody as a capture tool for various synthetic peptides and a graph of results for this assay using Antibody 2 as the capture tool.
Figure 28:
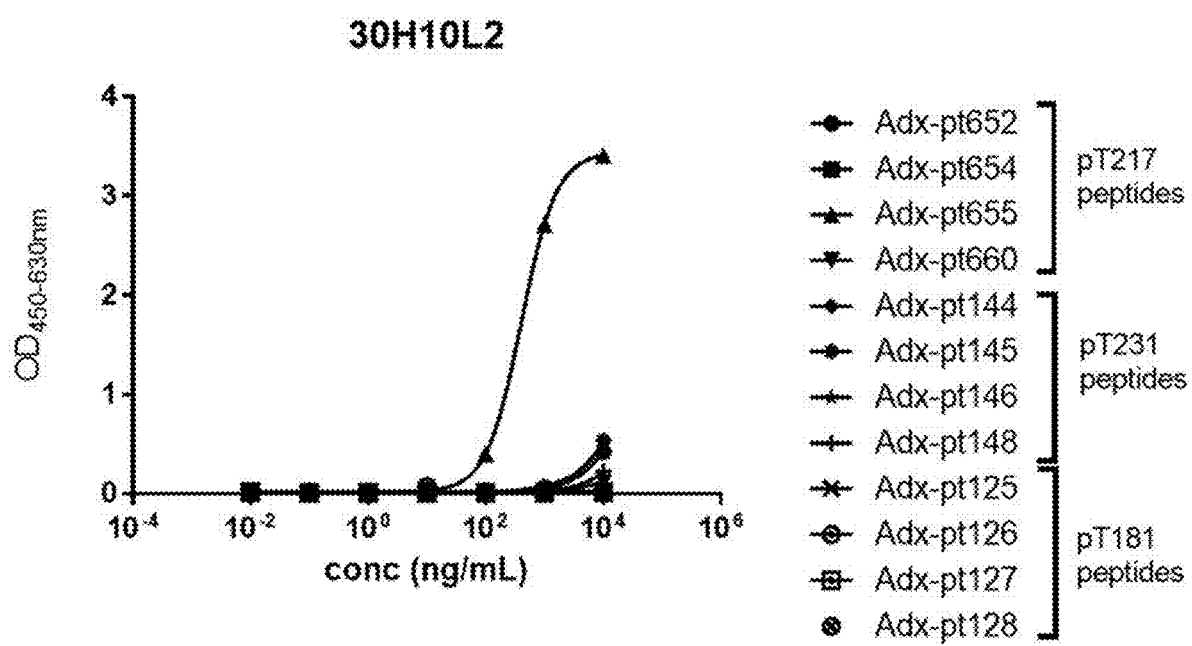

In FIG. 28, a diagram of an assay using Antibody 2 to detect capture of particular Tau peptides is depicted. In this assay, Antibody 2 is bound to a plate and sample wells from the plate are subjected to various biotinylated peptides under conditions conducive to forming specific antibody-ligand interactions. Samples are then washes to remove excess unbound biotinylated peptide. Streptavidin beads conjugated to peroxidase and then added to the samples to allow biotin-streptavidin complexes to form on peptide bound antibodies. TMBrea substrate is then added and samples are measured for colorimetric development using an ELISA plate reader. The results were graphed and out of various pTau-217, pTau-231, and pTau-181 peptides tested, Adx-pt655 yielded specific dose-dependent reactivity. These results illustrate the specificity of Antibody 2 to specific features of pTau (namely Tau phosphorylated at threonine 217). Antibody 5 and Antibody 6 tested by indirect ELISA under the same conditions using the same Tau peptides yielded no specific dose-dependent reactivity toward the Tau peptides tested.

Various pTau-217 antibodies corresponding to Antibody 1, Antibody 2, Antibody 3, Antibody 4, Antibody 5, and Antibody 5 described here were also evaluated as capture antibodies either directly coated onto or onto streptavidin-coated plates on the Mesoscale Discovery technology platform. This system uses non-radioactive, electrochemiluminescent labels, thereby conferring significant advantages over traditional ELISA assays. These advantages include lower background signal, improved sensitivity, and a dynamic range of detection.

Figure 29:
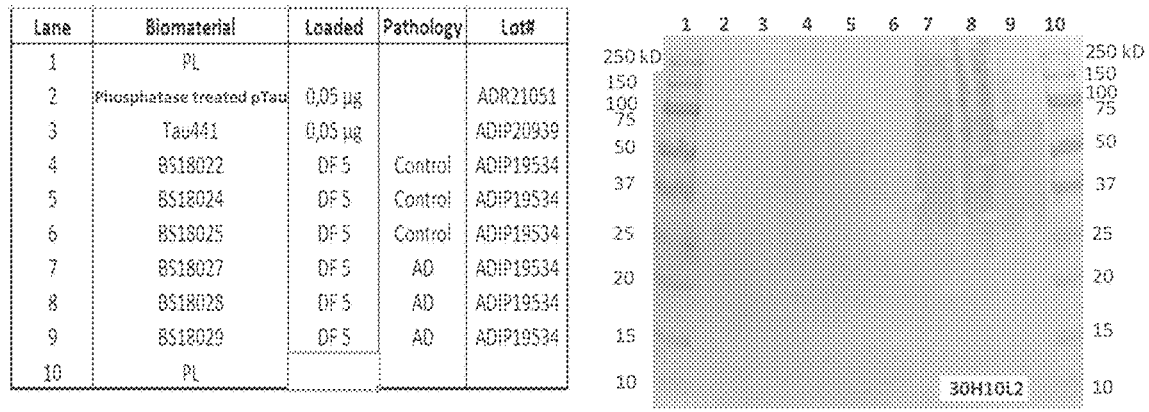
FIG. 29 depicts Western blot analysis using various Tau antibodies on brain lysate samples from AD patients or control subjects.
Figure 29:
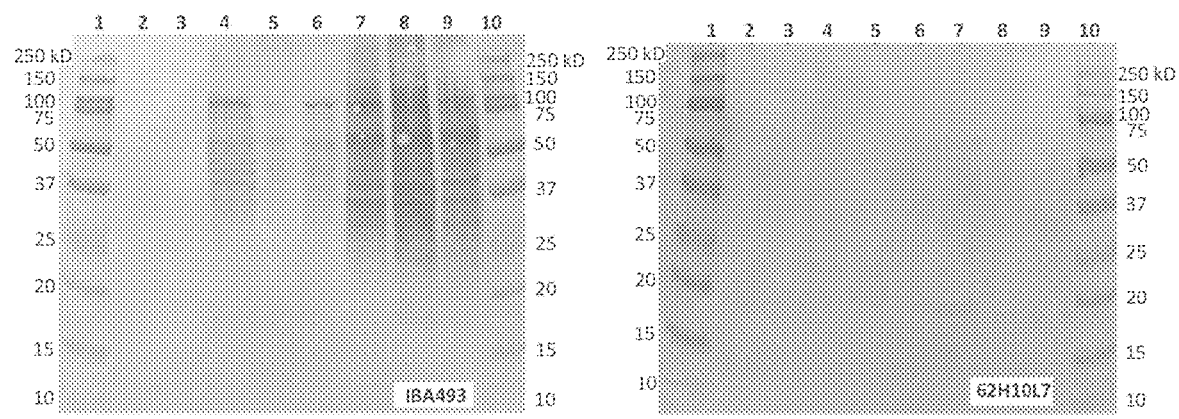
Figure 29:
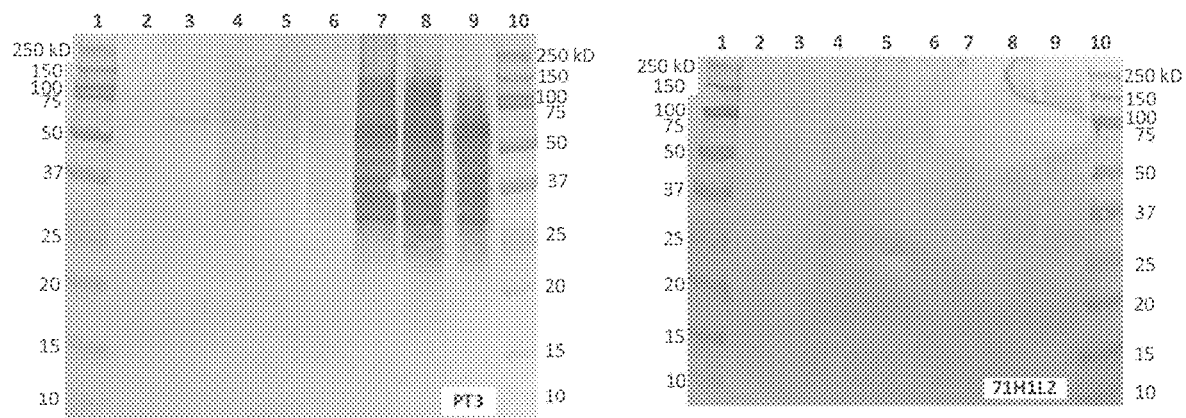

In FIG. 29, Western blots were used to assess binding of various antibodies to brain lysate samples from AD patients and Control subjects. In the five Western blots shown, samples are loaded according to the same sample key shown in FIG. 29. Protein ladders were run in lanes 1 and 10. Phosphatase treated pTau loaded in an amount of 0.05 ug was run in lane 2. Full-length Tau (Tau411) loaded in an amount of 0.05 ug was run in lane 3. Lanes 4-6 contain samples from different Control subjects with a dilution factor of 5. Lanes 7-9 contain samples from different AD subjects with a dilution factor of 5. The results indicated that IBA394 mAb and PT3 both bound to and immunoprecipitated different length isoforms of Tau in control samples and AD samples and immunoprecipitated significantly more Tau in AD samples while showing no interaction with synthetic full length Tau or phosphatase treated pTau. Antibody 2 (30H2L10) bound to and immunoprecipitated different length isoforms of Tau in AD samples but did not immunoprecipitate a significant amount to of Tau in samples from Control individuals. Antibody 5 and Antibody 6 did not yield detectable Western blot signals in this assay.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for detecting phosphorylated tau in a sample from an individual comprising: performing an immunoassay on the sample using an antibody or antibody fragment comprising a variable domain, heavy chain region (VH) and a variable domain, light chain region (VL), wherein:
   (a) the VH comprises SEQ ID NO: 31 and the VL comprises SEQ ID NO: 36;
   (b) the VH comprises SEQ ID NO: 33 and the VL comprises SEQ ID NO: 39;
   (c) the VH domain comprises SEQ ID NO: 34 and the VL comprises SEQ ID NO: 40;
   (d) the VH domain comprises SEQ ID NO: 30 and the VL comprises SEQ ID NO: 35;
   (e) the VH domain comprises SEQ ID NO: 31 and the VL comprises SEQ ID NO: 37; or
   (f) the VH domain comprises SEQ ID NO: 32 and the VL comprises SEQ ID NO: 38.

2. A method for detecting phosphorylated tau in a sample from an individual comprising: performing an immunoassay on the sample using an antibody or antibody fragment comprising a variable domain, heavy chain region (VH) and a variable domain, light chain region (VL),
   wherein the VH comprises an amino acid sequence at least about 90% identical to a sequence as set forth in any one of SEQ ID NOs: 30-34, and wherein the VL comprises an amino acid sequence at least about 90% identical to a sequence as set forth in any one of SEQ ID NOS: 35-40; and
   wherein the VH comprises a HCDR1 sequence, a HCDR2 sequence, and a HCDR3 sequence, and the VL comprises a LCDR1 sequence, a LCDR2 sequence, and a LCDR3 sequence, wherein:
   (a) the HCDR1 sequence comprises SEQ ID NO: 2, the HCDR2 sequence comprises SEQ ID NO: 7, the HCDR3 sequence comprises SEQ ID NO: 11, the LCDR1 sequence comprises SEQ ID NO: 15, the LCDR2 sequence comprises SEQ ID NO: 21, and the LCDR3 sequence comprises SEQ ID NO: 25;
   (b) the HCDR1 sequence comprises SEQ ID NO: 4, the HCDR2 sequence comprises SEQ ID NO: 7, the HCDR3 sequence comprises SEQ ID NO: 12, the LCDR1 sequence comprises SEQ ID NO: 18, the LCDR2 sequence comprises SEQ ID NO: 23, and the LCDR3 sequence comprises SEQ ID NO: 28;
   (c) the HCDR1 sequence comprises SEQ ID NO: 5, the HCDR2 sequence comprises SEQ ID NO: 9, the HCDR3 sequence comprises SEQ ID NO: 13, the LCDR1 sequence comprises SEQ ID NO: 19, the LCDR2 sequence comprises SEQ ID NO: 21, and the LCDR3 sequence comprises SEQ ID NO: 29;
   (d) the HCDR1 sequence comprises SEQ ID NO: 1, the HCDR2 sequence comprises SEQ ID NO: 6, the HCDR3 sequence comprises SEQ ID NO: 10, the LCDR1 sequence comprises SEQ ID NO: 14, the LCDR2 sequence comprises SEQ ID NO: 20, and the LCDR3 sequence comprises SEQ ID NO: 24;
   (e) the HCDR1 sequence comprises SEQ ID NO: 2, the HCDR2 sequence comprises SEQ ID NO: 7, the HCDR3 sequence comprises SEQ ID NO: 11, the LCDR1 sequence comprises SEQ ID NO: 16, the LCDR2 sequence comprises SEQ ID NO: 22, and the LCDR3 sequence comprises SEQ ID NO: 26; or
   (f) wherein the HCDR1 sequence comprises SEQ ID NO: 3, the HCDR2 sequence comprises SEQ ID NO: 8, the HCDR3 sequence comprises SEQ ID NO: 10, the LCDR1 sequence comprises SEQ ID NO: 17, the LCDR2 sequence comprises SEQ ID NO: 20, and the LCDR3 sequence comprises SEQ ID NO: 27.

3. A method for detecting phosphorylated tau in a sample from an individual comprising: performing an immunoassay on the sample using an antibody comprising a heavy chain and a light chain, wherein:
   (a) the heavy chain comprises SEQ ID NO: 43 and the light chain comprises SEQ ID NO: 44;
   (b) the heavy chain comprises SEQ ID NO: 48 and the light chain comprises SEQ ID NO: 49;
   (c) the heavy chain comprises SEQ ID NO: 50 and the light chain comprises SEQ ID NO: 51;
   (d) the heavy chain comprises SEQ ID NO: 41 and the light chain comprises SEQ ID NO: 42;
   (e) the heavy chain comprises SEQ ID NO: 43 and the light chain comprises SEQ ID NO: 45; or
   (f) the heavy chain comprises SEQ ID NO: 46 and the light chain comprises SEQ ID NO: 47.

4. The method of claim 2, wherein the phosphorylated tau is selected from the group consisting of pTau-181, pTau-212, pTau-217, pTau-231, pTau-214, and pTau-220.

5. The method of claim 2, wherein the phosphorylated tau is pTau-181, pTau-217, or pTau-231.

6. The method of claim 2, wherein the antibody is a monoclonal antibody.

7. The method of claim 2, wherein the antibody is a rabbit monoclonal antibody.

8. The method of claim 2, wherein the antibody is a chimeric antibody or antigen binding fragment thereof.

9. The method of claim 2, wherein the antibody comprises an IgG1 constant region.

10. The method of claim 2, wherein the sample is selected from the group consisting of a blood sample, a plasma sample, a serum sample, and a cerebrospinal fluid (CSF) sample.

11. The method of claim 2, further comprising:
detecting the antibody or antibody fragment bound to the phosphorylated tau, thereby detecting the phosphorylated tau in the sample; and
establishing Alzheimer's disease in the individual based on the phosphorylated tau that is detected.

12. The method of claim 2, further comprising:
detecting the antibody or antibody fragment bound to the phosphorylated tau, thereby detecting the phosphorylated tau in the sample; and
establishing a prognosis of the individual for developing Alzheimer's disease based on the phosphorylated tau that is detected.

13. The method of claim 2, further comprising determining the individual's age, genotype, or expression of a biomarker.

14. The method of claim 13, wherein the biomarker is selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof.

15. The method of claim 12, wherein the method has a specificity of at least about 85% for differentiating the Alzheimer's disease in the individual from a normal control based on the phosphorylated tau that is detected.

16. The method of claim 12, wherein the method has a sensitivity of at least about 85% for differentiating the Alzheimer's disease in the individual from a normal control based on the phosphorylated tau that is detected.

17. The method of claim 2, wherein the method is performed in vitro.

18. The method of claim 2, wherein the phosphorylated tau is pTau-217.

19. The method of claim 1, wherein the phosphorylated tau is selected from the group consisting of pTau-181, pTau-212, pTau-217, pTau-231, pTau-214, and pTau-220.

20. The method of claim 1, wherein the phosphorylated tau is pTau-181, pTau-217, or pTau-231.

21. The method of claim 1, wherein the phosphorylated tau is pTau-217.

22. The method of claim 1, wherein the antibody is a monoclonal antibody.

23. The method of claim 1, wherein the antibody is a rabbit monoclonal antibody.

24. The method of claim 1, wherein the antibody is a chimeric antibody or antigen binding fragment thereof.

25. The method of claim 1, wherein the antibody comprises an IgG1 constant region.

26. The method of claim 1, wherein the sample is selected from the group consisting of a blood sample, a plasma sample, a serum sample, and a cerebrospinal fluid (CSF) sample.

27. The method of claim 1, further comprising:
detecting the antibody or antibody fragment bound to the phosphorylated tau, thereby detecting the phosphorylated tau in the sample; and
establishing Alzheimer's disease in the individual based on the phosphorylated tau that is detected.

28. The method of claim 1, further comprising:
detecting the antibody or antibody fragment bound to the phosphorylated tau, thereby detecting the phosphorylated tau in the sample; and
establishing a prognosis of the individual for developing Alzheimer's disease based on the phosphorylated tau that is detected.

29. The method of claim 1, further comprising determining the individual's age, genotype, or expression of a biomarker.

30. The method of claim 29, wherein the biomarker is selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof.

31. The method of claim 28, wherein the method has a specificity of at least about 85% for differentiating the Alzheimer's disease in the individual from a normal control based on the phosphorylated tau that is detected.

32. The method of claim 28, wherein the method has a sensitivity of at least about 85% for differentiating the Alzheimer's disease in the individual from a normal control based on the phosphorylated tau that is detected.

33. The method of claim 1, wherein the method is performed in vitro.

34. The method of claim 3, wherein the phosphorylated tau is selected from the group consisting of pTau-181, pTau-212, pTau-217, pTau-231, pTau-214, and pTau-220.

35. The method of claim 3, wherein the phosphorylated tau is pTau-181, pTau-217, or pTau-231.

36. The method of claim 3, wherein the phosphorylated tau is pTau-217.

37. The method of claim 3, wherein the antibody is a monoclonal antibody.

38. The method of claim 3, wherein the antibody is a rabbit monoclonal antibody.

39. The method of claim 3, wherein the antibody is a chimeric antibody.

40. The method of claim 3, wherein the antibody comprises an IgG1 constant region.

41. The method of claim 3, wherein the sample is selected from the group consisting of a blood sample, a plasma sample, a serum sample, and a cerebrospinal fluid (CSF) sample.

42. The method of claim 3, further comprising:
detecting the antibody bound to the phosphorylated tau, thereby detecting the phosphorylated tau in the sample; and
establishing Alzheimer's disease in the individual based on the phosphorylated tau that is detected.

43. The method of claim 3, further comprising:
detecting the antibody bound to the phosphorylated tau, thereby detecting the phosphorylated tau in the sample; and
establishing a prognosis of the individual for developing Alzheimer's disease based on the phosphorylated tau that is detected.

44. The method of claim 3, further comprising determining the individual's age, genotype, or expression of a biomarker.

45. The method of claim 44, wherein the biomarker is selected from the group consisting of Aβ42, Aβ40, Aβ38, BACE1, hFABP, TREM2, YKL-40, IP-10, neurogranin, SNAP-25, synaptotagmin, alpha-synuclein, TDP-43, ferritin, VILIP-1, NfL, GFAP, and combinations thereof.

46. The method of claim 43, wherein the method has a specificity of at least about 85% for differentiating the Alzheimer's disease in the individual from a normal control based on the phosphorylated tau that is detected.

47. The method of claim 43, wherein the method has a sensitivity of at least about 85% for differentiating the Alzheimer's disease in the individual from a normal control based on the phosphorylated tau that is detected.

48. The method of claim 3, wherein the method is performed in vitro.

* * * * *